US010059751B2

(12) United States Patent
Lundegaard et al.

(10) Patent No.: US 10,059,751 B2
(45) Date of Patent: Aug. 28, 2018

(54) PEPTIDE COMBINATIONS AND USES THEREOF IN TREATING DUST MITE ALLERGY

(71) Applicants: Alk-Abello A/S, Horsholm (DK); La Jolla Institute For Allergy And Immunology, La Jolla, CA (US)

(72) Inventors: Claus Lundegaard, Soborg (DK); Lars Harder Christensen, Allerod (DK); Peter Adler Wurtzen, Vedbaek (DK); Alessandro Sette, La Jolla, CA (US); John Sidney, San Diego, CA (US); Gitte Lund, Allerod (DK); Peter Sejer Andersen, Vanløse (DK)

(73) Assignees: ALK-ABELLÓ A/S, Horsholm (DK); LA JOLLA INSTITUTE FOR ALLERGY AND IMMUNOGY, La Jolla, CA (US)

( * ) Notice: Subject to any disclaimer, the term of this patent is extended or adjusted under 35 U.S.C. 154(b) by 0 days.

(21) Appl. No.: 15/021,775

(22) PCT Filed: Dec. 23, 2014

(86) PCT No.: PCT/US2014/072228
§ 371 (c)(1),
(2) Date: Mar. 14, 2016

(87) PCT Pub. No.: WO2015/100360
PCT Pub. Date: Jul. 2, 2015

(65) Prior Publication Data
US 2016/0251403 A1 Sep. 1, 2016

Related U.S. Application Data

(60) Provisional application No. 61/919,925, filed on Dec. 23, 2013, provisional application No. 62/012,690, filed on Jun. 16, 2014.

(51) Int. Cl.
*A61K 39/00* (2006.01)
*C07K 14/00* (2006.01)
(Continued)

(52) U.S. Cl.
CPC ........ *C07K 14/43531* (2013.01); *A61K 39/35* (2013.01)

(58) Field of Classification Search
CPC .......................... A61K 39/35; C07K 14/43531
See application file for complete search history.

(56) References Cited

U.S. PATENT DOCUMENTS 5,194,596 A * 3/1993 Tischer .................. C07K 14/46
530/350
5,350,836 A * 9/1994 Kopchick .......... A01K 67/0275
435/69.4
(Continued)

FOREIGN PATENT DOCUMENTS

JP 2001231563 8/2001
WO WO 93/08280 A1 4/1993
(Continued)

OTHER PUBLICATIONS

Skolnick et al. (2000, Trends in Biotech. 18:34-39).*
(Continued)

*Primary Examiner* — Cherie M Stanfield
(74) *Attorney, Agent, or Firm* — Womble Bond Dickinson (US) LLP

(57) ABSTRACT

The invention relates to combinations of peptides or variants thereof derived from a portion of an amino sequence of a house dust mite allergen, e.g. the allergens Der p 1, Der f 1, Der p 2 and/or Der f 2. Such peptides comprise at least one T cell epitope and a significant high number of patients in a worldwide population will have HLA alleles with the potential to bind the peptides of the peptide combinations. The
(Continued)

invention also relates to the use of such peptide combinations in relieving an immune response caused by a dust mite.

15 Claims, 23 Drawing Sheets

Specification includes a Sequence Listing.

(51) Int. Cl.
    *C07K 14/435*     (2006.01)
    *A61K 39/35*     (2006.01)

(56) References Cited

U.S. PATENT DOCUMENTS

| | | | | |
|---|---|---|---|---|
| 5,820,862 | A * | 10/1998 | Garman | C07K 14/43531 424/184.1 |
| 7,288,256 | B1 | 10/2007 | Garman et al. | |
| 2010/0303866 | A1* | 12/2010 | Saint-Remy | A61K 35/17 424/275.1 |
| 2013/0302338 | A1 | 11/2013 | Wang | |

FOREIGN PATENT DOCUMENTS

| | | | |
|---|---|---|---|
| WO | WO 94/24281 A1 | 10/1994 | |
| WO | WO 95/28424 A1 | 10/1995 | |
| WO | WO 2009/022156 A2 | 2/2009 | |
| WO | WO 2009/022157 A2 | 2/2009 | |
| WO | WO 2009022156 A2 * | 2/2009 | ............ A61K 39/35 |
| WO | WO 2010/018384 A1 | 2/2010 | |
| WO | WO 2012/168487 A1 | 12/2012 | |
| WO | WO 2013/119863 A1 | 8/2013 | |

OTHER PUBLICATIONS

Bork (2000, Genome Research 10:398-400).*
Doerks et al. (1998, Trends in Genetics 14:248-250).*
Smith et al. (1997, Nature Biotechnology 15:1222-1223).*
Bork et al. (1996, Trends in Genetics 12:425-427).*
Cottingham et al., (Nature Biotechnology. 2001. 19:974-977).*
Oseroff et al., (J Immunol. ePub Jul. 11, 2012;189:1800-1811).*
Altschul, S., et al., "Basic Local Alignment Search Tool," *J. Mol Biol.*, 1990,vol. 215,pp. 403-410.
Bostick, D., et al., "A new topological method to measure protein structure similarity," *Biochemical and Biophysical Research Communications*, 2003, vol. 304, pp. 320-325.
Greenbaum, J., et al., "Functional classification of class II human leukocyte antigen (HLA) molecules reveals seven different supertypes and a surprising degree of repertoire sharing across supertypes," *Immunogenetics*, 2011, vol. 63, pp. 325-335.
Henmar, H., et al., "Allergenicity, immunogenicity and dose-relationship of three intact allergen vaccines and four allergoid vaccines for subcutaneous grass pollen immunotherapy," *Clinical and Experimental Immunology*, 2008, vol. 153, pp. 316-323.
Huynh-Hoa, B., et al., "Predicting population coverage of T-cell epitope-based diagnostics and vaccines," *BMC Bioinformatics*, 2006,vol. 7(153), pp. 1-5.
Karosiene, E., et al., "NetMHCIIpan-3.0, a common pan-specifi MNC class II prediction method including all three human MHC class II isotypes, HLA-DR, HLA-DP and HLA-DQ," *Immunogenetics*, 2013, vol. 65(10), pp. 1-25.

Mackenzie, K., et al., Combination peptide immunotherapy based on T-cell epitope mapping reduces allergen-specific IgE and eosinophilia in allergic airway inflammation, *Immunology*, 2013, vol. 138, pp. 258-268.
McKinney, D., et al., "A strategy to determine HLA class II restriction broadly covering the DR, DP and DQ allelic variants most commonly expressed in the general population," *Immunogenetics*, 2014, vol. 65(5), doi: 10.1007/s00251-013-0684-y, pp. 1-23.
Meyer, D., et al., "Chapter 4: Single locus polymorphism of classical HLA genes," *13th IHWS Anthropology/Human Genetic Diversity Report; Immunobiology of the Human MHC; Proceedings of the 13th International Histocompatibility Workshop and Conference*, 2006, pp. 653-704.
Middleton, D., et al., "New allele frequency database: www.allelefrequencies.net," *Tissue Antigens*, 2003, vol. 61, pp. 403-407.
Moldaver, D., et al, "Immunotherapy with peptides," *Allergy*, 2011, vol. 66, pp. 784-791.
Murugan, N., et al, "Prediction of MHC class II binding peptides based on an iterative learning model," *Immunome Research*, 2005, vol. 1(6), pp. 1-10.
Needleman, S., et al., "A General Method Applicable to the Search for Similarities in the Amino Acid Sequence of Two Proteins," *J. Mol. Biol.*, 1970, vol. 48, pp. 443-453.
Nielsen, M., et al, "NN-align. An artificial neural network-based alignment algorithm for MHC class II peptide binding prediction," *BMC Bioinformatics*, 2009, vol. 10(296), pp. 1-10.
Nielsen, M., et al., NetMHCIIpan-2.0—Improved pan-specific HLA-DR predictions using a novel concurrent alignment and weight optimization training procedure, *Immunome Research*, 2010, vol. 6(9), pp. 1-10.
Pearson, William R., Flexible Sequence Similarity Searching with the FASTA3 Program Package, *Methods in Molecular Biology*, 2000, vol. 132: Bioinformatics Methods and Protocols, pp. 185-219.
Pearson, W., et al., "Improved tools for biological sequence comparison," *Proc. Natl. Acad. Sci. USA*, 1988, vol. 85, pp. 2444-2448.
Prickett, S., et al., "Ara h 2 peptides containing dominant CD4+ T-cell epitopes: Candidates for a peanut allergy therapeutic," *J. Allergy Clin Immunol*, 2011, vol. 127(3), pp. 608-615e5.
Sidney, J., et al., "Measurement of MHC/Peptide Interactions by Gel Filtration," *Current Protocols in Immunology*, 1998, Supplement 31, pp. 18.3.1-18.3.19.
Sidney, J., et al., "Quantitative peptide binding motifs for 19 human and mouse MHC class I molecules derived using positional scanning combinatorial peptide libraries," *Immunome Research*, 2008, vol. 4(2), pp. 1-14.
Sidney, J., et al., "Divergent Motifs but Overlapping Binding Repertoires of Six HLA-DQ Molecules Frequently Expressed in the Worldwide Human Population," *The Journal of Immunology*, 2010, vol. 185, pp. 4189-4198.
Sidney, J., et al., "Five HLA-DP Molecules Frequently Expressed in the Worldwide Human Population Share a Common HLA Supertypic Biding Specificity," *The Journal of Immunology*, 2010, doi:10.4049/jimmunol.0903655, pp. 2492-2503, http://www.jimmunol.org/content/early/2010/02/05/jimmunol.0903655.full.pdf.
Smith, Temple F., "Comparison of Biosequences," *Advanced in Applied Mathematics*, 1981, vol. 2, pp. 482-489.
Smith, T., et al, "Identification of Common Molecular Subsequences," *J. Mol. Biol.*, 1981,vol. 147, pp. 195-197.
Bui H., et al., "Predicting population coverage of T-cell epitope-based diagnostics and vaccines," *BMC Bioinformatics*, 2006, vol. 7(153), pp. 1-5. (corrected citation).
Sidney, J., et al., "Measurement of MHC/Peptide Interactions by Gel Filtration of Monoclonal Antibody Capture," *Curr Protoc Immunol.* Published online 2013, Unit 18.3, pp. 1-47.

* cited by examiner

PEPTIDE COMBINATIONS AND USES THEREOF IN TREATING DUST MITE ALLERGY

CROSS-REFERENCE TO RELATED APPLICATIONS

This application is a national stage filing under 35 U.S.C. 371 of PCT/EP2014/072228 filed Dec. 23, 2014, which International Application was published by the International Bureau in English on Jul. 2, 2015, and application claims priority from U.S. Provisional Application No. 61/919,925, filed Dec. 23, 2013, and U.S. Provisional Application No. 62/012,690, filed on Jun. 16, 2014, which applications are hereby incorporated in their entirety by reference in this application.

FIELD OF THE INVENTION

The present invention relates to compositions of peptides derived from a house dust mite allergen and methods of using such compositions modulating an immune response, for treating a subject for an allergic response and/or for inducing or promoting immunological tolerance in a subject, and in diagnostic methods and kits.

BACKGROUND

Allergy to dust mites affects populations in most parts of the world. The most common dust mites are the European house dust mite (*Dermatophagoides pteronyssinus*) and the American house dust mite (*Dermatophagoides farinae*), which contain the major allergens Der p 1/Der p 2 and Der f 1/Der f 2, respectively. Other common dust mites are found in subtropical/tropical regions around the world, for example *Blomia tropicalis* containing the major allergens Blo t 1 and Blo t 2 and Euroglyphus maynei containing the major allergens Eur m 1 and Eur m 2.

Today, the treatment of dust mite allergy is performed with allergen-specific immunotherapy products based on whole, intact or modified allergens typically administered as a complex extract made from dust mites. Typically, such products are administered by subcutaneous injection or by the sublingual route to a subject over an extended period of time, frequently months or years and are now appreciated to induce a state of "tolerance" in the subject. The mechanism of action is thought to involve induction of IgG inhibitory antibodies, suppression of mast cell/basophil reactivity, suppression of T-cell responses, the promotion of T-cell anergy, and/or clonal deletion, and in the long term, decrease in the levels of allergen specific IgE.

Unfortunately, allergen-specific immunotherapy bears the risk of IgE-mediated adverse events including serious anaphylactic responses. Therefore, this therapy is not as widely offered to allergic subjects as its beneficial effect actually justifies. In the recent years, it has been suggested to treat allergy using smaller fragments (peptides) of the primary amino acid sequence of allergens (e.g. of the major allergens), that contain one or more epitope(s) recognized by T cells regulating the allergic reaction. This concept has been termed peptide immunotherapy (PIT), in which, repeated doses of the peptide is administered, typically by intradermal injection, to a subject (Moldaver and Larche 2011).

More specifically on the molecular level, peptides are bound by Human Leucocyte Antigen (HLA) class II on the surface of Antigen Presenting Cells (APC). This peptide-HLA complex is then recognized by specific T-cell receptors on the cell surface of T-cells that upon interaction with the APCs becomes activated. A major difference of peptide-based immunotherapy and therapies based on full-length allergens is that this interaction is thought to occur without a concomitant antibody mediated "danger signal" being elicited. This is thought to drive the T-cell response in a more tolerogenic direction.

Peptide-based immunotherapy (PIT) represents a potentially attractive alternative to allergen extracts, with a more favorable safety/tolerability profile and a significantly shorter treatment regimen than existing therapies. In contrast to therapies based on intact allergens, PIT solely addresses the T-cell compartment of the immune system without engaging existing antibody responses because of the lack of antibody epitopes due to the smaller size of peptides compared to allergens. Consequently, no IgE-mediated adverse events are expected although they are often seen when treating allergy with traditional allergen-based immunotherapy products. Peptide immunotherapy is today in clinical development and does seem to have a favorable safety profile over the whole-allergen based vaccines.

A shortcoming of using the T cell epitope-containing peptides is, however, associated with the restriction of each peptide to only bind a subset of the naturally occurring HLA Class II molecules within the human population. A mix of several peptides covering different HLA Class II alleles is therefore mandatory to generate a broadly acting immunotherapy allergy treatment. As this repertoire of HLA Class II alleles varies from one person to another and from one ethnic population to another, it is challenging to provide peptide-based immunotherapies that can be offered to allergic subjects of any geographic region in the world unless numerous peptides are included in the vaccine. Taken into consideration the enormous costs and risks in the clinical development of new vaccines and the increasing demands from regulatory bodies to meet high standards for toxicity testing, dose justification, safety and efficacy trials, it is desirable to provide peptide vaccines containing as few peptides as possible, but at the same time to be able to treat the majority of dust mite allergic subjects in a worldwide population with the same immunotherapy product.

Such a product should comprise a combination of peptides that in combination are able to bind the worldwide HLA Class II allele repertoire, and the resulting peptide-HLA complexes should be recognized as T cell epitopes in the subject so as to induce tolerogenic immunological reactions. Recent studies in mice have indicated that peptide immunotherapy using one peptide alone did not reduce the severity of allergic airway inflammation, but that it is at least required that the mice are treated with two peptides that match the MHC molecules of the mice being treated (Mackenzie K J et al 2013).

International patent applications WO93/08280, WO94/24281, WO95/28424, WO2009/022156, WO95/28424 and WO2010/018384, respectively, and US application US20130302338 relate to peptides of house dust mite allergens and their use in treating house dust mite allergy.

SUMMARY

The present inventors have found it possible to assemble peptide combinations consisting of few peptides, such as three, four, five or six peptides, which have HLA Class II allele repertoire covering a significantly high fraction of a worldwide population and which also produce a T cell response in a significantly high fraction of a donor population allergic to a house dust mite.

The invention provides a number of compositions comprising peptide combinations having high worldwide HLA Class II allele coverage. As disclosed herein, such peptide combinations may be assembled by first providing a set of T cell epitope containing peptides (for example as disclosed in Example 3), then estimating the HLA Class II allele coverage of individual T cell epitope containing-peptides (for example as disclosed in Examples 10), then combining peptides with different HLA alleles to cover the HLA Class II allele repertoire of a worldwide population (for example as disclosed in Example 6) and then verifying in a qualified donor population (for example as disclosed in Example 2) that the suggested peptide combinations are able to produce a T cell response in a high fraction of the population (For example as described in Example 7).

Thus, there is herein provided a combination of peptides (in the following also named "peptide combination" or "peptide mix") for use as an "allergy vaccine" in the treatment of allergy to a house dust mite allergen, which is eligible for the majority of the world population. The peptides selected for the herein disclosed peptide combinations derive from one or more of the house dust mite allergens Der p 1, Der p 2, Der f 1 and Der f 2, and optionally Der p 4, and are shown to produce a T cell response in many donors and to have a satisfactorily high worldwide HLA Class II coverage. It should be understood that peptides of a peptide combination as disclosed herein primarily are distinct peptides derived from different regions of the house dust mite allergens, optionally wherein the amino acid residues of one distinct peptide overlap with few amino acid residues of another distinct peptide such as overlapping with less than 13, such as less than 12, 11, 10 or 9 amino acid residues. Tables 9 and 10 report peptides shown to produce a T cell response in a high fraction of the donor population ("high responder peptides"-derived from FIGS. 1 to 8) and wherein peptides are collected in groups of distinct peptides. Therefore, the invention relates in a first aspect to a composition comprising at least three peptides, wherein the composition comprises peptides selected from at least three of the following peptide groups:

group 26.: a parent peptide with the amino acid sequence SEQ ID NOs: 82 (pep-110), 269 (pep-125), 70 (pep-099) or 253 (pep-012); or a variant thereof (e.g. SEQ ID NOs: 223, 247, 224, 248);
group 24.: a parent peptide with the amino acid sequence SEQ ID NOs: 271 (pep-131), 67 (pep-096), 79 (pep-108), 256 (pep-031) or 270 (pep-126); or a variant thereof (e.g. SEQ ID NOs: 279, 241);
group 14.: a parent peptide with the amino acid sequence SEQ ID NOs: 268 (pep-130) or 22 (pep-054); or a variant thereof;
group 1.: a parent peptide with the amino acid sequence SEQ ID NO: 90 or a variant thereof;
group 2.: a parent peptide with the amino acid sequence SEQ ID NO: 280 or a variant thereof (e.g. SEQ ID NO: 98);
group 3.: a parent peptide with the amino acid sequence SEQ ID NO: 9 (pep-041) or a variant thereof (e.g. SEQ ID NO: 99);
group 4.: a parent peptide with the amino acid sequence SEQ ID NO: 10 (pep-042) or a variant thereof (e.g. SEQ ID Nos: 259, 102, 161, 281, 282);
group 5.: a parent peptide with the amino acid sequence SEQ ID NO: 11 (pep-043) or a variant thereof (e.g. SEQ ID NO: 103, 281, 282);
group 6.: a parent peptide with the amino acid sequence SEQ ID NO: 12 (pep-044) or a variant thereof (e.g. SEQ ID NOs: 105, 283, 106);
group 7.: a parent peptide with the amino acid sequence SEQ ID NOs: 42 (pep-072) or 249 (pep-022); or a variant thereof (e.g. SEQ ID NOs: 166);
group 8.: a parent peptide with the amino acid sequence SEQ ID NO: 15 (pep-047) or a variant thereof (e.g. SEQ ID NOs: 111, 270, 112);
group 9.: a parent peptide with the amino acid sequence SEQ ID NOs: 266 (pep-123), 255 (pep-025), 46 (pep-075) or 17 (pep-049); or a variant thereof (e.g. SEQ ID NOs: 271, 114, 173, 115, 174);
group 10.: a parent peptide with the amino acid sequence SEQ ID NOs: 18 (pep-050), 258 (pep-122) or 267 (pep-124); or a variant thereof (e.g. SEQ ID NOs: 117, 176);
group 11.: a parent peptide with the amino acid sequence SEQ ID NO: 120; or a variant thereof;
group 12.: a parent peptide with the amino acid sequence SEQ ID NOs: 20 (pep-052) or 49 (pep-078); or a variant thereof (e.g. SEQ ID NOs: 121, 180);
group 13.: a parent peptide with the amino acid sequence SEQ ID NO: 21 (pep-053) or a variant thereof;
group 15.: a parent peptide with the amino acid sequence SEQ ID NOs: 52 (pep-081) or 23 (pep-055, 272); or a variant thereof (e.g. SEQ ID Nos: 273, 128, 187, 129, 188);
group 16.: a parent peptide with the amino acid sequence SEQ ID NO: 26 (pep-058) or a variant thereof (e.g. SEQ ID NOs: 133, 192, 274, 191);
group 17.: a parent peptide with the amino acid sequence SEQ ID NOs: 29 (pep-061), 58 (pep-087), 251 (pep-10) or 252 (pep-011); or a variant thereof (e.g. SEQ ID NOs: 140, 199);
group 18.: a parent peptide with the amino acid sequence SEQ ID NO: 71 (pep-100) or a variant thereof;
group 19.: a parent peptide with the amino acid sequence SEQ ID NO: 72 (pep-101) or a variant thereof (e.g. SEQ ID NOs: 60 (pep-089), 227);
group 20.: a parent peptide with the amino acid sequence SEQ ID NOs: 61 (pep-090), 73 (pep-102) or 276; or a variant thereof (e.g. SEQ ID NOs: 277, 205, 229, 206, 230);
group 21.: a parent peptide with the amino acid sequence SEQ ID NO: 62 (pep-091) or a variant thereof (e.g. SEQ ID NO: 208);
group 22.: a parent peptide with the amino acid sequence SEQ ID NOs: 63 (pep-092) or 278; or a variant thereof (e.g. SEQ ID NO: 222, 210);
group 23.: a parent peptide with the amino acid sequence SEQ ID NO: 77 (pep-106) or a variant thereof (e.g. SEQ ID NO: 238); and group 25.: a parent peptide with the amino acid sequence SEQ ID NO: 81 (pep-109) or a variant thereof (e.g. SEQ ID NOs: 221, 245, 246).

The invention provides in a second aspect a pharmaceutical composition comprising a composition as defined herein.

The invention provides in a third aspect to a method for relieving or reducing (e.g. treating) an immune response triggered by an allergen of a dust mite (e.g. house dust mite) in a subject in need thereof, comprising administering to the subject a therapeutically effective amount of a composition described herein.

The invention provides in a further aspect, a method for relieving one or more symptoms of an immune response triggered by an allergen of a dust mite in a subject in need thereof, comprising administering to the subject a therapeutically effective amount of a composition described herein.

The invention provides in a further aspect, a method for inducing immunological tolerance against an allergen of a dust mite, comprising administering to the subject a therapeutically effective amount of a composition described herein.

In further aspects, the invention relates to a composition as defined herein for use in a method defined herein, e.g. a composition as defined herein for use in relieving an immune response triggered by an allergen of a dust mite in a subject in need thereof; for use in relieving one or more symptoms of an immune response triggered by an allergen of a dust mite in a subject in need thereof; and/or for inducing immunological tolerance against an allergen of a dust mite in a subject in need thereof.

In further aspects, the invention relates to the use of a composition as defined herein for the preparation of a medicament for use in a method defined herein, e.g. the use of a composition as defined herein for the preparation of a medicament for use in relieving an immune response triggered by an allergen of a dust mite in a subject in need thereof; for use in relieving one or more symptoms of an immune response triggered by an allergen of a dust mite in a subject in need thereof; and/or for inducing immunological tolerance against an allergen of a dust mite in a subject in need thereof.

In still further aspects, the invention relates to a kit comprising a compartment and instructions, wherein the compartment comprises a composition described herein and wherein the instructions are for use in treating allergy to dust mites, such as house dust mites.

In still further aspects, the invention relates to a method of determining whether T cells of a subject in need of treatment recognize a composition as defined herein, comprising contacting T cells obtained from the subject with said composition or a single peptide thereof and detecting whether the T cells are stimulated by said composition or single peptide.

In still another aspect, the invention relates to a diagnostic kit comprising a composition defined herein.

BRIEF DESCRIPTION OF FIGURES

FIG. 1 shows the fraction of donors (y-axis=% responders) responding to a given peptide (x-axis shows peptide ID numbers found in Table 2).

FIG. 2 shows the fraction of donors (y-axis=% responders) responding to a given peptide (x-axis shows peptide ID numbers found in Table 2).

FIG. 3 shows the fraction of donors (y-axis=% responders) responding to a given peptide (x-axis shows peptide ID numbers found in Table 3).

FIG. 4 shows the fraction of donors (y-axis=% responders) responding to a given peptide (x-axis shows peptide ID numbers found in Table 3).

FIG. 5 shows the fraction of donors (y-axis=% responders) responding to a given peptide (x-axis shows peptide ID numbers found in Tables 4 and 6).

FIG. 6 shows the fraction of donors (y-axis=% responders) responding to a given peptide (x-axis shows peptide ID numbers found in Tables 4 and 6).

FIG. 7 shows the fraction of donors (y-axis=% responders) responding to a given peptide (x-axis shows peptide ID numbers found in Tables 5 and 6).

FIG. 8 shows the fraction of donors (y-axis=% responders) responding to a given peptide (x-axis shows peptide ID numbers found in Tables 5 and 6).

FIG. 9h: This Figure shows the average number of peptides in peptide combinations 17p, 17s, 17f, 3-pep-mix 110+130-131 and the 2-pep-mix 110+131 that a donor of the test population is able to respond to.

FIG. 9l: This figure shows % responders shown to respond to peptide combinations 17p, 17s, 17f, and 8 and a peptide combination consisting of only peptides pep-110, pep-130 and pep-131, when analyzed in a T cell assay using a subset of 31 donors having about 88% worldwide HLA Class II coverage.

FIGS. 10 to 19: These figures refer to the estimation of valency of various peptide combinations according to the description of valency disclosed in Example 10. The figures show the fraction of a virtual population of patients (Y-axis=% patients) that have HLA Class II alleles potentially able to bind (i.e. able to respond to) 0, 1, 2, 3, 4 and 5 peptides, respectively, in the combination (Data indicated with bars). Valency data are shown both with respect to peptides only derived from the HDM group 1 allergens Der p 1 or Der f 1 (indicated at the x-axis as Grp 1); peptides only derived from the HDM group 2 allergens Der p 2 or Der f 2 (indicated at the x-axis as Grp 2); peptides derived only from Der p (i.e. allergens Der p 1 or Der p 2 (indicated at the x-axis as Der p) and peptides derived only from Der f (i.e. allergens Der f 1 or Der f 2 (indicated at the x-axis as Der f). Finally, valency is also estimated with respect to all peptides in the combination (indicated at the X-axis as "all"). The Figures also shows the predicted fraction of patients (% patients) that will have HLA alleles potentially able to bind a given number of peptides or more in the peptide combination (data points shown as X)

FIG. 13 shows valency for peptide combination 9, wherein the estimation is based on predicted HLA allele coverage of alleles shown in Table 17.

FIG. 14 shows valency for peptide combination 17d, wherein the estimation is based on predicted HLA allele coverage of alleles shown in Table 17.

FIG. 15 shows valency for peptide combination 17f, wherein the estimation is based on predicted HLA allele coverage of alleles shown in Table 17.

FIG. 16 shows valency for peptide combination 17p, wherein the estimation is based on predicted HLA allele coverage of alleles shown in Table 17.

FIG. 17 shows valency for peptide combination 17s, wherein the estimation is based on predicted HLA allele coverage of alleles shown in Table 17.

FIG. 18 shows valency for peptide combination 17x, wherein the estimation is based on predicted HLA allele coverage of alleles shown in Table 17.

FIG. 19 shows valency for peptide combination 23, wherein the estimation is based on predicted HLA allele coverage of alleles shown in Table 17.

FIG. 20 shows that the patient population in average may be able to respond to 1.8 peptides of the peptide combination named "core 2" (peptides pep-110+pep-131). The patient population may in average be able to respond to 2.8 peptides of the peptide combination named Core 3 (peptides pep-110, pep-131 and pep-130), whereas the patient population may respond to 2.4 peptides of the three-peptide combination named Core 3_53 (peptides pep-110, pep-131 and pep-053). The peptides of Core 3 are present in the peptide combinations numbered 17f, 17p and 17s (contain 5 peptides), all comprising a high average number of peptides (3.5, 4.6, and 3.8, respectively) that the patient population can respond to. For comparison purposes, the peptide combination number 8 will on have 3 peptides that the patient population can respond to.

DETAILED DESCRIPTION

Figure 1:
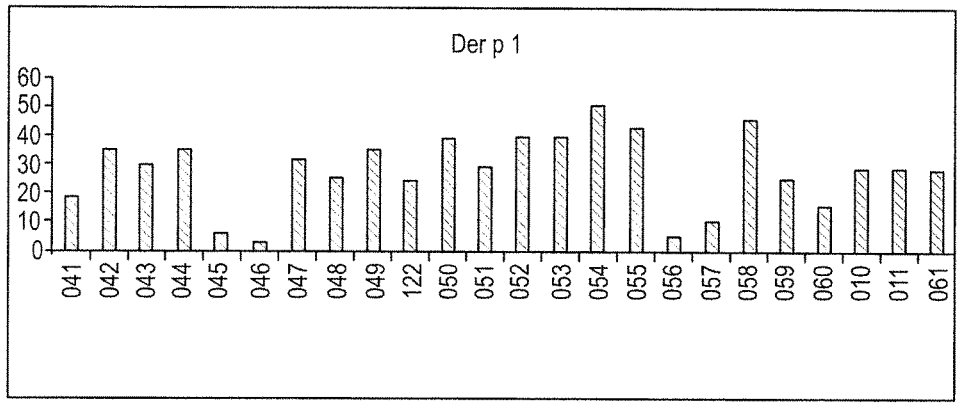
FIG. 1: This figure shows T-cell recognition of overlapping 20mers derived from Der p 1.
Figure 2:
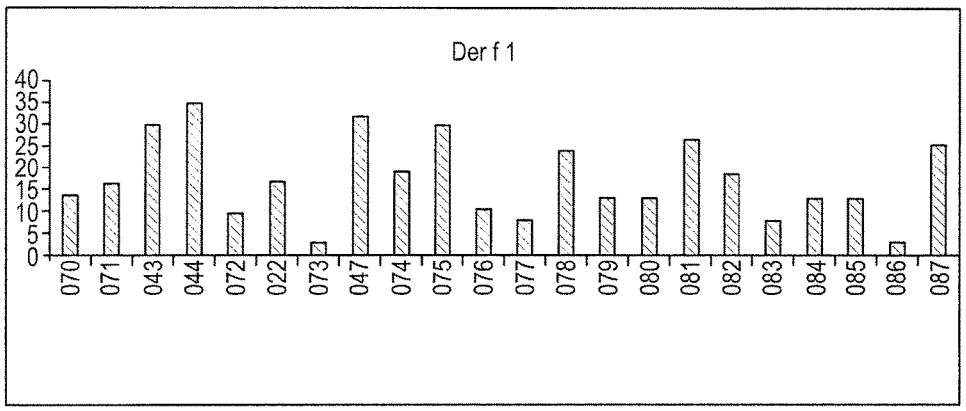
FIG. 2: This figure shows T-cell recognition of overlapping 20mers derived from Der f 1.
Figure 3:
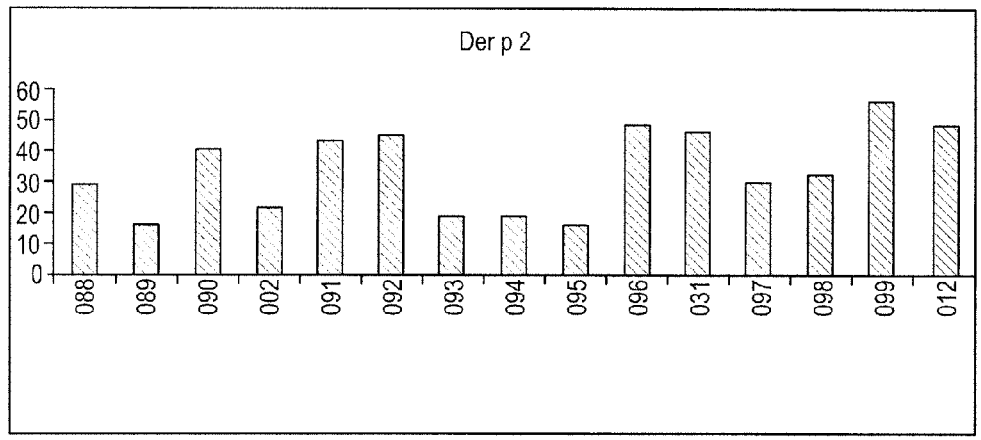
FIG. 3: This figure shows T-cell recognition of overlapping 20mers derived from Der p 2.
Figure 4:
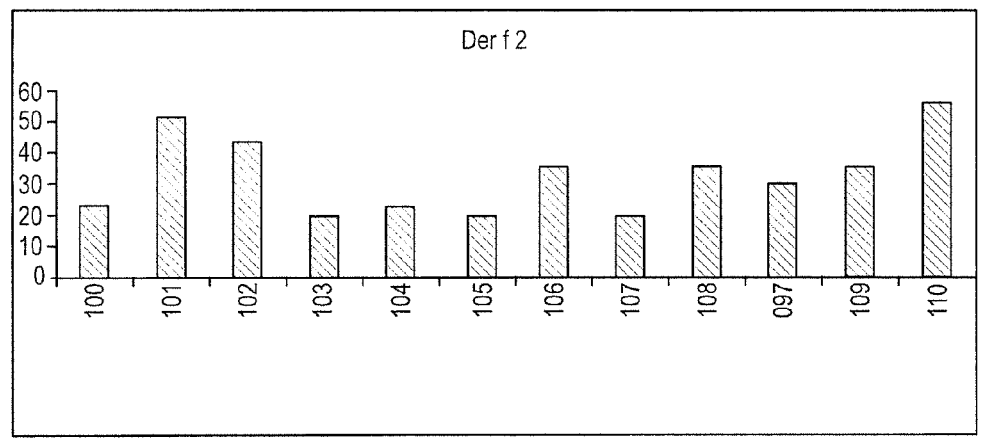
FIG. 4: This figure shows T-cell recognition of overlapping 20mers derived from Der f 2.
Figure 5:
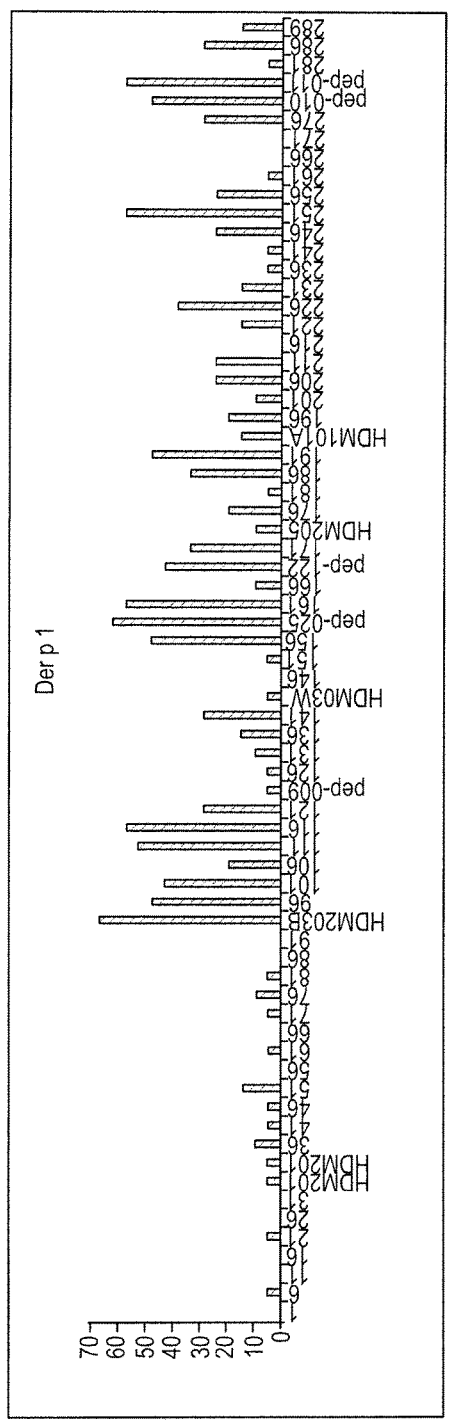
FIG. 5: This figure shows T-cell recognition of overlapping 15mers derived from Der p 1.
Figure 6:
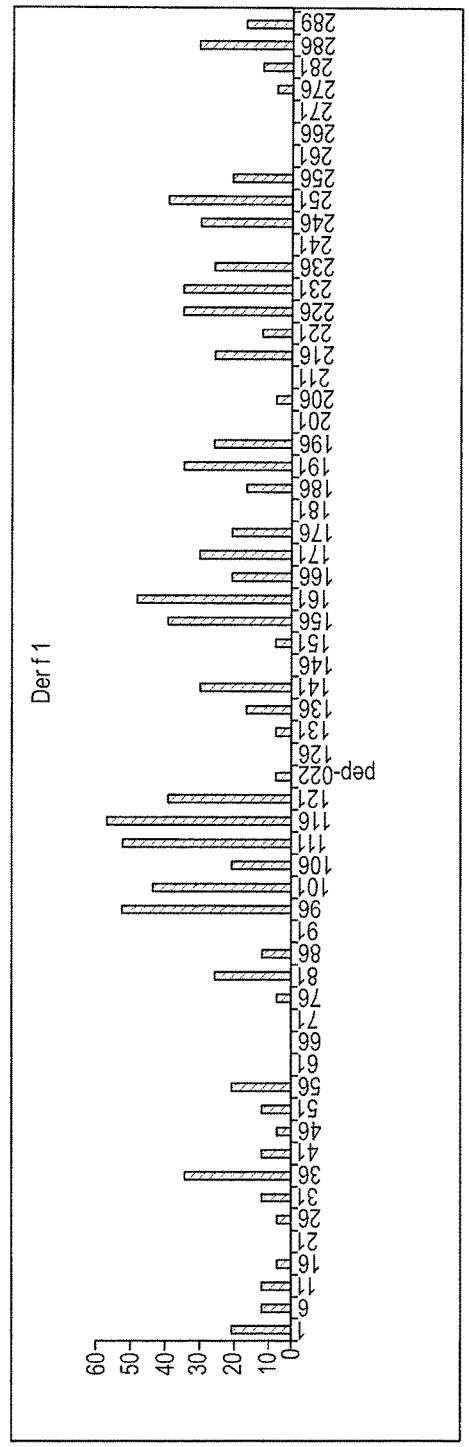
FIG. 6: This figure shows T-cell recognition of overlapping 15mers derived from Der f 1.
Figure 7:
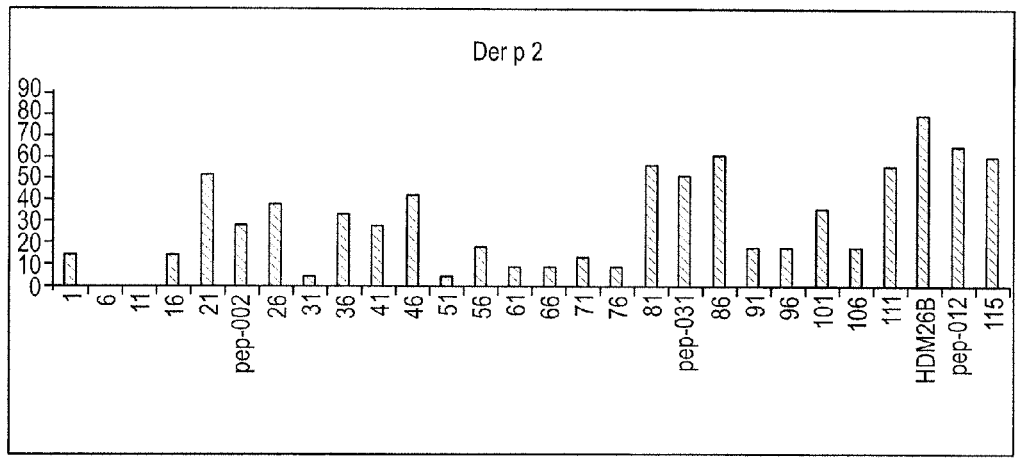
FIG. 7: This figure shows T-cell recognition of overlapping 15mers derived from Der p 2.
Figure 8:
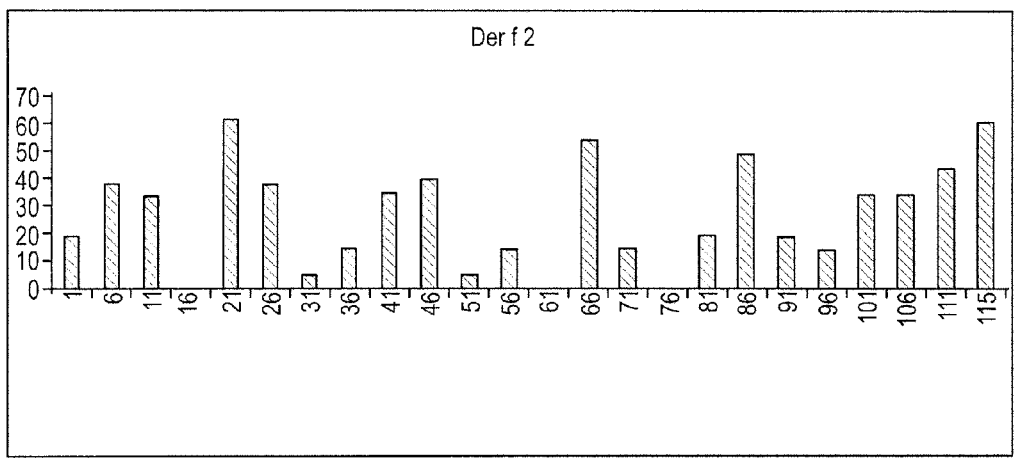
FIG. 8: This figure shows T-cell recognition of overlapping 15mers derived from Der f 2.

The following definitions and terminology are used herein:

The term "peptide" as used herein denotes an individual (e.g. isolated) amino acid molecule having a sequence length of about 12 to 30 amino acid residues. A peptide as referred to herein may be a linear peptide, which does not comprise a secondary helix structure. A peptide as used herein may be a parent peptide or a variant thereof.

The term "parent peptide" as used herein denotes an individual peptide that represents a region of the allergen it originates from, which region contains at least one T cell epitope that herein is reported to produce an in vitro T cell response in a high fraction of the donor population and to have broad HLA Class II coverage. In the present context, the individual peptides having an amino acid sequence of SEQ ID NOs: 9 (pep-041), 10 (pep-042), 11 (pep-043), 12 (pep-044), 42 (pep-072), 254 (pep-022), 15 (pep-047), 266 (pep-123), 255 (pep-025), 17 (pep-049), 46 (pep-075), 18 (pep-050), 258 (pep-122), 267 (pep-124), 20 (pep-052), 49 (pep-078), 21 (pep-053), 268 (pep-130), 22 (pep-054), 23 (pep-055), 52 (pep-081), 26 (pep-058), 29 (pep-061), 58 (pep-087), 251 (pep-010), 252 (pep-011), 272, 71 (pep-100), 72 (pep-101), 60 (pep-089), 61 (pep-090), 73 (pep-102), 249 (pep-002), 62 (pep-091), 63 (pep-092), 77 (pep-106), 67 (pep-096), 271 (pep-131), 79 (pep-108), 256 (pep-031), 270 (pep-126), 81 (pep-109), 269 (pep-125), 70 (pep-099) and 82 (pep-110), are considered parent peptides. As shown herein, an individual peptide derived from the same region of the allergen as the parent peptide and which overlaps with at least 15 contiguous amino acid residues of the parent peptide also produces a T cell response in a high fraction of the donor population. Such individual peptides are thus said to belong to the same peptide group of individual peptides as the parent peptide.

Thus, the term "a group of peptides" or "peptide group" is meant to denote a collection of individual peptides derived from the same region of an allergen and which have at least about 14 to 15 contiguous amino acids overlapping with the amino acid sequence of a parent peptide defined herein, optionally with 1, 2, or 3 modifications (e.g. substitutions or deletions of amino acid residues within the 14 to 15 contiguous amino acids). A group of peptides therefore contains one or more parent peptides defined herein and variants of said parent peptides. Tables 9 and 10 provide examples of parent peptides and variants thereof.

As used herein an "epitope" refers to a region or part of an antigen, such as a peptide disclosed herein, that elicits an immune response when administered to a subject. An epitope may be a T cell epitope, i.e., an epitope that elicits, stimulates, induces, promotes, increases or enhances a T cell activity, function or response. For example a Th2 cell epitope. Any peptide or combination of peptides of interest can be analyzed to determine whether they include at least one T cell epitope using any number of assays (e.g. T cell proliferation assays, lymphokine secretion assays, T cell non-responsiveness studies, etc.).

The term "allergen" refers to an antigen which elicits, induces, stimulates, or enhances an immune response by a cell of the immune system of an exposed animal (e.g., human). An antigen is an allergen when the specific immune response is the development of enhanced sensitivity or a hypersensitivity to the antigen, but the antigen itself is not typically innately harmful. An allergen is therefore a particular type of antigen that can cause development of enhanced or increased sensitivity or hypersensitivity in a subject. For example, an allergen can elicit production of IgE antibodies in predisposed subjects.

HLA alleles as disclosed herein uses a simpler notation, such as DRB1_0101 or DPA10102-DPB10101, respectively instead of the official HLA nomenclature, as presented at the web site "HLA Nomenclature" found at hla.alleles.org. The amino acid sequence of an expressed HLA allele can be identified as HLA-X*YY:ZZ where X denotes a specific locus, e.g. the DRB1 locus. YY is a two digit number referring to the allele group, formerly defined by the serotype. ZZ is a two or three digit number (herein always two digits) defining the specific HLA protein. Thus a specific beta chain may be referred to as e.g., HLA-DRB1*01:01, and a specific alpha-beta chain pair be denoted as HLA-DPA1*02:01-HLA-DPB1*01:01.

Compositions (Peptide Combinations)

As disclosed herein, compositions (e.g. peptide combinations) of the invention comprise at least three peptides selected from at least three of peptide groups 1 to 26 disclosed herein. In other embodiments, the composition comprises at least four peptides, wherein the composition comprises peptides selected from at least 3 or 4 of the peptide groups 1 to 26. In still other embodiments, the composition comprises at least five peptides, wherein the composition comprises peptides selected from at least 3, 4 or 5 of the peptide groups 1 to 26. Additional peptides in the compositions as disclosed herein is preferably selected from one or more peptide groups from which there is no other peptide in the composition. In some preferred embodiments, the peptides in the herein disclosed compositions are all from different peptide groups. In still other embodiments, a composition as disclosed herein comprises a maximum of three peptides selected from each of three different peptide groups, a maximum of four peptides selected from each of four different peptide groups, a maximum of five peptides selected from each of five different peptide groups, a maximum of six peptides selected from each of six different peptide groups, or a maximum of seven peptides selected from each of seven different peptide groups. Thus, a composition of the invention may comprise a maximum of three, four, five, six or seven peptides.

Figure 9A:
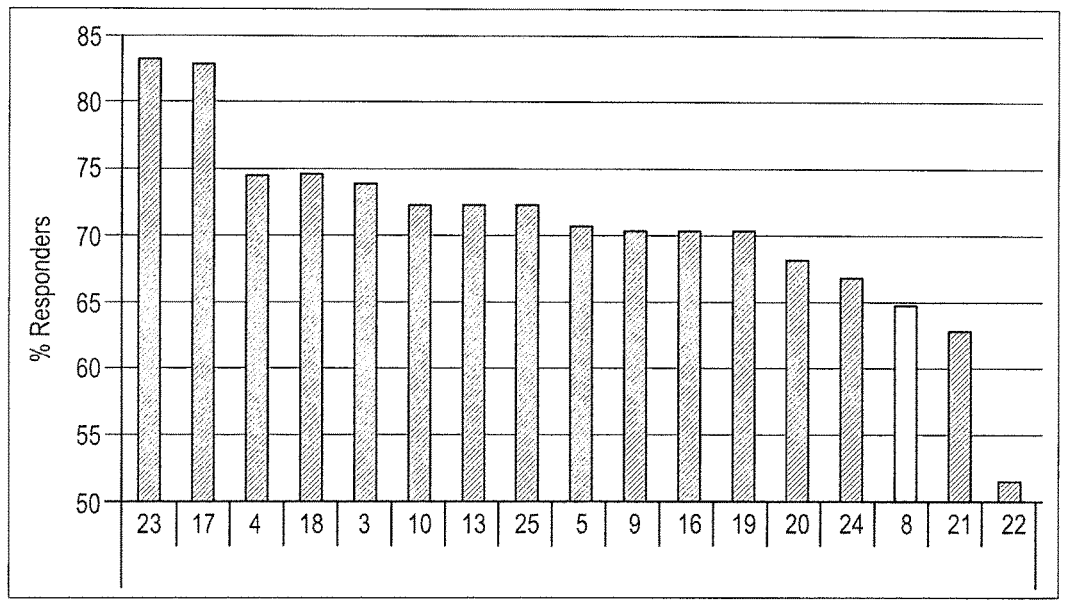
FIG. 9a: This figure shows the fraction of donors (% responders) responding to a peptide combination (shown in Table 14) in an in vitro T cell proliferation assay as described in Example 3.

By the present invention, there are provided several peptide combinations able to produce an in vitro T cell response in a high fraction of the donor population (see e.g. FIG. 9a, Table 14). In certain embodiments, the peptide combinations are assembled using a collection of peptides from peptide groups 3, 4, 5, 6, 7, 9, 10, 12, 13, 14, 15, 16, 17, 18, 19, 20, 21, 24, 25 and 26. Therefore, in some embodiments, the at least three peptides are selected from at least three of the following peptide groups 3, 4, 5, 6, 7, 9, 10, 12, 13, 14, 15, 16, 17, 18, 19, 20, 21, 24, 25 and 26.

Compositions of the invention may, but not necessarily, comprise peptides from an allergen of both the house dust mite species *Dermatophagoides farinae* and *Dermatophagoides pteronyssinus*. Also, the peptide combinations may, but not necessarily, comprise individual peptides derived from both a house dust mite (HDM) group 1 allergen (e.g. Der p 1 and/or Der f 1) and a house dust mite (HDM) group 2 allergen (e.g. Der p 2 and/or Der f 2). In some embodiments of the invention, the composition comprises at least three peptides, wherein one of the peptides derives from Der p 1 or Der f 1 and another peptide derives from Der p 2 or Der f 2.

Hence in some embodiments, at least one peptide is selected from any one of the peptide groups 1-17, these groups representing peptides derived from Der p 1 and/or Der f 1, for example a peptide consisting of an amino acid sequence selected from any one of SEQ ID NOs: 251 (pep-010), 252 (pep-011), 253 (pep-012), 254 (pep-022), 255 (pep-025), 9 (pep-041), 10 (pep-042), 11 (pep-043), 12 (pep-044), 17 (pep-049), 18 (pep-050), 20 (pep-052), 21 (pep-053), 22 (pep-054), 23 (pep-055), 26 (pep-058), 29 (pep-061), 42 (pep-072), 46 (pep-075), 49 (pep-078), 52 (pep-081), 58 (pep-087), 258 (pep-122), 266 (pep-123), 267 (pep-124), 268 (pep-130), 259 (pep-203B), 90, 98, 99, 280, 102, 161, 281, 282, 103, 105, 106, 283, 111, 112, 284, 114, 115, 173, 174, 285, 117, 176, 120, 121, 180, 128, 129, 272, 187, 188, 273, 191, 133, 274, 140 and 199, or a variant thereof.

In some embodiments, at least one peptide is selected from any one of the peptide groups 18-26, these groups representing peptides derived from Der p 2 and/or Der f 2, for example a peptide consisting of an amino acid sequence selected from any one of SEQ ID NOs: 249 (pep-002), 253 (pep-012), 256 (pep-031), 238 (pep-066), 60 (pep-089), 61 (pep-090), 62 (pep-091), 63 (pep-092), 67 (pep-096), 70 (pep-099), 71 (pep-100) 72 (pep-101), 73 (pep-102), 77 (pep-106), 79 (pep-108), 81 (pep-109), 82 (pep-110), 269 (pep-125), 270 (pep-126), 271 (pep-131), 264 (pep-26B), 226, 275, 227, 205, 206, 229, 230, 192, 276, 277, 208, 233, 278, 210, 234, 242, 243, 279, 221, 245, 246, 283, 223, 247, 224 and 248, or a variant thereof. In some embodiments at least one peptide is selected from any one of the peptide groups 1-17 and at least one peptide is selected from any one of the peptide groups 18-26.

As disclosed herein, compositions of the invention provide high HLA Class II coverage to a worldwide population. Therefore, in certain embodiments, the peptides of the peptide combination bind collectively to the majority of the alleles disclosed in Table 8 or Table 17. For example, a peptide combination of the invention may collectively bind to at least 20 of the 28 HLA alleles in the group consisting of DPA10201-DPB10101, DPA10103-DPB10201, DPA10103-DPB10301, DPA10103-DPB10401, DPA10103-DPB10402, DPA10202-DPB10501, DPA10201-DPB11401, DQA10501-DQB10201, DQA10501-DQB10301, DQA10301-DQB10302, DQA10401-DQB10402, DQA10101-DQB10501, DQA10102-DQB10602, DRB1_0101, DRB1_0301, DRB1_0401, DRB1_0405, DRB1_0701, DRB1_0901, DRB1_1101, DRB1_1201, DRB1_1302, DRB1_1501, DRB3_0101, DRB3_0202, DRB4_0101 and DRB5_0101. To increase the HLA Class II coverage, the peptides of a peptide combination may collectively bind to at least 21, 22, 23, 24, 25, 26, 27 or 28 of the 28 alleles. In other terms, a peptide combination of the invention may collectively bind to at least 70%, such as at least 75%, 80%, 85%, 88%, 90%, 92%, 94%, 95%, 96%, 97% or 98% of the HLA alleles consisting of the group of DPA10201-DPB10101, DPA10103-DPB10201, DPA10103-DPB10301, DPA10103-DPB10401, DPA10103-DPB10402, DPA10202-DPB10501, DPA10201-DPB11401, DQA10501-DQB10201, DQA10501-DQB10301, DQA10301-DQB10302, DQA10401-DQB10402, DQA10101-DQB10501, DQA10102-DQB10602, DRB1_0101, DRB1_0301, DRB1_0401, DRB1_0405, DRB1_0701, DRB1_0901, DRB1_1101, DRB1_1201, DRB1_1302, DRB1_1501, DRB3_0101, DRB3_0202, DRB4_0101 and DRB5_0101.

The HLA Class II coverage may be determined using numerous alleles. For example, the peptide combination may collectively bind to at least 70% of the 83 HLA alleles disclosed in Table 17, such as at least 75%, 80%, 85%, 88%, 90%, 92%, 94%, 95%, 96%, 97% or 98% of the HLA alleles consisting of the group of DRB1_0101, DRB1_0102, DRB1_0103, DRB1_0301, DRB1_0302, DRB1_0307, DRB1_0401, DRB1_0402, DRB1_0403, DRB1_0404, DRB1_0405, DRB1_0406, DRB1_0407, DRB1_0408, DRB1_0410, DRB1_0411, DRB1_0417, DRB1_0701, DRB1_0801, DRB1_0802, DRB1_0803, DRB1_0804, DRB1_0806, DRB1_0809 DRB1_0811, DRB1_0901, DRB1_1001 DRB1_1101, DRB1_1102, DRB1_1103 DRB1_1104, DRB1_1106, DRB1_1110 DRB1_1111, DRB1_1128, DRB1_1201 DRB1_1202, DRB1_1301, DRB1_1302, DRB1_1303, DRB1_1304, DRB1_1305, DRB1_1307, DRB1_1311 DRB1_1312, DRB1_1323, DRB1_1331, DRB1_1401, DRB1_1402, DRB1_1403, DRB1_1404, DRB1_1405, DRB1_1406, DRB1_1407, DRB1_1418, DRB1_1419, DRB1_1424, DRB1_1501, DRB1_1502, DRB1_1503, DRB1_1504, DRB1_1506, DRB1_1519, DRB1_1601 DRB1_1602, DRB1_1607, DRB3_0101, DRB3_0202, DRB4_0101, DRB5_0101 DPA10103-DPB10201, DPA10103-DPB10301, DPA10103-DPB10401, DPA10103-DPB1040, DPA10201-DPB10101, DPA10201-DPB11401, DPA10202-DPB10501, DQA10101-DQB10501, DQA10102-DQB10602, DQA10301-DQB10302, DQA10401-DQB10402, DQA10501-DQB10201 and DQA10501-DQB10301.

To assemble peptide combinations with high HLA Class II coverage, one may consider combining at least three peptides independently selected from peptides having high worldwide HLA class II coverage, for example peptides with the rating "A" shown in Table 12. Those peptides are regarded as "high T cell responders" and also possess high HLA class II coverage.

Thus, in some embodiments, the at least three peptides are selected from at least three of the peptide groups 4, 5, 6, 9, 10, 13, 14, 15, 16, 17, 20, 21, 24, 25 and 26. Exemplary peptide combinations of such embodiments are shown in Table 14 (peptide combinations 3, 4, 5, 6, 7, 9, 10, 11, 12, 13, 14, 15, 16, 18, 19, 20, 23, 24, 25, 17, 17a, 17b, 17c, 17d, 17f, 17p, 17l, 17q, 17s, 17t, 17u, 17v and 17x). As shown herein (e.g. FIGS. 9a, 9b, 9f and 9j), these peptide combinations have T cell responders in more than 65% of the donor population. Notably, the peptide combinations number 21 and 22, which do not comprise individual peptides from at least three of the peptide groups selected from 4, 5, 6, 9, 10, 13, 14, 15, 16, 17, 20, 21, 24, 25 and 26 produce T cell responses in considerable fewer donors. Peptide combination number 22 comprises an individual peptide from each of the peptide groups 7, 20 and 17.

Therefore, in some embodiments the composition does not comprise a peptide from peptide group 7, a peptide from peptide group 20 or a peptide from peptide group 17. In particularly, the composition does not comprise as two of the peptides, a peptide from peptide group 7 and a peptide from peptide group 20. Furthermore in some embodiments, the composition does not comprise as three of the peptides, a peptide from peptide group 7, a peptide from peptide group 20 and a peptide from peptide group 17.

Furthermore, some peptides are poorly soluble in aqueous solution, for example in solutions having a target pH in the range of pH 4 to 8 or are difficult to synthesize. Therefore, to assemble peptide combinations of the invention not having particular constraints with respect to solubility and manufacturability, a composition may comprise at least three peptides selected from any of the "first choice peptides" as set out in Table 15. Therefore, in some embodiments, the at least three peptides are selected from at least three of the peptide groups 9, 10, 13, 14, 16, 17, 20, 21, 24, 25 and 26.

Compositions may comprise at least four, five, six or seven peptides selected from at least four, five, six or seven of the peptide groups 1 to 26. Thus, a composition comprising the at least three peptides may comprise an additional peptide (e.g. one, two, three or more peptides) selected from any of the peptide groups 1-26, preferably from which group there is no other peptide in the composition. Thus, an additional peptide may be selected from any one of the group of peptides 1-26 that are not represented in the composition. For example, in some embodiments, a composition may comprise at least four peptides, wherein the composition comprises peptides selected from at least three or four of the peptide groups 1 to 26, for example selected from at least three or four of the peptide groups 4, 5, 6, 9, 10, 13, 14, 15, 16, 17, 20, 21, 24, 25 and 26, for example selected from at least three or four of the peptide groups 9, 10, 13, 14, 16, 17, 20, 21, 24, 25 and 26. In some embodiments, a composition may comprise at least five peptides, wherein the composition comprises peptides selected from at least three, four or five of the peptide groups 1 to 26, for example selected from at least three, four or five of the peptide groups 4, 5, 6, 9, 10, 13, 14, 15, 16, 17, 20, 21, 24, 25 and 26, for example selected from at least three, four or five of the peptide groups 9, 10, 13, 14, 16, 17, 20, 21, 24, 25 and 26. For example, the peptide combinations may be assembled by selecting a first, second or third peptide from any of the peptides disclosed in Table 15.

In some embodiments, the composition comprises as one of the peptides a peptide from peptide group 26 (e.g. parent peptide pep-110 or a variant thereof). Exemplary peptide combinations are combination numbers 3, 4, 5, 9, 10, 13, 16, 18, 19, 20, 23, 25, 17, 17a, 17b, 17c, 17d, 17f, 17p, 17l, 17q, 17s, 17t, 17v and 17x shown in Table 14. Such compositions may additionally comprise as one of the peptides a peptide derived from a HDM group 1 allergen, e.g. a peptide selected from any one of the peptide groups 1-17.

In some embodiments, the composition comprises as one of the peptides a peptide from peptide group 26 (e.g. parent peptide pep-110 or a variant thereof) and comprises as one of the peptides a peptide selected from any one of the peptide groups 24, 17, 9 and 16. Exemplary peptide combinations are combination numbers 3, 4, 5, 9, 10, 16, 18, 19, 20, 23, 25, 17, 17a, 17b, 17c, 17d, 17f, 17p, 17l, 17q, 17s, 17t, 17v and 17x shown in Table 14. The composition may comprise one or more additional peptides independently selected from any of the peptide groups 1-26 from which there is no other peptide in the composition, for example from peptide groups 3, 4, 6, 9, 10, 16, 17 and 21.

In some embodiments, the composition comprises as two of the peptides, a peptide from peptide group 26 (e.g. parent peptide pep-110 or a variant thereof) and a peptide from peptide group 24 (e.g. parent peptide pep-131 or a variant thereof). Exemplary peptide combinations are combination numbers 3, 5, 9, 17f, 17p, 17l, 17q, 17s, 17v, and 17x shown in Table 14.

In some embodiments, the composition comprises a third peptide selected from any one of the peptide groups 1-17, for example selected from any one of the peptide groups 4, 5, 6, 9, 10, 13, 14, 15, 16 and 17.

Figure 9B:
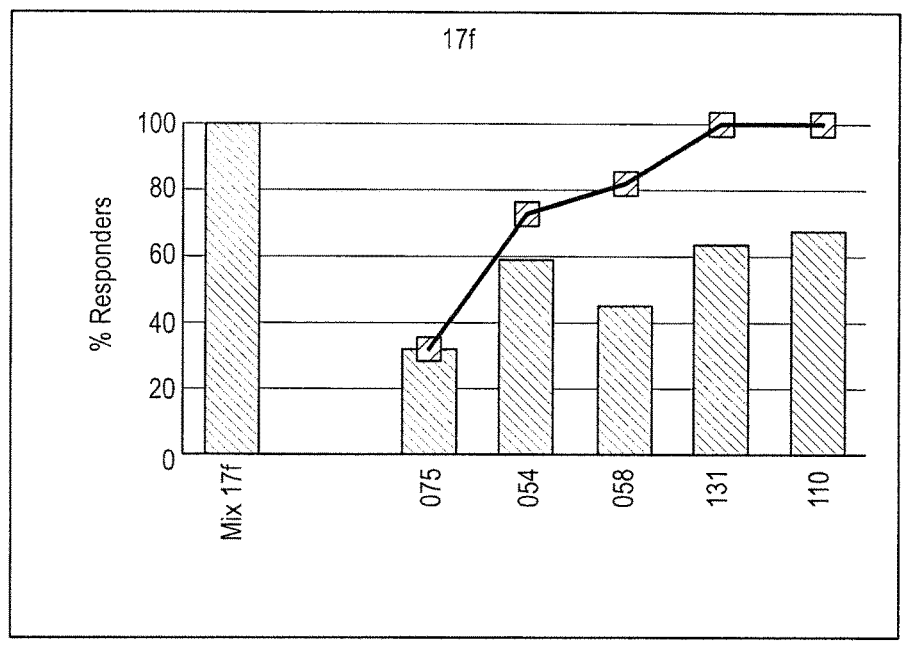
FIGS. 9b and 9c: The figures show the fraction of donors (% responders) responding to peptide combination 17f in comparison to peptide combination 17 in a T cell assay as described in Example 3. The T cell responses of individual peptides are also shown and their calculated cumulated responses add up to the responses measured for the peptide combination.
Figure 9C:
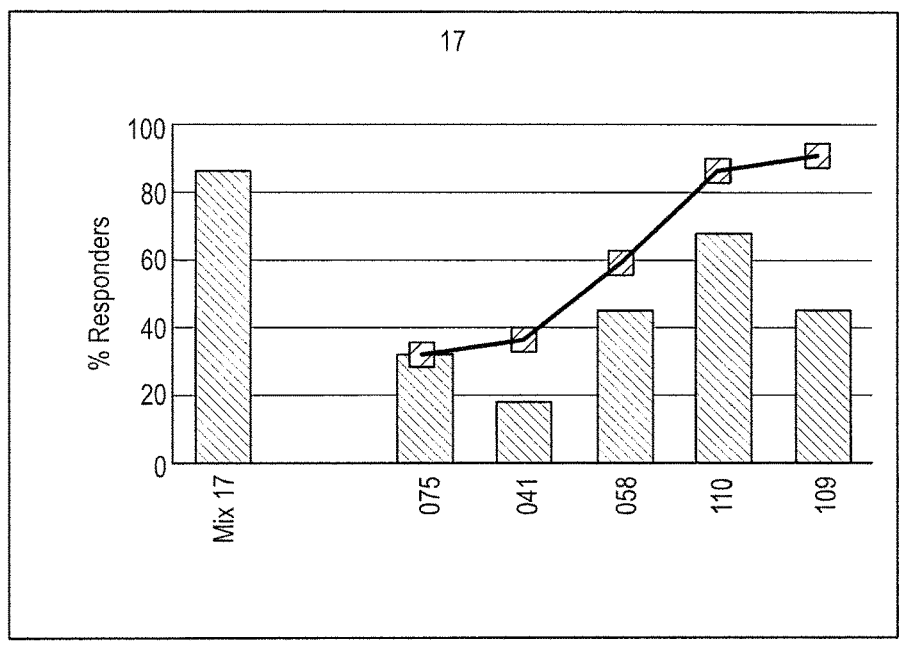
Figure 9D:
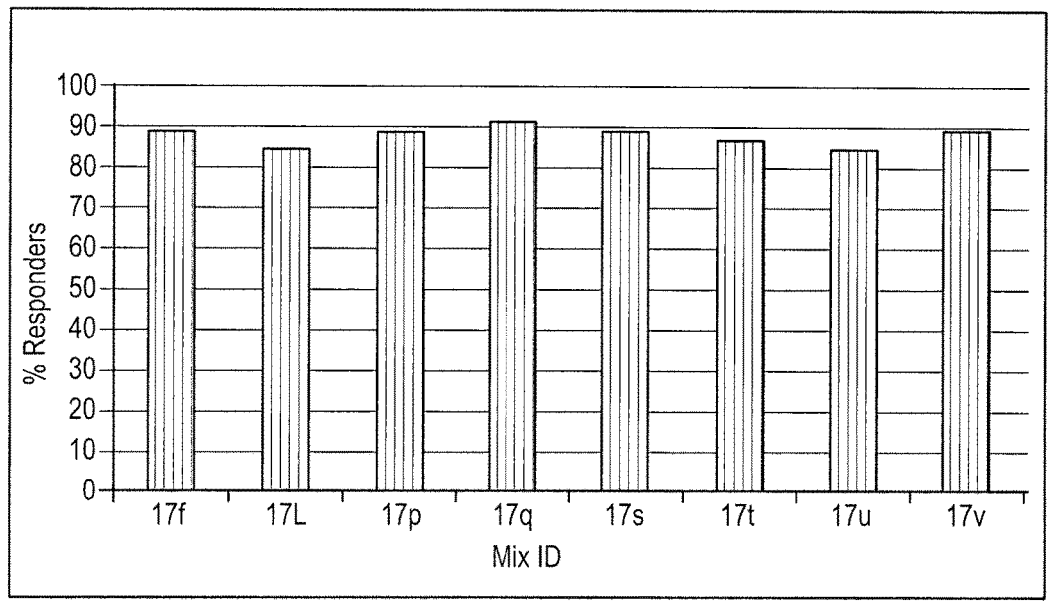
FIG. 9d: This figure shows the calculated percentage responders responding in an T cell assay to peptide combinations numbers 17f, 17l, 17p, 17q, 17s, 17t, 17u and 17v, respectively.
Figure 9E:
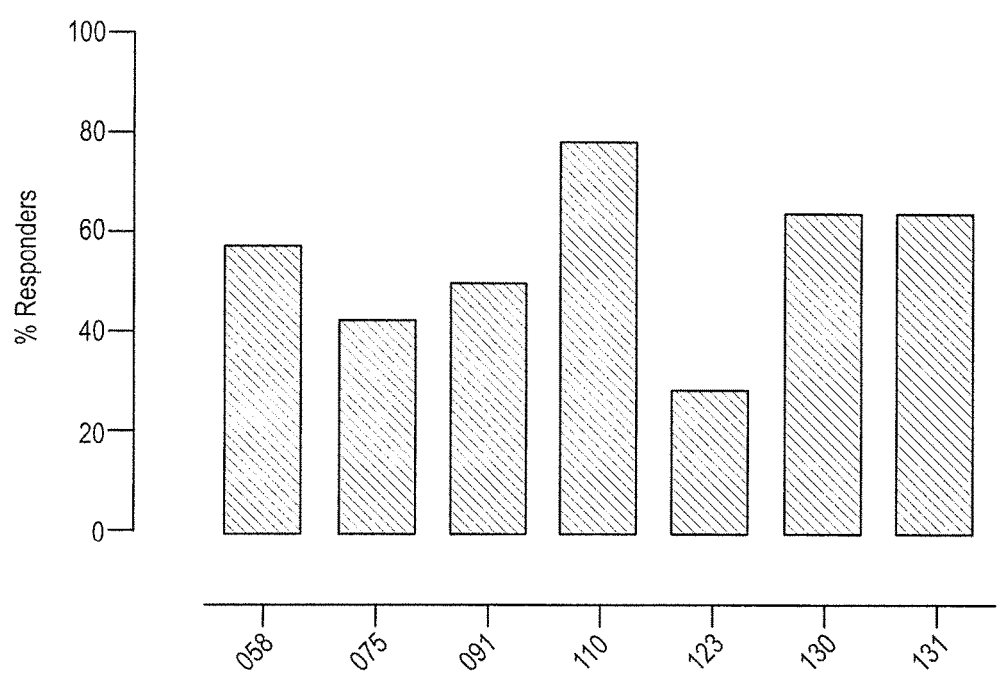
FIG. 9e: This figure shows % responders (as measured) in a T cell assay to a subset of individual peptides (pep-058, pep-075, pep-091, pep-110, pep-123, pep-130 and pep-131) using a subset of 31 donors having a worldwide HLA Class II coverage of about 88%.

As shown herein, a composition comprising three peptides may produce a T cell response in a high fraction of donors (FIG. 9e). Therefore, in some embodiments, the third peptide is from peptide group 14 (e.g. parent peptide pep-130 or pep-054; or a variant thereof). Exemplary peptide combinations are combination numbers 17f, 17p, 17q, 17s and 17v shown in Table 14.

The composition may in addition to the three peptides from each of the peptide groups 26, 24 and 14 comprise an additional peptide selected from any one of the peptide groups 1-13, 15-23 and 25, such as selected from any one of the peptide groups 9, 16 and 21.

Thus, in some embodiments, a composition comprises three, four, five, six or seven peptides, wherein the composition comprises peptides from each of the three peptide groups 26, 24 and 14 and in addition comprises a peptide selected from any one of the peptide groups 9, 16 and 21.

In more specific embodiments, such compositions comprise five peptides, wherein the composition comprises peptides from each of the five peptide groups 26, 24, 14, 9 and 16. For example, peptide combination 17q (shown in Table 14) that comprises:
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 266 (pep-123) or a variant thereof; and
e) a parent peptide with the amino acid sequence SEQ ID NO: 26 (pep-058) or a variant thereof.

Another example is peptide combination 17f (shown in Table 14) that comprises:
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 266 (pep-123) or a variant thereof; and
e) a parent peptide with the amino acid sequence SEQ ID NO: 26 (pep-058) or a variant thereof.

In still some specific embodiments, the composition comprises five peptides, wherein the composition comprises peptides selected from each of the five peptide groups 26, 24, 14, 9 and 21. For example, the peptide combination 17p (shown in Table 14) that comprises:
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 266 (pep-123) or a variant thereof; and
e) a parent peptide with the amino acid sequence SEQ ID NO: SEQ ID NO: 62 (pep-091) or a variant thereof.

Another examples is peptide combination 17s (shown in Table 14) that comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 46 (pep-075) or a variant thereof; and
e) a parent peptide with the amino acid sequence SEQ ID NO: 62 (pep-091) or a variant thereof.

In still other specific embodiments, the composition comprises five peptides, wherein the composition comprises peptides from each of the five peptide groups 26, 24, 14, 16 and 21. For example, peptide combination 17v (shown in Table 14) that comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 26 (pep-058) or a variant thereof; and
e) a parent peptide with the amino acid sequence SEQ ID NO: 62 (pep-091) or a variant thereof.

As mentioned, in some embodiments of the invention a composition comprises as two of the peptides, a peptide from peptide group 26 and a peptide from peptide group 24. In some embodiments thereof, a third peptide is from peptide group 9 or from peptide group 21. Exemplary peptide combinations are combination numbers 17f, 17p, 17l, 17q, 17s, 17v and 17x (shown in Table 14).

In some specific embodiments thereof, the composition comprises five peptides, wherein the composition comprises peptides from each of the five peptide groups 26, 24, 21, 9 and 13. For example peptide combination number 17x (shown in Table 14) that comprises:
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 62 (pep-091) or a variant thereof;
d) a parent peptide with the amino acid sequence SEQ ID NO: 266 (pep-123) or a variant thereof; and
e) a parent peptide with the amino acid sequence SEQ ID NO: 21 (pep-053) or a variant thereof.

In still other embodiments, a composition may comprise as two of the peptides, a peptide from peptide group 26 and a peptide from peptide group 24 and a third peptide from peptide group 17 (e.g. pep-010 or pep-011; or a variant thereof). Exemplary compositions are peptide combinations numbers 3, 5 and 9 (shown in Table 14). Thus, a composition may comprise at least three peptides, wherein the composition comprises a peptide from each of the three peptide groups 3, 5 and 9. Optionally, an additional peptide is selected from any one of the peptide groups 1-16, 18-23 and 25, such as peptide groups 3, 4, 6, 9, 10, 14, 16 and 21. In some embodiments thereof, the additional peptide(s) is selected from any one or both of the peptide groups 7 and 10. Thus, a composition may comprise three, four, five, six or seven peptides, wherein the composition comprises peptides from three of the peptide groups 26, 24 and 17 and wherein an additional peptide is selected from any of the peptide groups 7 and 10. In specific embodiments thereof, the composition comprises five peptides, wherein the composition comprises a peptide from each of the five peptide groups 26, 24, 17, 7 and 10. Exemplary compositions are peptide combinations number 5 (shown in Table 14) and 9 (shown in Table 14). For example peptide combination number 5 (shown in Table 14) that comprises:

a) a parent peptide with the amino acid sequence SEQ ID NO: 253 (pep-012) or a variant thereof;
b) a parent peptide with the amino acid sequence SEQ ID NO: 256 (pep-031) or a variant thereof;
c) a parent peptide with the amino acid sequence SEQ ID NO: 252 (pep-011) or a variant thereof;
d) a parent peptide with the amino acid sequence SEQ ID NO: 254 (pep-022) or a variant thereof; and
e) a parent peptide with the amino acid sequence SEQ ID NO: 258 (pep-122) or a variant thereof.

Another example is peptide combination number 9 (shown in Table 14) that comprises:

a) a parent peptide with the amino acid sequence SEQ ID NO: 253 (pep-012) or a variant thereof;
b) a parent peptide with the amino acid sequence SEQ ID NO: 256 (pep-031) or a variant thereof;
c) a parent peptide with the amino acid sequence SEQ ID NO: 251 (pep-010) or a variant thereof
d) a parent peptide with the amino acid sequence SEQ ID NO: 254 (pep-022) or a variant thereof; and
e) a parent peptide with the amino acid sequence SEQ ID NO: 258 (pep-122) or a variant thereof.

In still some embodiments, the composition comprises five peptides, wherein the composition comprises peptides from each of the four peptide groups 26, 24, 17 and 10; and a peptide with the amino acid sequence SEQ ID NO: 117 (pep-p4) or a variant thereof. For example peptide combination number 3 (shown in Table 14) that comprises:

a) a parent peptide with the amino acid sequence SEQ ID NO: 253 (pep-012) or a variant thereof;
b) a parent peptide with the amino acid sequence SEQ ID NO: 256 (pep-031) or a variant thereof;
c) a parent peptide with the amino acid sequence SEQ ID NO: 252 (pep-011) or a variant thereof;
d) a parent peptide with the amino acid sequence SEQ ID NO: 258 (pep-122) or a variant thereof; and
e) a parent peptide with the amino acid sequence SEQ ID NO: 117 or a variant thereof.

In some embodiments, the composition comprises as two of the peptides, a peptide from peptide group 26 (e.g. parent peptide pep-110 or a variant thereof) and a peptide from peptide group 17 (e.g. a parent peptide selected from any of pep-087, pep-010, pep-011, pep-061; or a variant thereof). Exemplary peptide combinations are combination numbers 3, 5, 9, 16, 19 and 20 shown in Table 14.

In some embodiments, the composition comprises three peptides, wherein the composition comprises peptides from each of the three peptide groups 26, 17 and 6. For example peptide combination number 16 (shown in Table 14) that comprises:

a) a parent peptide with the amino acid sequence SEQ ID NO: 70 (pep-099) or a variant thereof;
b) a parent peptide with the amino acid sequence SEQ ID NO: 251 (pep-010) or a variant thereof; and
c) a parent peptide with the amino acid sequence SEQ ID NO: 12 (pep-044) or a variant thereof.

In some embodiments, the composition comprises as two of the peptides, a peptide from peptide group 26 (e.g. parent peptide pep-110 or a variant thereof) and a peptide from peptide group 9 (e.g. a parent peptide selected from any of pep-123, pep-025, pep-075 or pep-049; or a variant thereof). Exemplary peptide combinations are combination numbers 10, 18, 23, 25, 17, 17c, 17f, 17p, 17l, 17q, 17s 17t and 17x shown in Table 14. In some embodiments thereof, the composition comprises five peptides, wherein the composition comprises peptides from each of the five peptide groups 26, 9, 6, 16 and 19. For example the composition of peptide combination number 10 (shown in Table 14) that comprises:

a) a parent peptide with the amino acid sequence SEQ ID NO: 70 (pep-099) or a variant thereof;
b) a parent peptide with the amino acid sequence SEQ ID NO: 46 (pep-075) or a variant thereof;
c) a parent peptide with the amino acid sequence SEQ ID NO: 12 (pep-044) or a variant thereof;
d) a parent peptide with the amino acid sequence SEQ ID NO: 26 (pep-058) or a variant thereof; and
e) a parent peptide with the amino acid sequence SEQ ID NO: 60 (pep-089) or a variant thereof.

In some embodiments thereof, the composition comprises five peptides, wherein the composition comprises peptides from each of the five peptide groups 26, 9, 6, 18 and 20.

For example the composition of peptide combination number 23 (shown in Table 14) that comprises:

a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 12 (pep-044) or a variant thereof;
d) a parent peptide with the amino acid sequence SEQ ID NO: 71 (pep-100) or a variant thereof; and
e) a parent peptide with the amino acid sequence SEQ ID NO: 73 (pep-102) or a variant thereof.

In still some embodiments thereof, the composition comprises five peptides, wherein the composition comprises peptides from each of the five peptide groups 26, 9, 6, 12 and 21. For example, the composition of peptide combination number 25 (shown in Table 14) that comprises:

a) a parent peptide with the amino acid sequence SEQ ID NO: 82 (pep-110) or a variant thereof;
b) a parent peptide with the amino acid sequence SEQ ID NO: 17 (pep-049)) or a variant thereof;
c) a parent peptide with the amino acid sequence SEQ ID NO: 12 (pep-044) or a variant thereof;
d) a parent peptide with the amino acid sequence SEQ ID NO: 20 (pep-052), or a variant thereof; and
e) a parent peptide with the amino acid sequence SEQ ID NO: 62 (pep-091) or a variant thereof.

In still some embodiments thereof, the composition comprises five peptides, wherein the composition comprises peptides from each of the five peptide groups 26, 9, 16, 3 and 25. For example, the composition of peptide combination number 17 (shown in Table 14) that comprises:

a) a parent peptide with the amino acid sequence SEQ ID NO: 82 (pep-110) or a variant thereof;
b) a parent peptide with the amino acid sequence SEQ ID NO: 46 (pep-075) or a variant thereof;

c) a parent peptide with the amino acid sequence SEQ ID NO: 26 (pep-058) or a variant thereof;
d) a parent peptide with the amino acid sequence SEQ ID NO: 9 (pep-041) or a variant thereof; and
e) a parent peptide with the amino acid sequence SEQ ID NO: 81 (pep-109) or a variant thereof.

In still some embodiments thereof, the composition comprises five peptides, wherein the composition comprises peptides from each of the five peptide groups 26, 9, 16, 14 and 25. For example, the composition of peptide combination number 17a (shown in Table 14) that comprises:
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 22 (pep-054) or a variant thereof; and
e) a parent peptide with the amino acid sequence SEQ ID NO: 81 (pep-109) or a variant thereof.

In still some embodiments thereof, the composition comprises five peptides, wherein the composition comprises peptides from each of the five peptide groups 26, 9, 16, 3 and 21. For example, the composition of peptide combination number 17c (shown in Table 14) that comprises:
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 9 (pep-041) or a variant thereof; and
e) a parent peptide with the amino acid sequence SEQ ID NO: 62 (pep-091) or a variant thereof.

In still some embodiments thereof, the composition comprises five peptides, wherein the composition comprises peptides from each of the five peptide groups 26, 9, 16, 14 and 21. For example, the composition of peptide combination number 17t (shown in Table 14) that comprises:
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 268 (pep-130) or a variant thereof; and
e) a parent peptide with the amino acid sequence SEQ ID NO: 62 (pep-091) or a variant thereof.

In some embodiments, the composition comprises as two of the peptides, a peptide from peptide group 26 (e.g. parent peptide pep-110 or a variant thereof) and a peptide from peptide group 16 (e.g. a parent peptide pep-058 or a variant thereof). Exemplary peptide combinations are combination numbers 10, 17a, 17b, 17c, 17d, 17f, 17l, 17q and 17t shown in Table 14. In some embodiments thereof, the composition comprises five peptides, wherein the composition comprises peptides from each of the five peptide groups 26, 16, 3, 15 and 25. For example the composition of peptide combination number 17b (shown in Table 14) that comprises:
a) a parent peptide with the amino acid sequence SEQ ID NO: 82 (pep-110) or a variant thereof;
b) a parent peptide with the amino acid sequence SEQ ID NO: 26 (pep-058) or a variant thereof;
c) a parent peptide with the amino acid sequence SEQ ID NO: 9 (pep-041) or a variant thereof;
d) a parent peptide with the amino acid sequence SEQ ID NO: 52 (pep-081) or a variant thereof; and
e) a parent peptide with the amino acid sequence SEQ ID NO: 81 (pep-109) or a variant thereof.

In some embodiments thereof, the composition comprises five peptides, wherein the composition comprises peptides from each of the five peptide groups 26, 16, 14, 15 and 21. For example the composition of peptide combination number 17d (shown in Table 14) that comprises:
a) a parent peptide with the amino acid sequence SEQ ID NO: 82 (pep-110) or a variant thereof;
b) a parent peptide with the amino acid sequence SEQ ID NO: 26 (pep-058) or a variant thereof;
c) a parent peptide with the amino acid sequence SEQ ID NO: 22 (pep-054) or a variant thereof;
d) a parent peptide with the amino acid sequence SEQ ID NO: 52 (pep-081) or a variant thereof; and
e) a parent peptide with the amino acid sequence SEQ ID NO: 62 (pep-091) or a variant thereof.

As should be understood, compositions of the invention preferably comprise only one peptide from a peptide group defined herein. However, in certain embodiments, the composition may comprise two peptides of the same peptide group, wherein one of the peptides derives from Der p and the other peptide of the same peptide group derives from Der f. Examples of such compositions are peptide combinations 13, 18, 19 and 20 of Table 14 that comprise two peptides from peptide group 26.

Therefore, in some embodiments, the composition comprises three peptides, wherein the composition comprises two peptides from peptide group 26 and one peptide from peptide group 6. For example the composition of peptide combination number 18 (shown in Table 14) that comprises:
a) a parent peptide with the amino acid sequence SEQ ID NO: 82 (pep-110) or a variant thereof;
b) a parent peptide with the amino acid sequence SEQ ID NO: 70 (pep-099) or a variant thereof; and
c) a parent peptide with the amino acid sequence SEQ ID NO: 12 (pep-044) or a variant thereof.

Still, in some embodiments, the composition comprises five peptides, wherein the composition comprises two peptides from peptide group 26 and one peptide from each of the three peptide groups 9, 6 and 3. For example the composition of peptide combination number 18 (shown in Table 14) that comprises:
a) a parent peptide with the amino acid sequence SEQ ID NO: 82 (pep-110) or a variant thereof;
b) a parent peptide with the amino acid sequence SEQ ID NO: 70 (pep-099) or a variant thereof;
c) a parent peptide with the amino acid sequence SEQ ID NO: 17 (pep-049) or a variant thereof;
d) a parent peptide with the amino acid sequence SEQ ID NO: 12 (pep-044) or a variant thereof; and
e) a parent peptide with the amino acid sequence SEQ ID NO: 9 (pep-041) or a variant thereof.

In still some embodiments, the composition comprises five peptides, wherein the composition comprises two peptides from peptide group 26 and one peptide from each of the three peptide groups 17, 10 and 3. For example the composition of peptide combination number 19 (shown in Table 14) that comprises:
a) a parent peptide with the amino acid sequence SEQ ID NO: 82 (pep-110) or a variant thereof;
b) a parent peptide with the amino acid sequence SEQ ID NO: 70 (pep-099) or a variant thereof;

c) a parent peptide with the amino acid sequence SEQ ID NO: 251 (pep-010) or a variant thereof;
d) a parent peptide with the amino acid sequence SEQ ID NO: 18 (pep-050) or a variant thereof; and
e) a parent peptide with the amino acid sequence SEQ ID NO: 9 (pep-041) or a variant thereof.

In still some embodiments, the composition comprises four peptides, wherein the composition comprises two peptides from peptide group 26 and one peptide from each of the two peptide groups 17 and 10. For example the composition of peptide combination number 20 (shown in Table 14) that comprises:
a) a parent peptide with the amino acid sequence SEQ ID NO: 82 (pep-110) or a variant thereof;
b) a parent peptide with the amino acid sequence SEQ ID NO: 70 (pep-099) or a variant thereof;
c) a parent peptide with the amino acid sequence SEQ ID NO: 251 (pep-010) or a variant thereof; and
d) a parent peptide with the amino acid sequence SEQ ID NO: 18 (pep-050) or a variant thereof.

In certain embodiments, the composition comprises as one of the peptides a peptide of peptide group 26, the composition does not comprise a peptide of any of the peptide groups 24, 17, 9 and 16, but may still achieve high T cell responder rate and worldwide HLA Class II coverage. For example, a composition of the peptide combination number 4 of Table 14. Therefore, in some embodiments, the composition comprises four peptides, wherein the composition comprises peptides from each of the four peptide groups 26, 7, 10 and 20. A composition of the peptide combination number 4 (shown in Table 14) comprises:
a) a parent peptide with the amino acid sequence SEQ ID NO: 253 (pep-012) or a variant thereof;
b) a parent peptide with the amino acid sequence SEQ ID NO: 254 (pep-022) or a variant thereof;
c) a parent peptide with the amino acid sequence SEQ ID NO: 258 (pep-122) or a variant thereof;
d) a parent peptide with the amino acid sequence SEQ ID NO: 249 (pep-002) or a variant thereof; and optionally
e) a parent peptide with the amino acid sequence SEQ ID NO: 257 (pep-117) or a variant thereof.

In certain embodiments, the composition comprises as one of the peptides a peptide of peptide group 26, but the composition does not comprise a peptide of any of the peptide groups 24, 17, 9 and 16. As shown in FIG. 9a for peptide combination number 24 (shown in Table 14), such a composition may still achieve high T cell responder rate and worldwide HLA Class II coverage. Therefore, in certain embodiments, the composition comprises five peptides, wherein the composition comprises peptides from each of the five peptide groups 10, 6, 12, 18 and 20. For example peptide combination number 24 (shown in Table 14) that comprises:
a) a parent peptide with the amino acid sequence SEQ ID NO: 18 (pep-050) or a variant thereof;
b) a parent peptide with the amino acid sequence SEQ ID NO: 12 (pep-044) or a variant thereof;
c) a parent peptide with the amino acid sequence SEQ ID NO: 49 (pep-078) or a variant thereof;
d) a parent peptide with the amino acid sequence SEQ ID NO: 71 (pep-100) or a variant thereof; and
e) a parent peptide with the amino acid sequence SEQ ID NO: 73 (pep-102) or a variant thereof.

It should be understood that compositions comprising three peptides, such as four peptides, such as five peptides, may comprise an additional peptide selected from any one of the peptide groups 1 to 26, wherein optionally the additional peptide(s) is from a peptide group from which there is no other peptide in the composition, thus the additional peptide is of any of the peptide groups 1 to 26 that is not represented in the peptide combination, for example from peptide groups 3, 4, 6, 10, 16, and 21. In certain embodiments, the additional peptide is from the same peptide group as another peptide of the composition, wherein the additional peptide is derived from another allergen species selected from Der p and Der f. For example, the composition may comprise one, two, three four or more additional peptides. For example, in certain embodiments the compositions may comprise up to four peptides, up to five peptides, up to six peptides, up to seven peptides.

The present invention has been exemplified with numerous peptide combinations shown in Table 14, but several other peptide combinations may be provided by substituting one of the peptides of the peptide combinations shown in Table 14 with another peptide from the same peptide group, i.e. a variant of the parent peptide or one of the other parent peptides or variants thereof also included in the same peptide group. Furthermore, one peptide from one peptide group may be substituted with a peptide from another group. For example, a peptide from a peptide group may be substituted with a peptide from another peptide group that has the same functionality, for example the functionality that the substitute peptide binds to the same or substantially the same group of HLA Class II alleles that the original peptide binds to. The ability of a peptide to bind HLA Class II alleles may be determined by a competitive MHC class II binding assay (For example as disclosed in Example 9) that determines the ability of a peptide to displace a known control binder from a human MHC class II allotype, for example the allotypes shown in Tables 8 or 17 herein. Thus, in some embodiments, a substitute peptide binds to the same, substantially the same or at least 70%, 75%, 80%, such as at least 85%, 88%, 90%, 92%, 94%, 95%, 96%, 97% or 98%, or more of the alleles binding to the peptide to be substituted, for example where the binding is determined by in-vitro binding assay or predicted binding to the alleles consisting of the group of DPA10201-DPB10101, DPA10103-DPB10201, DPA10103-DPB10301, DPA10103-DPB10401, DPA10103-DPB10402, DPA10202-DPB10501, DPA10201-DPB11401, DQA10501-DQB10201, DQA10501-DQB10301, DQA10301-DQB10302, DQA10401-DQB10402, DQA10101-DQB10501, DQA10102-DQB10602, DRB1_0101, DRB1_0301, DRB1_0401, DRB1_0405, DRB1_0701, DRB1_0901, DRB1_1101, DRB1_1201, DRB1_1302, DRB1_1501, DRB3_0101, DRB3_0202, DRB4_0101 and DRB5_0101 or optionally those listed in Table 17.

For example peptide 041 (SEQ ID NO: 9) is able to bind the alleles DRB1_1302, DRB3_0101, DRB3_0202, DQA10501-DQB10201 and DQA10401-DQB10402 and may be replaced by any of the peptides 011, 010 and 075 (SEQ ID NOs: 252, 251 and 46, respectively) that binds to at least the same alleles as peptide 041 as shown in Table 16a.

In the same way, it may be that a:
parent peptide with an amino acid sequence of SEQ ID NO: 17 (pep-058) may be substituted with parent peptide with an amino acid sequence of SEQ ID NOs: 22 (pep-054), 255 (pep-025) or 49 (pep-078);
parent peptide with an amino acid sequence of SEQ ID NO: 46 (pep-075) may be substituted with parent peptide with amino acid sequence SEQ ID NOs: 255 (pep-025), 285, 17 (pep-049), 20 (pep-052), 22 (pep-054), 21 (pep-053), 49 (pep-078) or 266 (pep-123);

parent peptide with an amino acid sequence of SEQ ID NO: 82 (pep-110) may be substituted with parent peptide with an amino acid sequence of SEQ ID NOs: 253 (pep-012), 70 (pep-099), 264 (pep-HDM26B), 269 (pep-125), 224 or 248;

parent peptide with an amino acid sequence of SEQ ID NO: 268 (pep-130) may be substituted with a parent peptide with an amino acid sequence of SEQ ID NOs: 255 (pep-025), 12 (pep-044), 22 (pep-054) or 21 (pep-053);

parent peptide with an amino acid sequence of SEQ ID NO: 271 (pep-131) may be substituted with a parent peptide with an amino acid sequence of SEQ ID NOs: 256 (pep-031), 81 (pep-109) or 67 (pep-096);

parent peptide with an amino acid sequence of SEQ ID NO: 81 (pep-109) may be substituted with a parent peptide with an amino acid sequence of SEQ ID NOs: 256 (pep-031), 67 (pep-096) or 271 (pep-131);

parent peptide with an amino acid sequence of SEQ ID NO: 17 (pep-049) may be substituted with a parent peptide with an amino acid sequence of SEQ ID NOs: 46 (pep-075) or 266 (pep-123);

parent peptide with an amino acid sequence of SEQ ID NO: 22 (pep-054) may be substituted with a parent peptide with an amino acid sequence of SEQ ID NO: 255 (pep-025), 12 (pep-044), 21 (pep-053), 26 (pep-058), 46 (pep-075) or 268 (pep-130);

parent peptide with an amino acid sequence of SEQ ID NO: 67 (pep-096) may be substituted with parent peptide with an amino acid sequence of SEQ ID NO: 256 (pep-031), 81 (pep-109) or 271 (pep-131);

parent peptide with an amino acid sequence of SEQ ID NO: 12 (peptide 044) may be substituted with a parent peptide with an amino acid sequence of SEQ ID NOs: 22 (pep-054), 268 (pep-130) or 283;

parent peptide with an amino acid sequence of SEQ ID NO: 15 (pep-050) may be substituted with a parent peptide with an amino acid sequence of SEQ ID NOs: 254 (pep-022), 26 (pep-058), 274, 52 (pep-081), 258 (pep-122) or 267 (pep-124);

parent peptide with an amino acid sequence of SEQ ID NO: 256 (pep-031) may be substituted with a parent peptide with an amino acid sequence of SEQ ID NOs: 81 (pep-109), 271 (pep-131), 67 (pep-096) or 270 (pep-126);

parent peptide with an amino acid sequence of SEQ ID NO: 251 (pep-010) may be substituted with a parent peptide with an amino acid sequence of SEQ ID NOs: 252 (pep-011), 58 (pep-087) or 29 (pep-061);

parent peptide with an amino acid sequence of SEQ ID NO; 258 (pep-122) may be substituted with a parent peptide with an amino acid sequence of SEQ ID NOs: 18 (pep-050), 52 (pep-081) or 267 (pep-124);

parent peptide with an amino acid sequence of SEQ ID NO: 253 (pep-012) may be substituted with a parent peptide with an amino acid sequence of SEQ ID NOs: 256 (pep-031), 70 (pep-099), 81 (pep-109), 82 (pep-110), 269 (pep-125);

parent peptide with an amino acid sequence of SEQ ID NO: 73 (pep-102) may be substituted with a parent peptide with an amino acid sequence of SEQ ID NOs: 249 (pep-002), 60 (pep-089), 61 (pep-090), 276, 277 or 82 (pep-110);

parent peptide with an amino acid sequence of SEQ ID NO: 70 (pep-099) may be substituted with a parent peptide with an amino acid sequence of SEQ ID NOs: 253 (pep-012), 264 (pep-26B), 82 (pep-110) or 269 (pep-125);

parent peptide with an amino acid sequence of SEQ ID NO: 52 (pep-081) may be substituted with a parent peptide with an amino acid sequence of SEQ ID NOs: 250 (pep-009), 254 (pep-022), 10 (pep-042), 18 (pep-050), 258 (pep-122) or 23 (pep-055).

In specific embodiments, parent peptide pep-075 (SEQ ID NO: 46) of peptide group 9 may be substituted with parent peptide pep-123 (SEQ ID NO: 266) or a variant thereof, and parent peptide pep-054 (SEQ ID NO: 22) may be substituted with parent peptide pep-091SEQ ID NO: 62) or a variant thereof.

Variants of Parent Peptides (Variants Thereof)

A parent peptide described herein may contain one or more modifications, which optionally may result in greater or less activity or function, for example in the ability to elicit, stimulate or induce an in vitro immune response (e.g. T cell proliferation or T cell cytokine production); in the ability to bind HLA Class II alleles; in the ability to induce or enhance immunological tolerance to a relevant antigen, e.g. a house dust mite allergen, such as Der p 1, Der f1, Der p 2 and/or Der f 2; or in the ability to dissolve in solvents e.g. in an aqueous solution.

A modification may include one or more deletions of amino acid residues from the N- and/or C-terminal end of the parent peptide, one or more additions of amino acid residues to the N- and/or C-terminal of the parent peptide and/or one or more amino acid substitutions, additions or deletions within the amino acid sequence of the parent peptide.

Typically, a longer variant of the parent peptide may be up to 60 amino acids in length, for example up to 55, 50, 45, 40, 35, 30, 28, 25, 24, or 22 amino acids in length. More typically, a longer variant peptide is up to about 30 amino acids in length, such as up to 25 amino acids in length. The longer variant may comprise the amino acid sequence of a parent peptide disclosed herein, or an amino acid sequence having at least 65% identity or similarity over the length of the amino acid sequence of the parent peptide or a fragment thereof, such as over at least 12 contiguous amino acids, for example over at least 13, 14, 15, 16, 17, 18, 19, 20 contiguous amino acids of the parent peptide or over the length of the parent peptide. Typically, the longer variant comprises an amino acid sequence having at least 70%, 75%, 80%, 85%, 90% or 95% identity or similarity over the length of the amino acid sequence of the parent peptide or over at least 12 contiguous amino acids, for example over at least 13, 14, 15, 16, 17, 18, 19 or 20 contiguous amino acids of the parent peptide. Therefore, in some embodiments, a variant of the parent peptide is a longer peptide up to 30 amino acid residues in length that comprises one or more additional amino acid residues at the N- and/or C-terminal end than the parent peptide or comprises an amino acid sequence having at least 80% identity over at least 14 contiguous amino acids of the parent peptide, such as over at least 15, 16, 17, 18 contiguous amino acids of the parent peptide.

A variant of the parent peptide may also include a fragment of a parent peptide disclosed herein. A fragment of the parent peptide can have one or more amino acids less than the parent peptide, either comprising deletions from within the amino acid sequence of the parent peptide and/or amino acid deletions from the N- and/or C-terminus of the parent peptide. Typically, a fragment will have a length of at least 12 amino acids, for example at least 13, 14, 15, 16 or 17 amino acids, and will have at least 65% identity or similarity over the length of the fragment, or over the length of at least 12 contiguous amino acids of the parent peptide, when aligned with the parent peptide. In some embodiments, the percentage identity or similarity is at least 70%, 75%, 80%, 85%, 90% or 95% over the length of the fragment, or over at least 12, 13, 14 or 15 contiguous amino acids of the parent peptide. Therefore, in some embodiments, a variant thereof may be a shorter peptide comprising an amino acid sequence having at least 80% identity over at least 14 contiguous amino acids of the parent peptide, such as over at least 15, 16, 17, 18 contiguous amino acids of the parent peptide. Examples of fragments of parent peptides disclosed herein may be selected from SEQ ID NOs: 90, 102, 161, 103, 105, 106, 111, 114, 115, 173, 174, 117, 176, 120, 121, 180, 128, 187, 188, 191, 133, 192, 199, 226, 227, 205, 229, 206, 230, 208, 233, 210, 234, 242, 243, 221, 245, 246, 283, 166, 223, 247, 224 and 248.

As mentioned, a variant of a parent peptide may comprise additional amino acids or may consist of a fragment of the parent peptide. Thus, a variant of a parent peptide may consist of 12-30 amino acids, for example 13-30, 14-30, 15-30, 16-30, 12-28, 13-28, 14-28, 15-28, 16-28, 13-26, 14-26, 15-26, 16-26, 13-25, 14-25, 15-25, 15-25, 13-24, 14-24, 15-24, 16-24, 3-22, 14-22, 15-22, 16-22, 13-20, 14-20, 15-20, 16-20 amino acids, such as particularly 12, 13, 14, 15, 16, 17, 18, 19, 20, 21, 22, 23, 24, 25, 26, 27, 28, 29 or 30 amino acids.

Moreover, a variant of a parent peptide may comprise an amino acid sequence having at least 65% sequence identity or similarity over at least 14 contiguous amino acids of the parent peptide sequence, optionally wherein the percent sequence identity or similarity is at least 70% 80%, 85%, 90% or 95% over at least 15 contiguous amino acids of the parent peptide sequence, such as over at least 16, 17, 18 or 20 contiguous amino acids of the parent peptide sequence.

In some embodiments, the variant of the parent peptides consists of 14-30 amino acids residues and comprises an amino acid sequence having at least 80% sequence identity or similarity over at least 14 contiguous amino acids of the parent peptide. In other embodiments, the variant consists of 15-30 amino acids residues and comprises an amino acid sequence having at least 80% sequence identity or similarity over at least 15 contiguous amino acids of the parent peptide. For example, the percent identity or similarity may be at least 85%, such as at least 90% or 95% over at least 14 contiguous amino acids, for example over at least 15, 16, 17, or 18 contiguous amino acids of the parent sequence. Thus, in such embodiments, the variant consists of 14-30 amino acid residues, such as 15-30 amino acid residues, wherein one, two or three amino acid residues within at least 14, such as at least 15, 16, 17 or 18 contiguous amino acids of the parent peptide are substituted.

In particular embodiments, the variant is a peptide consisting of 17-30 amino acids and comprises an amino acid sequence having at least 80%, such as at least 85%, 90% or 95% identity or similarity over at least 14 or 15 contiguous amino acids of the parent sequence.

In still other particular embodiments, the variant is a peptide consisting of 15-25 amino acids and comprises an amino acid sequence having at least 80% identity or similarity over at least 14 or 15 contiguous amino acids of the parent sequence.

In still other particular embodiments, the variant is a peptide consisting of 16-25 amino acids and comprises an amino acid sequence having at least 80% identity or similarity over at least 14 or 15 contiguous amino acids of the parent sequence.

In further embodiments, the at least 80% identity or similarity is over at least 16, 17, 18 or 19 contiguous amino acids of the parent peptide sequence and the percent identity or similarity may be at least is 85%, such as at least 90% or 95% over at least 16, 17, 18 or 19 contiguous amino acids of the parent peptide sequence.

The term "identity" and "identical" and grammatical variations thereof, as used herein, mean that two or more referenced entities are the same (e.g., amino acid sequences). Thus, where two peptides are identical, they have the same amino acid sequence. The identity can be over a defined area, e.g. over at least 12, 13, 14, 15 or 16 contiguous amino acids of the parent peptide sequence, optionally wherein the alignment is the best fit with gaps permitted.

For example, to determine whether a variant peptide has at least 80% similarity or identity over at least 15 contiguous amino acid residues of the parent peptide sequence, the variant peptide may be aligned with the parent peptide and the percent identity calculated with respect to the identical amino acid residues found within the amino acid sequence of the variant peptide that overlaps with the 15 contiguous amino acids of the parent peptide sequence.

Identity can be determined by comparing each position in aligned sequences. A degree of identity between amino acid sequences is a function of the number of identical or matching amino acids at positions shared by the sequences, i.e. over a specified region. Optimal alignment of sequences for comparisons of identity may be conducted using a variety of algorithms, as are known in the art, including the Clustal Omega program available at the website location at www.ebi.ac.uk/Tools/mas/clustalo/, the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at the website located at www.ncbi.nlm.nih-.gov). Such algorithms that calculate percent sequence identity (homology) generally account for sequence gaps and mismatches over the comparison region or area. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM 100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981). Programs for quantitating protein structural similarity using Delaunay-based topological mapping have also been developed (Bostick et al., *Biochem Biophys Res Commun.* 304: 320 (2003)).

The term "similarity" and "similar" and grammatical variations thereof, as used herein, mean that an amino acid sequence contains a limited number of conservative amino acid substitutions compared to a peptide reference sequence, e.g. the variant peptide versus the parent peptide. A variety of criteria can be used to indicate whether amino acids at a particular position in a peptide are similar. In making changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

Substitutions may be conservative or non-conservative amino acid substitutions. A "conservative substitution" is the replacement of one amino acid by a biologically, chemically or structurally similar residue. Biological similarity means that the substitution does not destroy a biological activity, e.g. T cell reactivity or HLA coverage. Structural similarity means that the amino acids have side chains with similar length, such as alanine, glycine and serine, or a similar size. Chemical similarity means that the residues have the same charge, or are both either hydrophilic or hydrophobic. For example, a conservative amino acid substitution is one in which an amino acid residue is replaced with an amino acid residue having a similar side chain, for example amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine, histidine); nonpolar side chains (e.g., alanine, valine, leucine, isoleucine, proline, phenylalanine, methionine, tryptophan); beta-branched side chains (e.g., threonine, valine, isoleucine), and aromatic side chains (e.g., tyrosine, phenylalanine, tryptophan). Particular examples include the substitution of one hydrophobic residue, such as isoleucine, valine, leucine or methionine, for another, or the substitution of one polar residue for another, such as the substitution of arginine for lysine, glutamic acid for aspartic acid, or glutamine for asparagine, serine for threonine, and the like. Proline, which is considered more difficult to classify, shares properties with amino acids that have aliphatic side chains (e.g., Leu, Val, Ile, and Ala). In certain circumstances, substitution of glutamine for glutamic acid or asparagine for aspartic acid may be considered a similar substitution in that glutamine and asparagine are amide derivatives of glutamic acid and aspartic acid, respectively.

A parent peptide disclosed herein is derived from the allergen isoforms Der p 1.0105, Der f 1.0101, Der p 2.0101 or Der f 2.0103, whereas a typical variant peptide may be derived from the same stretch found in another isoform of the same allergen shown in Table 1. Thus, the amino acid sequence of a parent peptide derived from one isoform of an allergen (e.g. isoform Der p 1.0105) may be substituted with one, two, three or four amino acid residues derived from another isoform of the same allergen (e.g. isoform Derp1.0101), where the amino acid residues have the same position number in the two isoforms.

As mentioned, a variant of a parent peptide disclosed herein may comprise one or more additional amino acid residues at the N- and/or C-terminal end than the parent peptide. Such amino acid residues may be naturally occurring amino acids or non-naturally occurring amino acids. In some embodiments, the one or more additional amino acids are the same amino acid or amino acid sequence flanking the N- and/or C-terminal ends of the parent peptide when aligned with the amino acid sequence of the allergen isoform it is present in, based upon or derived from or is aligned with another isoform of the same allergen. Thus, additional amino acids may be the amino acids flanking the N- and/or C-terminal ends of the parent peptide when aligned to Der p 1, Der f 1, Der p 2 or Der f 2. For example, wherein a peptide derives from Derp1.0105, the additional amino acids may be the amino acids flanking the N- and/or C-terminal ends of the peptide when aligned to Derp1.0105 or another isoform thereof set out in Table 1. Likewise, peptides derived from Derf1.0101, Derp2.0101 or Derf2.0103 may comprise additional amino acids flanking the N- and/or C-terminal ends of the peptide when aligned to Derf1.0101 or an isoform thereof, Derp2.0101 or an isoform thereof, Derf2.0103 or an isoform thereof, respectively. Various isoforms are shown in Table 1. For example, an isoform of Der p 1 may be selected from any of the isoforms with amino acid sequence with SEQ ID Nos: 287-311, an isoform of Der f 1 may be selected from any of the isoforms with amino acid sequence with SEQ ID Nos: 312-322, an isoform of Der p 2 may be selected from any of the isoforms with amino acid sequence with SEQ ID Nos: 323-337 and an isoform of Der f 2 may be selected from any of the isoforms with amino acid sequence with SEQ ID Nos: 338-354.

A variant peptide may include a number of modifications compared to the parent peptide, for example to increase or decrease physical or chemical properties of the parent peptide, for example to decrease its ability to resist oxidation, to improve or increase solubility in aqueous solution, to decrease aggregation, to decrease synthesis problems, etc.

Accordingly, in some embodiments of the invention, a variant of a parent peptide comprises:

a) one or more (e.g. 1, 2, or 3) amino acid substitutions in the parent peptide sequence, for example a glutamate residue at the N-terminus of the parent peptide may be replaced with pyroglutamate and/or one or more cysteine residues in the parent peptide may be replaced with serine or 2-aminobutyric acid; and/or b) one or more amino acid additions (e.g. 1, 2, 3, 5, 4, 6, 7, 8) to the parent peptide sequence, for example wherein the variant comprises one or more (e.g. 1, 2, 3, or 4) lysine residue(s) and/or one or more (e.g. 1, 2, 3, or 4) arginine residue(s) and/or one or more positively charged residues added at the N- and/or C-terminus of the parent peptide or to a fragment of the parent peptide consisting of at least 14 contiguous amino acids of the parent peptide (such as at least 15 contiguous amino acids); and/or c) one or more amino acid deletions from the parent peptide, for example wherein a hydrophobic residue the up to three amino acids from the N- or C-terminus of the parent peptide are deleted; and/or any two consecutive amino acids comprising the sequence Asp-Gly up to four amino acids from the N- or C-terminus of the parent peptide are deleted.

Furthermore, in some embodiments, a variant of a parent peptide may comprise one, two, three or more lysine or arginine amino acid residue(s) added to the N- and/or C-terminus of the parent peptide that have been extended with one or more, e.g. 1, 2, 3, 4, or 5 amino acid residues, optionally of the wild type sequence the peptide is based upon or another wild type isoform.

Typical examples of variants of parent peptides are shown in Tables 11a, 11b and 11c. Table 11a shows examples of the addition of one or more amino acid residues from the wild type allergen isoform to a parent peptide. Table 11b shows examples of parent peptides pep-058, pep-075, pep-123 with one or more Arginine residues added to the N- and/or C-terminus, e.g. variants with SEQ ID NOs: 274-278, 279-282 and 283-286, respectively. Table 11c shows examples of amidation of the C-terminal end of parent peptides pep-058, pep-075, pep-110, pep-130, pep-091 and pep-123.

A parent peptide or a variant peptide thereof may be derivatized. A derivative of a peptide (also named "derivatized peptide" herein) refers to a modified form of a peptide disclosed herein, including a modified form of a variant thereof. Typically, a derivative is formed by reacting a functional side group of an amino acid (e.g. amino, sulfhydryl or carboxy-group) with another molecule to form a covalent or non-covalent attachment of any type of molecule (naturally occurring or designed), such as a sugar moiety. Specific examples of derivatives of a peptide include glycosylation, acylation (e.g. acetylation), phosphorylation, amidation, formylation, ubiquitination and derivatization by protecting/blocking groups and any of numerous chemical modifications. Additional specific non-limiting examples are tagged peptides, fusion peptides, chimeric peptides including peptides having one or more non-amino acyl groups (q.v., sugar, lipid, etc.) covalently linked to the peptide. Typically, a derivative comprises one or more modifications, for example selected from any of: (a) N-terminal acylation (e.g. acetylation or formylation); (b) C-terminal amidation (e.g. reaction with ammonia or an amine); (c) one or more hydrogens on the side chain amines of arginine and/or lysine replaced with a methylene group; (d) glycosylation and/or (e) phosphorylation.

In a particular embodiment, the peptides are amidated at the C-terminal end, for example peptide pept-130 may be amidated.

In particular embodiments, a derivative comprises a fusion (chimeric) sequence of peptides, which optionally may contain an amino acid sequence having one or more molecules not normally present in a reference (wild type) sequence covalently attached to the peptide amino acid sequence. The term "chimeric" and grammatical variations thereof, when used in reference to a sequence, means that the sequence contains one or more portions that are derived from, obtained or isolated from, or based upon other physical or chemical entities.

Another particular example of a derivative is one in which a second heterologous sequence, i.e. a heterologous functional domain, is attached to a peptide disclosed herein, (covalent or non-covalent binding) that may confer a distinct or complementary function to a peptide disclosed herein. Heterologous functional domains are not restricted to amino acid residues. Thus, a heterologous functional domain can consist of any of a variety of different types of small or large functional moieties. Such moieties include nucleic acid, peptide, carbohydrate, lipid or small organic compounds, such as a drug (e.g., an antiviral), a metal (gold, silver), or a radioisotope.

Linkers, such as amino acid or peptidomimetic sequences, may be inserted between the peptide sequence and the addition (e.g., heterologous functional domain) so that the two entities maintain, at least in part, a distinct function or activity. Linkers may have one or more properties that may include a flexible conformation, an inability to form an ordered secondary structure or a hydrophobic or charged character, which could promote or interact with either domain. Amino acids typically found in flexible protein regions include Gly, Asn and Ser. Other near neutral amino acids, such as Thr and Ala, may also be used in the linker sequence.

In a particular aspect of the invention, the peptides of the peptide combination are not provided as individual peptides, but the peptides may be fused together or to a carrier molecule to form an isolated molecule. For example, the peptides may be fused to the N- and C-terminus of a surface polypeptide of a virus, e.g. a virus of the hepadnaviridae family as disclosed in international patent application WO12168487 A1.

A variant peptide or a derivative of a parent peptide may share the same functionality or activity as the parent peptide or may have improved functionality or activity. For example, a variant of a parent peptide may bind to at least 70% of the group of Class HLA II alleles that the parent peptide binds to. Thus, in some embodiments, the variant peptide binds to the same, substantially the same or at least 75%, 80%, such as at least 82%, 85%, 88%, 90%, 92%, 95%, 98% or more, of the group of HLA Class II alleles that binds to the parent peptide, optionally wherein this is determined under same test conditions, either using prediction tools or in-vitro binding assay. Optionally, the Class HLA II binding is determined with respect to a particular group of Class HLA II alleles, for example one or more or all of the following alleles: DPA1*02:01-DPB1*01:01, DPA1*01:03-DPB1*02:01, DPA1*01:03-DPB1*03:01, DPA1*01:03-DPB1*04:01, DPA1*01:03-DPB1*04:02, DPA1*02:02-DPB1*05:01, DPA1*02:01-DPB1*14:01, DQA1*05:01-DQB1*02:01, DQA1*05:01-DQB1*03:01, DQA1*03:01-DQB1*03:02, DQA1*04:01-DQB1*04:02, DQA1*01:01-DQB1*05:01, DQA1*01:02-DQB1*06:02, DRB1*01:01, DRB1*03:01, DRB1*04:01, DRB1*04:05, DRB1*07:01, DRB1*09:01, DRB1*11:01, DRB1*12:01, DRB1*13:02, DRB1*15:01, DRB3*01:01, DRB3*02:02, DRB4*01:01 and DRB5*01:01, or the alleles disclosed in Table 8 or in Table 17. Assays for measuring Class HLA II binding in vitro is well known in the art and some are described herein in Example 9.

Furthermore, a variant peptide may have one or more of the same T cell epitopes as the parent peptide. This may be determined by the ability to induce or stimulate in vitro T cell proliferation using cultured PBMCs (peripheral blood monocytes) in response to the variant peptide compared to the parent peptide, optionally using same test conditions, or by the ability to induce or stimulate production of cytokines, (e.g. cytokines, IL-5, IL-13 and/or IL-10) from T cells (obtained from cultured PBMC's) in response to the variant peptide compared to the parent peptide, as described herein in Example 3.

Therefore, in one particular embodiment, a variant of a parent peptide may include an overlap of at least 9 amino acid residues, preferably identical residues, when aligned with a parent peptide of the invention. The overlap is preferably more than 9 amino acid residues, e.g. 10, 11 or 12 amino acid residues or more, such as 13, 14 or 15 amino acid residues. The core binding sequence of MHC II molecules is known to be approximately 9 amino acids long, although MHC II molecules can accommodate longer peptides of 10-30 residues (Murugan and Dai, 2005). Therefore, in certain embodiments, an overlap of 9 amino acids or more with a parent sequence is sufficient for a variant to be able to share a T cell epitope with the parent peptide.

Peptides are typically provided in the form of a salt, for example as a pharmaceutically acceptable and/or a physiologically acceptable salt. For example, the salt may be an acid addition salt with an inorganic acid, an acid addition salt with an organic acid, a salt with a basic inorganic acid, a salt with a basic organic acid, a salt with an acidic or basic amino acid or a mixture thereof. Typical examples of an acid addition salts with an inorganic acid are selected from any of the salts with hydrochloric acid, hydrobromic acid, nitric acid, sulfuric acid, phosphoric acid, or the like. An acid salt with an organic acid may be selected from any of the salts with formic acid, acetic acid, trifluoroacetic acid, fumaric acid, oxalic acid, tartaric acid, maleic acid, succinic acid, malic acid, methanesulfonic acid, benzenesulfonic acid, p-toluenesulfonic acid, or the like. Salts with an inorganic base may be selected from a salt of an alkali metal salts such as sodium salts and potassium salts; alkali earth metal salts such as calcium salts and magnesium salts; and aluminum salts and ammonium salts. Salts with a basic organic base may be selected from any salt with trimethylamine, triethylamine, pyridine, picoline, ethanolamine, diethanolamine, triethanolamine, dicyclohexylamine, N,N-dibenzylethylenediamine, caffeine, piperidine, and pyridine. Salts with a basic amino acid may be selected from any salt with arginine, lysine, ornithine, or the like. Salts with an acidic amino acid may be selected from any salt with aspartic acid, glutamic acid, or the like.

In particular embodiments of the invention a salt, such as a pharmaceutically acceptable salt, is an acetate salt.

Typical examples of variants of parent peptides are listed in the following:

- a variant of a parent peptide of peptide group 26, e.g. a variant of any of the parent peptides with the amino acid sequence of SEQ ID NOs: 82 (pep-110), 269 (pep-125), 70 (pep-099) and 253 (pep-012) may be a peptide with the amino acid sequence of SEQ ID NOs: 223, 247, 224 or 248;
- a variant of a parent peptide of peptide group 24, e.g. a variant of any of the parent peptides with the amino acid sequence of SEQ ID NOs: 271 (pep-131), 67 (pep-096), 79 (pep-108), 256 (pep-031) and 270 (pep-126) may be a peptide with the amino acid sequence of SEQ ID NOs: 279 or 241;
- a variant of a parent peptide of peptide group 2, e.g. a variant of the parent peptide with the amino acid sequence of SEQ ID NO: 280 may be a peptide with the amino acid sequence of SEQ ID NO: 98;
- a variant of a parent peptide of peptide group 3, e.g. a variant of the parent peptide with the amino acid sequence of SEQ ID NO: 9 (pep-041) may be a peptide with the amino acid sequence of SEQ ID NO: 99;
- a variant of a parent peptide of peptide group 4, e.g. a variant of the parent peptide with the amino acid sequence of SEQ ID NO: 10 (pep-042) may be a peptide with the amino acid sequence of SEQ ID NOs: 259, 102, 161, 281 or 282;
- a variant of a parent peptide of peptide group 5, e.g. a variant of the parent peptide with the amino acid sequence of SEQ ID NO: 11 (pep-043) may be a peptide with the amino acid sequence of SEQ ID NOs: 103, 281 or 282;
- a variant of a parent peptide of peptide group 6, e.g. a variant of the parent peptide with the amino acid sequence of SEQ ID NO: 12 (pep-044) may be a peptide with the amino acid sequence of SEQ ID NOs: 105, 283 or 106;
- a variant of a parent peptide of peptide group 7, e.g. a variant of the parent peptide with the amino acid sequence of SEQ ID NOs: 42 (pep-072) or 249 (pep-022); may be a peptide with the amino acid sequence of SEQ ID NO: 166;
- a variant of a parent peptide of peptide group 8, e.g. a variant of the parent peptide with the amino acid sequence of SEQ ID NO: 15 (pep-047) may be a peptide with the amino acid sequence of SEQ ID NO: 111, 270 or 112;
- a variant of a parent peptide of peptide group 9, e.g. a variant of the parent peptide with the amino acid sequence of SEQ ID NOs: 266 (pep-123), 255 (pep-025), 46 (pep-075) and 17 (pep-049) may be a peptide with the amino acid sequence of SEQ ID NO: 271, 114, 173, 115 or 174;
- a variant of a parent peptide of peptide group 10, e.g. a variant of the parent peptide with the amino acid sequence of SEQ ID NOs: 18 (pep-050), 258 (pep-122) and 267 (pep-124) may be a peptide with the amino acid sequence of SEQ ID NO: 117 or 176;
- a variant of a parent peptide of peptide group 12, e.g. a variant of the parent peptide with the amino acid sequence of SEQ ID NOs: 20 (pep-052) or 49 (pep-078) may be a peptide with the amino acid sequence of SEQ ID NO: 121 or 180;
- a variant of a parent peptide of peptide group 15, e.g. a variant of the parent peptide with the amino acid sequence of SEQ ID NO: 26 (pep-058) may be a peptide with the amino acid sequence of SEQ ID NO: 133, 192, 274 or 191;
- a variant of a parent peptide of peptide group 16, e.g. a variant of the parent peptide with the amino acid sequence of SEQ ID NOs: 52 (pep-081), 23 (pep-055) and 272) may be a peptide with the amino acid sequence of SEQ ID NO: 273, 128, 187, 129 or 188;
- a variant of a parent peptide of peptide group 17, e.g. a variant of the parent peptide with the amino acid sequence of SEQ ID NOs: 29 (pep-061), 58 (pep-087), 251 (pep-10) or 252 (pep-011) may be a peptide with the amino acid sequence of SEQ ID NO: 140 or 199;
- a variant of a parent peptide of peptide group 19, e.g. a variant of the parent peptide with the amino acid sequence of SEQ ID NO: 72 (pep-101) and 60 (pep-089) may be a peptide with the amino acid sequence of SEQ ID NO: 227;
- a variant of a parent peptide of peptide group 20, e.g. a variant of the parent peptide with the amino acid sequence of SEQ ID NOs: 61 (pep-090), 73 (pep-102) and 276 may be a peptide with the amino acid sequence of SEQ ID NO: 277, 205, 229, 206 or 230;
- a variant of a parent peptide of peptide group 21, e.g. a variant of the parent peptide with the amino acid sequence of SEQ ID NOs: SEQ ID NO: 62 (pep-091) may be a peptide with the amino acid sequence of SEQ ID NO: 208;
- a variant of a parent peptide of peptide group 22, e.g. a variant of the parent peptide with the amino acid sequence of SEQ ID NOs: 63 (pep-092) and 278 may be a peptide with the amino acid sequence of SEQ ID NO: 222 or 210;
- a variant of a parent peptide of peptide group 23, e.g. a variant of the parent peptide with the amino acid sequence of SEQ ID NOs: 77 (pep-106) may be a peptide with the amino acid sequence of SEQ ID NO: 238;
- a variant of a parent peptide of peptide group 25, e.g. a variant of the parent peptide with the amino acid sequence of SEQ ID NOs: SEQ ID NO: 81 (pep-109) may be a peptide with the amino acid sequence of SEQ ID NO: 221, 245 or 246.

As mentioned any parent peptide or a variant thereof may be amidated. Therefore, in some embodiments, a variant of a parent peptide is amidated at the C-terminus.

Peptides disclosed herein and variants, derivatives or salts thereof are typically manufactured synthetically. Thus, in certain embodiments, peptides, variants, derivatives and salts thereof are synthetic. The peptides, variants, derivatives and salts may be isolated and/or purified, e.g. made by the hand of man, such as by peptide synthesis. Typically, the peptides may be combined after synthesis and freeze-dried or dissolved in aqueous solutions, DMSO, glycerol or the like or mixtures thereof. Typically, each peptide of a peptide combination is present in equimolar concentrations or substantially equimolar ranges. Typically, the peptides are freeze-dried (lyophilized), such as to provide them in a storage-stable form and in a form ready to be re-dissolved. The concentration of each of the re-dissolved peptides may be in a molar concentration in the range of 1 to 1000 µM, for example in the range of 10 to 800 µM, for example in the range of 20 to 500 µM, for example in the range of 20 to 300 µM.

Pharmaceutical Compositions

The invention also features a pharmaceutical composition comprising a composition, e.g. a peptide combination, defined herein. The pharmaceutical composition may be a vaccine, e.g. a product for use in conducting immunotherapy, including but not limited to a vaccine for treating an allergic immune response to a house dust mite allergen.

A pharmaceutical composition comprises in addition to the peptide combination, therapeutically inactive ingredients, such as a pharmaceutically acceptable or physiologically acceptable excipient, carrier and/or adjuvants, which are well-known to the person skilled in the art and may include, but are not limited to, solvents, emulsifiers, wetting agents, plasticizers, solubilizers (e.g. solubility enhancing agents) coloring substances, fillers, preservatives, anti-oxidants, anti-microbial agents, viscosity adjusting agents, buffering agents, pH adjusting agents, isotonicity adjusting agents, mucoadhesive substances, and the like. Examples of formulation strategies are well-known to the person skilled in the art.

In some embodiments, the peptide may be formulated (e.g. mixed together) with immune-modifying agents like adjuvants. The adjuvant may be any conventional adjuvant, including but not limited to oxygen-containing metal salts, e.g. aluminium hydroxide, chitosan, heat-labile enterotoxin (LT), cholera toxin (CT), cholera toxin B subunit (CTB), polymerized liposomes, mutant toxins, e.g. LTK63 and LTR72, microcapsules, interleukins (e.g. IL-1 BETA, IL-2, IL-7, IL-12, INFGAMMA), GM-CSF, MDF derivatives, CpG oligonucleotides, LPS, MPL, MPL-derivatives, phosphophazenes, Adju-Phos(R), glucan, antigen formulation, liposomes, DDE, DHEA, DMPC, DMPG, DOC/Alum Complex, Freund's incomplete adjuvant, ISCOMs(R), LT Oral Adjuvant, muramyl dipeptide, monophosphoryl lipid A, muramyl peptide, and phospatidylethanolamine. Additional examples of adjuvants are described, for example, in "Vaccine Design—the subunit and adjuvant approach" (Edited by Powell, M. F. and Newman, M. J.; 1995, Pharmaceutical Biotechnology (Plenum Press, New York and London, ISBN 0-306-44867-X) entitled "Compendium of vaccine adjuvants and excipients" by Powell, M. F. and Newman M.

In some embodiments, the pharmaceutical composition may be formulated for parenteral administration, such as formulated for injection, e.g. subcutaneous and/or intradermal injection. Therefore, in some embodiments, the pharmaceutical composition may be a liquid (i.e. formulated as a liquid), including a solution, a suspension, a dispersion, and a gelled liquid. For example, a liquid pharmaceutical composition may be formed by dissolving a powder, granulate or lyophilizate of a peptide combination described herein in a suitable solvent and then administering to a subject. Suitable solvents may be any solvent having physiologically acceptable properties and able to dissolve the peptide combination in desired concentrations. A desired concentration may depend on the aliquot to be administered (i.e. to be injected) and the desired single dose. It is emphasized that for the purposes of injection the aliquot is in the range of about 10 to 500 microliters, e.g. 50 to 300 microliters or less and a desired single dose is within range of 1 to 1000 nanomole. Therefore, a suitable solvent should be able to dissolve any peptide of the combination to achieve a final concentration of about 1 to 1000 µM for each of the peptides. Thus, in one embodiment, a liquid composition comprises each of the peptides of the combination in a concentration of 10 to 800 µM, for example 20 to 500 µM or 20 to 300 µM. Typically, the concentration of each peptide is the same, such as in an equimolar concentration, but each peptide of the composition may be present in different concentrations. Typically, the solvent is an aqueous solution, optionally mixed with other solvents. Thus, a solvent may comprise at least 60% w/w of water, e.g. at least 65% w/w, 70% w/w, 75% w/w, 80% w/w, 85% w/w, 90% w/w or 95% w/w, 99% w/w of water, such as distilled water, such as sterile water. In some embodiments, the solvent is sterile distilled water, e.g. water for injection. An aqueous solution may comprise other solvents than water, for example DMSO (dimethylsulfoxide), glycerol, ethanol, acetonitrile, vegetable or synthetic oils. The pH of the aqueous phase of the solvent may be in a physiological acceptable range, typically in the range of 3 to 9, such as in the range of pH 3 to 8, such as in the range of pH 4 to 8, such as in the range of 5 to 8, such as in the range of 6 to 8. Thus, the liquid formulation may comprise a pH controlling agent or buffering agent (e.g. citrate buffer, phosphate buffer, acetate buffer), optionally the pH may be adjusted with dilutions of strong base (e.g. sodium hydroxide or the like) and/or dilutions of strong acids (e.g. hydrochloric acid).

Typically, the liquid formulation is isotonic, and optionally sterile. Therefore, in some embodiments, the formulation comprises saline, such as isotonic saline. The liquid may contain additional excipients, such as another solvent, a solubilizing enhancing agent (e.g. polyoxyethylene (20) sorbitan monolaurate (Tween® 20), ionic and non-ionic emulsifiers (e.g. poloxamers (Kolliphor®)), a dispersant, a thickener, a preservative, an anti-microbial agent, and/or an antioxidant. Non-limiting illustrative examples of solvents include water, saline, DMSO, glycerol, ethanol, acetonitrile, vegetable or synthetic oils.

Some peptides are known to be prone to oxidation or being unstable when exposed to water for a long period. Therefore, to achieve storage stable compositions, a pharmaceutical composition may be formulated to contain only a limited amount of water or aqueous solution, e.g. containing less than 10% w/w of water or aqueous solution, such as less than 9, 8, 7, 6, 5, 4, 3, 2, 1, 0.5% w/w of water or aqueous solution. Examples of pharmaceutical compositions with limited levels of water may include granulates, powders, for example lyophilizates, i.e. freeze-dried powders. Typically, the freeze-dried composition may be dissolved before use, for example dissolved in an aqueous, optionally sterile, solution, for example a solution having a pH in the range of 3-9, such as pH in the range of 3 to 8, such as pH in the range of 4 to 8. A lyophilizate may contain additional ingredients, e.g. bulking agents and lyoprotectants (e.g. sucrose, lactose, trehalose, mannose, mannitol, sorbitol, glucose, raffinose, glycine, histidine or mixtures thereof), buffering agents (e.g. sodium citrate, sodium phosphate, disodium phosphate, sodium hydroxide, Tris base, Tris acetate, Tris HCl or mixtures thereof), antioxidants, antimicrobial agents, solubilizers (e.g. polyoxyethylene (20) sorbitan monolaurate (Tween® 20)).

A freeze-dried composition may also be formulated into a solid dosage form that is administered for example by the oral route such as by oral mucosa. Thus, in some embodiments, the pharmaceutical composition may be formulated for oral administration, for example for sublingual administration. Therefore, the pharmaceutical composition may be a solid dosage form, such as a freeze-dried solid dosage form, typically a tablet, a capsule or sachet, which optionally may be formulated for fast disintegration. Pharmaceutical formulations and delivery systems appropriate for the compositions, methods and uses of the invention are known in the art (see, e.g., Remington: The Science and Practice of Pharmacy (2003) 20th ed., Mack Publishing Co., Easton, Pa.; Remington's Pharmaceutical Sciences (1990) 18th ed., Mack Publishing Co., Easton, Pa.; The Merck Index (1996) 12th ed., Merck Publishing Group, Whitehouse, N.J.; Pharmaceutical Principles of Solid Dosage Forms (1993), Technonic Publishing Co., Inc., Lancaster, Pa.; Ansel ad Soklosa, Pharmaceutical Calculations (2001) 11th ed., Lippincott Williams & Wilkins, Baltimore, Md.; and Poznansky et al., Drug Delivery Systems (1980), R. L. Juliano, ed., Oxford, N.Y., pp. 253-315).

As mentioned, pharmaceutical compositions can be formulated to be compatible with a particular route of administration, such as by intradermal or by sublingual administration. Thus, pharmaceutical compositions may include carriers, diluents, or excipients suitable for administration by various routes. Exemplary routes of administration for contact or in vivo delivery for which a composition can optionally be formulated include inhalation, intranasal, oral, buccal, sublingual, subcutaneous, intradermal, epicutaneous, rectal, transdermal, or intralymphatic.

For oral, buccal or sublingual administration, a composition may take the form of, for example, tablets or capsules, optionally formulated as fast-integrating tablets/capsules or slow-release tablets/capsules. In some embodiments, the tablet is freeze-dried, optionally a fast-disintegrating tablet or capsule suitable for being administered under the tongue.

The pharmaceutical composition may also be formulated into a "unit dosage form", which used herein refers to physically discrete units, wherein each unit contains a predetermined quantity of a peptide or peptide combination, optionally in association with a pharmaceutical carrier (excipient, diluent, vehicle or filling agent) which, when administered in one or more doses, may produce a desired effect. Unit dosage forms also include, for example, ampules and vials, which may include a composition in a freeze-dried or lyophilized state (a lyophilizate) or a sterile liquid carrier, for example that can be added prior to administration or delivery in vivo. Unit dosage forms additionally include, for example, ampules and vials with liquid compositions disposed therein.

Peptides may be prone to degradation when exposed to oxygen, for example when exposed to air or solvents containing air. Therefore, in some embodiments, the pharmaceutical composition comprises an inert gas, e.g. argon or nitrogen.

Another aspect of the invention relates to a kit comprising a compartment and instructions, wherein the compartment comprises a pharmaceutical composition as described herein and wherein the instructions are for use in treating allergy to dust mites, such as house dust mites. A kit may further comprise packaging material comprising corrugated fiber, glass, plastic, foil, ampules, vials, blister pack, preloaded syringes or tubes, optionally that maintain sterility of the components. A kit may further comprise labels or inserts comprising printed matter or computer readable medium optionally including identifying components, dose amounts, clinical pharmacology and instructions for the clinician or for a subject using one or more of the kit components, prophylactic or therapeutic benefits, adverse side effects or manufacturer information.

In one embodiment, the kit additionally comprises a container comprising a solvent for dissolving the composition before use. Examples of suitable solvents are described supra. Optionally, the kit may also comprise a device for use in parenteral injection, e.g. for injecting the composition (e.g. dissolved composition) to a subcutaneous or intradermal tissue. A device may be any suitable device for that purpose, such as a needle or microneedle adapted for intradermal or subcutaneous delivery of the composition. For example, the device may be a microneedle or a device comprising a plurality of microneedles designed for intradermal delivery of liquids, e.g. as described in international patent applications WO14064543 A1, WO05049107 A2, WO06054280 A2, WO07066341 A3 and WO14188429 A1.

Therapy

Compositions (e.g. peptide combinations) described herein may be used for the treatment of an immune response or allergy to a dust mite, such as a house dust mite, in a subject in need thereof. Allergy to a dust mite may be clinically presented in the subject as atopic dermatitis, urticaria, contact dermatitis, allergic conjunctivitis, allergic rhinitis, allergic asthma, anaphylaxis, and/or hay fever. Therefore, in some aspects of the present invention, the method comprises decreasing, reducing, suppressing or inhibiting atopic dermatitis, urticaria, contact dermatitis, allergic conjunctivitis, allergic rhinitis, allergic asthma, anaphylaxis, and/or hay fever.

The phrase "treatment of an immune response" or "treating an immune response" may encompass preventing, relieving, alleviating, reducing, inhibiting, decreasing, or suppressing an immune response, for example an allergic immune response, such as an immune response against a mite allergen (e.g. house dust mite allergen). The treatment of an immune response may also include the decrease, inhibition, suppression or reduction of a T cell response, which may include but is not limited to a Th2 cell response or a memory T cell response. Furthermore, the treatment of an immune response described herein may also comprise inducing, promoting, increasing or enhancing proliferation of regulatory T cells while optionally decreasing, reducing, inhibiting, suppressing or reducing production of pro-inflammatory lymphokines/cytokines.

Therefore, in some aspects, the invention relates to a method for relieving an immune response to an allergen of a dust mite (e.g. a house dust mite) in a subject in need thereof, comprising administering to said subject a therapeutically effective amount of a composition described herein (e.g. a peptide combination described herein).

In other aspects, the administration of a composition described herein may induce immunological tolerance against the allergen(s) of said dust mite.

Thus, compositions disclosed herein may produce a therapeutic or beneficial effect, which optionally may be objectively or subjectively measurable. A therapeutic or beneficial effect can but need not be complete ablation of all or any immune response, or one or more symptoms caused by or associated with an allergen. Thus, a satisfactory clinical result is achieved when there is an incremental improvement or a partial reduction in an immune response or one or more symptoms caused by or associated with an allergen, or there is an inhibition, decrease, reduction, suppression, prevention, limit or control of worsening or progression of an immune response or one or more symptoms caused by or associated with an allergen over a short or long duration (hours, days, weeks, months, etc.).

Therefore, in still other aspects, the subject's administration of a therapeutically effective amount of a composition described herein may relieve one or more symptoms of the immune response. For example, the method may comprise relieving one or more symptoms associated with allergic rhinitis, allergic conjunctivitis, allergic asthma and/or allergic eczema (e.g. atopic dermatitis).

In some embodiments, the one or more symptoms may be associated with allergic rhinitis. For example, the method may comprise reducing one or more of the following symptoms: intensity of itchy nose; number of sneezes within a given period (e.g. daily, weekly, monthly); intensity of blocked nose (e.g. congestion); amount of nasal secretions; eosinophilic count in nasal secretions; specific IgE antibody level (titer) in nasal secretions or in serum; and basophil histamine release of blood.

In other embodiments, the one or more symptoms may be associated with allergic conjunctivitis. For example, the method may comprise reducing one or more of the following symptoms: intensity of itchy eyes, redness in the white of the eyes and/or watery eyes; eosinophilic count in conjunctival tissue scrapings; specific IgE antibody level (titer) in conjunctival tissue scrapings or in serum; and basophil histamine release in blood.

In some embodiments, the one or more symptoms may be associated with allergic asthma. For example, the method may comprise reducing one or more of the following symptoms: number of or frequency of asthma exacerbations (optionally that require hospitalization), intensity and/or number of coughs within a given period (e.g. daily, weekly, monthly); intensity of wheezes; intensity of shortness of breath or congestion (e.g. improvement of being short of breath); reducing Forced Expiratory Volume (FEV1); reducing specific IgE antibody level (titer) in lung fluid or in serum and basophil histamine release in blood; or the method may comprise improving lung function.

In some embodiments, the one or more symptoms may be symptoms associated with atopic dermatitis. For example, the method may comprise reducing one or more of the following symptoms: itch intensity of the skin; eczema score, and number of (peripheral) blood eosinophils.

A therapeutic or beneficial effect also includes reducing or eliminating the need, dosage frequency or amount of a second therapeutic method or therapeutically active drug (e.g. anti-inflammatory, decongestants or anti-allergic agent) used for treating a subject having an immune response or one or more symptoms caused by or associated with an allergen. For example, administration of a peptide combination described herein may reduce the amount of an adjunct therapy administered to a subject, such as reducing the subject's need for concomitant treatment with fast or long-acting β2-agonists, leukotriene modifiers, theophylline corticosteroids or H1 antihistamines (e.g. inhaled or oral) to reduce, relieve, or suppress one or more symptoms of the immune response.

As used herein, the term "immune response" includes T cell (cellular) mediated and/or B cell (humoral) mediated immune responses, or both cellular and humoral responses. In particular, the term "immune response" may include an IgE-mediated immune response (i.e. an allergic immune response). Exemplary immune responses include T cell responses, such as Th2 responses resulting in cytokine production and/or cellular cytotoxicity. In addition, the term "immune response" includes responses that are indirectly affected by T cell activation, e.g., antibody production (humoral responses) and activation of cytokine responsive cells, e.g., eosinophils, macrophages. Immune cells involved in the immune response include lymphocytes, such as T cells (CD4+, CD8+, Th1 and Th2 cells, memory T cells) and B cells; antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer (NK) cells; and myeloid cells, such as macrophages, eosinophils, mast cells, basophils, and granulocytes. A particular immune response is production of immunoglobulin (Ig) isotypes antibodies or decreasing IgE antibodies.

Therefore, in some embodiments, the method comprises inducing or increasing an IgG antibody (e.g. specific IgG) response in a subject to an allergen of a dust mite. In still some embodiments, the method comprises decreasing an IgE antibody (e.g. specific IgE) response in a subject to an allergen of a dust mite. In still some embodiments, the method comprises decreasing a T cell response in a subject to an allergen of a dust mite, for example decreasing the production of Th-2 associated cytokines, like IL-5, IL-4, IL-13 in response to said allergen.

The term "modulating an immune response" or "modulate an immune response" may include to stimulate, induce, promote, increase or enhance an immune response, e.g. a T cell regulatory response, or may include inhibiting, decreasing, suppressing or reducing a T cell response, which may include, but is not limited to a Th2 cell response.

Without being limited to a particular mechanism of action, a peptide combination of the invention may modulate, such as suppress a T cell or an antibody response. For example, a T cell response and/or antibody response triggered by a dust mite allergen (e.g. house dust mite allergen) may be suppressed or inhibited by a peptide combination described herein. Typically, a T cell response is associated with a cytokine response, e.g. IL-2, IL-3, IL-4, IL-5, IL-6, IL-9, IL-10, IL-12, IL-13, IL-17, IL-22, IL-31 or IFN-g response. In particular embodiments, the T cell response against a dust mite allergen may result in decreased production in a subset of the cytokines, for example cytokines associated with a Th2-mediated response (e.g. IL-4, IL-5 and/or IL-13), and may optionally also result in increased production of cytokines associated with a Tregs (e.g. IL-10).

As mentioned, peptide combinations described herein may provide a beneficial effect on an immune response against a dust mite allergen. Exemplary dust mites are the house dust mites of the genus *Dermatophagoides* that include, but are not limited to, the species *Dermatophagoides farinae* (American house dust mite) and *Dermatophagoides pteronyssinus* (European house dust mite); the house dust mites of the genus Euroglyphus that include, but are not limited to, the species Euroglyphus maynei; and the house dust mites of the genus *Blomia* that include, but are not limited to, the species *Blomia tropicalis*. The two latter house dust mite species are mainly found in subtropical/tropical regions around the world and both species are known to comprise allergens that cross-react with antibodies produced in response to allergens of *Dermatophagoides* mites.

A dust mite allergen may be any allergen detected in a house dust mite (e.g. of the genus *Dermatophagoides*, Euroglyphus and/or *Blomia*). Exemplary dust mite allergens of *Dermatophagoides farinae* are: Der f 1, Der f 2, Der f 3, Der f 6, Der f 7, Der f 10, Der f 11, Der f 13, Der f 14, Der f 15, Der f 16, Der f 17, Der f 18 and Der f 22; exemplary dust mite allergens of *Dermatophagoides pteronyssinus* are: Der p 1, Der p 2, Der p 3, Der p 4, Der p 5, Der p 6, Der p 7, Der p 8, Der p 9, Der p 10, Der p 11, Der p 14, Der p 20, Der p 21 and Der p 23; exemplary dust mite allergens of *Blomia tropicalis* are: Blo t 1, Blo t 2, Blo t 3, Blo t 4, Blo t 5, Blo t 6, Blo t 10, Blo t 11, Blo t 12, Blo t 13, Blo t 19 and Blo t 21; exemplary dust mite allergens of Euroglyphus maynei are: Eur m 1, Eur m 2, Eur m 3, Eur m 4 and Eur m 14.

Typically, the dust mite allergen is a major dust mite allergen, for example a house dust mite Group 1 allergen, like Der p 1 and Der f 1, optionally Blo t 1 and Eur m 1, or a house dust mite Group 2 allergen like Der p 2 and Der f 2, optionally Blo t 2 and Eur m 2.

Typically, the treatment comprises repeated administration of the composition with weekly, bi-weekly, monthly or quarterly intervals. Thus, in a particular embodiment, the treatment comprises immunotherapy with single doses repeatedly administered until a persistent effect is achieved. Immunotherapy is thought to produce immunological tolerance in the subject undergoing therapy. Thus, in still other embodiments, the compositions, such as peptide combinations, may be used to induce immunological tolerance in a subject in need thereof.

As used herein, the term "immunological tolerance" refers to a) a decreased or reduced level of a specific immunological response (thought to be mediated at least in part by antigen-specific effector T lymphocytes, B lymphocytes, antibodies, or a combination thereof); b) a delay in the onset or progression of a specific immunological response; or c) a reduced risk of the onset or progression of a specific immunological response (e.g. to a house dust mite allergen). An increase, improvement, enhancement or induction of "tolerance" may refer to a decrease, reduction, inhibition, suppression, or limiting or controlling or clearing of specific immunological reactivity to an allergen as compared to reactivity to the allergen in a previous exposure to the same allergen. Thus, in certain embodiments, the method comprises inducing immunological tolerance in a subject to an allergen (e.g. house dust mite allergen) to suppress an allergic immune response to the allergen. Immunological tolerance in a subject to an allergen can also be reflected by reducing the occurrence, frequency, severity, progression, or duration of an allergic response of the subject to the allergen. Induction of immune tolerance (also referred to as desensitization), and the relative amount of immune tolerance, can be measured by methods disclosed herein or known to the skilled artisan. For example, induction of immune tolerance can be measured by the modulated lymphokine and/or cytokine level in a subject or animal before versus after administering a peptide combination described herein for the first time. A modulated cytokine level can be an increase of a cytokine level, for instance an increase of a lymphokine and/or cytokine level of at least 1.5, 2, 3, 4, 5, 6, 7, 8, 10, 20, 50 times or more relative to before administering the peptide combination for the first time. Alternatively, modulation can be a decrease of the level of a particular cytokine level, for instance a decrease of the lymphokine and/or cytokine level of at least 1.5, 2, 3, 4, 5, 6, 7, 8, 10, 20, 50 times or more relative to before administering the peptide combination for the first time. The lymphokines/cytokines chosen to measure can be from any relevant lymphokines/cytokines, such as IL-2, IL-5, IL-4, IL-6, IL-10, IL-12, IL-13, IL-17, TNF-alfa, IFN-gamma, TGF-beta, MCP-1, RANK-L and Flt3L. Accordingly, the term "inducing immunological tolerance" may include eliciting, stimulating, promoting, increasing or enhancing immunological tolerance. Immunological tolerance may involve modulation of T cell activity, including but not limited to CD4+ T cells, CD8+ T cells, Th1 cells, Th2 cells and regulatory T cells (Tregs), and memory T cells, including inflammatory lymphokines/cytokines produced by T cells.

A peptide combination is typically administered by injection, such as by subcutaneous or intradermal administration, but may also include other routes of administration, such as epicutaneous, rectal, sublingual, oral, buccal, intranasal, respiratory and intralymphatic route of administration.

The peptide combination may be administered to any subject in need thereof, for example a human, a pet such as a dog or a cat, a domestic animal such as a horse, or a laboratory animal like a mouse, a guinea pig or a rabbit. The subject may be sensitized to an allergen of a dust mite (e.g. having specific IgE antibodies against an allergen of a dust mite and/or having a T cell response against an allergen of a dust mite). Therefore, a subject in need thereof may produce specific IgE antibodies or a T cell response against house dust mite allergens Der p 1, Der p 2, Der f 1 and/or Der f 2, and optionally other dust mite allergens as described supra including an aqueous extract of a house dust mite or a house dust mite faeces.

The peptide combination may be administered in clinically relevant doses, such as therapeutically sufficient doses. For example, a single dose of each peptide of the composition may be in the range of 1 to 1000 nanomole, for example 1 to 500 nanomole, for example 1 to 250 nanomole, for example 5 to 250 nanomole, which single dose may be repeated once daily, weekly, biweekly or monthly or quarterly. Typically, the peptide combination is a liquid administered in a volume of about 50 to 150 microliter, such as by intradermal administration.

The compositions described herein may be dosed in a dosage regimen usually applied in the field of allergy immunotherapy, such peptide allergy immunotherapy. For example, compositions may be administered as a single dose (e.g. one injection) with daily, weekly, bi-weekly, monthly or quarterly intervals over a period of at least 2-6 months or even longer until a more persistent effect is achieved. The term "persistent effect" means that one or more clinically relevant symptoms of the immune response is reduced in the subject when exposed to an allergen of a house dust mite compared to before the subject is administered the first dose. A persistent effect may be evaluated at least two months after the subject has stopped treatment, such as after at least three, four, five, six, nine or twelve months. It is also envisaged that the treatment is initiated by an up-dosing phase with the peptide combination being administered in increasing doses within one day or with daily, weekly or bi-weekly intervals until the target maintenance dose is achieved.

The subject administered a peptide combination described herein may optionally also be administered another therapeutic agent used for treating an immune response against a dust mite allergen. However, in some embodiments, the subject is not co-administered the peptide combination of another immunogen, e.g. an allergen extract or allergen, e.g. allergen extract or allergen of a house dust mite. Thus, in certain embodiments, a composition described herein may not comprise an allergen extract.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. The invention is further exemplified by way of the following non-limited examples.

A still other aspect of the invention relates to an in vitro method of determining whether T cells of a subject in need of treatment recognize a composition as described herein, comprising contacting T cells obtained from the subject with said composition or a single peptide thereof and detecting whether the T cells are stimulated by said composition or single peptide. The in vitro method may be used to determine whether the subject has, or is at risk of developing, an allergy to a dust mite allergen.

The invention is further described by the following embodiments 1 to 119:

Embodiment 1. A composition comprising at least three peptides, wherein the composition comprises peptides selected from at least three of the following peptide groups:
group 26.: a parent peptide with the amino acid sequence SEQ ID NOs: 82 (pep-110), 269 (pep-125), 70 (pep-099) or 253 (pep-012); or a variant thereof;
group 24.: a parent peptide with the amino acid sequence SEQ ID NOs: 271 (pep-131), 67 (pep-096), 79 (pep-108), 256 (pep-031) or 270 (pep-126); or a variant thereof;
group 14.: a parent peptide with the amino acid sequence SEQ ID NOs: 268 (pep-130) or 22 (pep-054); or a variant thereof;
group 1.: a parent peptide with the amino acid sequence SEQ ID NO: 90 or a variant thereof;
group 2.: a parent peptide with the amino acid sequence SEQ ID NO: 280 or a variant thereof;
group 3.: a parent peptide with the amino acid sequence SEQ ID NO: 9 (pep-041) or a variant thereof;
group 4.: a parent peptide with the amino acid sequence SEQ ID NO: 10 (pep-042) or a variant thereof;
group 5.: a parent peptide with the amino acid sequence SEQ ID NO: 11 (pep-043) or a variant thereof;
group 6.: a parent peptide with the amino acid sequence SEQ ID NO: 12 (pep-044) or a variant thereof;
group 7.: a parent peptide with the amino acid sequence SEQ ID NOs: 42 (pep-072) or 249 (pep-022); or a variant thereof;
group 8.: a parent peptide with the amino acid sequence SEQ ID NO: 15 (pep-047) or a variant thereof;
group 9.: a parent peptide with the amino acid sequence SEQ ID NOs: 266 (pep-123), 255 (pep-025), 46 (pep-075) or 17 (pep-049); or a variant thereof;
group 10.: a parent peptide with the amino acid sequence SEQ ID NOs: 18 (pep-050), 258 (pep-122) or 267 (pep-124); or a variant thereof;
group 11.: a parent peptide with the amino acid sequence SEQ ID NO: 120; or a variant thereof;
group 12.: a parent peptide with the amino acid sequence SEQ ID NOs: 20 (pep-052) or 49 (pep-078); or a variant thereof;
group 13.: a parent peptide with the amino acid sequence SEQ ID NO: 21 (pep-053) or a variant thereof;
group 15.: a parent peptide with the amino acid sequence SEQ ID NOs: 52 (pep-081) or 23 (pep-055, 272); or a variant thereof;
group 16.: a parent peptide with the amino acid sequence SEQ ID NO: 26 (pep-058) or a variant thereof;
group 17.: a parent peptide with the amino acid sequence SEQ ID NOs: 29 (pep-061), 58 (pep-087), 251 (pep-10) or 252 (pep-011); or a variant thereof;
group 18.: a parent peptide with the amino acid sequence SEQ ID NO: 71 (pep-100) or a variant thereof;
group 19.: a parent peptide with the amino acid sequence SEQ ID NO: 72 (pep-101) or a variant thereof;
group 20.: a parent peptide with the amino acid sequence SEQ ID NOs: 61 (pep090), 73 (pep-102) or 276; or a variant thereof;
group 21.: a parent peptide with the amino acid sequence SEQ ID NO: 62 (pep-091) or a variant thereof;
group 22.: a parent peptide with the amino acid sequence SEQ ID NOs: 63 (pep-092) or 278; or a variant thereof;
group 23.: a parent peptide with the amino acid sequence SEQ ID NO: 77 (pep-106) or a variant thereof; and
group 25.: a parent peptide with the amino acid sequence SEQ ID NO: 81 (pep-109) or a variant thereof.

Embodiment 2. The composition according to embodiment 1, wherein at least one peptide is selected from any one of the peptide groups 1-17.

Embodiment 3. The composition according to any one of the preceding embodiments, wherein at least one peptide is selected from any one of the peptide groups 18-26.

Embodiment 4. The composition according to any one of the preceding embodiments, wherein the at least three peptides are selected from three of the peptide groups 4, 5, 6, 9, 10, 13, 14, 15, 16, 17, 20, 21, 24, 25 and 26.

Embodiment 5. The composition according to any one of the preceding embodiments, wherein the at least three peptides are selected from three of the peptide groups 9, 10, 13, 14, 16, 20, 21, 24, 25 and 26.

Embodiment 6. The composition according to any one of the preceding embodiments, wherein the composition comprises an additional peptide selected from any one of the peptide groups 1-26 from which there is no other peptide in the composition.

Embodiment 7. The composition according to any one of the preceding embodiments, wherein the composition does not comprise a peptide from peptide group 7 and/or peptide group 20.

Embodiment 8. The composition according to embodiment 7, wherein the composition does not comprise as three of the peptides, peptides from each of the peptide groups 7, 20 and 17.

Embodiment 9. The composition according to any one of the preceding embodiments, wherein the composition comprises as one of the peptides a peptide from peptide group 26 (e.g. parent peptide pep-110 or a variant thereof).

Embodiment 10. The composition according to embodiment 9, wherein the composition comprises as one of the peptides a peptide selected from any one of the peptide groups 1-17.

Embodiment 11. The composition according to any one of the preceding embodiments, wherein the composition comprises as one of the peptides a peptide from peptide group 26 (e.g. parent peptide pep-110) and comprises as one of the peptides a peptide selected from any one of the peptide groups 24, 17, 9 or 16.

Embodiment 12. The composition according to embodiment 11, wherein the composition comprises as two of the peptides, a peptide from peptide group 26 (e.g. parent peptide pep-110) and a peptide from peptide group 24 (e.g. parent peptide pep-131).

Embodiment 13. The composition according to embodiment 12, wherein the third peptide is selected from any one of the peptide groups 4, 5, 6, 9, 10, 13, 14, 15, 16 and 17.

Embodiment 14. The composition according to any one of embodiments 12 and 13, wherein the third peptide is from peptide group 14.

Embodiment 15. The composition according embodiment 14, wherein an additional peptide is selected from any one of the peptide groups 1-13, 15-23 and 25.

Embodiment 16. The composition according to embodiment 14, wherein an additional peptide is selected from any one of the peptide groups 9, 16 and 21.

Embodiment 17. The composition according to any one of embodiments 12 to 16, comprising five peptides, wherein the composition comprises peptides from each of the five peptide groups 26, 24, 14, 9 and 16.

Embodiment 18. The composition according to embodiment 17, wherein the composition comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 266 (pep-123) or a variant thereof; and
e) a parent peptide with the amino acid sequence SEQ ID NO: 26 (pep-058) or a variant thereof.

Embodiment 19. The composition according to embodiment 17, wherein the composition comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 266 (pep-123) or a variant thereof; and
e) a parent peptide with the amino acid sequence SEQ ID NO: 26 (pep-058) or a variant thereof.

Embodiment 20. The composition according to any one of embodiments 12 to 16, comprising five peptides, wherein the composition comprises peptides from each of the five peptide groups 26, 24, 14, 9 and 21.

Embodiment 21. The composition according to embodiment 20, wherein the composition comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 266 (pep-123) or a variant thereof; and
e) a parent peptide with the amino acid sequence SEQ ID NO: 62 (pep-091) or a variant thereof.

Embodiment 22. The composition according to embodiment 20, wherein the composition comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 46 (pep-075) or a variant thereof; and
e) a parent peptide with the amino acid sequence SEQ ID NO: 62 (pep-091) or a variant thereof.

Embodiment 23. The composition according to any one of embodiments 12 to 16, comprising five peptides, wherein the composition comprises peptides from each of the five peptide groups 26, 24, 14, 16 and 21.

Embodiment 24. The composition according to embodiment 23, wherein the composition comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 268 (pep-130) or a variant thereof;
d) a parent peptide with the amino acid sequence SEQ ID NO: 26 (pep-058) or a variant thereof; and
e) a parent peptide with the amino acid sequence SEQ ID NO: 62 (pep-091) or a variant thereof.

Embodiment 25. The composition according to any one of embodiments 12 and 13, wherein the third peptide is from peptide group 9 or from peptide group 21.

Embodiment 26. The composition according to embodiment 25, comprising five peptides, wherein the composition comprises peptides from each of the five peptide groups 26, 24, 21, 9 and 13.

Embodiment 27. The composition according to embodiment 26, wherein the composition comprises
a) a parent peptide with the amino acid sequence SEQ ID NO: 82 (pep-110) or a variant thereof;
b) a parent peptide with the amino acid sequence SEQ ID NO: 271 (pep-131) or a variant thereof;
c) a parent peptide with the amino acid sequence SEQ ID NO: 62 (pep-091) or a variant thereof;
d) a parent peptide with the amino acid sequence SEQ ID NO: 266 (pep-123) or a variant thereof; and
e) a parent peptide with the amino acid sequence SEQ ID NO: 21 (pep-053) or a variant thereof.

Embodiment 28. The composition according to any one of embodiments 12 and 13, wherein the third peptide is from peptide group 17.

Embodiment 29. The composition according embodiment 28, comprising an additional peptide selected from any one of the peptide groups 1-16, 18-23 and 25.

Embodiment 30. The composition according to any one of embodiments 28 and 29, wherein an additional peptide is selected from any one or both of the peptide groups 7 and 10.

Embodiment 31. The composition according to embodiment 30, comprising five peptides, wherein the composition comprises a peptide from each of the five peptide groups 26, 24, 17, 7 and 10.

Embodiment 32. The composition according to embodiment 31, wherein the composition comprises
a) a parent peptide with the amino acid sequence SEQ ID NO: 253 (pep-012) or a variant thereof;
b) a parent peptide with the amino acid sequence SEQ ID NO: 256 (pep-031) or a variant thereof;
c) a parent peptide with the amino acid sequence SEQ ID NO: 252 (pep-011) or a variant thereof;
d) a parent peptide with the amino acid sequence SEQ ID NO: 254 (pep-022) or a variant thereof; and
e) a parent peptide with the amino acid sequence SEQ ID NO: 258 (pep-122) or a variant thereof.

Embodiment 33. The composition according to embodiment 31, wherein the composition comprises
a) a parent peptide with the amino acid sequence SEQ ID NO: 253 (pep-012) or a variant thereof;
b) a parent peptide with the amino acid sequence SEQ ID NO: 256 (pep-031) or a variant thereof;
c) a parent peptide with the amino acid sequence SEQ ID NO: 251 (pep-010) or a variant thereof;
d) a parent peptide with the amino acid sequence SEQ ID NO: 254 (pep-022) or a variant thereof; and
e) a parent peptide with the amino acid sequence SEQ ID NO: 258 (pep-122) or a variant thereof.

Embodiment 34. The composition according to embodiment 30, comprising five peptides, wherein the composition comprises peptides from each of the four peptide groups 26, 24, 17 and 10; and a peptide with the amino acid sequence SEQ ID NO: 117 (pep-p4) or a variant thereof.

Embodiment 35. The composition according to embodiment 34, comprising
a) a parent peptide with the amino acid sequence SEQ ID NO: 253 (pep-012) or a variant thereof;
b) a parent peptide with the amino acid sequence SEQ ID NO: 256 (pep-031) or a variant thereof;
c) a parent peptide with the amino acid sequence SEQ ID NO: 252 (pep-011) or a variant thereof;
d) a parent peptide with the amino acid sequence SEQ ID NO: 258 (pep-122) or a variant thereof; and
e) a parent peptide with the amino acid sequence SEQ ID NO: 117 or a variant thereof.

Embodiment 36. The composition according to embodiment 11, wherein the composition comprises as two of the peptides, a peptide from peptide group 26 (e.g. parent peptide 110) and a peptide from peptide group 17. (e.g. parent peptide pep-058, pep-010, pep-011 or pep-061).

Embodiment 37. The composition according to embodiment 36, comprising three peptides, wherein the composition comprises peptides from each of the three peptide groups 26, 17 and 6.

Embodiment 38. The composition according to embodiment 37, comprising
a) a parent peptide with the amino acid sequence SEQ ID NO: 70 (pep-099) or a variant thereof;
b) a parent peptide with the amino acid sequence SEQ ID NO: 251 (pep-010) or a variant thereof; and
c) a parent peptide with the amino acid sequence SEQ ID NO: 12 (pep-044) or a variant thereof.

Embodiment 39. The composition according to embodiment 11, wherein the composition comprises as two of the peptides, a peptide from peptide group 26 (e.g. parent peptide 110) and a peptide from peptide group 9. (e.g. parent peptide pep-123, pep-025, pep-075 or pep-049).

Embodiment 40. The composition according to embodiment 39, comprising five peptides, wherein the composition comprises peptides from each of the five peptide groups 26, 9, 6, 16 and 19.

Embodiment 41. The composition according to embodiment 40, comprising
a) a parent peptide with the amino acid sequence SEQ ID NO: 70 (pep-099) or a variant thereof;
b) a parent peptide with the amino acid sequence SEQ ID NO: 46 (pep-075) or a variant thereof;
c) a parent peptide with the amino acid sequence SEQ ID NO: 12 (pep-044) or a variant thereof;
d) a parent peptide with the amino acid sequence SEQ ID NO: 26 (pep-058) or a variant thereof; and
e) a parent peptide with the amino acid sequence SEQ ID NO: 60 (pep-089) or a variant thereof.

Embodiment 42. The composition according to embodiment 39, comprising five peptides, wherein the composition comprises peptides from each of the five peptide groups 26, 9, 6, 18 and 20.

Embodiment 43. The composition according to embodiment 42, comprising
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 12 (pep-044) or a variant thereof;
d) a parent peptide with the amino acid sequence SEQ ID NO: 71 (pep-100) or a variant thereof; and
e) a parent peptide with the amino acid sequence SEQ ID NO: 73 (pep-102) or a variant thereof.

Embodiment 44. The composition according to embodiment 39, comprising five peptides, wherein the composition comprises peptides from each of the five peptide groups 26, 9, 6, 12 and 21.

Embodiment 45. The composition according to embodiment 44, comprising
a) a parent peptide with the amino acid sequence SEQ ID NO: 82 (pep-110) or a variant thereof;
b) a parent peptide with the amino acid sequence SEQ ID NO: 17 (pep-049)) or a variant thereof;
c) a parent peptide with the amino acid sequence SEQ ID NO: 12 (pep-044) or a variant thereof;
d) a parent peptide with the amino acid sequence SEQ ID NO: 20 (pep-052) or a variant thereof; and
e) a parent peptide with the amino acid sequence SEQ ID NO: 62 (pep-091) or a variant thereof.

Embodiment 46. The composition according to embodiment 39, comprising five peptides, wherein the composition comprises peptides from each of the five peptide groups 26, 9, 16, 3 and 25.

Embodiment 47. The composition according to embodiment 46, wherein the composition comprises
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 9 (pep-041) or a variant thereof; and
e) a parent peptide with the amino acid sequence SEQ ID NO: 81 (pep-109) or a variant thereof.

Embodiment 48. The composition according to embodiment 39, comprising five peptides, wherein the composition comprises peptides from each of the five peptide groups 26, 9, 16, 14 and 25.

Embodiment 49. The composition according to embodiment 48, wherein the composition comprises
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 22 (pep-054) or a variant thereof; and
e) a parent peptide with the amino acid sequence SEQ ID NO: 81 (pep-109) or a variant thereof.

Embodiment 50. The composition according to embodiment 39, comprising five peptides, wherein the composition comprises peptides from each of the five peptide groups 26, 9, 16, 3 and 21.

Embodiment 51. The composition according to embodiment 50, wherein the composition comprises
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 9 (pep-041) or a variant thereof; and
e) a parent peptide with the amino acid sequence SEQ ID NO: 62 (pep-091) or a variant thereof.

Embodiment 52. The composition according to embodiment 39, comprising five peptides, wherein the composition comprises peptides from each of the five peptide groups 26, 9, 16, 14 and 21.

Embodiment 53. The composition according to embodiment 52, wherein the composition comprises
a) a parent peptide with the amino acid sequence SEQ ID NO: 82 (pep-110) or a variant thereof;
b) a parent peptide with the amino acid sequence SEQ ID NO: 46 (pep-075) or a variant thereof;
c) a parent peptide with the amino acid sequence SEQ ID NO: 26 (pep-058) or a variant thereof;
d) a parent peptide with the amino acid sequence SEQ ID NO: 268 (pep-130) or a variant thereof; and
e) a parent peptide with the amino acid sequence SEQ ID NO: 62 (pep-091) or a variant thereof.

Embodiment 54. The composition according to embodiment 11, wherein the composition comprises as two of the peptides, a peptide from peptide group 26 (e.g. parent peptide pep-110 or a variant thereof) and a peptide from peptide group 16 (e.g. parent peptide pep-058 or a variant thereof).

Embodiment 55. The composition according to embodiment 54, comprising five peptides, wherein the composition comprises peptides from each of the five peptide groups 26, 16, 3, 15 and 25.

Embodiment 56. The composition according to embodiment 55, wherein the composition comprises
a) a parent peptide with the amino acid sequence SEQ ID NO: 82 (pep-110) or a variant thereof;
b) a parent peptide with the amino acid sequence SEQ ID NO: 26 (pep-058) or a variant thereof;
c) a parent peptide with the amino acid sequence SEQ ID NO: 9 (pep-041) or a variant thereof;
d) a parent peptide with the amino acid sequence SEQ ID NO: 52 (pep-081) or a variant thereof; and
e) a parent peptide with the amino acid sequence SEQ ID NO: 81 (pep-109) or a variant thereof.

Embodiment 57. The composition according to embodiment 54, comprising five peptides, wherein the composition comprises peptides from each of the five peptide groups 26, 16, 14, 15 and 21.

Embodiment 58. The composition according to embodiment 57, wherein the composition comprises
a) a parent peptide with the amino acid sequence SEQ ID NO: 82 (pep-110) or a variant thereof;
b) a parent peptide with the amino acid sequence SEQ ID NO: 26 (pep-058) or a variant thereof;
c) a parent peptide with the amino acid sequence SEQ ID NO: 22 (pep-054) or a variant thereof;
d) a parent peptide with the amino acid sequence SEQ ID NO: 52 (pep-081) or a variant thereof; and
e) a parent peptide with the amino acid sequence SEQ ID NO: 62 (pep-091) or a variant thereof.

Embodiment 59. The composition according to any one of the preceding embodiments, wherein the peptides in the composition are all selected from different peptide groups, for example a maximum of 3 peptides selected from each of 3 different peptide groups, for example a maximum of 4 peptides selected from each of 4 different peptide groups, for example a maximum of 5 peptides selected from each of 5 different peptide groups, for example a maximum of 6 peptides selected from each of 6 different peptide groups, or for example a maximum of 7 peptides selected from each of 7 different peptide groups.

Embodiment 60. The composition according to any one of the preceding embodiments, wherein the variant is a peptide comprising one or more additional amino acids than the parent peptide and comprises up to 30 amino acid residues in length, optionally wherein the variant peptide comprises an amino acid sequence having at least 80% identity over at least 14 contiguous amino acids of the parent peptide.

Embodiment 61. The composition according to any one of the preceding embodiments, wherein the variant is a peptide comprising fewer amino acids than the parent peptide and wherein the amino acid sequence has at least 80% identity over at least 14 contiguous amino acids of the parent peptide.

Embodiment 62. The composition according to any one of embodiments 60 and 61, wherein the variant consists of 14 to 30 amino acid residues and comprises an amino acid sequence having at least 80% sequence identity over at least 15 contiguous amino acids of the parent peptide.

Embodiment 63. The composition according to any one of embodiments 60 and 61, wherein the variant consists of 15-30 amino acids residues and comprises an amino acid sequence having at least 80% sequence identity over at least 15 contiguous amino acids of the parent peptide.

Embodiment 64. The composition according to any one of embodiments 60 and 61, wherein the variant consists of 15-25 amino acids residues and comprises an amino acid sequence having at least 80% sequence identity over at least 15 contiguous amino acids of the parent peptide.

Embodiment 65. The composition according to any one of the preceding embodiments, wherein the variant comprises one or more (e.g. 1, 2, 3, or 4) arginine residue(s) (R), one or more lysine residue(s) (K), one or more glutamic residues (E), and/or one or more aspartic acid residues (D) added to the N- or C-terminus of the parent peptide or to a fragment of the parent peptide consisting of at least 14 contiguous amino acids of the parent peptide.

Embodiment 66. The composition according to any one of the preceding embodiments, wherein the variant comprises one or more additional amino acid residues added at the N- and/or C-terminal ends of the parent peptide, wherein the one or more additional amino acid residues are the same amino acid or amino acid sequence flanking the N- and/or C-terminal ends of the parent peptide when it is aligned with the wild type amino acid sequence it is present in, based upon or derived from or is aligned with another isoform of the same wild type amino acid sequence.

Embodiment 67. The composition according to any one of the preceding embodiments, wherein the variant comprises a deletion of a hydrophobic residue up to three amino acids from the N- or C-terminus of the parent peptide; and/or deletion of any two consecutive amino acids comprising the sequence Asp-Gly up to four amino acids from the N- or C-terminus of the parent peptide.

Embodiment 68. The composition according to any one of the preceding embodiments, wherein a peptide of the composition including a variant thereof contains at least one T cell epitope, optionally a Th-2 cell epitope.

Embodiment 69. The composition according to any one of the preceding embodiments, wherein the variant binds to at least 70% of the group of HLA Class II alleles that the parent peptide binds to.

Embodiment 70. The composition according to any one of the preceding embodiments, wherein the parent peptide or the variant thereof is derivatized.

Embodiment 71. The composition according to embodiment 70, wherein the parent peptide or the variant thereof is amidated at the C-terminal end.

Embodiment 72. The composition according to embodiment 70, wherein the derivative comprises (a) N-terminal acetylation; (b) C-terminal amidation (c) one or more hydrogens on the side chain amines of arginine and/or lysine replaced with a methylene group; (d) glycosylation and/or (e) phosphorylation.

Embodiment 73. The composition according to any one of the preceding embodiments, wherein the parent peptide or the variant thereof, or a derivative of the parent peptide or variant thereof is a salt.

Embodiment 74. The composition according to embodiment 73, wherein the salt is an acetate salt.

Embodiment 75. The composition according to any one of the preceding embodiments, wherein the peptides are synthetically made.

Embodiment 76. The composition according to any one of the preceding embodiments, wherein the peptides are freeze-dried.

Embodiment 77. The composition according to any one of the preceding embodiments, wherein each peptide in the composition is present in equimolar concentrations or in substantially equimolar concentrations.

Embodiment 78. The composition according to any one of the preceding embodiments, wherein each peptide in the composition is present in a molar concentration of 1 to 1000 µM.

Embodiment 79. The composition according to any one of embodiments 1 to 78, wherein the composition is a pharmaceutical composition.

Embodiment 80. The pharmaceutical composition according to embodiment 79, further comprising a pharmaceutically acceptable carrier, excipient and/or adjuvant, optionally sterile.

Embodiment 81. The pharmaceutical composition according to any one of embodiments 79 and 80 formulated as a vaccine for parenteral administration.

Embodiment 82. The pharmaceutical composition according to any one of embodiments 79 to 81, wherein the pharmaceutical composition is a powder.

Embodiment 83. The pharmaceutical composition according to any one of embodiments 79 to 82, wherein the composition is formulated to be re-dissolved before use.

Embodiment 84. The pharmaceutical composition according to any one of embodiments 79 to 83, wherein the composition is isotonic.

Embodiment 85. A kit comprising a compartment and instructions, wherein the compartment comprises the composition according to any one of embodiments 1 to 84 and wherein the instructions are for use in treating allergy to dust mites, such as house dust mites.

Embodiment 86. The kit according to embodiment 85, wherein the kit further comprises packaging material comprising corrugated fiber, glass, plastic, foil, ampules, vials, blister pack, preloaded syringes or tubes, optionally that maintains sterility of the components.

Embodiment 87. The kit according to any one of embodiments 85 to 86, wherein the kit further comprises labels or inserts comprising printed matter or computer readable medium optionally including identifying components, dose amounts, clinical pharmacology, instructions for the clinician or for a subject using one or more of the kit components, prophylactic or therapeutic benefits, adverse side effects or manufacturer information.

Embodiment 88. A method for relieving or reducing (e.g. treating) an immune response triggered by an allergen of a dust mite (e.g. house dust mite) in a subject in need thereof, comprising administering to the subject a therapeutically effective amount of the composition according to any one of embodiments 1 to 84.

Embodiment 89. A method for relieving one or more symptoms of an immune response triggered by an allergen of a dust mite (e.g. house dust mite) in a subject in need thereof, comprising administering to the subject a therapeutically effective amount of the composition according to any one of embodiments 1 to 84.

Embodiment 90. A method for inducing (developing) immunological tolerance against an allergen of a dust mite (e.g. house dust mite), comprising administering to a subject a therapeutically effective amount of the composition according to any one of embodiments 1 to 84.

Embodiment 91. The method according to any one of embodiments 88 to 90, wherein the method comprises relieving one or more symptom(s) associated with allergic rhinitis, allergic conjunctivitis, allergic asthma and/or allergic eczema (e.g. atopic dermatitis).

Embodiment 92. The method according to embodiment 91, wherein the one or more symptom(s) are symptoms associated with allergic rhinitis.

Embodiment 93. The method according to embodiment 92, wherein the method comprises reducing the intensity of itchy nose; reducing the number of sneezes within a given period (e.g. daily, weekly, monthly); reducing the intensity of blocked nose (congestion); reducing the amount of nasal fluid; reducing the eosinophilic count in nasal fluid; reducing specific IgE antibody level (titer) in nasal fluid or in serum and/or reducing basophil histamine release of blood.

Embodiment 94. The method according to embodiment 91, wherein the one or more symptom(s) are symptoms associated with allergic conjunctivitis.

Embodiment 95. The method according to embodiment 94, wherein the method comprises reducing the intensity of itchy eyes, redness in the white of the eyes and/or watery eyes; reducing the eosinophilic count in conjunctival tissue scrapings; reducing specific IgE antibody level (titer) in conjunctival tissue scrapings or in serum and/or reducing basophil histamine release of blood.

Embodiment 96. The method according to embodiment 91, wherein the one or more symptom(s) are symptoms associated with allergic asthma.

Embodiment 97. The method according to embodiment 96, wherein the method comprises reducing the intensity and/or number of coughs within a given period (e.g. daily, weekly, monthly); reducing the intensity of wheezes; improving being short of breath; improving lung function; reducing specific IgE antibody level (titer) in lung fluid or in serum and/or reducing basophil histamine release of blood.

Embodiment 98. The method according to embodiment 91, wherein the one or more symptom(s) are symptoms associated with atopic dermatitis.

Embodiment 99. The method according to embodiment 98, wherein the method comprises reducing itch intensity of the skin; reducing eczema score and/or reducing number of (peripheral) blood eosinophils.

Embodiment 100. The method according to any one of embodiments 88 to 99, wherein the method comprises reducing the subject's need for concomitant treatment with corticosteroids or H1 antihistamines to reduce, relieve or suppress one or more symptoms of the immune response.

Embodiment 101. The method according to any one of embodiments 88 to 100, wherein the dust mite allergy is clinically presented as atopic dermatitis, urticaria, contact dermatitis, allergic conjunctivitis, allergic rhinitis, allergic asthma, anapylaxis, and/or hay fever.

Embodiment 102. The method according to any one of embodiments 88 to 101, wherein the method decreases, reduces, suppresses or inhibits atopic dermatitis, urticaria, contact dermatitis, allergic conjunctivitis, allergic rhinitis, allergic asthma, anaphylaxis, and/or hay fever.

Embodiment 103. The method according to any one of embodiments 88 to 102, wherein the method comprises inducing or increasing an IgG antibody response in the subject to an allergen of a dust mite.

Embodiment 104. The method according to any one of embodiments 88 to 103, wherein the method comprises decreasing an IgE antibody response in the subject to an allergen of a dust mite.

Embodiment 105. The method according to any one of embodiments 88 to 105, wherein the method comprises decreasing a T cell response in the subject to an allergen of a dust mite.

Embodiment 106. The method according to any one of embodiments 88 to 105, wherein the subject is sensitized to an allergen of a dust mite (e.g. has specific IgE antibodies against an allergen of a dust mite and/or has a T cell response against an allergen of a dust mite).

Embodiment 107. The method according to any one of embodiments 88 to 106, wherein the dust mite is of the genus *Dermatophagoides*.

Embodiment 108. The method according to any one of embodiments 88 to 107, wherein the allergen of a dust mite is Der p 1, Der p 2, Der f 1 and/or Der f 2.

Embodiment 109. The method according to any one of embodiments 88 to 108, wherein the treatment comprises repeated administration of the composition in weekly, bi-weekly, monthly or quarterly intervals.

Embodiment 110. The method according to any one of embodiments 88 to 109, wherein the treatment is by immunotherapy.

Embodiment 111. The method according to any one of embodiments 88 to 110, wherein a single dose of each single peptide of the composition is in the range of 1 to 1000 nanomoles.

Embodiment 112. The method according to any one of embodiments 88 to 111, wherein the administration comprises administering a volume of about 50 to 150 microliters of the composition (e.g. by intradermal administration).

Embodiment 113. The method according to any one of embodiments 88 to 112, wherein the administration is by a route of administration selected from any one of subcutaneous, intradermal, epicutaneous, rectal, topical, sublingual, oral, buccal, intranasal, respiratory and intralymphatic route.

Embodiment 114. The method according to any one of embodiments 88 to 113, wherein the subject is a human, a pet such as a dog or a cat or a domestic animal such as a horse.

Embodiment 115. A composition according to any one of embodiments 1-84 for use in a method according to any one of embodiments 88-114.

Embodiment 116. Use of a composition according to any one of embodiments 1-84 for the preparation of a medicament for use in a method according to any one of embodiments 88-114.

Embodiment 117. An in vitro method of determining whether T cells of a subject in need of treatment recognize a composition as defined in any of embodiments 1 to 784, comprising contacting T cells obtained from the subject with said composition or a single peptide thereof and detecting whether the T cells are stimulated by said composition or single peptide.

Embodiment 118. The method of embodiment 117 carried out to determine whether a subject has, or is at risk of developing, an allergy to a dust mite allergen.

Embodiment 119. A diagnostic kit comprising a composition according to any one of embodiments 1-84..

The invention is still further described by the following embodiments A1 to A191:

Embodiment A1. A composition comprising a peptide combination comprising three peptides or more, wherein each peptide of the combination is independently selected from:
(a) any of the peptides consisting of an amino acid sequence of SEQ ID NOS:249 (peptide 002), 251 (peptide 010), 252 (peptide 011), 253 (peptide 012), 254 (peptide 022), 255 (peptide 025), 256 (peptide 031), 9 (peptide 041), 10 (peptide 042), 11 (peptide 043), 12 (peptide 044), 15 (peptide 047), 17 (peptide 049), 18 (peptide 050), 20 (peptide 052), 21 (peptide 053), (peptide 054), 23 (peptide 055), 26 (peptide 058), 29 (peptide 061), 238 (peptide 066), 42 (peptide 072), 46 (peptide 075), 49 (peptide 078), 52 (peptide 081), 58 (peptide 087), 60 (peptide 089), 61 (peptide 090), 62 (peptide 091), 63 (peptide 092), 67 (peptide 096), 70 (peptide 099), 71 (peptide 100), 72 (peptide 101), 73 (peptide 102), 77 (peptide 106), 79 (peptide 108), 81 (peptide 109), 82 (peptide 110), 257 (peptide 117), 258 (peptide 122), 266 (peptide 123), 267 (peptide 124), 269 (peptide 125), 270 (peptide 126), 268 (peptide 130), 271 (peptide 131), 259 (peptide 203B), 264 (peptide 26B), 90, 98, 99, 280, 102, 161, 281, 282, 103, 105, 106, 166, 111, 112, 284, 114, 115, 173, 174, 285, 117, 176, 120, 121, 180, 128, 129, 272, 187, 188, 273, 191, 133, 192, 274, 140, 199, 226, 275, 227, 205, 206, 229, 230, 276, 277, 208, 233, 278, 210, 234, 242, 243, 279, 221, 245, 246, 166, 223, 247, 224 or 248; or (b) a variant sequence, a derivative or a salt of any of the peptides in (a).

Embodiment A2. The composition according to embodiment A1, wherein at least one of the peptides of the peptide combination is a peptide of allergen der p 1 or allergen der f 1 and is selected from:
(a) any of the peptides consisting of an amino acid sequence of SEQ ID NOS:251 (peptide 010), 252 (peptide 011), 253 (peptide 012), 254 (peptide 022), 255 (peptide 025), 9 (peptide 041), 10 (peptide 042), 11 (peptide 043), 12 (peptide 044), 17 (peptide 049), 18 (peptide 050), 20 (peptide 052), 21 (peptide 053), 22 (peptide 054), 23 (peptide 055), 26 (peptide 058), 29 (peptide 061), 42 (peptide 072), 46 (peptide 075), 49 (peptide 078), 52 (peptide 081), 58 (peptide 087), 258 (peptide 122), 266

(peptide 123), 267 (peptide 124), 268 (peptide 130), 259 (peptide 203B), 90, 98, 99, 280, 102, 161, 281, 282, 103, 105, 106, 283, 166, 111, 112, 284, 114, 115, 173, 174, 285, 117, 176, 120, 121, 180, 128, 129, 272, 187, 188, 273, 191, 133, 274, 140 or 199; or (b) a variant sequence, a derivative or a salt of any of the peptides in (a).

Embodiment A3. The composition according to any one of the preceding embodiments A1 to A2, wherein at least one peptide of the peptide combination is a peptide of allergen Der p 2 or allergen Der f 2 and is selected from:
(a) any of the peptides consisting of an amino acid sequence of SEQ ID NOS:249 (peptide 002), 253 (peptide 012), 256 (peptide 031), 238 (peptide 066), 60 (peptide 089), 61 (peptide 090), 62 (peptide 091), 63 (peptide 092), 67 (peptide 096), 70 (peptide 099), 71 (peptide 100), 72 (peptide 101), 73 (peptide 102), 77 (peptide 106), 79 (peptide 108), 81 (peptide 109), 82 (peptide 110), 269 (peptide 125), 270 (peptide 126), 285 (peptide 131), 264 (peptide 26B), 226, 275, 227, 205, 206, 229, 230, 276, 277, 208, 233, 192, 278, 210, 234, 242, 243, 279, 221, 245, 246, 166, 223, 247, 224 or 248; or (b) a variant sequence, a derivative or a salt of any of the peptides in (a).

Embodiment A4. The composition according to any of the preceding embodiments A1 to A3, wherein at least three peptides are independently selected from any of the peptides denoted with the rating "A" as set out in Table 12.

Embodiment A5. The composition according to embodiment A4, wherein at least three peptides are independently selected from:
(a) any of the peptides comprising an amino acid sequence of SEQ ID NOS:249 (peptide 002), 251 (peptide 010), 252 (peptide 011), 253 (peptide 012), 256 (peptide 031), 10 (peptide 042), 11 (peptide 043), 12 (peptide 044), 17 (peptide 049), 18 (peptide 050), 21 (peptide 053), 22 (peptide 054), 26 (peptide 058), 29 (peptide 061), 52 (peptide 081), 58 (peptide 087), 61 (peptide 090), 62 (peptide 091), 67 (peptide 096), 70 (peptide 099), 73 (peptide 102), 81 (peptide 109), 82 (peptide 110), 258 (peptide 122), 266 (peptide 123), 267 (peptide 124), 269 (peptide 125), 270 (peptide 126), 268 (peptide 130), 271 (peptide 131), 259 (peptide 203B), 264 (peptide 26B), 280, 281, 282, 166, 284, 285, 272, 273, 274, 275, 276 or 277; or (b) a variant sequence, a derivative or a salt of any of the peptides in (a).

Embodiment A6. The composition according to any of the preceding embodiments A1 to A5, wherein at least three peptides are selected from any of the "first choice peptides" set out in Table 15.

Embodiment A7. The composition according to embodiment A6, wherein at least three peptides are selected from:
(a) any of the peptides consisting of an amino acid sequence of SEQ ID NOS: 253 (peptide 012), 256 (peptide 031), 270 (peptide 126), 17 (peptide 049), 266 (peptide 123), 18 (peptide 050), 267 (peptide 124), 21 (peptide 053), 22 (peptide 054), 268 (peptide 130), 26 (peptide 058), 52 (peptide 081), 61 (peptide 090), 62 (peptide 091), 67 (peptide 096), 271 (peptide 131), 70 (peptide 099), 269 (peptide 125), 73 (peptide 102), 81 (peptide 109) or 82 (peptide 110); or (b) a variant sequence, a derivative or a salt of any of the peptides in (a).

Embodiment A8. The composition according to any of the preceding embodiments A1 to A7, wherein at least one peptide of the combination consists of an amino acid sequence selected from SEQ ID NOS: 22 (peptide 054) or 268 (peptide 130), or a variant sequence, a derivative or a salt thereof.

Embodiment A9. The composition according to any of the preceding embodiments A1 to A8, wherein at least one peptide of the combination consists of an amino acid sequence selected from any of SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof.

Embodiment A10. The composition according to any of the preceding embodiments A1 to A9, wherein at least one peptide of the combination consists of an amino acid sequence selected from any of SEQ ID NOS:, 7 (peptide 096), 271 (peptide 131), 79 (peptide 108), 256 (peptide 031), 270 (peptide 126), 242 or 279, or a variant sequence, a derivative thereof or a salt thereof.

Embodiment A11. The composition according to any of the preceding embodiments A1 to A10, wherein at least one peptide of the combination consists of an amino acid sequence selected from SEQ ID NOS: 26 (peptide 058), 133, 192, or 274, or a variant sequence, a derivative or a salt thereof.

Embodiment A12. The composition according to any of the preceding embodiments A1 to A11, wherein at least one peptide of the combination consists of an amino acid sequence selected from SEQ ID NOS: 17 (peptide 049), 266 (peptide 123), SEQ ID NO: 46 (peptide 075), SEQ ID NO: 173, 174 or 285, or a variant sequence, a derivative or a salt thereof.

Embodiment A13. The composition according to any of the preceding embodiments A1 to A12, wherein at least one peptide of the combination consists of an amino acid sequence selected from SEQ ID NOS: 12 (peptide 044), 105, 106 or 283, or a variant sequence, a derivative or a salt thereof.

Embodiment A14. The composition according to any of the preceding embodiments A1 to A13, wherein at least one peptide of the combination consists of an amino acid sequence selected from SEQ ID NO: 251 (peptide 010), 252 (peptide 11), 58 (peptide 087), 29 (peptide 061), 140 or 199, or a variant sequence, a derivative or a salt thereof.

Embodiment A15. The composition according to any of the preceding embodiments A1 to A14, wherein at least one peptide of the combination consists of an amino acid sequence selected from any of SEQ ID NOS: 62 (peptide 091) or 208, or a variant sequence, a derivative or a salt thereof.

Embodiment A16. The composition according to any of the preceding embodiments A1 to A15, wherein at least one peptide of the combination consists of an amino acid sequence selected from SEQ ID NOS: 18 (peptide 050), 258 (peptide 122), 267 (peptide 124), 117 or 176, or a variant sequence, a derivative or a salt thereof.

Embodiment A17. The composition according to any of the preceding embodiments A1 to A16, wherein at least one peptide of the combination consists of an amino acid sequence of SEQ ID NO: 9 (peptide 041), 98, 99 or 280, or a variant sequence, a derivative or a salt thereof.

Embodiment A18. The composition according to any of the preceding embodiments A1 to A17, wherein at least one peptide of the combination consists of an amino acid sequence selected from any of SEQ ID NOS: 10 (peptide 042), 259 (HDM203B), 102, 161, 281 or 282, or a variant sequence, a derivative or a salt thereof.

Embodiment A19. The composition according to any of the preceding embodiments A1 to A18, wherein at least one peptide of the combination consists of an amino acid sequence selected from SEQ ID NOS: 11 (peptide 043), SEQ ID NO: 103, 281 or 282, or a variant sequence, a derivative or a salt thereof.

Embodiment A20. The composition according to any of the preceding embodiments A1 to A19, wherein at least one peptide of the combination consists of an amino acid sequence selected from SEQ ID NOS: 42 (peptide 072), 254 (peptide 022) or 166, or a variant sequence, a derivative or a salt thereof.

Embodiment A21. The composition according to any of the preceding embodiments A1 to A20, wherein at least one peptide of the combination consists of an amino acid sequence selected from SEQ ID NOS: 15 (peptide 047), 111, 112 or 284, or a variant sequence, a derivative or a salt thereof.

Embodiment A22. The composition according to any of the preceding embodiments A1 to A21, wherein at least one peptide of the combination consists of an amino acid sequence selected from SEQ ID NOS: 265 (peptide 025), 115, 173 or 285, or a variant sequence, a derivative or a salt thereof.

Embodiment A23. The composition according to any of the preceding embodiments A1 to A22, wherein at least one peptide of the combination consists of an amino acid sequence selected from SEQ ID NOS: 20 (peptide 052) 49 (peptide 078), 121 or 180, or a variant sequence, a derivative or a salt thereof.

Embodiment A24. The composition according to any of the preceding embodiments A1 to A23, wherein one peptide of the combination consists of an amino acid sequence of SEQ ID NO: 21 (peptide 053), or a variant sequence, a derivative or a salt thereof.

Embodiment A25. The composition according to any of the preceding embodiments A1 to A24, wherein at least one peptide of the combination consists of an amino acid sequence selected from SEQ ID NOS: 23 (peptide 055), 52 (peptide 081), 128, 129, 272, 187, 188 or 273, or a variant sequence, a derivative or a salt thereof.

Embodiment A26. The composition according to any of the preceding embodiments A1 to A25, wherein at least one peptide of the combination consists of an amino acid sequence selected from any of SEQ ID NOS: 61 (peptide 090), 73 (peptide 102), 205, 206, 229, 230, 276 or 277, or a variant sequence, a derivative or a salt thereof.

Embodiment A27. The composition according to any of the preceding embodiments A1 to A26, wherein at least one peptide of the combination consists of an amino acid sequence selected from any of SEQ ID NOS: 249 (peptide 002), 206 or 230, or a variant sequence, a derivative or a salt thereof.

Embodiment A28. The composition according to any of the preceding embodiments A1 to A27, wherein at least one peptide of the combination consists of an amino acid sequence selected from any of SEQ ID NOS: 63 (peptide 092), 233, 210, 234 or 278, or a variant sequence, a derivative or a salt thereof.

Embodiment A29. The composition according to any of preceding embodiments A1 to A28, wherein at least one peptide of the combination consists of an amino acid sequence selected from any of SEQ ID NOS: 81 (peptide 109), 221 or 245, or a variant sequence, a derivative or a salt thereof.

Embodiment A30. The composition according to any of embodiments A1 to A29, wherein a first peptide of the combination consists of an amino acid sequence selected from SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; and a second peptide of the combination consists of an amino acid sequence selected from SEQ ID NOS: 26 (peptide 058), 133, 192, or 274, or a variant sequence, a derivative or a salt thereof.

Embodiment A31. The composition according to any of embodiments A1 to A29, wherein a first peptide of the combination consists of an amino acid sequence selected from any of SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; and a second peptide of the combination consists of an amino acid sequence selected from SEQ ID NOS: 12 (peptide 044) 105 or 106, or a variant sequence, a derivative or a salt thereof.

Embodiment A32. The composition according to any of embodiments A1 to A29, wherein a first peptide of the combination consists of an amino acid sequence selected from SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; and a second peptide of the combination consists of an amino acid sequence selected from SEQ ID NOS: 251 (peptide 010), 252 (peptide 011), 58 (peptide 087) 29 (peptide 061), 140 or 199, or a variant sequence, a derivative or a salt thereof.

Embodiment A33. The composition according to embodiment 31, wherein the peptide combination comprises at least three peptides, wherein a first peptide and a second peptide of the combination are selected from any of SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; and a third peptide of the combination consists of an amino acid sequence selected from SEQ ID NOS: 12 (peptide 044) 105, 106 or 283, or a variant sequence, a derivative or a salt thereof (peptides of peptide combination number 13 set out in Table 14).

Embodiment A34. The composition according to embodiment A33, wherein the peptide combination comprises at least three peptides consisting of an amino acid sequence of SEQ ID NOS: 12 (peptide 044), 70 (peptide 099) and 82 (peptide 110), respectively, or a variant sequence, a derivative or a salt thereof. (peptides of peptide combination number 13 set out in Table 14)

Embodiment A35. The composition according to any of embodiments A31 or 32, wherein the peptide combination comprises at least three peptides, wherein a first peptide consists of an amino acid sequence selected from SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; a second peptide consists of an amino acid sequence selected from SEQ ID NOS: 12 (peptide 044) 105, 106 or 283, or a variant sequence, a derivative or a salt thereof; and a third peptide consists of an amino acid sequence selected from SEQ ID NO: 251 (peptide 010), 252 (peptide 11), 58 (peptide 087), 29 (peptide 061), 140 or 199, or a variant sequence, a derivative and a salt thereof (peptides of peptide combination number 16 set out in Table 14).

Embodiment A36. The composition according to embodiment A35, wherein the peptide combination comprises at least three peptides consisting of an amino acid sequence of SEQ ID NOS: 12 (peptide 044), 82 (peptide 110) and 251 (peptide 010), respectively, or a variant sequence, a derivative or a salt thereof (peptides of peptide combination number 16 set out in Table 14).

Embodiment A37. The composition according to embodiment A32, wherein the peptide combination comprises at least four peptides, wherein a first peptide and a second peptide consist of an amino acid sequence selected from SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; a third peptide consists of an amino acid sequence selected from SEQ ID NO: 251 (peptide 010), 252 (peptide 11), 58 (peptide 087), 29 (peptide 061), 140 or 199, or a variant sequence, a derivative or a salt thereof; and a fourth peptide consists of an amino acid sequence selected from SEQ ID NOS: 18 (peptide 050), 258 (peptide 122), 267 (peptide 124), 117 or 176, a variant sequence, a derivative or a salt thereof (peptides of peptide combination number 20 set out in Table 14).

Embodiment A38. The composition according to embodiment A37, wherein the peptide combination comprises at least four peptides consisting of an amino acid sequence of SEQ ID NOS: 18 (peptide 050), 82 (peptide 110), 251 (peptide 010) and 70 (peptide 070), respectively, or a variant sequence, a derivative or a salt thereof (peptides of peptide combination number 20 set out in Table 14).

Embodiment A39. The composition according to any of embodiments A30 to A38, wherein a further peptide of the peptide combination comprises of an amino acid sequence selected from SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof.

Embodiment A40. The composition according to any of embodiments A30 to A39, wherein a further peptide of the peptide combination consists of an amino acid sequence selected from SEQ ID NOS: 22 (peptide 054) or 268 (peptide 130), or a variant sequence, a derivative or a salt thereof.

Embodiment A41. The composition according to any of embodiments A30 to A40, wherein a further peptide of the peptide combination consists of an amino acid sequence selected from SEQ ID NOS:, 7 (peptide 096), 271 (peptide 131), 79 (peptide 108), 256 (peptide 031), 270 (peptide 126), 242 or 279, or a variant sequence, a derivative or a salt thereof.

Embodiment A42. The composition according to any of embodiments A30 to A41, wherein a further peptide of the peptide combination consists of an amino acid sequence selected from SEQ ID NOS: 26 (peptide 058), 133, 192 or 274, or a variant sequence, a derivative or a salt thereof.

Embodiment A43. The composition according to any of embodiments A30 to A42, wherein a further peptide of the peptide combination consists of an amino acid sequence selected from SEQ ID NOS: 17 (peptide 049), 266 (peptide 123), 46 (peptide 075), 173, 174 or 285, or a variant sequence, a derivative or a salt thereof.

Embodiment A44. The composition according to any of embodiments A30 to A43, wherein a further peptide of the peptide combination consists of an amino acid sequence selected from SEQ ID NOS: 12 (peptide 044), 105, 106 or 283, or a variant sequence, a derivative or a salt thereof.

Embodiment A45. The composition according to any of embodiments A30 to A44, wherein a further peptide of the peptide combination consists of an amino acid sequence selected from SEQ ID NO: 251 (peptide 010), 252 (peptide 11), 58 (peptide 087), 30 (peptide 061), 140 or 199, or a variant sequence, a derivative or a salt thereof.

Embodiment A46. The composition according to any of embodiments A30 to A45, wherein a further peptide of the peptide combination consists of an amino acid sequence selected from SEQ ID NOS: 62 (peptide 091) or 208, or a variant sequence, a derivative or a salt thereof.

Embodiment A47. The composition according to any of embodiments A30 to A46, wherein a further peptide of the peptide combination consists of an amino acid sequence selected from SEQ ID NOS: 18 (peptide 050), 258 (peptide 122), 267 (peptide 124), 117 or 176, or a variant sequence, a derivative or a salt thereof.

Embodiment A48. The composition according to any of embodiments A30 to A47, wherein a further peptide of the peptide combination consists of an amino acid sequence selected from SEQ ID NO: 9 (peptide 041), 98, 99 or 280, or a variant sequence thereof, a derivative thereof or a salt thereof.

Embodiment A49. The composition according to any of embodiments A30 to A48, wherein a further peptide of the peptide combination consists of an amino acid sequence selected from SEQ ID NOS: 10 (peptide 042), 259 (HDM203B), 102, 161, 281 or 282, a variant sequence, a derivative or a salt thereof.

Embodiment A50. The composition according to any of embodiments A30 to A49, wherein a further peptide of the peptide combination consists of an amino acid sequence selected from SEQ ID NOS: 11 (peptide 043) or SEQ ID NO: 103, or a variant sequence, a derivative or a salt thereof.

Embodiment A51. The composition according to any of embodiments A30 to A50, wherein a further peptide of the peptide combination consists of an amino acid sequence selected from SEQ ID NOS: 42 (peptide 072), 254 (peptide 022) or 166, or a variant sequence, a derivative or a salt thereof.

Embodiment A52. The composition according to any of embodiments A30 to A51, wherein a further peptide of the peptide combination consists of an amino acid sequence selected from SEQ ID NOS: 15 (peptide 047), 111, 112 or 284, or a variant sequence, a derivative or a salt thereof.

Embodiment A53. The composition according to any of embodiments A30 to A52, wherein a further peptide of the peptide combination consists of an amino acid sequence selected from SEQ ID NOS: 265 (peptide 025), 115, 173 or 285, or a variant sequence, a derivative or a salt thereof.

Embodiment A54. The composition according to any of embodiments A30 to A53, wherein a further peptide of the peptide combination consists of an amino acid sequence selected from SEQ ID NOS: 20 (peptide 052) 49 (peptide 078), 121 or 180, or a variant sequence, a derivative or a salt thereof.

Embodiment A55. The composition according to any of embodiments A30 to A54, wherein a further peptide of the peptide combination consists of an amino acid sequence selected from SEQ ID NO: 21 (peptide 053), or a variant sequence, a derivative or a salt thereof.

Embodiment A56. The composition according to any of embodiments A30 to A55, wherein a further peptide of the peptide combination consists of an amino acid sequence selected from SEQ ID NOS: 23 (peptide 055), 52 (peptide 081), 128, 129, 272, 187, 188 or 273, or a variant sequence, a derivative or a salt thereof.

Embodiment A57. The composition according to any of embodiments A30 to A56, wherein a further peptide of the peptide combination consists of an amino acid sequence selected from SEQ ID NOS: 61 (peptide 090), 73 (peptide 102), 205, 206, 229, 230, 276 or 277, or a variant sequence, a derivative or a salt thereof.

Embodiment A58. The composition according to any of embodiments A30 to A57, wherein a further peptide of the peptide combination consists of an amino acid sequence selected from SEQ ID NOS: 249 (peptide 002), 206 or 230, or a variant sequence, a derivative or a salt thereof.

Embodiment A59. The composition according to any of embodiments A30 to A58, wherein a further peptide of the peptide combination consists of an amino acid sequence selected from SEQ ID NOS: 63 (peptide 092), 233, 210, 234 or 278, or a variant sequence, a derivative or a salt thereof.

Embodiment A60. The composition according to any of embodiments A30 to A59, wherein the peptide combination comprises at least one peptide consisting of an amino acid sequence derived from allergen Der p 4, or a variant sequence, a derivative or a salt thereof; such as a peptide consisting of an amino acid sequence selected from SEQ ID NO: 257 (peptide 117), or a variant sequence, a derivative or a salt thereof.

Embodiment A61. The composition according to any of the preceding embodiments, wherein the peptide combination consists of or comprises the peptides of a peptide combination selected from peptide combination number 3, 4, 5, 6, 7, 9, 10, 11, 12, 13, 14, 15, 16, 18, 19, 20, 23, 24, 25, 17, 17a, 17b, 17c, 17d, 17f and 17p set out in Table 14, wherein the amino acid sequences of said peptides are set out in Table 12, or variant sequences, derivatives or salts thereof.

Embodiment A62. The composition according to any of embodiments A30 or A33 to A61, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 246, 223, 247, 224 or 248, or a variant sequence, a derivative or a salt thereof; a second peptide consists of an amino acid sequence selected from SEQ ID NOS: 26 (peptide 058) 133, 192 or 274, or a variant sequence, a derivative or a salt thereof; a third peptide consists of an amino acid sequence of SEQ ID NO: 9 (peptide 041), 98, 99 or 280, or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence selected from SEQ ID NOS: 81 (peptide 109), 221 or 245 a variant sequence, a derivative or a salt thereof (peptides of peptide combination number 17 set out in Table 14).

Embodiment A63. The composition according to embodiment A62, wherein the peptide combination comprises at least five peptides consisting of an amino acid sequence of SEQ ID NOS: 82 (peptide 110), 26 (peptide 058), 9 (peptide 041), 46 (peptide 075) and 81 (peptide 109), respectively, or a variant sequence, a derivative or a salt thereof (peptide combination number 17 set out in Table 14).

Embodiment A64. The composition according to any of embodiments A30 and A33 to 61, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 26 (peptide 058) 133, 192 or 274, or a variant sequence, a derivative or a salt thereof; a third peptide consists of an amino acid sequence selected from SEQ ID NOS: 22 (peptide 054) or 268 (peptide 130), or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, a variant sequence, a derivative or a salt thereof; and a fifth peptide consists of an amino acid sequence selected from SEQ ID NOS: 81 (peptide 109), 221 or 245, or a variant sequence, a derivative or a salt thereof (peptides of peptide combination number 17a set out in Table 14).

Embodiment A65. The composition according to embodiment A64, wherein the peptide combination comprises at least five peptides consisting of an amino acid sequence of SEQ ID NO: 22 (peptide 054), 26 (peptide 058), 46 (peptide 075), 81 (peptide 109) and 82 (peptide 110), respectively, or a variant sequence, a derivative or a salt thereof (peptides of peptide combination number 17a set out in Table 14).

Embodiment A66. The composition according to any of embodiments A30 and A33 to A61, wherein the peptide combination comprises at least 5 peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 26 (peptide 058) 133, 192 or 274, or a variant sequence, a derivative or a salt thereof; a third peptide consists of an amino acid sequence of SEQ ID NO: 9 (peptide 041), 98, 99 or 280, or a variant sequence, a derivative or a salt thereof; a fourth peptide consists of an amino acid sequence selected from SEQ ID NOS: 23 (peptide 055), 52 (peptide 081), 128, 129, 272, 187, 188 or 273, or a variant sequence, a derivative or a salt thereof; and a fifth peptide consists of an amino acid sequence selected from SEQ ID NOS: 81 (peptide 109), 221 or 245, or a variant sequence, a derivative or a salt thereof (peptides of peptide combination number 17b set out in Table 14).

Embodiment A67. The composition according to embodiment A66, wherein the peptide combination comprises at least five peptides consisting of an amino acid sequence of SEQ ID NO: 9 (peptide 041), 26 (peptide 058), 52 (peptide 081), 81 (peptide 109) and 82 (peptide 110), respectively, or a variant sequence, a derivative or a salt thereof (peptides of peptide combination number 17b set out in Table 14).

Embodiment A68. The composition according to any of embodiments A30 and A33 to A61, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 26 (peptide 058) 133, 192 or 274, or a variant sequence, a derivative or a salt thereof; a third peptide consists of an amino acid sequence of SEQ ID NO: 9 (peptide 041), 98, 99 or 280, or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence of an amino acid sequence selected from SEQ ID NOS: 62 (peptide 091) or 208, or a variant sequence, a derivative or a salt thereof (peptides of peptide combination number 17c set out in Table 14).

Embodiment A69. The composition according to embodiment A68, wherein the peptide combination comprises at least five peptides consisting of an amino acid sequence of SEQ ID NO: 9 (peptide 041), 26 (peptide 058), 46 (peptide 075), 62 (peptide 091) and 82 (peptide 110), respectively, or a variant sequence, a derivative or a salt thereof (peptides of peptide combination number 17c set out in Table 14).

Embodiment A70. The composition according to any of embodiments A30 and A33 to A61, wherein the peptide combination comprises at least 5 peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 26 (peptide 058) 133, 192 or 274, or a variant sequence, a derivative or a salt thereof; a third peptide consists of an amino acid sequence selected from SEQ ID NOS: 22 (peptide 054) or 268 (peptide 130), or a variant sequence, a derivative or a salt thereof; a fourth peptide consists of an amino acid sequence selected from SEQ ID NOS: 23 (peptide 055), 52 (peptide 081), 128, 129, 272, 187, 188 or 273, or a variant sequence, a derivative or a salt thereof; and a fifth peptide consists of an amino acid sequence selected from SEQ ID NOS: 62 (peptide 091) or 208, or a variant sequence, a derivative or a salt thereof (peptides of peptide combination number 17d set out in Table 14).

Embodiment A71. The composition according to embodiment A70, wherein the peptide combination comprises at least five peptides consisting of an amino acid sequence of SEQ ID NO: 22 (peptide 054), 26 (peptide 058), 52 (peptide 081), SEQ ID NO: 62 (peptide 091) and SEQ ID NO: 82 (peptide 110), respectively, or a variant sequence, a derivative or a salt thereof. (peptides of peptide combination number 17d set out in Table 14).

Embodiment A72. The composition according to any of embodiments A30 and A33 to A61, wherein the peptide combination comprises at least 5 peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 26 (peptide 058) 133, 192 or 274, or a variant sequence, a derivative or a salt thereof; a third peptide consists of an amino acid sequence selected from SEQ ID NOS: 22 (peptide 054) or 268 (peptide 130), or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence selected from SEQ ID NOS: 256 (peptide 031), 7 (peptide 096), 271 (peptide 131), 79 (peptide 108), 270 (peptide 126), 242 or 279, or a variant sequence, a derivative or a salt thereof (peptides of peptide combination number 17f set out in Table 14).

Embodiment A73. The composition according to embodiment A72, wherein the peptide combination comprises at least five peptides consisting of an amino acid sequence of SEQ ID NO: 26 (peptide 058), 46 (peptide 075), 82 (peptide 110), 268 (peptide 130) and 271 (peptide 131), respectively or a variant sequence, a derivative or a salt thereof (peptides of peptide combination number 17f set out in Table 14).

Embodiment A74. The composition according to embodiment 72, wherein the second peptide consisting of an amino acid sequence selected from SEQ ID NOS: 26 (peptide 058) 133, 192 or 274, or a variant sequence, a derivative or a salt thereof is substituted by a peptide consisting of an amino acid sequence selected from SEQ ID NOS: 62 (peptide 091) or 208, or a variant sequence, a derivative or a salt thereof.

Embodiment A75. The composition according to embodiment A74, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 62 (peptide 091) or 208, or a variant sequence, a derivative or a salt thereof; a third peptide consists of an amino acid sequence selected from SEQ ID NOS: 22 (peptide 054) or 268 (peptide 130), or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence selected from SEQ ID NOS: 256 (peptide 031), 7 (peptide096), 271 (peptide 131), 79 (peptide 108), 270 (peptide 126), 242 or 279, or a variant sequence, a derivative or a salt thereof (peptides of peptide combination number 17p set out in Table 14).

Embodiment A76. The composition according to embodiment A75, wherein the peptide combination consists of or comprises the five peptides consisting of an amino acid sequence of SEQ ID NO: 62 (peptide 091), 82 (peptide 110), 266 (peptide 123), 268 (peptide 130) and 271 (peptide 131), respectively, or a variant sequence, a derivative or a salt thereof (peptides of peptide combination number 17p set out in Table 14).

Embodiment A77. The composition according to any of embodiments A31 or A33 to A61, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 12 (peptide 044) 105, 106 or 283, or a variant sequence, a derivative or a salt thereof; a third peptide consists of an amino acid sequence of SEQ ID NO: 71 (peptide 100), 226 or 275, or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence of an amino acid sequence selected from SEQ ID NOS: 62 (peptide 090), 73 (peptide 102), 60 (peptide 089), 205, 206, 229, 230, 276 or 277, or a variant sequence, a derivative or a salt thereof (peptides of peptide combination number 23 set out in Table 14).

Embodiment A78. The composition according to embodiment A77, wherein the peptide combination comprises at least the five peptides consisting of an amino acid sequence of SEQ ID NOS: 82 (peptide 110), 12 (peptide 044), 73 (peptide 102), 46 (peptide 075) and 71 (peptide 100), respectively, or a variant sequence, a derivative or a salt of any thereof (peptide combination number 23 set out in Table 14).

Embodiment A79. The composition according to any of embodiments A31 or A33 to A61, wherein the peptide combination comprises at least five peptides, wherein a first and second peptide consist of an amino acid sequence selected from SEQ ID NOs: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a third peptide consists of an amino acid sequence selected from SEQ ID NOS: 12 (peptide 044) 105, 106 or 283, or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence of SEQ ID NO: 9 (peptide 041), 98, 99 or 280, or a variant sequence, a derivative or a salt thereof (peptides of peptide combination number 18 set out in Table 14).

Embodiment A80. The composition according to embodiment A80, wherein the peptide combination comprises at least the five peptides consisting of an amino acid sequence of SEQ ID NOS: 9 (041), 12 (044), 17 (049), SEQ ID NO: 70 (peptide 099) and 82 (110), respectively, or a variant sequence, a derivative or a salt thereof. (peptides of peptide combination number 18 set out in Table 14).

Embodiment A81. The composition according to any of embodiments A31 or A33 to A61, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 12 (peptide 044) 105, 106 or 283, or a variant sequence, a derivative or a salt thereof; a third peptide consists of an amino acid sequence selected from SEQ ID NOS: 17 (peptide 049), 266 (peptide 123), 46 (peptide 075), 173, 174 or 285, or a variant sequence, a derivative or a salt thereof; a fourth peptide consists of an amino acid sequence selected from SEQ ID NOS:62 (peptide 091) or 208, or a variant sequence, a derivative or a salt thereof; and a fifth peptide consists of an amino acid sequence selected from SEQ ID NOS: 20 (peptide 052), 49 (peptide 078), 121 or 180, or a variant sequence, a derivative or a salt thereof (peptides of peptide combination number 25 set out in Table 14).

Embodiment A82. The composition according to embodiment A83, wherein the peptide combination comprises at least the five peptides consisting of an amino acid sequence of SEQ ID NOS: 82 (peptide 110), 12 (peptide 044), 17 (peptide 049), 62 (peptide 091) and 20 (peptide 052), respectively, or a variant sequence, a derivative or a salt thereof (peptides of peptide combination number 25 set out in Table 14).

Embodiment A83. The composition according to any of embodiments A31 or A33 to A61, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 12 (peptide 044) 105, 106 or 283, or a variant sequence, a derivative or a salt thereof; a third peptide consists of an amino acid sequence selected from SEQ ID NOS: 26 (peptide 058) 133, 192 or 274, or a variant sequence, a derivative or a salt thereof; a fourth peptide consists of an amino acid sequence selected from SEQ ID NOS: 17 (peptide 049), 266 (peptide 123), 46 (peptide 075), 173, 174 or 285, or a variant sequence, a derivative or a salt thereof; and a fifth peptide consists of an amino acid sequence selected from SEQ ID NOS: 61 (peptide 090), 73 (peptide 102), 60 (peptide 089), 205, 206, 229, 230, 276 or 277, or a variant sequence, a derivative or a salt thereof (peptides of peptide combination number 10 set out in Table 14).

Embodiment A84. The composition according to embodiment A84, wherein the peptide combination comprises at least five peptides consisting of an amino acid sequence of SEQ ID NOS: 70 (peptide 099), 12 (peptide 044): 26 (peptide 058), 46 (peptide 075), and 60 (peptide 089), respectively, or a variant sequence, a derivative or a salt thereof (peptides of peptide combination number 10 set out in Table 14).

Embodiment A85. The composition according to any of embodiments A32 and A33 to A61, wherein the peptide combination comprises at least five peptides, wherein a first peptide of the peptide combination consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide of the peptide combination consists of an amino acid sequence selected from SEQ ID NOS: 251 (peptide 010), 252 (peptide 011), 58 (peptide 087) 29 (peptide 061), 140 or 199, or a variant sequence, a derivative or a salt thereof; a third peptide consists of an amino acid sequence selected from SEQ ID NOS: 256 (peptide 031), 7 (peptide 096), 271 (peptide 131), 79 (peptide 108), 270 (peptide 126), 242 or 279, or a variant sequence, a derivative or a salt thereof; a fourth peptide consists of an amino acid sequence of SEQ ID NO: 257 (peptide 117) or a variant sequence, a derivative or a salt thereof; and a fifth peptide consists of an amino acid sequence selected from SEQ ID NOS: 18 (peptide 050), 258 (peptide 122), 267 (peptide 124), 117 or 176, or a variant sequence, a derivative or a salt thereof (peptides of peptide combination number 3 set out in Table 14).

Embodiment A86. The composition according to embodiment A87, wherein the peptide combination comprises at least five peptides consisting of an amino acid sequence of SEQ ID NOS: 252 (peptide 011), 253 (peptide 012), 256 (peptide 031), 257 (peptide 117) and 258 (peptide 122), respectively, or a variant sequence, or a derivative or a salt thereof. (peptides of peptide combination number 3 set out in Table 14).

Embodiment A87. The composition according to any of embodiments A32 and A33 to A61, wherein the peptide combination comprises at least five peptides, wherein a first peptide of the peptide combination consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide of the peptide combination consists of an amino acid sequence selected from SEQ ID NOS: 251 (peptide 010), 252 (peptide 011), 58 (peptide 087) 29 (peptide 061), 140 or 199, or a variant sequence, a derivative or a salt thereof; a third peptide consists of an amino acid sequence selected from SEQ ID NOS: 256 (peptide 031), 7 (peptide 096), 271 (peptide 131), 79 (peptide 108), 270 (peptide 126), 242 or 279, or a variant sequence, a derivative or a salt thereof; a fourth peptide consists of an amino acid sequence selected from SEQ ID NOS: 42 (peptide 072), 254 (peptide 022) or 166, or a variant sequence, a derivative or a salt thereof; and a fifth peptide consists of an amino acid sequence selected from SEQ ID NOS: 18 (peptide 050), 258 (peptide 122), 267 (peptide 124), 117 or 176, or a variant sequence, a derivative or a salt thereof (peptides of peptide combination number 5 set out in Table 14).

Embodiment A88. The composition according to embodiment A88, wherein the peptide combination comprises at least five peptides consisting of an amino acid sequence of SEQ ID NOS: 252 (peptide 011), 253 (peptide 012), 254 (peptide 022), 256 (peptide 031) and 258 (peptide 122), respectively, or a variant sequence, a derivative or a salt thereof. (peptides of peptide combination number 5 set out in Table 14)

Embodiment A89. The composition according to embodiment A88, wherein the peptide combination comprises at least five peptides consisting of an amino acid sequence of SEQ ID NOS: 251 (peptide 010), 253 (peptide 012), 254 (peptide 022), 256 (peptide 031) and SEQ ID NO: 258 (peptide 122), respectively, or a variant sequence, a derivative or a salt thereof. (peptides of peptide combination number 9 set out in Table 14)

Embodiment A90. The composition according to any of embodiments A32 and A33 to A63, wherein the peptide combination comprises at least five peptides, wherein a first and a second peptide consist of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a third peptide consists of an amino acid sequence selected from SEQ ID NOS: 251 (peptide 010), 252 (peptide 011), 58 (peptide 087) 29 (peptide 061), 140 or 199, or a variant sequence, a derivative or a salt thereof; a third peptide consists of an amino acid sequence selected from SEQ ID NOS: 256 (peptide 031), 7 (peptide 096), 271 (peptide 131), 79 (peptide 108), 270 (peptide 126), 242 or 279, or a variant sequence, a derivative or a salt thereof; a fourth peptide consists of an amino acid sequence selected of SEQ ID NO: 9 (peptide 041), 98, 99 or 280, or a variant sequence, a derivative or a salt thereof; and a fifth peptide consists of an amino acid sequence selected from SEQ ID NOS: 18 (peptide 050), 258 (peptide 122), 267 (peptide 124), 117 or 176, or a variant sequence, a derivative or a salt thereof (peptides of peptide combination number 19 set out in Table 14).

Embodiment A91. The composition according to embodiment A91, wherein the peptide combination comprises at least five peptides consisting of an amino acid sequence of SEQ ID NOS: 251 (peptide 010), 9 (peptide 041), SEQ ID NO: 18 (peptide 050), SEQ ID NO: 70 (peptide 099) and SEQ ID NO: 82 (peptide 110), respectively, (peptides of a peptide combination number 19 set out in Table 14), or a variant sequence, a derivative or a salt thereof.

Embodiment A92. The composition according to any of embodiments A1 to A29, wherein the peptide combination comprises at least five peptides, wherein a first peptide consists of an amino acid sequence selected from SEQ ID NOS: 12 (peptide 044) 105, 106 or 283, or a variant sequence, a derivative or a salt thereof; a second peptide consists of an amino acid sequence selected from SEQ ID NOS: 20 (peptide 052) 49 (peptide 078), 121 or 180, or a variant sequence, a derivative or a salt thereof; a third peptide consists of an amino acid sequence of SEQ ID NOS: 71 (peptide 100), 226 or 275, or a variant sequence, a derivative or a salt thereof; a fourth peptide consists of an amino acid sequence selected from any of SEQ ID NOS: 18 (peptide 050), 258 (peptide 122), 267 (peptide 124), 117 or 176, or a variant sequence, a derivative or a salt thereof; and a fifth peptide consists of an amino acid sequence selected from SEQ ID NOS: 61 (peptide 090), 73 (peptide 102), 60 (peptide 089), 205, 206, 229, 230, 276 or 277, or a variant sequence, a derivative or a salt thereof (peptides of peptide combination number 24 set out in Table 14).

Embodiment A93. The composition according to embodiment A93, wherein the peptide combination consists of or comprises the five following peptides consisting of an amino acid sequence of SEQ ID NO: 12 (peptide 044), 18 (peptide 050), 49 (peptide 078), 71 (peptide 100) and 73 (peptide 102), respectively, or a variant sequence, a derivative or a salt thereof. (peptides of peptide combination number 24 set out in Table 14)

Embodiment A94. The composition according to any of embodiments A1 to A29, wherein the peptide combination comprises at least five peptides, wherein a first peptide consists of an amino acid sequence selected from SEQ ID NOS: 70 (peptide 099), 269 (peptide 125), 82 (peptide 110), 264 (peptide 26B), 253 (peptide 012), 166, 246, 223, 247, 224 or 248, or a variant sequence, a derivative or a salt thereof; a second peptide consists of an amino acid sequence selected from SEQ ID NOS: 249 (peptide 002), 206 or 230, or a variant sequence, a derivative or a salt thereof; a third peptide consists of an amino acid sequence of SEQ ID NOS: 42 (peptide 072), 254 (peptide 022) or 166, or a variant sequence, a derivative or a salt thereof; a fourth peptide consists of an amino acid sequence selected from any of SEQ ID NOS: 18 (peptide 050), 258 (peptide 122), 267 (peptide 124), 117 or 176, or a variant sequence, a derivative or a salt thereof; and a fifth peptide consists of amino acid sequence 257 (peptide 117), a variant sequence, a derivative or a salt thereof (peptides of peptide combination number 4 set out in Table 14).

Embodiment A95. The composition according to embodiment A95, wherein the peptide combination consists of or comprises the five following peptides consisting of an amino acid sequence of SEQ ID NO: 249 (peptide 002), 253 (peptide 12), 254 (peptide 022), 257 (peptide 117) and 258 (peptide 122), respectively, or a variant sequence, a derivative or a salt thereof. (peptides of peptide combination number 4 set out in Table 14).

Embodiment A96. The composition according to any of embodiments A62 to A95, wherein the peptide combination comprises a peptide consisting of an amino sequence of SEQ ID NO: 264 (peptide HDM 203B), 281 or 282, or a variant sequence, a derivative or a salt thereof.

Embodiment A97. The composition according to any of embodiments A62 to A96, wherein the peptide combination comprises a peptide consisting of an amino sequence of SEQ ID NO: 259 (peptide HDM 26B), or a variant sequence, a derivative or a salt thereof.

Embodiment A98. The composition according to any of embodiments A62 to A97, wherein the combination comprises at least one additional peptide independently selected from peptides consisting of an amino acid sequence selected from SEQ ID NOS:249 (peptide 002), 251 (peptide 010), 252 (peptide 011), 253 (peptide 012), 254 (peptide 022), 255 (peptide 025), 256 (peptide 031), 9 (peptide 041), 10 (peptide 042), 11 (peptide 043), 12 (peptide 044), 15 (peptide 047), 17 (peptide 049), 18 (peptide 050), 20 (peptide 052), 21 (peptide 053), 22 (peptide 054), 23 (peptide 055), 26 (peptide 058), 29 (peptide 061), 238 (peptide 066), 42 (peptide 072), 46 (peptide 075), 49 (peptide 078), 52 (peptide 081), 58 (peptide 087), 60 (peptide 089), 61 (peptide 090), 62 (peptide 091), 63 (peptide 092), 67 (peptide 096), 70 (peptide 099), 72 (peptide 101), 73 (peptide 102), 77 (peptide 106), 79 (peptide 108), 81 (peptide 109), 82 (peptide 110), 257 (peptide 117), 258 (peptide 122), 266 (peptide 123), 267 (peptide 124), 269 (peptide 125), 270 (peptide 126), 268 (peptide 130), 271 (peptide 131), 259 (peptide 203B), 264 (peptide 26B), 90, 98, 99, 280, 102, 161, 281, 282, 103, 105, 106, 283, 111, 112, 284, 114, 115, 173, 174, 117, 176, 120, 121, 180, 128, 129, 272, 187, 188, 273, 191, 133, 192, 274, 140, 199, 226, 227, 205, 206, 229, 230, 276, 277, 208, 233, 278, 210, 234, 242, 243, 279, 221, 245, 246, 223, 247, 224 or 248, or a variant sequence, a derivative or a salt thereof.

Embodiment A99. The composition according to any of the preceding embodiments A1 to A99, wherein a peptide consisting of an amino acid sequence set out in Table 12 is replaced by a substitute peptide specified for said peptide in Table 12, or a variant sequence thereof, a derivative thereof or a salt thereof.

Embodiment A100. The composition according to any of the preceding embodiments A1 to A100, wherein the peptide consisting of an amino acid sequence of SEQ ID NO: 17 (peptide 058) is replaced by a substitute peptide consisting of an amino acid sequence selected from SEQ ID NOS: 22 (peptide 054), 255 (peptide 025), 49 (peptide 078), 133, 192 or 274, or a variant sequence thereof, a derivative thereof or a salt thereof.

Embodiment A101. The composition according to any of the preceding embodiments A1 to A101, wherein the peptide consisting of an amino acid sequence of SEQ ID NO: 46 (peptide 075) is replaced by a substitute peptide consisting of an amino acid sequence selected from SEQ ID NOS: 255 (peptide 025), 271, 17 (peptide 049), 20 (peptide 052), 22 (peptide 054), 21 (peptide 053), 49 (peptide 078) or 266 (peptide 123), or a variant sequence thereof a derivative thereof or a salt thereof.

Embodiment A102. The composition according to any of the preceding embodiments A1 to A101, wherein the peptide consisting of an amino acid sequence of SEQ ID NO: 82 (peptide 110) is replaced by a substitute peptide consisting of an amino acid sequence selected from SEQ ID NOS: 253 (peptide 012), 70 (peptide 099), 264 (peptide 26B), 269 (peptide 125), 224 or 248, or a variant sequence thereof, a derivative thereof or a salt thereof.

Embodiment A103. The composition according to any of the preceding embodiments A1 to A102, wherein the peptide consisting of an amino acid sequence of SEQ ID NO: 268 (peptide 130) is replaced by a substitute peptide consisting of an amino acid sequence selected from SEQ ID NOS: 255 (peptide 025), 285, 12 (peptide 044), 283, 22 (peptide 054) or 21 (peptide 053), or a variant sequence thereof, a derivative thereof or a salt thereof.

Embodiment A104. The composition according to any of the preceding embodiments A1 to A103, wherein the peptide consisting of an amino acid sequence of SEQ ID NO: 271 (peptide 131) is replaced by a substitute peptide consisting of an amino acid sequence selected from SEQ ID NOS: 256 (peptide 031), 81 (peptide 109), or 67 (peptide 096) or a variant sequence thereof, a derivative thereof or a salt thereof.

Embodiment A105. The composition according to any of the preceding embodiments A1 to A104, wherein the peptide consisting of an amino acid sequence of SEQ ID NO: 81 (peptide 109) is replaced by a substitute peptide consisting of an amino acid sequence selected from SEQ ID NO: 256 (peptide 031), 67 (peptide 096) or 271 (peptide 131), or a variant sequence thereof, a derivative thereof or a salt thereof.

Embodiment A106. The composition according to any of the preceding embodiments A1 to A105, wherein the peptide consisting of an amino acid sequence of SEQ ID NO: 17 (peptide 049) is replaced by a substitute The composition according to any of the preceding embodiments, wherein the peptide consisting of an amino acid sequence of SEQ ID NO: 46 (peptide 075), 266 (peptide 123) or 174, or a variant sequence thereof, a derivative thereof or a salt thereof.

Embodiment A107. The composition according to any of the preceding embodiments A1 to A106, wherein the peptide consisting of an amino acid sequence of SEQ ID NO: 22 (peptide 054) is replaced by a substitute peptide consisting of an amino acid sequence selected from SEQ ID NOS: 255 (peptide 025), 285, 12 (peptide 044), 283, 21 (peptide 053), 26 (peptide 058), 274, 46 (peptide 075) or 268 (peptide 130), or a variant sequence thereof, a derivative thereof or a salt thereof.

Embodiment A108. The composition according to any of the preceding embodiments A1 to A107, wherein the peptide consisting of an amino acid sequence of SEQ ID NO: 67 (peptide 096) is replaced by a substitute peptide consisting of an amino acid sequence selected from SEQ ID NOS: 256 (peptide 031), 81 (peptide 109) or 271 (peptide 131), or a variant sequence thereof, a derivative thereof or a salt thereof.

Embodiment A109. The composition according to any of the preceding embodiments A1 to A108, wherein the peptide consisting of an amino acid sequence of SEQ ID NO: 12 (peptide 044) is replaced by a substitute peptide consisting of an amino acid sequence selected from SEQ ID NOS: 22 (peptide 054), 268 (peptide 130) or 283, or a variant sequence thereof, a derivative thereof or a salt thereof.

Embodiment A110. The composition according to any of the preceding embodiments A1 to A109, wherein the peptide consisting of an amino acid sequence of SEQ ID NO: 15 (peptide 050) is replaced by a substitute peptide consisting of an amino acid sequence selected from SEQ ID NOS: 254 (peptide 022), 26 (peptide 058), 274, 52 (peptide 081), 258 (peptide 122) or 267 (peptide 124), or a variant sequence thereof, a derivative thereof or a salt thereof.

Embodiment A111. The composition according to any of the preceding embodiments A1 to A110, wherein the peptide consisting of an amino acid sequence of SEQ ID NO: 256 (peptide 031) is replaced by a substitute peptide consisting of an amino acid sequence selected from SEQ ID NOS: 81 (peptide 109), 271 (peptide 131), 67 (peptide 096) or 270 (peptide 126), or a variant sequence thereof, a derivative thereof or a salt thereof.

Embodiment A112. The composition according to any of the preceding embodiments A1 to A111, wherein the peptide consisting of an amino acid sequence of SEQ ID NO: 251 (peptide 010) is replaced by a substitute peptide consisting of an amino acid sequence selected from SEQ ID NOS: 252 (peptide 011), 58 (peptide 087) or 29 (peptide 061), or a variant sequence thereof, a derivative thereof or a salt thereof.

Embodiment A113. The composition according to any of the preceding embodiments A1 to A112, wherein the peptide consisting of an amino acid sequence of SEQ ID NO: 258 (peptide 122) is replaced by a substitute peptide consisting of an amino acid sequence selected from SEQ ID NOS: 18 (peptide 050), 52 (peptide 081) or 267 (peptide 124), or a variant sequence thereof, a derivative thereof or a salt thereof.

Embodiment A114. The composition according to any of the preceding embodiments A1 to A113, wherein the peptide consisting of an amino acid sequence of SEQ ID NO: 253 (peptide 012) is replaced by a substitute peptide consisting of an amino acid sequence selected from SEQ ID NOS: 256 (peptide 031), 70 (peptide 099), 81 (peptide 109), 82 (peptide 110) or 269 (peptide 125), or a variant sequence thereof, a derivative thereof or a salt thereof.

Embodiment A115. The composition according to any of the preceding embodiments A1 to A114, wherein the peptide consisting of an amino acid sequence of SEQ ID NO: 73 (peptide 102) is replaced by a substitute peptide consisting of an amino acid sequence selected from SEQ ID NOS: 249 (peptide 002), 60 (peptide 089), 61 (peptide 090), 276, 277 or 82 (peptide 110), or a variant sequence thereof, a derivative thereof or a salt thereof.

Embodiment A116. The composition according to any of the preceding embodiments A1 to A115, wherein the peptide consisting of an amino acid sequence of SEQ ID NO: 70 (peptide 099) is replaced by a substitute peptide consisting of an amino acid sequence selected from SEQ ID NOS: 253 (peptide 012), 264 (peptide 26B), 82 (peptide 110) or 269 (peptide 125), or a variant sequence thereof, a derivative thereof or a salt thereof.

Embodiment A117. The composition according to any of the preceding embodiments A1 to A116, wherein the peptide consisting of an amino acid sequence of SEQ ID NO: 52 (peptide 081) is replaced by a substitute peptide consisting of an amino acid sequence selected from SEQ ID NOS: 250 (peptide 009), 254 (peptide 022), 10 (peptide 042), 18 (peptide 050), 258 (peptide 122), 23 (peptide 055), 128, 129, 272, 187, 188 or 273, or a variant sequence thereof, a derivative thereof or a salt thereof.

Embodiment A118. The composition according to any of the preceding embodiments A1 to A117, wherein the peptide combination comprises at least one peptide consisting of an amino acid sequence derived from allergen Der p 1, or a variant sequence thereof, a derivative thereof or a salt thereof.

Embodiment A119. The composition according to any of the preceding embodiments A1 to A118, wherein the peptide combination comprises at least one peptide consisting of an amino acid sequence derived allergen Der p 2, or a variant sequence thereof, a derivative thereof or a salt thereof.

Embodiment A120. The composition according to any of the preceding embodiments A1 to A119, wherein the peptide combination comprises at least one peptide consisting of an amino acid sequence derived from allergen Der f 1, or a variant sequence thereof, a derivative thereof or a salt thereof.

Embodiment A121. The composition according to any of the preceding embodiments A1 to A120, wherein the peptide combination comprises at least one peptide consisting of an amino acid sequence derived from allergen Der f 2, or a variant sequence thereof, a derivative thereof or a salt thereof.

Embodiment A122. The composition according to any of embodiments A119 to A122, wherein the peptide combination comprises at least one peptide derived from each of the allergens Der p 1 and Der p 2.

Embodiment A123. The composition according to any of embodiments A119 to A122, wherein the peptide combination comprises at least one peptide derived from each of the allergens Der p 1 and Der f 2.

Embodiment A124. The composition according to any of embodiments A119 to A122, wherein the peptide combination comprises at least one peptide derived from each of the allergens Der p 1, Der p 2, Der f 1 and Der f 2.

Embodiment A125. The composition according to any of the preceding embodiments A1 to A124, wherein the allergens Der p 1, Der p 2, Der f 1 and Der f 2, respectively, consist of the amino acid sequences set out in Table 1.

Embodiment A126. The composition according to any of the preceding embodiments A1 to A125, wherein the peptide combination comprises 3, 4, 5, 6, 7, 8, 9 or 10 or more peptides, preferably no more than 5, 6 or 7 peptides.

Embodiment A127. The composition according to any of the preceding embodiments A1 to A126, wherein a variant sequence thereof comprises additional amino acid residues at the N- and/or C-terminal end.

Embodiment A128. The composition according to embodiment A127, wherein the additional amino acids are selected from amino acids flanking the N- and/or C-terminal ends when the peptide is aligned with the allergen it is present in, based upon or derived from.

Embodiment A129. The composition according to embodiment A128, wherein the allergen is selected from an allergen set out in Table 1, for example the allergens Derp1.0105 or an isoform thereof, Derf1.0101 or an isoform thereof, Derp2.0101 or an isoform thereof, Derf2.0103 or an isoform thereof.

Embodiment A130. The composition according to any of the preceding embodiments A1 to A129, wherein the variant sequence of a peptide is a longer peptide of up to 60 amino acids in length, which longer peptide comprises an amino acid sequence having at least 65% identity or homology over the length of the amino acid sequence of the peptide Embodiment A131. The composition according to any of the preceding embodiments A1 to A130, wherein the variant sequence of peptide is a longer peptide of up to 60, 55, 50, 45, 40, 35, 30, 28, 25, 24, or 22 amino acids in length, which longer peptide comprises an amino acid sequence having at least 65%, 70%, 75%, 80%, 85%, 90%, 95% identity or homology over the length of the amino acid sequence of the peptide.

Embodiment A132. The composition according to any of the embodiments A131 and A132, wherein the variant sequence of a peptide is a longer peptide of up to 30 amino acids in length, which longer peptide comprises an amino acid sequence having at least 80% identity or homology over the length of the amino acid sequence of the peptide.

Embodiment A133. The composition according to any of the preceding embodiments A1 to A132, wherein the variant sequence of a peptide is a fragment of the peptide comprising at least 15 amino acids in length, which fragment has at least 65% identity or homology over the length of the fragment when aligned with the peptide.

Embodiment A134. The composition according to any of the preceding embodiments A1 to A133, wherein the variant sequence is a fragment of the peptide comprising at least 15, such as at least 16, 17 or 18, amino acids in length with at least 65%, such as at least 70%, 75%, 80%, 85%, 90%, 95%, identity or homology over the length of the fragment when aligned with the peptide.

Embodiment A135. The composition according to any of embodiments A134 and A135, wherein the fragment consist of or comprises an amino sequence selected from SEQ ID NOS: 90, 102, 161, 103, 105, 106, 111, 114, 115, 173, 174, 117, 176, 120, 121, 180, 128, 187, 188, 191, 133, 192, 199, 226, 227, 205, 229, 206, 230, 208, 233, 210, 234, 242, 243, 221, 245, 246, 283, 223, 247, 224, 248, or a variant sequence, a derivative or a salt thereof.

Embodiment A136. The composition according to any of the preceding embodiments A1 to A135, wherein the variant sequence thereof has at least 65% identity or homology over at least 15 contiguous amino acids of the peptide.

Embodiment A137. The composition according to any of the preceding embodiments A1 to A136, wherein the variant sequence thereof has at least 65%, such as at least 70%, 75%, 80%, 85%, 90%, 95% identity or homology over at least 15, such as over at least 16, 17, 18, 19, 20 contiguous amino acids of the peptide.

Embodiment A138. The composition according to any of the preceding embodiments A1 to A137, wherein a variant sequence thereof comprises a glutamate residue present at the N-terminus of a peptide replaced with pyroglutamate.

Embodiment A139. The composition according to any of the preceding embodiments A1 to A138, wherein a variant sequence thereof comprises the addition of one or more lysine amino residue(s) or arginine amino acid residue(s) at the N- or C-terminus of the peptide.

Embodiment A140. The composition according to any one of the preceding embodiments A1 to A139, wherein a variant sequence thereof comprises one or more modifications selected from the following: (a) any cysteine residues in the native sequence of the peptide are replaced with serine or 2-aminobutyric acid; (b) hydrophobic residues in the up to three amino acids at the N or C terminus of the native sequence of the peptide are deleted; (c) any two consecutive amino acids comprising the sequence Asp-Gly in the up to four amino acids at the N or C terminus of the native sequence of the peptide are deleted; and/or (d) one or more positively charged residues are added at the N- and/or C-terminus Embodiment A141. The composition according to any one of the preceding embodiments A1 to A140, wherein a derivative thereof comprises one or more modifications selected from the following: (a) N terminal acetylation; (b) C terminal amidation; (c) one or more hydrogens on the side chain amines of Arginine and/or Lysine replaced with a methylene group; (d) glycosylation and/or (e) phosphorylation.

Embodiment A142. The composition according to any one of the preceding embodiments A1 to A141, wherein the salt is a pharmaceutically acceptable and/or a physiologically acceptable salt.

Embodiment A143. The composition according to any one of the preceding embodiments A1 to A142 wherein the salt is an acid addition salt with an inorganic acid, acid addition salt with an organic acid, salt with a basic inorganic acid, salt with a basis organic acid, salt with an acidic or basic amino acid or a mixture thereof, Embodiment A144. The composition according to embodiment A144, wherein an acid addition salt with an inorganic acid is selected from salts with hydrochloric acid, hydrobromic acid, nitric acid, sulfuric acid, phosphoric acid, or the like.

Embodiment A145. The composition according to embodiment A144, wherein an acid salt with an organic acids is selected from salts with formic acid, acetic acid, trifluoroacetic acid, fumaric acid, oxalic acid, tartaric acid, maleic acid, succinic acid, malic acid, methanesulfonic acid, benzenesulfonic acid, p-toluenesulfonic acid, or the like.

Embodiment A146. The composition according to embodiment A144, wherein a salt with an inorganic base is selected from a salt of an alkali metal salts such as sodium salts and potassium salts; alkali earth metal salts such as calcium salts and magnesium salts; and aluminum salts and ammonium salts;

Embodiment A147. The composition according to embodiment A144, wherein a salt with a basic organic bases is selected from any salt with trimethylamine, triethylamine, pyridine, picoline, ethanolamine, diethanolamine, triethanolamine, dicyclohexylamine, N,N-dibenzylethylenediamine, caffeine, piperidine, and pyridine;

Embodiment A148. The composition according to embodiment A144, wherein a salt with a basic amino acid is selected from any salt with arginine, lysine, ornithine, or the like;

Embodiment A149. The composition according to embodiment A144, wherein a salt with an acidic amino acid is selected from any salt with aspartic acid, glutamic acid, or the like.

Embodiment A150. The composition according to embodiment A144, wherein a salt thereof is an acetate salt.

Embodiment A151. The composition according to any one of the preceding embodiments A1 to A150, wherein the peptides are synthetically made.

Embodiment A152. The composition according to any one of the preceding embodiments A1 to A151, wherein the peptides are freeze-dried.

Embodiment A153. The composition according to any one of the preceding embodiments A1 to A152, wherein each peptide is present in equimolar concentrations or in substantially equimolar concentrations.

Embodiment A154. The composition according to any one of the preceding embodiments A1 to A153, wherein each peptide is present in a molar concentration 1 to 1000 µM, for example in the range of 10 to 800 µM, for example in the range of 20 to 500 µM, for example in the range of 20 to 300 µM.

Embodiment A155. A pharmaceutical composition comprising a composition according to any of embodiments A1 to A154.

Embodiment A156. The pharmaceutical composition according to embodiment A155, further comprising a pharmaceutically acceptable carrier, excipient and/or adjuvant, optionally sterile.

Embodiment A157. The pharmaceutical composition according to any of embodiments A155 and A156 formulated as a vaccine, optionally sterile.

Embodiment A158. The pharmaceutical composition according to any of embodiments A155 to A157, wherein the pharmaceutical composition is a powder, for example in freeze-dried form, optionally sterile.

Embodiment A159. The pharmaceutical composition according to any of embodiments A155 to A158, wherein the composition is adapted to be re-dissolved before use, for example in an aqueous, optionally sterile, solution, for example a solution having a pH in the range of 3 to 9, such as pH of 3 to 8, such as pH of 4 to 8.

Embodiment A160. The pharmaceutical composition according to any of embodiments A155 to A159, wherein the composition comprises saline, optionally sterile, and optionally further comprising a pH controlling or buffering agent, a wetting agent, a dispersant, a thickener or a preservative or anti-microbial agent.

Embodiment A161. A kit comprising a compartment and instructions, wherein the compartment comprises one or more of the compositions of any one of embodiments A1 to A160 and wherein the instructions are for use in treating allergy to dust mites, such as house dust mites.

Embodiment A162. The kit of embodiment A161, wherein the kit further comprises packaging material comprising corrugated fiber, glass, plastic, foil, ampules, vials, blister pack, preloaded syringes or tubes, optionally that maintains sterility of the components.

Embodiment A163. The kit of embodiment A161 or A162, wherein the kit further comprises labels or inserts comprising printed matter or computer readable medium optionally including identifying components, dose amounts, clinical pharmacology, instructions for the clinician or for a subject using one or more of the kit components, prophylactic or therapeutic benefits, adverse side effects or manufacturer information.

Embodiment A164. A method for treating allergy to dust mites, such as house dust mites, in a subject in need thereof, comprising administering a therapeutically sufficient amount of a composition according to any of embodiments A1 to A160.

Embodiment A165. A composition according to any of embodiments A1 to A160 for use in the treatment of allergy to dust mites, such as house dust mites in a subject in need thereof.

Embodiment A166. Use of a composition according to any of embodiments A1 to A160 for the preparation of a medicament for the treatment of allergy to dust mites, such as house dust mites, in a subject in need thereof.

Embodiment A167. The method and uses according to any of embodiments A164 to A166, wherein the treatment of allergy to dust mite, such as to a house dust mite, is by immunotherapy.

Embodiment A168. The method and uses according to any of embodiments A164-A167, wherein the house dust mite allergy is clinically presented as atopic dermatitis, urticaria, contact dermatitis, allergic conjunctivitis, allergic rhinitis, allergic asthma, anapylaxis, and/or hay fever.

Embodiment A169. The method and uses according to embodiments any of A164-A167, wherein the method or use decreases, reduces, suppresses or inhibits atopic dermatitis, urticaria, contact dermatitis, allergic conjunctivitis, allergic rhinitis, allergic asthma, anaphylaxis, and/or hay fever.

Embodiment A170. The method and uses according to any of embodiments A164-A167, wherein the method or use comprises modulating, decreasing, reducing, suppressing or inhibiting a T cell or antibody response.

Embodiment A171. The method and uses according to embodiment A170, wherein the T cell response is an IL-2, IL-3, IL-4, IL-5, IL-6, IL-9, IL-10, IL-12, IL-13, IL17, IL-22, IL-31 or IFN-g response.

Embodiment A172. The method and uses according to any of embodiments A164 to A171, wherein the method or use comprises the repeated administration of the composition (peptide combination).

Embodiment A173. The method and uses according to any of embodiments A164 to A172, wherein the administration is by a route of administration selected from subcutaneous, intradermal, epicutaneous, rectal, topical, sublingual, oral, buccal, intranasal, respiratory and intralymphatic route.

Embodiment A174. The method and uses according to any of embodiments A164 to A173, wherein the subject in need thereof is a human, a pet such as a dog or a cat or a domestic animal such as a horse.

Embodiment A175. The method and uses according to any of embodiments A164 to A174, wherein the house dust mite is of the genus *Dermatophagoides*, such as of the species *Dermatophagoides farinae* and/or *Dermatophagoides pteronyssinus*.

Embodiment A176. The method and uses according to any of embodiments A164 to A175, wherein the treatment of allergy to a dust mite is for the treatment of allergy to a dust mite allergen, such as to a house dust mite allergen, for example allergens Der p 1, Der p 2, Der f 1 and/or Der f 2, or another allergen of the genus *Dermatophagoides* (e.g. Der p 4) or another allergen of the species *Dermatophagoides farinae* and/or *Dermatophagoides pteronyssinus*.

Embodiment A177. The method and uses according to any of embodiments A164 to A176, wherein the subject in need thereof has specific IgE antibodies against Der p 1, Der p 2, Der f 1 and/or Der f 2.

Embodiment A178. The method and uses according to any of embodiments A164 to A177, wherein the subject in need thereof has a T cell response to the composition, such as to the peptide combination or single peptides thereof.

Embodiment A179. The method and uses according to any of embodiments A164 to A178, wherein a single dose of each single peptide of the composition is in the range of 1 to 1000 nanomole, for example in the range of 1 to 500 nanomole, for example in the range of 5 to 250 nanomole.

Embodiment A180. The method and uses according to any of embodiments A164 to A179, wherein an amount of about 50 to 150 microliter is administered, such as by intradermal administration.

Embodiment A181. An in vitro method of determining whether T cells of a subject in need of treatment recognize a composition as defined in any one of embodiments A1 to A160 comprising contacting said T cells obtained from the subject in need thereof with said peptide combination or single peptides thereof and detecting whether said T cells are stimulated by said peptide.

Embodiment A182. The method according to embodiment A181, which is carried out to determine whether a subject has, or is at risk of developing, an allergy to dust mite allergy.

Embodiment A183. The method and uses according to any of the preceding embodiments A1 to A182, wherein a T cell is a helper T cell, such as a Th2 cell.

LIST OF REFERENCES

Altschul, S. F., Gish, W., Miller, W., Myers, E. W. & Lipman D. J. Basic local alignment search tool, J. Mol. Biol. 215, 403-410, 1990

Bostick D, Vaisman II. A new topological method to measure protein structure similarity. Biochem Biophys Res Commun. 304, 320-325, 2003.

Bui H, Sidney J, Dinh K, Southwood S, Newman M J, Sette A (2006) Predicting population coverage of T-cell epitope-based diagnostics and vaccines. BMC Bioinformatics 7:153

Greenbaum 3, Sidney 3, Chung J, Brander C, Peters B, Sette A. Functional classification of class II human leukocyte antigen (HLA) molecules reveals seven different supertypes and a surprising degree of repertoire sharing across supertypes. Immunogenetics, 63, 325-335, 2011.

Henmar H et al, 2008: Henmar H, Lund G, Lund L, Petersen A, Würtzen P A. Allergenicity, immunogenicity and dose-relationship of three intact allergen vaccines and four allergoid vaccines for subcutaneous grass pollen immunotherapy. Clin Exp Immunol. 153β):316-23, 2008

Mackenzie K J, Fitch P M, Leech M D, Ilchmann A, Wilson C, McFarlane A J, Howie S E, Anderton S M, Schwarze J. Combination peptide immunotherapy based on T-cell epitope mapping reduces allergen-specific IgE and eosinophilia in allergic airway inflammation. Immunology, 138β), 258-268, 2013.

McKinney D M, Southwood S, Hinz D, Oseroff C, Arlehamn C S, Schulten V, et al. A strategy to determine HLA class II restriction broadly covering the D R, D P, and D Q allelic variants most commonly expressed in the general population. Immunogenetics; 65:357-70, 2013.

Middleton D, Menchaca L, Rood H, Komerofsky R. New allele frequency database: found at the website located at www.ailfrequencies.net. Tissue antigens 2003; 61:403-7.

Meyer D, Singe R, Mack S, Lancaster A, Nelson M, Erlich H, Frenandez-Vina M, Thomson G. Single Locus Polymorphism of Classical HLA Genes. Immunobiology of the Human MHC: Proceedings of the 13th International Histocompatibility Workshop and Conference; Seattle, Wash. pp. 653-704, 2007.

Moldaver and Larche. Immunotherapy with peptides. Allergy 66(6), 784-791, 2011.

Murugan and Dai. Prediction of MHC class II binding peptides based on an iterative learning model. Immunome Research 1:6, 2005.

Karosiene, Edita, Michael Rasmussen, Thomas Blicher, Ole Lund, Søren Buus, and Morten Nielsen. "NetMHCIIpan-3.0, a Common Pan-specific MHC Class II Prediction Method Including All Three Human MHC Class II Isotypes, HLA-DR, HLA-DP and HLA-DQ." Immunogenetics Needleman S B, Wunsch C D. A general method applicable to the search for similarities in the amino acid sequence of two proteins, J. Mol. Biol. 48:443, 1970.

Nielsen, Morten, Sune Justesen, Ole Lund, Claus Lundegaard, and Soren Buus. "NetMHCIIpan-2.0-Improved Pan-specific HLA-DR Predictions Using a Novel Concurrent Alignment and Weight Optimization Training Procedure." Immunome research 6, no. 1 doi:10.1186/1745-7580-6-9, 2010, Nielsen, Morten, and Ole Lund. "NN-align. An Artificial Neural Network-based Alignment Algorithm for MHC Class II Peptide Binding Prediction." BMC bioinformatics 10. doi:10.1186/1471-2105-10-296, 2009.

Pearson and Lipman, 1988: Pearson W R, Lipman D J. Improved tools for biological sequence comparison, Proc. Natl. Acad. Sci. USA 85(8): 2444-2448, 1988.

Pearson W R1, Flexible sequence similarity searching with the FASTA3 program package, Methods Mol Biol. 132, 185-219, 2000.

Sidney J, Southwood S, Oseroff C, del Guercio M F, Sette A, Grey H M. Measurement of MHC/peptide interactions by gel filtration. Curr Protoc Immunol. Chapter 18(Unit 18):13. doi: 10.1002/0471142735. im1803s31, 2001

Sidney J, Assarsson E, Moore C, Ngo S, Pinilla C, Sette A, Peters B. Quantitative peptide binding motifs for 19 human and mouse MHC class I molecules derived using positional scanning combinatorial peptide libraries. Immunome Res. 4:2, doi: 10.1186/1745-7580-4-2, 2008

Sidney J, Steen A, Moore C, Ngo S, Chung J, Peters B, Sette A. Divergent motifs but overlapping binding repertoires of six HLA-D Q molecules frequently expressed in the worldwide human population. J Immunol, 185(7), 4189-4198, 2010a.

Sidney J, Steen A, Moore C, Ngo S, Chung J, Peters B, Sette A. Five HLA-D P molecules frequently expressed in the worldwide human population share a common HLA supertypic binding specificity. 3 Immunol, 184(5), 2492-2503, 2010b.

Sidney J, Southwood S, Grey H M, Moore C, Oseroff C, Pinilla C, Sette A. Measurement of MHC/peptide interactions by gel filtration or monoclonal antibody capture.

Current protocols in immunology/edited by John E. Coligan et al, Chapter 18( ):Unit 18.3, 2013.

Smith and Waterman 1981: Smith and Waterman. Comparison of biosequences, Adv. Appl. Math 2: 482, 1981.

Smith et al. J. Mol. Biol. 147:195, 1981.

EXAMPLES

Example 1

House Dust Mite Peptide Library

This example includes a description of the peptide library used to map T-cell epitopes of major house dust mite allergens.

A complete set of overlapping 20mer peptides deriving from the full length amino acid sequences of allergens proDer p 1, proDer f 1, Der p 2 and Der f 2, were purchased from Thermo Scientific Custom Biopolymers, Germany having a purity of >95%. For the present study the following isoforms of the allergens were used for peptide design: Der p 1.0105 (variant of UniProt number P08176), Der f 1.0101 (UniProt number Q58A71), Der p 2.0101 (UniProt number P49278) and Der f 2.0103 (variant of UniProt number Q00855). These isoforms were confirmed to be abundant isoforms in house dust mite extracts by mass spectrometry (LC-MS/MS), but alternatively other isoforms of these allergens could have been used (see www.allergen.org for a complete and updated list of isoforms). Examples of isoforms of Der p 1, Der f 1, Der p 2 and Der f 2 are shown in Table 1. To avoid dimerization and polymerization of peptides by intra- and intermolecular disulfide bond formation between cysteine residues, this amino acid was consistently substituted by a serine residue in the set of overlapping 20mer peptides. The set of 20mer peptides is shown in Tables 2 and 3.

A complete set of overlapping 15mer peptides deriving from the same isoforms of proDer p 1, proDer f 1, Der p 2 and Der f 2 was purchased from A and A (San Diego, Calif.) as crude material on a small (1 mg) scale. Cysteine residues were not substituted by a serine in the set of 15mers peptide library. The set of 15mer peptides is shown in Tables 4 and 5.

Additional peptides were added to the peptide library by selecting house dust mite allergen group 1 or group 2 peptides previously shown in the art to induce T cell activation in house dust mite allergic donor population. The additional peptides were selected based on their broad HLA Class II allele coverage. Table 6 shows ten additional peptides (SEQ ID NOs: 249-258) together with 7 peptides (SEQ ID NOs: 259-265) previously suggested for a peptide combination for treating house dust mite allergy (International patent application WO2009 022156).

TABLE 1

Sequences of isoforms of house dust mite allergens Der p 1, Der f 1, Der p 2 and Der f 2.

| SEQ ID NO: | Table 1 |
|---|---|
| 287 | >Derp1.0101<br>RPSSIKTFEEYKKAFQKSYATFEDEEAARKNFLESVKYVQSNGGAINHLSDLSLDEFKNRFLMS<br>AEAFEHLKTQFDLNAETNASSINGNAPAEIDLRQMRTVTPIRMQGGSGSSWAFSGVAATESAYL |

TABLE 1-continued

Sequences of isoforms of house dust mite allergens Der p 1,
Der f 1, Der p 2 and Der f 2.

| SEQ ID NO: | Table 1 |
|---|---|
| | AHRNQSLDLAEQELVDSASQHGSHGDTIPRGIEYIQHNGVVQESYYRYVAREQSSRRPNAQRF<br>GISNYSQIYPPNANKIREALAQTHSAIAVIIGIKDLDAFRHYDGRTIIQRDNGYQPNYH<br>AVNIVGYSNAQGVDYWIVRNSWDTNWGDNGYGYFAANIDLMMIEEYPYVVIL |
| 288 | >Derp1.0102<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNVNKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 289 | >Derp1.0103<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIKYIQHNGVVQES<br>YYRYVAREQSSRRPNAQRFGISNYSQIYPPNVNKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 290 | >Derp1.0104<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAHRNQSLDLAEQELVDSASQHGSHGDTIPRGIEYIQHNGVVQES<br>YYRYVAREQSSRRPNAQRFGISNYSQIYPPNANKIREALAQTHTAIAVIIGIKDLDAFR<br>HYDGRTIIQRDNGYQPNYHAVNIVGYSNAQGVDYWIVRNSWDTNWGDNGYGYFAA<br>NIDLMMIEQYPYVVIL |
| 291 | >Derp1.0105<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNANKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 292 | >Derp1.0106<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNVNKIREALAQTHSAIAVIIGIKDLDAFR<br>HYDGRTIIQHDNGYQPNYHAVNIVGYSNAQGVDYWIVRNSWDTNWGDNGYGYFAA<br>NIDLMMIEEYPYVVIL |
| 293 | >Derp1.0107<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNAN KIREALAQTHTAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 294 | >Derp1.0108<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQLRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNVNKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 295 | >Derp1.0109<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRPVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNANKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 296 | >Derp1.0110<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATDSAYLAYRNQSLDLAEQELVDSASQHGSHGDTIPRGIEYIQHNGVVQES<br>YYRYVAREQSSRRPNAQRFGISNYSQIYPPNANKIREALAQTHSAIAVIIGIKDLDAFR |

TABLE 1-continued

Sequences of isoforms of house dust mite allergens Der p 1, Der f 1, Der p 2 and Der f 2.

| SEQ ID NO: | Table 1 |
|---|---|
| | HYDGRTIIQRDNGYQPNYHAVNIVGYSNAQGVDYWIVRNSWDTNWGDNGYGYFAA<br>NIDLMMIEEYPYVVIL |
| 297 | >Derp1.0111<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNASKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEKYPYVVIL |
| 298 | >Derp1.0112<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNVNKIRKALAQTHSAMAVIIGIKDLDAFR<br>HYDGRTIIQRDNGYQPNYHAVNIVGYSNAQGVDYWIVRNSWDTNWGDNGYGYFAA<br>NIDLMMIEKYPYVVIL |
| 299 | >Derp1.0113<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQIRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNASKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEGYPYVVIL |
| 300 | >Derp1.0114<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIAYIQHNGVVQES<br>YYRYVAREQSSRRPNAQRFGISNYSQIYPPNANKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 301 | >Derp1.0115<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRWTPIRMQGGSGSSW<br>AFSGVAATESAYLAYRNQSLDLAEQELVDSASQHGSHGDTIPRGIEYIQHNGVVQES<br>YYRYVAREQSSRRPNTQRFGISNYSQTYPPNANKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 302 | >Derp1.0116<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQLRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNANKIREALAQTHSAIAVIIGIKDLDAFR<br>HYDGRTIIQRDNGYQPNYYAVNIVGYSNAQGVDYWIVRNSWDTNWGDNGYGYFAA<br>NIDLMMIEEYPYVVIL |
| 303 | >Derp1.0117<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNAN KIREALTQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 304 | >Derp1.0118<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQIRIVTPIRMQGGSGSSW<br>AFSGVAATESAYLAYRNQSLDLAEQELVDSASQHGSHGDTIPRGIEYIQHNGVVQES<br>YYRYVAREQSSRRPNAQRFGISNYSQIYPPNANKIREALAQTHSAIAVIIGIKDLDAFR<br>HYDGRTIIQRDNGYQPNYHAVNIVGYSNAQGVDYWIVRNSWDTNWGDNGYGYFAA<br>NIDLMMIEEYPYVVIL |
| 305 | >Derp1.0119<br>RPSSIKTFEEYKKAFQKSYATFEDEEAARKNFLESVKYVQSNGGAINHLSDLSLDEFK<br>NRFLMSAEAFEHLKTQFDLNAETNASSINGNAPAEIDLRQMRTVTPIRMQGGSGSSW<br>AFSGVAATESAYLAYRNQSLDLAEQELVDSASQHGSHGDTIPRGIGYIQHNGVVQES |

TABLE 1-continued

Sequences of isoforms of house dust mite allergens Der p 1,
Der f 1, Der p 2 and Der f 2.

SEQ
ID
NO:    Table 1

YYRYVAREQSSRRPNAQRFGISNYSQIYPPNVNKIREALAQTHSAIAVIIGIKDLDAFR
       HYDGRTIIQRDNGYQPNYHAVNIVGYSNAQGVDYWIVRNSWDTNWGDNGYGYFAA
       NIDLMMIEEYPYVVIL

306    >Derp1.0120
       RPSSIKTFEEYKKAFQKSYATFEDEEAARKNFLESVKYVQSNGGAINHLSDLSLDEFK
       NRFLMSAEAFEHLKTQFDLNAETNASSINGNAPAEIDLRQMRTVTPIRMQGGSGSSW
       AFSGVAATESAYLAYRNQSLDLAEQELVDSASQHGSHGDTIPRGIEYIQHNGVVQES
       YYRYVAREQSSRRPNAQRFGISNYSQIYPPNAN KIREALAQTHSAIAVIIGIKDLDAFR
       HYDGRTIIRRDNGYQPNYHAVNIVGYSNAQGVDYWIVRNSWDTNWGDNGYGYFAA
       NIDLMMIEEYPYVVIL 307    >Derp1.0121
       RPSSIKTFEEYKKAFQKSYATFEDEEAARKNFLESVKYVQSNGGAINHLSDLSLDEFK
       NRFLMSAEAFEHLKTQFDLNAETNASSINGNAPAEIDLRQMRTVTPIRMQGGSGSSW
       AFSGVAATESAYLAYRSQSLDLAEQELVDSASQHGSHGDTIPRGIEYIQHNGVVQES
       YYRYVAREQSSRRPNAQRFGISNYSQIYPPNVNKIREALAQTHSAIAVIIGIKDLDAFR
       HYDGRTIIQRDNGYQPNYHAVNIVGYSNAQGVDYWIVRNSWDTNWGDNGYGYFAA
       NIDLMMIEGYPYVVIL 308    >Derp1.0122
       RPSSIKTFEEYKKAFQKSYATFEDEEAARKNFLESVKYVQSNGGAINHLSDLSLDEFK
       NRFLMSAEAFEHLKTQFDLNAETNASSINGNAPAEIDLRQMRTVTPIRMQGGSGSSW
       AFSGVAATESAYLAYRNQSLDLAEQELVDSASQHGSHGDTIPRGIEYIQHNGVVQES
       YYRYVAREQSSRRPNAQRFGTSNYSQIYPPNANKIREALAQTHSAIAVIIGIKDLDAFR
       HYDGRTIIQRDNGYQPNYHAVNIVGYSNAQGVDYWIVRNSWDTNWGDNGYGYFAA
       NIDLMMIEEYPYVVIL 309    >Derp1.0123
       RPSSIKTFEEYKKAFQKSYATFEDEEAARKNFLESVKYVQSNGGAINHLSDLSLDEFK
       NRFLMSAEAFEHLKTQFDLNAETNASSINGNAPAEIDLRQMRTVTPIRMQGGSGSSW
       AFSGVAATESAYLAYRNQSLDLAEQELVDSASQHGSHGDTIPRGIEYIQHNGVVQES
       YYRYVAREQSSRRPNAQRFGISNYSQIYPPNANKIREALAQTHSAIAVIIGIKDLDAFR
       HYDGRTIIQRDNGYQPNYHAVNIVGYSNAQGVDYWIVRNSWDTNWGDNGYGYFAA
       NIDLMMIEGYPYVVIL 310    >Derp1.0124
       RPSSIKTFEEYKKAFQKSYATFEDEEAARKNFLESVKYVQSNGGAINHLSDLSLDEFK
       NRFLMSAEAFEHLKTQFDLNAETNASSINGNAPAEIDLRQMRTVTPIRMQGGSGSSW
       AFSGVAATESAYLAYRNQSLDLAEQELVDSASQHGSNGDTIPRGIEYIQHNGVVQES
       YYRYVAREQSSRRPNAQRFGISNYSQIYPPNANKIREALAQTHSAIAVIIGIKDLDAFR
       HYDGRTIIQRDNGYQPNYHAVNIVGYSNAQGVDYWIVRNSWDTNWGDNGYGYFAA
       NIDLMMIEEYPYVVIL 311    >Derp1.0105r
       RPSSIKTFEEYKKAFQKSYATFEDEEAARKNFLESVKYVQSNGGAINHLSDLSLDEFK
       NRFLMSAEAFEHLKTQFDLNAETNASSINGNAPAEIDLRQMRTVTPIRMQGGSGSSW
       AFSGVAATESAYLAYREQSLDLAEQELVDSASQHGSHGDTIPRGIEYIQHNGVVQES
       YYRYVAREQSSRRPNAQRFGISNYSQIYPPNANKIREALAQTHSAIAVIIGIKDLDAFR
       HYDGRTIIQRDNGYQPNYHAVNIVGYSNAQGVDYWIVRNSWDTNWGDNGYGYFAA
       NIDLMMIEEYPYVVIL 312    >Derf1.0101
       RPASIKTFEEFKKAFNKNYATVEEEEVARKNFLESLKYVEANKGAINHLSDLSLDEFKN
       RYLMSAEAFEQLKTQFDLNAETSASRINSVNVPSELDLRSLRTVTPIRMQGGSGSSW
       AFSGVAATESAYLAYRNTSLDLSEQELVDSASQHGSHGDTIPRGIEYIQQNGVVEERS
       YPYVAREQQSRRPNSQHYGISNYSQIYPPDVKQIREALTQTHTAIAVIIGIKDLRAFQH
       YDGRTIIQHDNGYQPNYHAVNIVGYGSTQGVDYWIVRNSWDTTWGDSGYGYFQAG
       NNLMMIEQYPYVVIM 313    >Derf1.0102
       RPASIKTFEEFKKAFNKNYATVEEEEVARKNFLESLKYVEANKGAINHLSDLSLDEFKN
       RYLMSAEAFEQLKTQFDLNAETSASRINSVNVPSELDLRSLRTVTPIRMQGGSGSSW
       AFSGVAATESAYLAYRNTSLDLSEQELVDSASQHGSHGDTIPRGIEYIQQNGVVEERS
       YPYVAREQQSRRPNSQHYGISNYSQIYPPDVKQIREALTQTHTAIAVIIGIKDLRAFQH
       YDGRTIIQRDNGYQPNYHAVNIVGYGSTQGVDYWIVRNSWDTTWGDSGYGYFQAG
       NNLMMIEQYPYVVIM 314    >Derf1.0103
       RPASIKTFEEFKKAFNKNYATVEEEEVARKNFLESLKYVEANKGAINHLSDLSLDEFKN
       RYLMSAEAFEQLKTQFDLNAETSASRINSVNVPSELDLRSLRTVTPIRMQGGSGSSW
       AFSGVAATESAYLAYRNTSLDLSEQELVDSASQHGSHGDTIPRGIEYIQQNGVVEERS TABLE 1-continued Sequences of isoforms of house dust mite allergens Der p 1, Der f 1, Der p 2 and Der f 2.

| SEQ ID NO: | Table 1 |
|---|---|
| | YPYVAREQQSRRPNSQHYGISNYSQIYPPDVKQIREALTQTHTAIAVIIGIKDLRAFQH<br>YGGRTIIQHDNGYQPNYHAVNIVGYGSTQGVDYWIVRNSWDTTWGDSGYGYFQAG<br>NNLMMIEQYPYVVIM |
| 315 | >Derf1.0104<br>RPASIKTFEEFKKAFNKNYATVEEEEVARKNFLESLKYVEANKGAINHLSDLSLDEFKN<br>RYLMSAEAFEQLKTQFDLNAEISASRINSVNVPSELDLRSLRTVTPIRMQGSGSSWA<br>FSGVAATESAYLAYRNTSLDLSEQELVDSASQHGRHGDTIPRGIEYIQQNGVVEERSY<br>PYVAREQQSRRPNSQHYGISNYSQIYPPDVKQIREALTQTHTAIAVIIGIKDLRAFQHY<br>DGRTIIQHDNGYQPNYHAVNIVGYGSTQGVDYWIVRNSWDTTWGDSGYGYFQAGN<br>NLMMIEQYPYVVIM |
| 316 | >Derf1.0105<br>RPASIKTFEEFKKAFNKNYATVEEEEVARKNFLESLKYVEANKGAINHLSDLSLDEFKN<br>RYLMSAEAFEQLKTQFDLNAETSASRINSVNVPSELDLRSLRTVTPIRMQGGSGSSW<br>AFSGVAATESAYLAYRNTSLDLSEQELVDSASQHGSHGDTIPRGIEYIQQNGVVEERS<br>YPYVAREQQSRRPNSQHYDISNYSQIYPPDVKQIREALTQTHTAIAVIIGIKDLRAFQH<br>YDGRTIIQHDNGYQPNYHAVNIVGYGSTQGVDYWIVRNSWDTTWGDSGYGYFQAG<br>NNLMMIEQYPYVVIM |
| 317 | >Derf1.0106<br>RPASIKTFEEFKKAFNKNYATVEEEEVARKNFLESLKYVEANKGAINHLSDLSLDEFKN<br>RYLMSAEAFEQLKTQFDLNAETSASRINSVNVPSELDLRSLRTVTPIRMQGGSGSSW<br>AFSGVAATESAYLAYRNTSLDLSEQELVDSASQHGSHGDTIPRGIEYIQQNGVVEERS<br>YPYVAREQRSRRPNSQHYGISNYSQIYPPDVKQIREALTQTHTAIAVIIGIKDLRAFQH<br>YDGRTIIQHDNGYQPNYHAVNIVGYGSTQGDDYWIVRNSWDTTWGDSGYGYFQAG<br>NNLMMIEQYPYVVIM |
| 318 | >Derf1.0107<br>RPASIKTFEEFKKAFNKNYATVEEEEVARKNFLESLKYVEANKGAINHLSDLSLDEFKN<br>RYLMSAEAFEQLKTQFDLNAETSASRINSVNVPSELDLRSLRTVTPIRMQGGSGSSW<br>AFSGVAATESAYLAYRNTSLDLSEQELVDSASQHGSHGDTIPRGIEYIQQNGVVEERS<br>YPYVAREQRSRRPNSQHYGISNYSQIYPPDVKQIREALTQTHTAIAVIIGIKDLRAFQH<br>YDGRTIIQHDNGYQPNYHAVNIVGYGSTQGVDYWIVRNSWDTTWGDSGYGYFQAG<br>NNLMMIEQYPYVVIM |
| 319 | >Derf1.0108<br>RPASIKTFEEFKKAFNKNYATVEEEEVARKNFLESLKYVEANKGAINHLSDLSLDEFKN<br>RYLMSAEAFEQLKTQFDLNAETSASRINSVNVPSELDLRSLRTATPIRMQGGSGSSW<br>AFSGVAATESAYLAYRNTSLDLSEQELVDSASQHGSHGDTIPRGIEYIQQNGVVEERS<br>YPYVAREQQSRRPNSQHYGISNYSQIYPPDVKQIREALTQTHTAIAVIIGIKDLRAFQH<br>YDGRTIIQHDNGYQPNYHAVNIVGYGSTQGVDYWIVRNSWDTTWGDSGYGYFQAG<br>NNLMMIEQYPYVVIM |
| 320 | >Derf1.0109<br>RPASIKTFEEFKKAFNKNYAIVEEEEVARKNFLESLKYVEANKGAINHLSDLSLDEFKN<br>RYLMSAEAFEQLKTQFDLNAETSASRINSVNVPSELDLRSLRTVTPIRMQGGSGSSW<br>AFSGVAATESAYLAYRNTSLDLSEQKLVDSASQHGSHGDTIPRGIEYIQQNGVVEERS<br>YPYVAREQQSRRPNSQHYGISNYSQIYPPDVKQIREALTQTHTAIAVIIGIKDLRAFQH<br>YDGRTIIQHDNGYQPNYHAVNIVGYGSTQGVDYWIVRNSWDTTWGDSGYGYFQAG<br>NNLMMIEQYPYVVIM |
| 321 | >Derf1.0110<br>RPASIKTFEEFKKAFNKNYATVEEEEVARKNFLESLKYVEANKGAINHLSDLSLDEFKN<br>RYLMSAEAFEQLKTQFDLNAETSASRINSVNVPSELDLRSLRTVTPIRMQGGSGSSW<br>AFSGVAATESAYLAYRNTSLDLSEQELVDSASQHGSHGDTIPRGIEYIQQNGVVEERS<br>YPYVAREQQSRRPNSQHYGISNYSQIYPPDVKQIREALTQTHTAIAVIIGIKDLRAFQH<br>YDGRTIIRHDNGYQPNYHAVNIVGYGSTQGVDYWIVRNSWDTTWGDSGYGYFQAG<br>NNLMMIEQYPYVVIM |
| 322 | >Derf1.0107r<br>RPASIKTFEEFKKAFNKNYATVEEEEVARKNFLESLKYVEANKGAINHLSDLSLDEFKN<br>RYLMSAEAFEQLKTQFDLNAETSASRINSVNVPSELDLRSLRTVTPIRMQGGSGSSW<br>AFSGVAATESAYLAYRQTSLDLSEQELVDSASQHGSHGDTIPRGIEYIQQNGVVEERS<br>YPYVAREQRSRRPNSQHYGISNYSQIYPPDVKQIREALTQTHTAIAVIIGIKDLRAFQH<br>YDGRTIIQHDNGYQPNYHAVNIVGYGSTQGVDYWIVRNSWDTTWGDSGYGYFQAG<br>NNLMMIEQYPYVVIM |
| 323 | >Derp2.0101<br>DQVDVKDSANHEIKKVLVPGSHGSEPSIIHRGKPFQLEAVFEANQNTKTAKIEIKASI<br>DGLEVDVPGIDPNASHYMKSPLVKGQQYDIKYTWNVPKIAPKSENVVVTVKVMGDD<br>GVLASAIATHAKIRD |

TABLE 1-continued

Sequences of isoforms of house dust mite allergens Der p 1, Der f 1, Der p 2 and Der f 2.

| SEQ ID NO: | Table 1 |
|---|---|
| 324 | >Derp2.0102<br>DQVDVKDSANHEIKKVLVPGSHGSEPSIIHRGKPFQLEAVFEANQNSKTAKIEIKASI<br>DGLEVDVPGIDPNASHYMKSPLVKGQQYDIKYTWNVPKIAPKSENVVVTVKVMGDN<br>GVLASAIATHAKLRD |
| 325 | >Derp2.0103<br>DQVDVKDSANHEIKKVLVPGSHGSEPSIIHRGKPFQLEALFEANQNSKTAKIEIKASI<br>DGLEVDVPGIDPNASHYMKSPLVKGQQYDIKYTWNVPKIAPKSENVVVIVKVMGDN<br>GVLASAIATHAKIRD |
| 326 | >Derp2.0104<br>DQVDVKDSANHEIKKVLVPGSHGSEPSIIHRGKPFQLEALFEANQNSKTAKIEIKASI<br>DGLEVDVPGIDPNASHYMKSPLVKGQQYDIKYTWNVPKIAPKSENVVVTVKVLGDNG<br>VLASAIATHAKIRD |
| 327 | >Derp2.0105<br>DQVDVKDSANHEIKKVLVPGSHGSEPSIIHRGKPFQLEALFEANQNSKTAKIEIKASI<br>DGLEVDVPGIDPNASHYMKSPLVKGQQYDIKYTWNVPKIAPKSENVVVIVKVMGDD<br>GVLASAIATHAKIRD |
| 328 | >Derp2.0106<br>DQVDVKDSANHEIKKVLVPGSHGSEPSIIHRGKPFQLEAVFEANQNTKTAKIEIKASI<br>DGLEVDVPGIDPNASHYMKSPLVKGQQYDIKYTWNVPKITPKSENVVVTVKVMGDD<br>GVLASAIATHAKIRD |
| 329 | >Derp2.0107<br>DQVDVKDSANHEIKKVLVPGSHGSEPSIIHRGKPFQLEAVFEANQNSKTAKIEIKASI<br>DGLEVDVPGIDPNASHYMKSPLVKGQQYDIKYTWNVPKIAPKSENVVVTVKVMGDD<br>GVLASAIATHAKIRD |
| 330 | >Derp2.0108<br>DQVDVKDSANHEIKKVLVPGSHGSEPSIIHRGKPFQLEAVFEANQNSKTAKIEIKASI<br>DGLEVDVPGIDPNASHYMKSPLVKGQQYDIKYTWNVPKIAPKSENVVVTVKVMGDD<br>GALASAIATHAKIRD |
| 331 | >Derp2.0109<br>DQVDVKDSANHEIKKVLVPGSHGSEPSIIHRGKPFQLEAVFEANQNSKTAKIEIKASI<br>DGLEVDVPGIDPNASHYMKSPLVKGQQYDIKYTWNVPKIAPKSENVVVTVKVLGDNG<br>VLASAIATHAKIRD |
| 332 | >Derp2.0110<br>DQVDVKDSANHEIKKVLVPGSHGSEPSIIHRGKPFQLEAVFEANQNSKTAKIEIKASI<br>DGLEVDVPGIDPNASHYMKSPLVKGQQYDIKYTWNVPKIAPKSENVVVTVKVLGDNG<br>VLASAIATHAKIRD |
| 333 | >Derp2.0111<br>DQVDVKDSANHEIKKVLVPGSHGSEPSIIHRGKPFQLEALFEANQNSKTAKIEIKASI<br>DGLEVDVPGIDPNASHYVKSPLVKGQQYDIKYTWNVPKIAPKSENVVVTVKVMGDN<br>GVLASAIATHAKIRD |
| 334 | >Derp2.0112<br>DQVDVKDSANHEIKKVLVPGSHGSEPSIIHRGKPFQLEAVFEANQNTKTAKIEIKASI<br>DGLEVDVPGIDPNASHYVKSPLVKGQQYDIKYTWNVPKIAPKSENVVVIVKVIGDNG<br>VLASAIATHAKIRD |
| 335 | >Derp2.0113<br>DQVDVKDSANHEIKKVLVPGSHGSEPSIIHRGKPFQLEAVFEANQNTKNAKIEIKASI<br>DGLEVDVPGIDPNASHYVKSPLVKGQQYDIKYTWNVPKIAPKSENVVVTVKVMGDN<br>GVLASAIATHAKIRD |
| 336 | >Derp2.0114<br>DQVDVKDSANHEIKKVLVPGSHGSEPSIIHRGKPFQLEALFEANQNTKNAKIEIKASI<br>DGLEVDVPGIDPNASHYVKSPLVKGQQYDIKYTWNVPKIAPKSENVVVIVKVLGDNG<br>VLASAIATHAKIRD |
| 337 | >Derp2.0115<br>DQVDVKDSANHEIKKVLVPGSHGSEPSIIHRGKPFQLEAVFEANQNSKTAKIEIKASI<br>DGLEVDVPGIDPNASHYMKSPLVKGQQYDIKYTWNVPKIAPKSENVVVTVKVMGDN<br>GVLASAIATHAKIRD |

TABLE 1-continued

Sequences of isoforms of house dust mite allergens Der p 1, Der f 1, Der p 2 and Der f 2.

| SEQ ID NO: | Table 1 |
|---|---|
| 338 | >Derf2.0101<br>DQVDVKDSANNEIKKVMVDGSHGSDPSIIHRGKPFTLEALFDANQNTKTAKIEIKASL<br>DGLEIDVPGIDTNASHFVKSPLVKGQQYDIKYTWNVPKIAPKSENVVVTVKLIGDNGV<br>LASAIATHGKIRD |
| 339 | >Derf2.0102<br>DQVDVKDSANNEIKKVMVDGSHGSDPSIIHRGKPFTLEALFDANQNTKTAKIEIKASL<br>DGLEIDVPGIDTNASHFMKSPLVKGQQYDIKYTWNVPKIAPKSENVVVIVKLIGDNG<br>VLASAIATHGKIRD |
| 340 | >Derf2.0103<br>DQVDVKDSANNEIKKVMVDGSHGSDPSIIHRGKPFTLEALFDANQNTKTAKIEIKASL<br>DGLEIDVPGIDTNASHFMKSPLVKGQQYDAKYTWNVPKIAPKSENVVVIVKLVGDNG<br>VLASAIATHAKIRD |
| 341 | >Derf2.0104<br>DQVDVKDSANNEIKKVMVDGSHGSDPSIIHRGKPFTLEALFDANQNTKTAKTEIKAS<br>LDGLEIDVPGIDTNASHFMKSPLVKGQQYDAKYTWNVPKIAPKSENVVVTVKLVGDN<br>GVLASAIATHAKIRD |
| 342 | >Derf2.0105<br>DQVDVKDSANNEIKKVMVDGSHGSDPSIIHRGKPFTLEALFDANQNTKTAKIEIKASL<br>DGLEIDVPGIDTNASHFMKSPLVKGQQYDAKYTWNVPKIAPESENVVVIVKLVGDNG<br>VLASAIATHAKIRD |
| 343 | >Derf2.0106<br>DQVDVKDSANHEIKKVMVDGSHGSDPSIIHRGKPFNLEAIFDANQNTKTAKIEIKANI<br>DGLEVDVPGIDTNASHYIKSPLVKGQQYDAKYTWNVPKIAPKSENVVVIVKLVGDNG<br>VLASAIATHAKIRD |
| 344 | >Derf2.0107<br>DQVDVKDSANNEIKKVMVDGSHGSDPSIIHRGKPFTLEALFDANQNTKTAKIEIKANI<br>NGLEVDVPGIDTNASHYIKSPLVKGQQYDAKYTWNVPKIAPKSENVVVIVKLIGDNG<br>VLASAIATHAKIRD |
| 345 | >Derf2.0108<br>DQVDVKDSANNEIKKVMVDGSHGSDPSIIHRGKPFTLEALFDANQNTKTAKIEIKANI<br>DGLEVDVPGIDTNASHYIKSPLVKGQQYDAKYTWNVPKIAPKSENVVVIVKLVGDNG<br>VLASAIATHAKIRD |
| 346 | >Derf2.0109<br>DQVDVKDSANNEIKKVMVDGRHGSDPSIIHRGKPFTLEALFDANQNTKTAKIEIKANI<br>NGLEVDVPGIDTNASHFVKSPLVKGQQYDIKYTWNVPKIAPKSENVVVIVKLIGDNG<br>VLASAIATHAKIRD |
| 347 | >Derf2.0110<br>DQVDVKDSANNEIKKVMVDGSHGSDPSIIHRGKPFTLEALFDANQNTKTAKIEIKANI<br>NGLEADVPGIDTNASHYIKSPLVKGQQYDAKYTWNVPKIAPKSENVVVIVKLIGDNG<br>VLASAIATHAKIRD |
| 348 | >Derf2.0111<br>DQVDVKDSANNEIKKVMVDGRHGSDPSIIHRGKPFTLEALFDANQNTKTAKIEIKANI<br>NGLEVDVPGIDTNASHFVKSPLVKGQQYDIKYTWNVPKIAPKSENVVVIVKLIGDNG<br>VLASAIATHAKIRD |
| 349 | >Derf2.0112<br>DQVDVKDSANNEIKKVMVDGSHGSDPSIIHRGKPFTLEALFDANQNTKTAKIEIKASL<br>DGLEIDVPGIDTNASHFMKSPLVKGQQYDAKYTWNVPKIAPKSENVVVIVKLVGDNG<br>VLASAIATHGKIRD |
| 350 | >Derf2.0113<br>DQVDVKDSANNEIKKVMVDGSHGSDPSIIHRGKPFTLEALFDANQNTKTAKIEIKASL<br>DGLETDVPGIDTNASHFMKSPLVKGQQYDAKYTWNVPKIAPKSENVVVTVKLIGDNG<br>VLASAIATHGKIRD |
| 351 | >Derf2.0114<br>DQVDVKDSANNEIKKVMVDGSHGSDPSIIHRGKPFTLEALFDANQNTKTAKIEIKANI<br>NGLEVDVPGIDTNASHFVKSPLVKGQQYDIKYTWNVPKIAPKSENVVVTVKLIGDNG<br>VLASAIATHGKIRD |

TABLE 1-continued

Sequences of isoforms of house dust mite allergens Der p 1, Der f 1, Der p 2 and Der f 2.

| SEQ ID NO: | Table 1 |
|---|---|
| 352 | >Derf2.0115<br>DQVDVKDSANNEIKKVMVDGSHGSDPSIIHRGKPFTLEALFDANQNTKTAKIEIKANI<br>NGLEVDVPGIDTNASHFVKSPLVKGQQYDIKYTWNVPKIAPKSENVVVTVKLIGDNG<br>VLASAIATHGKISD |
| 353 | >Derf2.0116<br>DQVDVKDSANNEIKKVMVDGSHGSDPSIIHRGKPFTLEALFDANQNTKTAKIEIKANI<br>NGLEVDVPGIDTNASHYIKSPLVKGQQYDAKYTWNVPKIAPKSENVVVTVKLIGDNG<br>VLASAIATHGKIRD |
| 354 | >Derf2.0117<br>DQVDVKDSANNEIKKVMVDGSHGSDPSIIHRGKPFTLEALFDANQNTKTAKIEIKANI<br>NGLEVDVPGIDTNASHYIKSPLVKGQQYDIKYTWNVPKIAPKSENVVV1VKLIGDNGV<br>LASAIATHGKIRD |

TABLE 2

Peptide library of Der p 1 and Der f 1 (20 mers peptides)

| SEQ ID NO: | Pep No | Start pos | Sequence derived from Der p 1 | SEQ ID NO: | Pep No | Start pos | Sequence derived from Der f 1 |
|---|---|---|---|---|---|---|---|
| Pro-protein | | | | | | | |
| 1 | 33 | 1 | RPSSIKTFEEYKKAFNKSYA | 30 | 62 | 1 | RPASIKTFEEFKKAFNKNYA |
| 2 | 34 | 11 | YKKAFNKSYATFEDEEAARK | 31 | 63 | 11 | FKKAFNKNYATVEEEEVARK |
| 3 | 35 | 21 | TFEDEEAARKNFLESVKYVQ | 32 | 64 | 21 | TVEEEEVARKNFLESLKYVE |
| 4 | 36 | 31 | NFLESVKYVQSNGGAINHLS | 33 | 65 | 31 | NFLESLKYVEANKGAINHLS |
| 5 | 37 | 41 | SNGGAINHLSDLSLDEFKNR | 34 | 66 | 41 | ANKGAINHLSDLSLDEFKNR |
| 6 | 38 | 51 | DLSLDEFKNRFLMSAEAFEH | 35 | 67 | 51 | DLSLDEFKNRYLMSAEAFEQ |
| 7 | 39 | 61 | FLMSAEAFEHLKTQFDLNAE | 36 | 68 | 61 | YLMSAEAFEQLKTQFDLNAE |
| 8 | 40 | 71 | LKTQFDLNAETNASSINGN | 37 | 69 | 71 | LKTQFDLNAETSASRINSVN |
| Mature protein | | | | | | | |
| 9 | 41 | 81 | TNASSINGNAPAEIDLRQM | 38 | 70 | 81 | TSASRINSVNVPSELDLRSL |
| 10 | 42 | 90 | APAEIDLRQMRTVTPIRMQG | 39 | 71 | 91 | VPSELDLRSLRTVTPIRMQG |
| 11 | 43 | 100 | RTVTPIRMQGGSGSSWAFSG | 40 | 43 | 101 | RTVTPIRMQGGSGSSWAFSG |
| 12 | 44 | 110 | GSGSSWAFSGVAATESAYLA | 41 | 44 | 111 | GSGSSWAFSGVAATESAYLA |
| 13 | 45 | 120 | VAATESAYLAYRNQSLDLAE | 42 | 72 | 121 | VAATESAYLAYRNTSLDLSE |
| 14 | 46 | 130 | YRNQSLDLAEQELVDSASQH | 43 | 73 | 131 | YRNTSLDLSEQELVDSASQH |
| 15 | 47 | 140 | QELVDSASQHGSHGDTIPRG | 44 | 47 | 141 | QELVDSASQHGSHGDTIPRG |
| 16 | 48 | 150 | GSHGDTIPRGIEYIQHNGVV | 45 | 74 | 151 | GSHGDTIPRGIEYIQQNGVV |
| 17 | 49 | 160 | IEYIQHNGVVQESYYRYVAR | 46 | 75 | 161 | IEYIQQNGVVEERSYPYVAR |
| 18 | 50 | 170 | QESYYRYVAREQSSRRPNAQ | 47 | 76 | 171 | EERSYPYVAREQQSRRPNSQ |
| 19 | 51 | 180 | EQSSRRPNAQRFGISNYSQI | 48 | 77 | 181 | EQQSRRPNSQHYGISNYSQI |
| 20 | 52 | 190 | RFGISNYSQIYPPNANKIRE | 49 | 78 | 191 | HYGISNYSQIYPPDVKQIRE |
| 21 | 53 | 200 | YPPNANKIREALAQTHSAIA | 50 | 79 | 201 | YPPDVKQIREALTQTHTAIA |

TABLE 2-continued

Peptide library of Der p 1 and Der f 1 (20 mers peptides)

| SEQ ID NO: | Pep No | Start pos | Sequence derived from Der p 1 | SEQ ID NO: | Pep No | Start pos | Sequence derived from Der f 1 |
|---|---|---|---|---|---|---|---|
| 22 | 54 | 210 | ALAQTHSAIAVIIGIKDLDA | 51 | 80 | 211 | ALTQTHTAIAVIIGIKDLRA |
| 23 | 55 | 220 | VIIGIKDLDAFRHYDGRTII | 52 | 81 | 221 | VIIGIKDLRAFQHYDGRTII |
| 24 | 56 | 230 | FRHYDGRTIIQRDNGYQPNY | 53 | 82 | 231 | FQHYDGRTIIQHDNGYQPNY |
| 25 | 57 | 240 | QRDNGYQPNYHAVNIVGYSN | 54 | 83 | 241 | QHDNGYQPNYHAVNIVGYGS |
| 26 | 58 | 250 | HAVNIVGYSNAQGVDYWIVR | 55 | 84 | 251 | HAVNIVGYGSTQGVDYWIVR |
| 27 | 59 | 260 | AQGVDYWIVRNSWDTNWGDN | 56 | 85 | 261 | TQGVDYWIVRNSWDTTWGDS |
| 28 | 60 | 270 | NSWDTNWGDNGYGYFAANID | 57 | 86 | 271 | NSWDTTWGDSGYGYFQAGNN |
| 29 | 61 | 280 | GYGYFAANIDLMMIEEYPYVVIL | 58 | 87 | 281 | GYGYFQAGNNLMMIEQYPYVVIM |

Table 2 shows overlapping 20mers peptides of allergen Der p 1 (isoform 1.0105) and allergen Der f 1 (isoform 1.0101). Underlined amino acid S indicated that a cysteine residue is replaced with serine)

TABLE 3

Peptide library of Der p 2 and Der f 2 (20 mers peptides)

| SEQ ID NO: | Pep No | Start pos | Sequence derived from Der p 2 | SEQ ID NO: | Pep No | Start pos | Sequence derived from Der f 2 |
|---|---|---|---|---|---|---|---|
| 59 | 88 | 1 | DQVDVKDSANHEIKKVLVP | 71 | 100 | 1 | DQVDVKDSANNEIKKVMVD |
| 60 | 89 | 10 | NHEIKKVLVPGSHGSEPSII | 72 | 101 | 10 | NNEIKKVMVDGSHGSDPSII |
| 61 | 90 | 20 | GSHGSEPSIIHRGKPFQLEA | 73 | 102 | 20 | GSHGSDPSIIHRGKPFTLEA |
| 62 | 91 | 30 | HRGKPFQLEAVFEANQNTKT | 74 | 103 | 30 | HRGKPFTLEALFDANQNTK |
| 63 | 92 | 40 | VFEANQNTKTAKIEIKASID | 75 | 104 | 40 | LFDANQNTKTAKIEIKASLD |
| 64 | 93 | 50 | AKIEIKASIDGLEVDVPGID | 76 | 105 | 50 | AKIEIKASLDGLEIDVPGID |
| 65 | 94 | 60 | GLEVDVPGIDPNASHYMKSP | 77 | 106 | 60 | GLEIDVPGIDTNASHFMKSP |
| 66 | 95 | 70 | PNASHYMKSPLVKGQQYDIK | 78 | 107 | 70 | TNASHFMKSPLVKGQQYDAK |
| 67 | 96 | 80 | LVKGQQYDIKYTWNVPKIAP | 79 | 108 | 80 | LVKGQQYDAKYTWNVPKIAP |
| 68 | 97 | 90 | YTWNVPKIAPKSENVVVTVK | 80 | 97 | 90 | YTWNVPKIAPKSENVVVTVK |
| 69 | 98 | 100 | KSENVVVTVKVMGDDGVLAS | 81 | 109 | 100 | KSENVVVTVKLVGDNGVLAS |
| 70 | 99 | 110 | VMGDDGVLASAIATHAKIRD | 82 | 110 | 110 | LVGDNGVLASAIATHAKIRD |

TABLE 4

Peptide library of Der p 1 and Der f 1 (15 mers peptides)

| SEQ ID NO: | Start pos | Sequence derived from Der p 1 | SEQ ID NO: | Start pos | Sequence derived from Der f 1 |
|---|---|---|---|---|---|
| 83 | 1 | RPSSIKTFEEYKKAF | 142 | 1 | RPASIKTFEEFKKAF |
| 84 | 6 | KTFEEYKKAFNKSYA | 143 | 6 | KTFEEFKKAFNKNYA |
| 85 | 11 | YKKAFNKSYATFEDE | 144 | 11 | FKKAFNKNYATVEEE |
| 86 | 16 | NKSYATFEDEEAARK | 145 | 16 | NKNYATVEEEEVARK |

TABLE 4-continued

Peptide library of Der p 1 and Der f 1 (15 mers peptides)

| SEQ ID NO: | Start pos | Sequence derived from Der p 1 | SEQ ID NO: | Start pos | Sequence derived from Der f 1 |
|---|---|---|---|---|---|
| 87 | 21 | TFEDEEAARKNFLES | 146 | 21 | TVEEEEVARKNFLES |
| 88 | 26 | EAARKNFLESVKYVQ | 147 | 26 | EVARKNFLESLKYVE |
| 89 | 31 | NFLESVKYVQSNGGA | 148 | 31 | NFLESLKYVEANKGA |
| 90 | 36 | VKYVQSNGGAINHLS | 149 | 36 | LKYVEANKGAINHLS |
| 91 | 41 | SNGGAINHLSDLSLD | 150 | 41 | ANKGAINHLSDLSLD |
| 92 | 46 | INHLSDLSLDEFKNR | 151 | 46 | INHLSDLSLDEFKNR |
| 93 | 51 | DLSLDEFKNRFLMSA | 152 | 51 | DLSLDEFKNRYLMSA |
| 94 | 56 | EFKNRFLMSAEAFEH | 153 | 56 | EFKNRYLMSAEAFEQ |
| 95 | 61 | FLMSAEAFEHLKTQF | 154 | 61 | YLMSAEAFEQLKTQF |
| 96 | 66 | EAFEHLKTQFDLNAE | 155 | 66 | EAFEQLKTQFDLNAE |
| 97 | 71 | LKTQFDLNAETNACS | 156 | 71 | LKTQFDLNAETSACR |
| 98 | 76 | DLNAETNACSINGNA | 157 | 76 | DLNAETSACRINSVN |
| 99 | 81 | TNACSINGNAPAEI | 158 | 81 | TSACRINSVNVPSEL |
| 100 | 86 | INGNAPAEIDLRQM | 159 | 86 | INSVNVPSELDLRSL |
| 101 | 91 | PAEIDLRQMRTVTP | 160 | 91 | VPSELDLRSLRTVTP |
| 102 | 96 | DLRQMRTVTPIRMQG | 161 | 96 | DLRSLRTVTPIRMQG |
| 103 | 101 | RTVTPIRMQGGCGSC | 162 | 101 | RTVTPIRMQGGCGSC |
| 104 | 106 | IRMQGGCGSCWAFSG | 163 | 106 | IRMQGGCGSCWAFSG |
| 105 | 111 | GCGSCWAFSGVAATE | 164 | 111 | GCGSCWAFSGVAATE |
| 106 | 116 | WAFSGVAATESAYLA | 165 | 116 | WAFSGVAATESAYLA |
| 107 | 121 | VAATESAYLAYRNQS | 166 | 121 | VAATESAYLAYRNTS |
| 108 | 126 | SAYLAYRNQSLDLAE | 167 | 126 | SAYLAYRNTSLDLSE |
| 109 | 131 | YRNQSLDLAEQELVD | 168 | 131 | YRNTSLDLSEQELVD |
| 110 | 136 | LDLAEQELVDCASQH | 169 | 136 | LDLSEQELVDCASQH |
| 111 | 141 | QELVDCASQHGCHGD | 170 | 141 | QELVDCASQHGCHGD |
| 112 | 146 | CASQHGCHGDTIPRG | 171 | 146 | CASQHGCHGDTIPRG |
| 113 | 151 | GCHGDTIPRGIEYIQ | 172 | 151 | GCHGDTIPRGIEYIQ |
| 114 | 156 | TIPRGIEYIQHNGVV | 173 | 156 | TIPRGIEYIQQNGVV |
| 115 | 161 | IEYIQHNGVVQESYY | 174 | 161 | IEYIQQNGVVEERSY |
| 116 | 166 | HNGVVQESYYRYVAR | 175 | 166 | QNGVVEERSYPYVAR |
| 117 | 171 | QESYYRYVAREQSCR | 176 | 171 | EERSYPYVAREQQCR |
| 118 | 176 | RYVAREQSCRRPNAQ | 177 | 176 | PYVAREQQCRRPNSQ |
| 119 | 181 | EQSCRRPNAQRFGIS | 178 | 181 | EQQCRRPNSQHYGIS |
| 120 | 186 | RPNAQRFGISNYCQI | 179 | 186 | RPNSQHYGISNYCQI |
| 121 | 191 | RFGISNYCQIYPPNA | 180 | 191 | HYGISNYCQIYPPDV |
| 122 | 196 | NYCQIYPPNANKIRE | 181 | 196 | NYCQIYPPDVKQIRE |
| 123 | 201 | YPPNANKIREALAQT | 182 | 201 | YPPDVKQIREALTQT |

TABLE 4-continued

Peptide library of Der p 1 and Der f 1 (15 mers peptides)

| SEQ ID NO: | Start pos | Sequence derived from Der p 1 | SEQ ID NO: | Start pos | Sequence derived from Der f 1 |
|---|---|---|---|---|---|
| 124 | 206 | NKIREALAQTHSAIA | 183 | 206 | KQIREALTQTHTAIA |
| 125 | 211 | ALAQTHSAIAVIIGI | 184 | 211 | ALTQTHTAIAVIIGI |
| 126 | 216 | HSAIAVIIGIKDLDA | 185 | 216 | HTAIAVIIGIKDLRA |
| 127 | 221 | VIIGIKDLDAFRHYD | 186 | 221 | VIIGIKDLRAFQHYD |
| 128 | 226 | KDLDAFRHYDGRTII | 187 | 226 | KDLRAFQHYDGRTII |
| 129 | 231 | FRHYDGRTIIQRDNG | 188 | 231 | FQHYDGRTIIQHDNG |
| 130 | 236 | GRTIIQRDNGYQPNY | 189 | 236 | GRTIIQHDNGYQPNY |
| 131 | 241 | QRDNGYQPNYHAVNI | 190 | 241 | QHDNGYQPNYHAVNI |
| 132 | 246 | YQPNYHAVNIVGYSN | 191 | 246 | YQPNYHAVNIVGYGS |
| 133 | 251 | HAVNIVGYSNAQGVD | 192 | 251 | HAVNIVGYGSTQGVD |
| 134 | 256 | VGYSNAQGVDYWIVR | 193 | 256 | VGYGSTQGVDYWIVR |
| 135 | 261 | AQGVDYWIVRNSWDT | 194 | 261 | TQGVDYWIVRNSWDT |
| 136 | 266 | YWIVRNSWDTNWGDN | 195 | 266 | YWIVRNSWDTTWGDS |
| 137 | 271 | NSWDTNWGDNGYGYF | 196 | 271 | NSWDTTWGDSGYGYF |
| 138 | 276 | NWGDNGYGYFAANID | 197 | 276 | TWGDSGYGYFQAGNN |
| 139 | 281 | GYGYFAANIDLMMIE | 198 | 281 | GYGYFQAGNNLMMIE |
| 140 | 286 | AANIDLMMIEEYPYV | 199 | 286 | QAGNNLMMIEQYPYV |
| 141 | 289 | IDLMMIEEYPYVVIL | 200 | 289 | NNLMMIEQYPYVVIM |

Table 4 shows overlapping 15mers peptides of Der p1 (isoform 1.0105) and Der f 1 (isoform 1.0101)

TABLE 5

Peptide library of Der p 2 and Der f 2 (15 mers peptides)

| SEQ ID NO: | Start pos | Sequence derived from Der p 2 | SEQ ID NO: | Start pos | Sequence derived from Der f 2 |
|---|---|---|---|---|---|
| 201 | 1 | DQVDVKDCANHEIKK | 225 | 1 | DQVDVKDCANNEIKK |
| 202 | 6 | KDCANHEIKKVLVPG | 226 | 6 | KDCANNEIKKVMVDG |
| 203 | 11 | HEIKKVLVPGCHGSE | 227 | 11 | NEIKKVMVDGCHGSD |
| 204 | 16 | VLVPGCHGSEPCIIH | 228 | 16 | VMVDGCHGSDPCIIH |
| 205 | 21 | CHGSEPCIIHRGKPF | 229 | 21 | CHGSDPCIIHRGKPF |
| 206 | 26 | PCIIHRGKPFQLEAV | 230 | 26 | PCIIHRGKPFTLEAL |
| 207 | 31 | RGKPFQLEAVFEANQ | 231 | 31 | RGKPFTLEALFDANQ |
| 208 | 36 | QLEAVFEANQNTKTA | 232 | 36 | TLEALFDANQNTKTA |
| 209 | 41 | FEANQNTKTAKIEIK | 233 | 41 | FDANQNTKTAKIEIK |
| 210 | 46 | NTKTAKIEIKASIDG | 234 | 46 | NTKTAKIEIKASLDG |
| 211 | 51 | KIEIKASIDGLEVDV | 235 | 51 | KIEIKASLDGLEIDV |
| 212 | 56 | ASIDGLEVDVPGIDP | 236 | 56 | ASLDGLEIDVPGIDT |

TABLE 5-continued

Peptide library of Der p 2 and Der f 2 (15 mers peptides)

| SEQ ID NO: | Start pos | Sequence derived from Der p 2 | SEQ ID NO: | Start pos | Sequence derived from Der f 2 |
|---|---|---|---|---|---|
| 213 | 61 | LEVDVPGIDPNACHY | 237 | 61 | LEIDVPGIDTNACHF |
| 214 | 66 | PGIDPNACHYMKCPL | 238 | 66 | PGIDTNACHFMKCPL |
| 215 | 71 | NACHYMKCPLVKGQQ | 239 | 71 | NACHFMKCPLVKGQQ |
| 216 | 76 | MKCPLVKGQQYDIKY | 240 | 76 | MKCPLVKGQQYDAKY |
| 217 | 81 | VKGQQYDIKYTWNVP | 241 | 81 | VKGQQYDAKYTWNVP |
| 218 | 86 | YDIKYTWNVPKIAPK | 242 | 86 | YDAKYTWNVPKIAPK |
| 219 | 91 | TWNVPKIAPKSENVV | 243 | 91 | TWNVPKIAPKSENVV |
| 220 | 96 | KIAPKSENVVVTVKV | 244 | 96 | KIAPKSENVVVTVKL |
| 221 | 101 | SENVVVTVKVMGDDG | 245 | 101 | SENVVVTVKLVGDNG |
| 222 | 106 | VTVKVMGDDGVLACA | 246 | 106 | VTVKLVGDNGVLACA |
| 223 | 111 | MGDDGVLACAIATHA | 247 | 111 | VGDNGVLACAIATHA |
| 224 | 115 | GVLACAIATHAKIRD | 248 | 115 | GVLACAIATHAKIRD |

Table 5 shows overlapping 15mers peptides of Der p 2 (isoform 2.0101) and Der f 2 (isoform 2.0103)

TABLE 6

Additional Peptide Library

| SEQ ID NO: | Peptide ID No | Species | Position Start | Sequence |
|---|---|---|---|---|
| 249 | 002 | Der p 2 | 26 | SIIHRGKPFQLEA |
| 250 | 009 | Der p 1 | 24 | ESAYLAYRNQSLDLAE |
| 251 | 010 | Der p 1 | 277 | DNGYGYFAANIDLMMIEE |
| 252 | 011 | Der p 1 | 278 | NGYGYFAANIDLMM |
| 253 | 012 | Der p 2 | 115 | VLASAIATHAKIRD |
| 254 | 022 | Der f 1 | 122 | ATESAYLAYRNTSLD |
| 255 | 025 | Der p 1 | 159 | RGIEYIQHNGVVQES |
| 256 | 031 | Der p 2 | 83 | QQYDIKYTWNVPKIA |
| 257 | 117 | Der p 4 | 383 | EIYNMVKFRMIAGQE |
| 258 | 122 | Der p 1 | 169 | QESYYRYVAREQSSRR |
| 259 | HDM203B | Der p 1 | | DLRQMRTVTPIRMQGGSGS |
| 260 | HDM03W | Der p 1 | | ELVDSASQHG |
| 261 | HDM101A | Der p 1 | | NYSQIYPPNVNKIREA |
| 262 | HDM201 | Der p 1 | | ESVKYVQSNGGAI |
| 263 | HDM205 | Der p 1 | | SYYRYVAREQS |
| 264 | HDM26B | Der p 2 | | GVLASAIATHAKIR |
| 265 | HDM35A | Der p 7 | | RGLKQMKRVGDANV |

Table 6 shows additional peptides suggested for peptide combinations of the invertion.

Example 2

Assembling a Donor Population

This example includes a description of how to compose a donor population of house dust mite allergic individuals that represent a worldwide population with respect to HLA Class II allele repertoire.

Donors (n=59) from the Copenhagen area were recruited by determining immunological reactivity to house dust mite allergen extract and by confirming clinical history consistent with house dust mite allergy. Donors with detectable specific IgE levels towards Der p (extract) or Der f (extract) were included.

Each donor was genotyped with respect to their HLA loci DRB1, DRB3, DRB4, DRB5, DP, and DQ by the vendor Proimmune using PCR amplification by the Tier 1 method. In short, the PCR-sequence specific oligonucleotides (PCR-SSOP) were used to resolve major allele groups to 4 digits, with a certain degree of degeneracy between highly related alleles. PCR-SSOP: The genomic DNA was amplified using PCR and then incubated with a panel of different oligonucleotide probes, which have distinctive reactivity with different HLA-types. Table 7 shows the HLA class II allele repertoire of the initial donor population and that this donor population represent 23 different HLA-DRB1 alleles.

For the purpose of calculating worldwide HLA coverage of the donor population, there were selected a fraction (28 alleles) of the originally detected alleles of Table 7, because this fraction of alleles were available for determining which HLA alleles the peptides are able to bind to. Table 8 shows the worldwide HLA allele frequencies (calculated) of the limited set of 28 alleles (Table 8). The frequencies represent an average frequency across several world-wide populations. In detail: Average haplotype and phenotype frequencies for individual HLA-DRB1 alleles are based on MHC data available at The Allele Frequency Net Database (AFND) found at the website located at www.allelefrequencie.net. As an estimated world wide allele distribution is used frequencies from the four major ethnical groups, Hispanics, Caucasians, African Americans, and Asians. The frequencies are calculated as the simple mean of the frequencies from population IDs, 1514, 1513, 2419, and 2420, respectively. Each ethnical group consists of data from more than 1000 individuals. Average haplotype and phenotype frequencies for other alleles are based on MHC data available at dbMHC (available at the internet site located at www.ncbi.nlm.nih.gov/projects/gv/mhc/). dbMHC data considers prevalence in Europe, North Africa, North-East Asia, the South Pacific (Australia and Oceania), Hispanic North, South America, American Indian, South-East Asia, South-West Asia, and Sub-Saharan Africa populations. DP and DRB3/4/5 frequencies consider only the beta chain frequency, given that the DRA chain is largely monomorphic, and that differences in DPA are not hypothesized to significantly influence binding. Frequency data are not available for DRB3/4/5 alleles. However, because of linkage with DRB1 alleles, coverage for these specificities may be assumed as follows: DRB3 with DR3, DR11, DR12, DR13 and DR14; DRB4 with DR4, DR7 and DR9; DRB5 with DR15 and DR16. Specific allele frequencies at each B3/B4/B5 locus are based on published associations with various DRB1 alleles, and assume only limited variation at the indicated locus.

Figure 21:
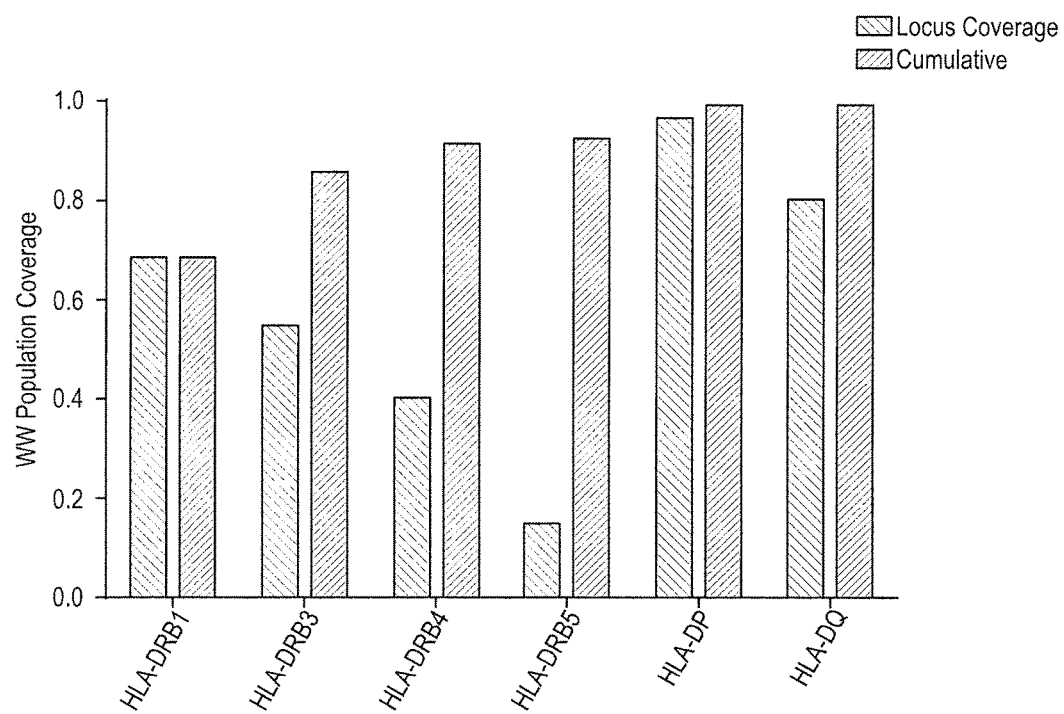
FIG. 21: This figure shows the selected subset of HLA alleles from single loci (Table 8) that would individually be present in between 15% and 97% of a worldwide population and together the alleles would be present in 99% of the worldwide population.
Figure 22:
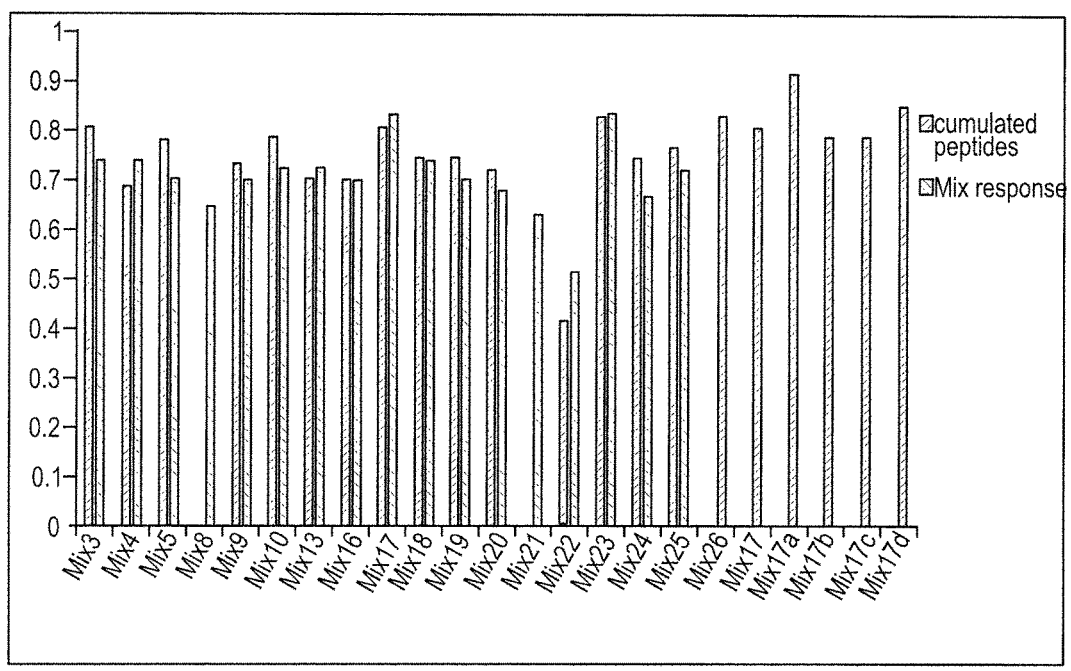
FIG. 22: This figure refers to the cumulated T cell responses of various peptide combinations. The figure shows T cell response frequencies of peptide combinations calculated from the actual single peptide T cell responses and compared to the actual T cell responses determined on peptide combinations. There is found a high correlation between cumulated single T cell responses of each peptide in the peptide combination and the actual T cell response of the peptide combination, thereby indicating that the T cell response of additional suggested peptide combinations can be estimated with high probability using the single peptide responses.

HLA allele frequencies shown in Table 8 were used to calculate the fraction of a worldwide population that would be covered by this subset of alleles. As shown in FIG. 21 the selected allele subset from each single locus individually represents between 15 and 97% of a worldwide population, and the cumulated population coverage amounts to about 100%.

21 different HLA-DRB1 alleles were found in the donor population and are shown in Table 7. These alleles will be present in 89% of a worldwide population according to the frequencies of Table 8. A final donor population of 47 individuals was then assembled, and the HLA-DRB1 alleles from this group are found in 85% instead of 89% of a worldwide population. The final donor population (n=47) has 25 of the 28 alleles shown in Table 8 and a global population HLA coverage of about 100% could be estimated. Thus, the donor population may represent a global donor population with respect to the most frequent HLA Class II alleles.

TABLE 7

HLA alleles
Table 7 - HLA Class II alleles found in the initial donor population

| DRB | DPA | DQA |
|---|---|---|
| DRB1_0101 | DPA10103-DPB10101 | DQA10101-DQB10201 |
| DRB1_0103 | DPA10103-DPB10201 | DQA10101-DQB10202 |
| DRB1_0301 | DPA10103-DPB10301 | DQA10101-DQB10301 |
| DRB1_0401 | DPA10103-DPB10401 | DQA10101-DQB10302 |
| DRB1_0404 | DPA10103-DPB10402 | DQA10101-DQB10501 |
| DRB1_0405 | DPA10103-DPB10501 | DQA10101-DQB10503 |
| DRB1_0406 | DPA10103-DPB10601 | DQA10101-DQB10603 |
| DRB1_0407 | DPA10103-DPB11001 | DQA10102-DQB10201 |
| DRB1_0701 | DPA10103-DPB110401 | DQA10102-DQB10202 |
| DRB1_0801 | DPA10103-DPB110501 | DQA10102-DQB10301 |
| DRB1_0803 | DPA10103-DPB11101 | DQA10102-DQB10302 |
| DRB1_0901 | DPA10103-DPB111101 | DQA10102-DQB10303 |
| DRB1_1101 | DPA10103-DPB11301 | DQA10102-DQB10402 |
| DRB1_1103 | DPA10103-DPB11501 | DQA10102-DQB10502 |
| DRB1_1104 | DPA10103-DPB11601 | DQA10102-DQB10602 |

TABLE 7-continued

HLA alleles
Table 7 - HLA Class II alleles found in the initial donor population

| DRB | DPA | DQA |
|---|---|---|
| DRB1_1109 | DPA10103-DPB11701 | DQA10102-DQB10603 |
| DRB1_1201 | DPA10103-DPB12301 | DQA10102-DQB10604 |
| DRB1_1301 | DPA10103-DPB15901 | DQA10102-DQB10609 |
| DRB1_1302 | DPA10201-DPB10101 | DQA10103-DQB10201 |
| DRB1_1303 | DPA10201-DPB10201 | DQA10103-DQB10202 |
| DRB1_1401 | DPA10201-DPB10301 | DQA10103-DQB10301 |
| DRB1_1501 | DPA10201-DPB10401 | DQA10103-DQB10302 |
| DRB1_1601 | DPA10201-DPB10402 | DQA10103-DQB10501 |
| DRB3_0101 | DPA10201-DPB10501 | DQA10103-DQB10601 |
| DRB3_0201 | DPA10201-DPB10901 | DQA10103-DQB10603 |
| DRB3_0202 | DPA10201-DPB11001 | DQA10201-DQB10201 |
| DRB3_0301 | DPA10201-DPB11101 | DQA10201-DQB10202 |
| DRB4_0101 | DPA10201-DPB11301 | DQA10201-DQB10301 |
| DRB4_0103 | DPA10201-DPB11401 | DQA10201-DQB10302 |
| DRB5_0101 | DPA10201-DPB11701 | DQA10201-DQB10303 |
| DRB5_0202 | DPA10201-DPB12301 | DQA10201-DQB10501 |
| | DPA10202-DPB10101 | DQA10201-DQB10602 |
| | DPA10202-DPB10201 | DQA10201-DQB10603 |
| | DPA10202-DPB10401 | DQA10201-DQB10604 |
| | DPA10202-DPB10402 | DQA10201-DQB10609 |
| | DPA10202-DPB10501 | DQA10301-DQB10201 |
| | | DQA10301-DQB10202 |
| | | DQA10301-DQB10301 |
| | | DQA10301-DQB10302 |
| | | DQA10301-DQB10303 |
| | | DQA10301-DQB10402 |
| | | DQA10301-DQB10501 |
| | | DQA10301-DQB10502 |
| | | DQA10301-DQB10503 |
| | | DQA10301-DQB10601 |
| | | DQA10301-DQB10602 |
| | | DQA10301-DQB10603 |
| | | DQA10301-DQB10604 |
| | | DQA10401-DQB10301 |
| | | DQA10401-DQB10302 |
| | | DQA10401-DQB10402 |
| | | DQA10401-DQB10602 |
| | | DQA10501-DQB10201 |
| | | DQA10501-DQB10202 |
| | | DQA10501-DQB10301 |
| | | DQA10501-DQB10302 |
| | | DQA10501-DQB10303 |
| | | DQA10501-DQB10402 |
| | | DQA10501-DQB10501 |
| | | DQA10501-DQB10602 |
| | | DQA10501-DQB10603 |
| | | DQA10505-DQB10202 |
| | | DQA10505-DQB10301 |
| | | DQA10505-DQB10302 |
| | | DQA10505-DQB10501 |
| | | DQA10510-DQB10301 |
| | | DQA10510-DQB10604 |

This table shows the HLA Class II allele repertoire of the initial donor population.

TABLE 8

HLA alleles selected for prediction of HLA worldwide coverage
Table 8 - HLA frequencies in a worldwide population

| Alleles (n = 13) | Frequency | Alleles (n = 15) | Frequency |
|---|---|---|---|
| DPA10201-DPB10101 | 0.084 | DRB1_0101 | 0.043 |
| DPA10103-DPB10201 | 0.092 | DRB1_0301 | 0.077 |
| DPA10103-DPB10301 | 0.07 | DRB1_0401 | 0.034 |
| DPA10103-DPB10401 | 0.201 | DRB1_0405 | 0.023 |
| DPA10103-DPB10402 | 0.236 | DRB1_0701 | 0.102 |
| DPA10202-DPB10501 | 0.115 | DRB1_0802 | 0.027 |
| DPA10201-DPB11401 | 0.038 | DRB1_0901 | 0.040 |
| DQA10501-DQB10201 | 0.058 | DRB1_1101 | 0.057 |
| DQA10501-DQB10301 | 0.195 | DRB1_1201 | 0.023 |
| DQA10301-DQ810302 | 0.1 | DRB1_1302 | 0.045 |
| DQA10401-DQB10402 | 0.066 | DRB1_1501 | 0.074 |

TABLE 8-continued

HLA alleles selected for prediction of HLA worldwide coverage
Table 8 - HLA frequencies in a worldwide population

| Alleles (n = 13) | Frequency | Alleles (n = 15) | Frequency |
|---|---|---|---|
| DQA10101-DQB10501 | 0.076 | DRB3_0101 | 0.14 |
| DQA10102-DQB10602 | 0.076 | DRB3_0202 | 0.189 |
|  |  | DRB4_0101 | 0.237 |
|  |  | DRB5_0101 | 0.083 |

Figure 18:
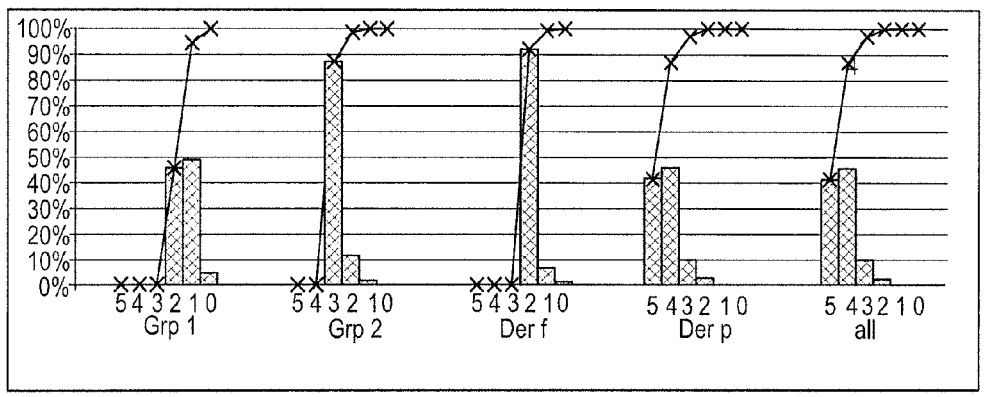
Figure 19:
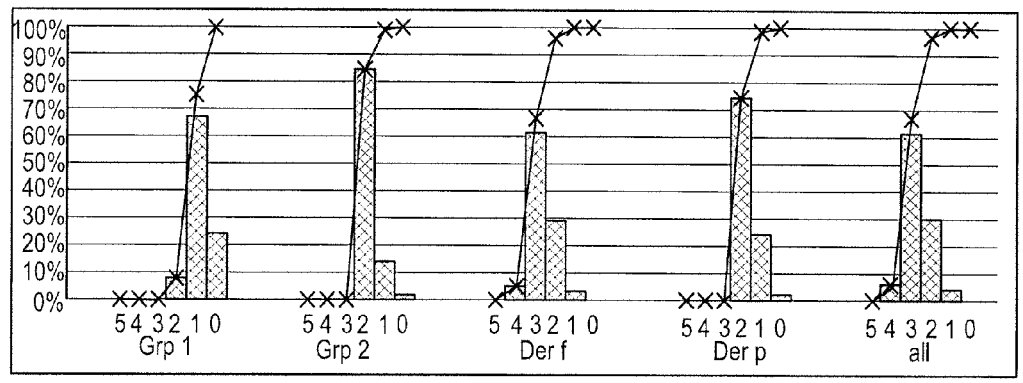
Figure 20:
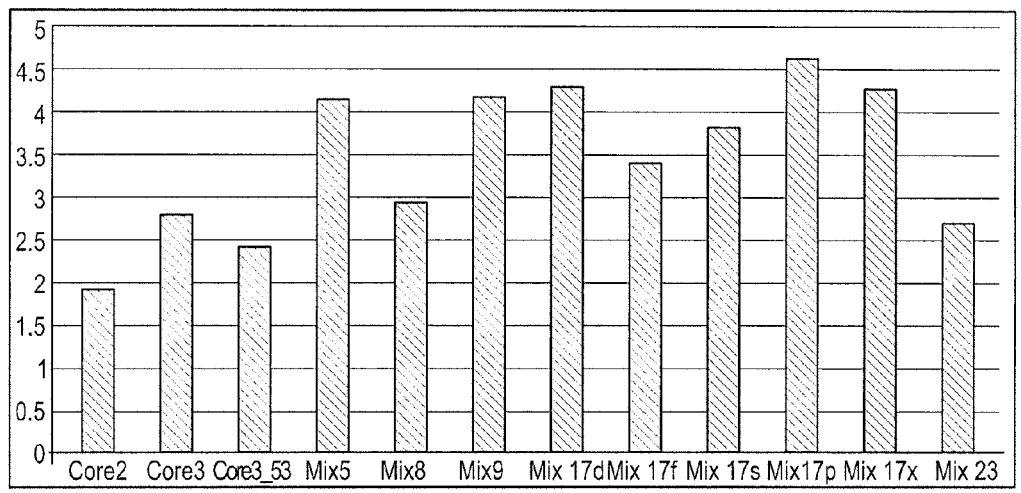
FIG. 20 shows the predicted average number of peptides that a patient of the virtual patient population described in Example 10 potentially can respond to in the peptide combinations shown (i.e. have HLA Class II alleles potentially able to bind to peptides in the combination, wherein the estimation is based on predicted HLA allele coverage of alleles shown in Table 17.

Table 8 shows the HLA allele frequencies in a worldwide population for a fraction (28 HLA alleles) of the alleles found in the initial donor population. These allele frequencies were used in the prediction of donor HLA worldwide coverage shown in FIG. 18.

Example 3

Screening for T Cell Reactivity

This example includes a description of how peptides (singly or in combination) were screened for T cell reactivity in the donor population.

The T cell reactivity to peptides disclosed herein was determined either by measuring T cell proliferation of T cell lines specific to the allergens investigated or by measuring the cytokine production of allergen-specific T cells obtained from cultured PBMCs.

Establishing cultured PBMCs and T-cell lines (TCL): TCL specific to the six allergens rproDer p 1, rproDer f 1, rDer p 2, rDer f 2, Der p 4 and Der p 7, respectively or specific to the combination of all six allergens were established from peripheral blood mononuclear cells (PBMCs) of each donor.

PBMCs were isolated from freshly drawn heparinized blood by gradient centrifugation on lymphoprep (Nycomed, Norway), washed twice and re-suspended in RPMI 1640 medium with HEPES and ultraglutamine (Cambrex, Belgium) supplemented with 5% v/v AB-serum (Cambrex, Belgium), 100 units/ml penicillin, and 0.1 mg/ml streptomycin (Sigma, St Louis, USA) (referred to as AB-medium). Isolated PBMCs were CD8 depleted by Macs magnetic depletion according to the manufacturer's instructions (Miltenyi Biotec, Bergisch Gladbach, Germany). CD8-depleted PBMC ($2\times10^6$/ml) were stimulated in 1 ml bulk cultures in AB medium in 24 well plates (Nunc, Denmark) with a mixture of recombinant allergens: rDer p1, rDer f1, r Derp2, rDerf2, rDerp4, rDerp7, 1 μg/ml of each, for 14 days. An amount of 65 U, 30 U, and 30 U recombinant IL-2 (Chiron, USA) were added per well at days 5, 6 and 7, respectively.

After 14 days, T-cells were isolated, washed and one aliquot was used for determination of the cytokine production, e.g. IL-5, by ELISpot assay (Enzyme-Linked ImmunoSpot) as described below. The remaining T-cells were re-stimulated in AB-medium with autologous PBMCs ($10^6$/well, irradiated 2500 Rad), allergens as above (1 μg/ml), and PHA-P (0.5 μg/ml, Difco, Detroit, Mich., USA). rIL-2 was added at day 3, 4 and 5. 10 days after re-stimulation T-cells are isolated, washed and used for T cell proliferation assay as described below. Remaining cells are frozen for later thawing and re-stimulation. The lines are kept in culture with re-stimulation every 10 days with allogeneic EBV B-cells ($10^5$/well, irradiated 3500 Rad), allogeneic PBMCs ($10^6$/well, irradiated 2500 Rad), and 0.5 μg/ml PHA-P and addition of rIL-2 at days 3-5. The cell line cultures are terminated after a period of 5 weeks, so all ELISpot data are obtained after 14 days of culture whereas proliferative responses are obtained after 24 or 34 days in culture Alternatively, allergen-specific T cells were obtained in the following manner; PBMCs were thawed and cultured in RPMI 1640 (Ω Scientific, Tarzana, Calif.) supplemented with 5% human AB serum (Cellgro, Herndon, Va.) at a density of $2\times10^6$ cells/ml in 24-well plates (BD Biosciences, San Jose, Calif.) and stimulated with a mixture of recombinant allergens: rDer p1, rDer f1, r Derp2, rDerf2, rDerp4, rDerp7, 1 μg/ml of each. Cells were kept at 37° C., 5% $CO_2$ and additional IL-2 (10 U/ml, eBioscience, San Diego, Calif.) was added every 3 days after initial antigenic stimulation. On day 14, cells were harvested and screened for reactivity against either selected peptides from Der p1, Der f1, Der p2, Der f2, Der p4 or Der p7 or peptide pools consisting on average of 20 peptides. On day 17, peptides from positive pools were tested individually to identify the reactive epitopes.

ELISpot assays. The production of IL-5 and IFN-γ from the cultured PBMCs described above in response to stimulation with a peptide described herein was measured by ELISpot as described in Oseroff C et al, 2010. Briefly, flat-bottom 96-well nitrocellulose plates (Millipore, Bedford, Mass.) were prepared according to the manufacturer's instructions and coated with 10 μg/ml anti-human IL-5 and anti-human IFN-γ. The next day, plates were washed, blocked and cells ($1\times10^5$ cells/well) were plated and incubated with single peptide, peptide pool or a mixture of Der p and Der f (10 μg/ml, 5 μg/ml and 5 μg/ml, respectively). After 24 hours, cells were removed and plates were incubated with 2 μg/ml biotinylated anti-human IL-5 Ab (clone 5A10; Mabtech) and anti-human IFN-γ-HRP (clone 7-B6-1-HRP; Mabtech) at 37° C. After 2 hours, plates were washed and avidin-alkaline phosphatase-complex was added (Vector Laboratories, Burlingame, Calif.) for 1 h at RT. Alkaline phosphatase-conjugated spots were developed with Vector Blue Substrate Kit (Vector Labs, Burlingame, Calif.). Horseradish Peroxidase-conjugated spots were developed with 3-amino-9-ethylcarvazole solution (Sigma-Aldrich, St. Louis, Mo.). Criteria for peptide positivity were 20 SFCs/$10^6$ PBMCs, $p \le 0.05$ stimulated cells compared to background, and a stimulation index (SI)≥2.

T cell proliferation assay: The capacity of the different peptides to stimulate allergen specific T cells is analyzed in a standard 72 h T cell proliferation assay, as described in Henmar H et al., Clin Exp Immunol 2008; 153β):316-23.

Cytokine measurements: Alternative to the ELISpot assay, the cytokine production of T cells can be measured in cell culture supernatants harvested at day 1 of the procedure for ELISpot assays or at day 2 of the procedure use for proliferation assays by analyzing the supernatants by MesoScale or MagPix analysis. The design of both assays resemble ELISA assays with the capture antibodies of several different specificities spotted in each well of a 96 well plate (Mesoscale, #144259) or the individual catching antibodies attached to beads that can be mixed to the final assay reagent (MagPix #230608) and both assays are developed to analyze various different cytokines or cellular mediators in a single sample. The cytokines IL-2, IL-4, IL-5, IL-10, IL-12, IL-13, and IFN-g can be measured by Mesoscale, whereas IL-4, IL-5, IL-9, IL-10, IL-12, IL-13, IL-17, IL-22, IL-31 can be measured by MagPix.

In the present set-up, the cytokine production was evaluated with respect to cytokine IL-5, which is predominantly produced by Th2 cells, but the evaluation could have been performed for other Th2-cytokines as well, e.g. IL-4, IL-13 or others. Finally, the cytokine production could have been evaluated with IL-10, which may be an indication of generation of regulatory T cells. This can be performed with FluoroSpot technique as replacement of ELISpot.

In addition, future evaluation of cytokine production from Peptide Mixes may be performed by Ex-Vivo FluoroSpot or EliSpot analysis of cytokines induced following peptide stimulation of PBMCs without any previous allergen stimulation.

Results:

FIGS. 1 to 4 show the percentage of donors that respond in the T-cell proliferation assay when T cells in vitro are exposed to the 20mers peptides of Tables 2 and 3. FIGS. 5 to 8 show the percentage of donors that responds in the T-cell proliferation assay when T cells in vitro are exposed to the 15mers peptides of Tables 4 and 5. Peptides to which a higher fraction of the donor population respond to (e.g. more than 20%, 25%, 30%, 40%, 50% of the donor population responds to) can be extracted from the figures and are listed in Tables 9 and 10 shown below. Those peptides are herein named "high responder peptides". Where two overlapping 15mers peptides both are considered high responder peptides, the redundant amino acid sequence having a length of 20 amino acids was assembled and is also shown in Tables 9 and 10 (SEQ ID NOS: 272-285). The two tables also indicate peptides that were selected for initial screening of peptide combinations in order to assemble peptide combinations with high coverage. These are herein named "parent peptides" (parent peptides are indicated with their Pep ID or SEQ ID in bold in Tables 9 and 10). Among peptides screened from Der p 1 and Der f 1, the following peptides were considered "parent peptides": peptides having an amino acid sequence of SEQ ID NOs: 9 (pep-041), 10 (pep-042), 11 (pep-043), 12 (pep-044), 42 (pep-072), 254 (pep-022), 15 (pep-047), 266 (pep-123), 255 (pep-025), 17 (pep-049), 46 (pep-075), 18 (pep-050), 258 (pep-122), 267 (pep-124), 20 (pep-052), 49 (pep-078), 21 (pep-053), 268 (pep-130), 22 (pep-054), 23 (pep-055), 52 (pep-081), 26 (pep-058), 29 (pep-061), 58 (pep-087), 251 (pep-010), 252 (pep-011) and 272.

Among peptides screened from Der p 2 and Der f 2, the following peptides were considered "parent peptides": Peptides with SEQ ID NOs: 71 (pep-100), 72 (pep-101), 60 (pep-089), 61 (pep-090), 73 (pep-102), 249 (pep-002), 62 (pep-091), 63 (pep-092), 77 (pep-106), 67 (pep-096), 271 (pep-131), 79 (pep-108), 256 (pep-031), 270 (pep-126), 81 (pep-109), 269 (pep-125), 70 (pep-099) and 82 (pep-110).

TABLE 9

Peptides from Der p 1 and Der f 1 with "high" responder frequency in T cell assays

| SEQ ID NO: | Pep ID: | Species: | aa length: | Peptide group: | Peptide sequence from Der p 1 or Der f 1 or both (pf1) |
|---|---|---|---|---|---|
| | | | | 1 | 36 (position number) |
| 90 | | p1 | 15 | | VKYVQSNGGAINHLS |
| | | | | 2 | 76 |
| 280 | | p1 | 20 | | DLNAETNACSINGNAPAEI |
| 98 | | p1 | 15 | | DLNAETNACSINGNA |
| 9 | 041 | p1 | 20 | 3 | TNASSINGNAPAEIDLRQM |
| 99 | | p1 | 15 | | TNACSINGNAPAEI |
| 10 | 042 | p1 | 20 | 4 | APAEIDLRQMRTVTPIRMQG |
| 259 | 203B | p1 | 19 | | DLRQMRTVTPIRMQGGSG |
| 102 | | p1 | 15 | | DLRQMRTVTPIRMQG |
| 161 | | f1 | 15 | | DLRSLRTVTPIRMQG |
| 281 | | p1 | 20 | | DLRQMRTVTPIRMQGGCGSC |
| 282 | | f1 | 20 | | DLRSLRTVTPIRMQGGCGSC |
| 11 | 043 | pf1 | 20 | 5 | RTVTPIRMQGGSGSSWAFSG |
| 103 | | pf1 | 15 | | RTVTPIRMQGGCGSC |
| 281 | | p1 | 20 | | DLRQMRTVTPIRMQGGCGSC |
| 282 | | f1 | 20 | | DLRSLRTVTPIRMQGGCGSC |
| | | | | 6 | 110 |
| 12 | 044 | pf1 | 20 | | GSGSSWAFSGVAATESAYLA |
| 105 | | pf1 | 15 | | GCGSCWAFSGVAATE |
| 283 | | pf1 | 20 | | GCGSCWAFSGVAATESAYLA |
| 106 | | pf1 | 15 | | WAFSGVAATESAYLA |
| 42 | 072 | f1 | 20 | 7 | VAATESAYLAYRNTSLDLSE |
| 166 | | f1 | 15 | | VAATESAYLAYRNTS |
| 254 | 022 | f1 | 15 | | AATESAYLAYRNTSLD |
| | | | | 8 | 140 |
| 15 | 047 | pf1 | 20 | | QELVDSASQHGSHGDTIPRG |
| 111 | | pf1 | 15 | | QELVDCASQHGCHGD |
| 270 | | pf1 | 20 | | QELVDCASQHGCHGDTIPRG |
| 112 | | pf1 | 15 | | CASQHGCHGDTIPRG |
| | | | | 9 | 158 |
| 266 | 123 | p1 | 22 | | RGIEYIQHNGVVQESYYRYVAR |
| 255 | 025 | p1 | 15 | | RGIEYIQHNGVVQES |
| 17 | 049 | p1 | 20 | | IEYIQHNGVVQESYYRYVAR |
| 46 | 075 | f1 | 20 | | IEYIQQNGVVEERSYPYVAR |
| 271 | | f1 | 20 | | TIPRGIEYIQQNGVVEERSY |

TABLE 9-continued

Peptides from Der p 1 and Der f 1 with "high" responder frequency in T cell assays

| SEQ ID NO: | Pep ID: | Species: | aa length: | Peptide group: | Peptide sequence from Der p 1 or Der f 1 or both (pf1) |
|---|---|---|---|---|---|
| 114 | | p1 | 15 | | TIPRGIEYIQHNGVV |
| 173 | | f1 | 15 | | TIPRGIEYIQQNGVV |
| 115 | | p1 | 15 | | IEYIQHNGVVQESYY |
| 174 | | f1 | 15 | | IEYIQQNGVVEERSY |
| 18 | 050 | p1 | 20 | 10 | QESYYRYVAREQSSRRPNAQ |
| 258 | 122 | p1 | 16 | | QESYYRYVAREQSSRR |
| 267 | 124 | p1 | 21 | | VQESYYRYVAREQSSRRPNAQ |
| 117 | | p1 | 15 | | QESYYRYVAREQSCR |
| 176 | | f1 | 15 | | EERSYPYVAREQQCR |
| 120 | | p1 | 15 | 11 | 185 RPNAQRFGISNYCQI |
| 20 | 052 | p1 | 20 | 12 | RFGISNYSQIYPPNANKIRE |
| 49 | 078 | f1 | 20 | | HYGISNYSQIYPPDVKQIRE |
| 121 | | p1 | 15 | | RFGISNYCQIYPPNA |
| 180 | | f1 | 15 | | HYGISNYCQIYPPDV |
| 21 | 053 | p1 | 20 | 13 | YPPNANKIREALAQTHSAIA |
| 268 | 130 | p1 | 22 | 14 | 208 REALAQTHSAIAVIIGIKDLDA |
| 22 | 054 | p1 | 20 | | ALAQTHSAIAVIIGIKDLDA |
| 23 | 055 | p1 | 20 | 15 | VIIGIKDLDAFRHYDGRTII |
| 52 | 081 | f1 | 20 | | VIIGIKDLRAFQHYDGRTII |
| 272 | | p1 | 20 | | KDLDAFRHYDGRTIIQRDNG |
| 273 | | f1 | 20 | | KDLRAFQHYDGRTIIQHDNG |
| 128 | | p1 | 15 | | KDLDAFRHYDGRTII |
| 187 | | f1 | 15 | | KDLRAFQHYDGRTII |
| 129 | | p1 | 15 | | FRHYDGRTIIQRDNG |
| 188 | | f1 | 15 | | FQHYDGRTIIQHDNG |
| 26 | 058 | p1 | 20 | 16 | 250 HAVNIVGYSNAQGVDYWIVR |
| 133 | | p1 | 15 | | HAVNIVGYSNAQGVD |
| 192 | | f1 | 15 | | HAVNIVGYGSTQGVD |
| 274 | | p1 | 20 | | YQPNYHAVNIVGYSTQGVD |
| 191 | | f1 | 15 | | YQPNYHAVNIVGYGS |
| 29 | 061 | p1 | 22 | 17 | 280 GYGYFAANIDLMMIEEYPYVVI |
| 58 | 087 | f1 | 23 | | GYGYFQAGNNLMMIEQYPYVVIM |
| 251 | 010 | | 18 | | DNGYGYFAANIDLMMIEE |
| 252 | 011 | p1 | 14 | | NGYGYFAANIDLMM |
| 140 | | p1 | 15 | | AANIDLMMIEEYPYV |
| 199 | | f1 | 15 | | QAGNNLMMIEQYPYV |

TABLE 10

Peptides from Der p 2 and f 2 showing high responder frequency in T cell assays.

| SEQ ID NO: | Pep ID: | Species: | aa length: | Peptide group: | Peptide sequence from Der p 2 or Der f 2 both (pf2) |
|---|---|---|---|---|---|
| 71 | 100 | f2 | 18 | 1 | DQVDVKDSANNEIKKVMVD |
| 72 | 101 | f2 | 20 | 19 | NNEIKKVMVDGSHGSDPSII |
| 227 | | f2 | 15 | | NEIKKVMVDGCHGSD |
| 60 | 089 | p2 | | | NHEIKKVLVPGSHGSEPSII |
| 275 | | f2 | 20 | | KDCANNEIKKVMVDGCHGSD |
| 226 | | f2 | | | KDCANNEIKKVMVDG |
| 61 | 090 | p2 | 20 | 20 | GSHGSEPSIIHRGKPFQLEA |
| 73 | 102 | f2 | 20 | | GSHGSDPSIIHRGKPFTLEA |
| 276 | | p2 | 20 | | CHGSEPCIIHRGKPFQLEAV |

TABLE 10-continued

Peptides from Der p 2 and f 2 showing high responder frequency in T cell assays.

| SEQ ID NO: | Pep ID: | Species: | aa length: | Peptide group: | Peptide sequence from Der p 2 or Der f 2 both (pf2) |
|---|---|---|---|---|---|
| 277 |  | f2 | 20 |  | CHGSDPCIIHRGKPFTLEAL |
| 205 |  | p2 | 15 |  | CHGSEPCIIHRGKPF |
| 229 |  | f2 | 15 |  | CHGSDPCIIHRGKPF |
| 249 | 002 | p2 | 13 |  | SIIHRGKPFQLEA* |
| 206 |  | p2 | 15 |  | PCIIHRGKPFQLEAV |
| 230 |  | f2 | 15 |  | PCIIHRGKPFTLEAL |
|  |  |  |  | 21  30 |  |
| 62 | 091 | p2 | 20 |  | HRGKPFQLEAVFEANQNTKT |
| 208 |  | p2 | 15 |  | QLEAVFEANQNTKTA |
| 63 | 092 | p2 | 20 | 22 | VFEANQNTKTAKIEIKASID |
| 278 |  | f2 | 20 |  | FDANQNTKTAKIEIKASLDG |
| 233 |  | f2 | 15 |  | FDANQNTKTAKIEIK |
| 210 |  | p2 | 15 |  | NTKTAKIEIKASIDG |
| 234 |  | f2 | 15 |  | NTKTAKIEIKASLDG |
|  |  |  |  | 23  60 |  |
| 77 | 106 | f2 | 20 |  | GLEIDVPGIDTNASHFMKSP |
| 238 |  | f2 | 15 |  | PGIDTNACHFMKCPL |
|  |  |  |  | 24  80 |  |
| 67 | 096 | p2 | 20 |  | LVKGQQYDIKYTWNVPKIAP |
| 271 | 131 | p2 | 21 |  | LVKGQQYDIKYTWNVPKIAPK |
| 79 | 108 | f2 | 20 |  | LVKGQQYDAKYTWNVPKIAP |
| 256 | 031 | p2 | 15 |  | QQYDIKYTWNVPKIA |
| 270 | 126 | p2 | 15 |  | KGQQYDIKYTWNVPKIA |
| 279 |  | f2 | 20 |  | YDAKYTWNVPKIAPKSENVV |
| 242 |  | f2 | 15 |  | YDAKYTWNVPKIAPK |
| 243 |  | f2 | 15 |  | TWNVPKIAPKSENVV |
|  |  |  |  | 100 |  |
| 81 | 109 | f2 | 20 | 25 | KSENVVVTVKLVGDNGVLAS |
| 221 |  | p2 | 15 |  | SENVVVTVKVMGDDG |
| 245 |  | f2 | 15 |  | SENVVVTVKLVGDNG |
| 246 |  | f2 | 15 |  | VTVKLVGDNGVLACA |
| 269 | 125 | p2 | 20 | 26 | VMGDNGVLASAIATHAKIRD |
| 70 | 099 | p2 | 20 |  | VMGDDGVLASAIATHAKIRD |
| 82 | 110 | f2 | 20 |  | LVGDNGVLASAIATHAKIRD |
| 223 |  | p2 | 15 |  | MGDDGVLACAIATHA |
| 247 |  | f2 | 15 |  | VGDNGVLACAIATHA |
| 264 | 26B | p2 | 14 |  | GVLASAIATHAKIR* |
| 224 |  | p2 | 15 |  | GVLACAIATHAKIRD |
| 248 |  | f2 | 15 |  | GVLACAIATHAKIRD |
| 253 | 012 | p2 | 14 |  | VLASAIATHAKIRD* |

Example 4

Modification of Parent Peptides

This example describes modifications of parent peptides to improve the aqueous solubility, in particular to increase the solubility in an aqueous solution having pH in a physiologically acceptable range, e.g. from 6 to 8. Solubility is closely related to the ratio between hydrophilic and hydrophobic amino acid residues and the net charge state of the peptide. Peptides have zero net charge at pH=pI, and would be expected to show the lowest solubility at this pH. Table 11b demonstrates that the pI (theoretically estimated) increases along with the net charge by adding one or more arginine residues to the parent peptides pep-058, pep-075 and pep-130 and that it is possible to increase the pI to above 8. Table 11b also shows that the solubility at pH 7 (evaluated by visual inspection) is increased for some of the modified peptides by adding one or more arginine residues to the N- and/or C-terminus. The solubility of these peptides was increased at pH values outside the physiological range (data not shown).

Table 11a shows other examples on how to modify the pI and the net charge by adding one or more amino acid residues from the wild type allergen to the N- and/or C-terminus of the peptides pep-049, pep-054, pep-031, pep-096, pep-075 and pep-130. The pI and net charge were estimated using known tools in the art. Table 11a also shows modifications made with the purpose of avoiding an N-terminal "Q" amino acid residue in pep-050 and to avoid the two adjacent amino acids "DG" in the sequence of pep-099.

The net charge of a peptide may be changed by acetylation of the N-terminal amino acid residue, which removes one positive charge (=net charge decreased by 1) or by the amidation of the C-terminal amino acid residue, which removes one negative charge (=net charge increased by 1). Table 11c shows examples on C-terminus amidation of peptides pep-058, pep-075 (along with addition of the RG amino acid residues at the N-terminus), pep-110, pep-130, pep-091 and pep-123, which demonstrate that the pI and net charge increase.

Peptides were tested for their ability to dissolve in aqueous solutions at different pH values. In short, each of the peptides were dissolved in water (pH about 5-6), hydrochloride solution at pH 2 (10 mM HCl), acetate buffer with pH 5 (20 mM acetate and 140 mM sodium chloride), phosphate buffer with pH 7 (20 mM phosphate and 140 mM sodium chloride) or bistrispropate buffer with pH 9 (20 mM bistrispropane and 140 mM sodium chloride, respectively, to produce a final molar concentration of the peptide of about 0.25 mM or 1 mM. Optionally, about 20% DMSO may be part of the solution. For comparison reasons, peptides were also dissolved in acetonitrile or DMSO. The solutions were inspected visually before and after centrifugation for turbidity, presence of particles/aggregates. In addition, presence of turbidity/particles/aggregates were detected by optical density (OD), but might also be detected by size-exclusion chromatography. Sub-visual particles may also be detected by dynamic light scattering (DLS) analysis. The solubility and stability of each peptide were also investigated using HPLC, e.g. RP-HPLC. For example, each of the solutions were injected onto the HPLC and the peak height or peak area of each of the peptides were compared to the corresponding peptide of a chromatogram of peptides dissolved in acetonitrile or DMSO—as peptides were assumed to be fully dissolved and stable in these solvents.

Table 11a to 11c—Examples of Peptides with Changes in Solubility

TABLE 11a

Addition of amino acid residue(s) from wild type isoform

| SEQ ID NO | Pep ID No | Sequence | Modified from Peptide: | Change in pI | Change in charge at pH 7 | Solubility at pH 7 |
|---|---|---|---|---|---|---|
| 266 | 123 | RGIEYIQHNGVVQESYYRYVAR | 049 | 7.6 to 9.3 | 0.1 to 1.1 | Slight turbid |
| 267 | 124 | VQESYYRYVAREQSSRRPNAQ | 050 | | | |
| 268 | 130 | REALAQTHSAIAVIIGIKDLDA | 054 | 5.1 to 5.3 | Unchanged (-0.9) | Slight turbid |
| 269 | 125 | VMGDNGVLASAIATHAKIRD | 099 | | | |
| 270 | 126 | KGQQYDIKYTWNVPKIA | 031 | 9.5 to 9.9 | 1 to 2 | Clear |
| 271 | 131 | LVKGQQYDIKYTWNVPKIAPK | 096 | 9.9 to 10.1 | 2 to 3 | Clear |
| 272 | 134 | RGIEYIQQNGVVEERSYPYVAR | 075 | 4.6 to 7.0 | -1 to 0 | Clear |
| 273 | 135 | KIREALAQTHSAIAVIIGIKDLDA | 130 | 5.3 to 7.8 | -0.9 to 0.1 | Slight turbid |

TABLE 11b

Addition of Arginine(s)

| SEQ ID NO | Peptide ID | Sequence | pI | Net charge at pH 7 | Solubility at pH 7 (visual inspection) |
|---|---|---|---|---|---|
| | 058 | HAVNIVGYSNAQGVDYWIVR | 7.7 | 0.1 | Slight turbid |
| 276 | 136 | RHAVNIVGYSNAQGVDYWIVR | 9.6 | 1.1 | Slight turbid |
| 277 | 137 | RHAVNIVGYSNAQGVDYWIVRR | 10.2 | 2.1 | Clear |
| 278 | 138 | RRHAVNIVGYSNAQGVDYWIVRR | 11.1 | 3.1 | Slight turbid |
| 274 | 132 | RRRHAVNIVGYSNAQGVDYWIVR | 11.8 | 4.1 | Slight turbid |
| 275 | 133 | RRHAVNIVGYSNAQGVDYWIVRRR | 11.8 | 4.1 | Clear |
| | 075 | IEYIQQNGVVEERSYPYVAR | 4.6 | -1 | Turbid |
| 279 | 139 | RIEYIQQNGVVEERSYPYVAR | 7 | 0 | Clear |
| 280 | 140 | RIEYIQQNGVVEERSYPYVARR | 9.4 | 1 | Clear |
| 281 | 141 | RRIEYIQQNGVVEERSYPYVARR | 9.9 | 2 | Clear |
| 282 | 142 | RRIEYIQQNGVVEERSYPYVARRR | 10.4 | 3 | Clear |
| 268 | 130 | REALAQTHSAIAVIIGIKDLDA | 5.3 | -0.9 | Slight turbid |

TABLE 11b-continued

Addition of Arginine(s)

| SEQ ID NO | Peptide ID | Sequence | pI | Net charge at pH 7 | Solubility at pH 7 (visual inspection)^ |
|---|---|---|---|---|---|
| 283 | 143 | RREALAQTHSAIAVIIGIKDLDA | 7.8 | 0.1 | Slight turbid |
| 284 | 144 | RREALAQTHSAIAVIIGIKDLDAR | 10.1 | 1.1 | Clear |
| 285 | 145 | RRREALAQTHSAIAVIIGIKDLDAR | 11.2 | 2.1 | Clear |
| 286 | 146 | RRREALAQTHSAIAVIIGIKDLDARR | 11.8 | 3.1 | Clear |

TABLE 11c

Amidation (-NH2)

| Corresp. SEQ ID NO (peptide SEQ ID NO without amidation) | Pep ID No | Sequence | From Peptide: | Change in pI* | Change in charge at pH 7* | Solubility at pH 7 |
|---|---|---|---|---|---|---|
| 26 | 147 | HAVNIVGYSNAQGVDYWIVR-NH2 | 058 | 7.7 to 9.6 | 0.1 to 1.1 | ND |
| 272 | 148 | RGIEYIQQNGVVEERSYPYVAR-NH2 | 075 | 4.6 to 9.4 | -1 to 1 | Slight turbid |
| 82 | 149 | LVGDNGVLASAIATHAKIRD-NH2 | 110 | 7.8 to 10.1 | 0.1 to 1.1 | Clear |
| 273 | 150 | KIREALAQTHSAIAVIIGIKDLDA-NH2 | 130 | 5.3 to 9.9 | -0.9 to 1.1 | Clear |
| 62 | 151 | HRGKPFQLEAVFEANQNTKT-NH2 | 091 | 9.9 to 10.6 | 1.1 to 2.1 | Clear |
| 266 | 152 | RGIEYIQHNGVVQESYYRYVAR-NH2 | 123 | 9.3 to 9.8 | 1.1 to 2.1 | ND |

Example 5

Selecting Candidates for Peptide Combinations

This example includes a description of how to assemble peptide combinations (pep-mixes), which with high likelihood would cover the worldwide (WW) HLA Class II allele repertoire and which will explore satisfactorily high frequency of T cell recognition in a worldwide population. Such peptide combinations would be eligible for peptide vaccines offered to a subject of any geographic region in the world with the expectation that the immune system will recognize at least one of the peptides in the peptide combination.

A peptide may be eligible for peptide combinations of the invention if it meets a first criterion of having high WW HLA coverage, preferably of above 0.4 (40% of WW population). The potential WW population coverage afforded by a peptide was determined on the basis of predicted capacity to bind a panel of 83 different HLA DR, DQ and DP molecules (Table 17). The coverage was calculated essentially as previously described in the literature (Bui et al. 2006; Sidney et al. 1996; Sidney et al. 2010a; Sidney et al. 2010b) based on MHC data available at dbMHC (available at the internet sites located at www.ncbi.nlm.nih.gov/projects/gv/mhc/.) (Meyer et al. 2007) and at www.allelefrequencie.net/ Middleton et al. 2003). These databases consider prevalence in Australia, Europe, North Africa, North America, North-East Asia, Oceania, Other, South America, South-East Asia, South-West Asia, and Sub-Saharan Africa. These populations are additionally inclusive of several sub-populations. The predictions and coverage calculations were performed with respect to the 30most prevalent alleles/haplotypes within the HLA loci, HLA-DRB1, HLA-DQ, and HLA-DP. For HLA-DQ and HLA-DP based MHC molecules both the alpha and the beta chains are in principle polymorphic, and the peptide specificity of the complete molecule thus determined by both alleles. As accurate haplotype data are not available concerning the coupling between the genetically linked alpha and beta chains for HLA-DQ and HLA-DP loci, respectively, it was assumed that they are genetically unlinked in the frequency calculation of the final haplotypes. The 83 considered alleles and the corresponding frequency data are displayed in Table 17. HLA-peptide binding predictions were conducted using the tool NetMHCIIpan-3.0 (Karosiene, Edita, Michael Rasmussen, Thomas Blicher, Ole Lund, Søren Buus, and Morten Nielsen. "NetMHCII-pan-3.0, a Common Pan-specific MHC Class II Prediction Method Including All Three Human MHC Class II Isotypes, HLA-DR, HLA-DP and HLA-DQ." Immunogenetics) available at the internet site located at www.cbs.dtu.dk/services/NetMHCIIpan-3.0. The peptides were considered positive to a given allele if the affinity was predicted to be lower than 300 nM and have a fractile score lower than 30% as reported by the prediction tool. For each peptide the frequency of each predicted positive allele was summed for each of the loci and the final predicted population coverage was calculated.

According to a second criterion, a peptide eligible for a peptide combination of the invention may have high frequency of T cell recognition in the donor population, which may be found among the parent peptides shown in Tables 9 and 10 or a variant thereof.

Table 12 lists examples of parent peptides initially selected for assembling peptide combinations in accordance with the first and second criterion described above together with their predicted worldwide HLA Class II coverage. Each peptide is also rated as A, B, C or D. The rating A denotes that the peptide has predicted WW HLA coverage above 0.4 (40% of WW population) and is recognized by T cells with a high frequency in the donor population. The rating B means that despite predicted low HLA WW coverage, the peptide gave a high frequency in T cell responses in the donor population investigated. The rating C means a peptide having high HLA prediction, but seems to give a low frequency in T cell recognition. The rating D means that the peptide had a borderline satisfactorily WW HLA coverage and T cell recognition frequency.

Table 13 shows the predicted WW HLA coverage of each of seven peptides of a peptide combination suggested for treating house dust mite allergy (International patent application WO2009 022156).

TABLE 12

Example Candidate Peptides

| SEQ ID No | Parent peptide | Peptide group | Sequence | Predicted WW HLA coverage | Rating |
|---|---|---|---|---|---|
| 9 | 041 | 3 | TNASSINGNAPAEIDLRQM | 0.8309 | C |
| 10 | 042 | 4 | APAEIDLRQMRTVTPIRMQG | 0.8684 | A |
| 11 | 043 | 5 | RTVTPIRMQGGSGSSWAFSG | 0.6903 | A |
| 12 | 044 | 6 | GSGSSWAFSGVAATESAYLA | 0.9639 | A |
| 42 | 072 | 7 | VAATESAYLAYRNTSLDLSE | | |
| 249 | 022 | 7 | ATESAYLAYRNTSLD | 0.6262 | C |
| 15 | 047 | 8 | QELVD$\underline{S}$ASQHG$\underline{S}$HGDTIPRG | 0 | D |
| 255 | 025 | 9 | RGIEYIQHNGVVQES | ND | B |
| 17 | 049 | 9 | IEYIQHNGVVQESYYRYVAR | 0.9434 | A |
| 46 | 075 | 9 | IEYIQQNGVVEERSYPYVAR | 0.0924 | B |
| 266 | 123 | 9 | RGIEYIQHNGVVQESYYRYVAR | | A |
| 258 | 122 | 10 | QESYYRYVAREQSSRR | 0.5776 | A |
| 18 | 050 | 10 | QESYYRYVAREQSSRRPNAQ | 0.5776 | A |
| 20 | 052 | 12 | RFGISNYSQIYPPNANKIRE | 0.3248 | B |
| 49 | 078 | 12 | HYGISNYSQIYPPDVKQIRE | 0.1907 | B |
| 21 | 053 | 13 | YPPNANKIREALAQTHSAIA | 0.785 | A |
| 22 | 054 | 14 | ALAQTHSAIAVIIGIKDLDA | 0.9148 | A |
| 268 | 130 | 14 | REALAQTHSAIAVIIGIKDLDA | | A |
| 23 | 055 | 15 | VIIGIKDLDAFRHYDGRTII | 0.287 | B |
| 52 | 081 | 15 | VIIGIKDLRAFQHYDGRTII | 0.8372 | A |
| 26 | 058 | 16 | HAVNIVGYSNAQGVDYWIVR | 0.7899 | A |
| 251 | 010 | 17 | DNGYGYFAANIDLMMIEE | 1 | A |
| 252 | 011 | 17 | NGYGYFAANIDLMM | 0.9996 | A |
| 58 | 087 | 17 | GYGYFQAGNNLMMIEQYPYVVIM | 0.9996 | A |
| 29 | 061 | 17 | GYGYFAANIDLMMIEEYPYVVIL | 1 | A |
| 71 | 100 | 18 | DQVDVKDSANNEIKKVMVD | | |

TABLE 12-continued

Example Candidate Peptides

| SEQ ID No | Parent peptide | Peptide group | Sequence | Predicted WW HLA coverage | Rating |
|---|---|---|---|---|---|
| 72 | 101 | 19 | NNEIKKVMVDGSHGSDPSII | | B |
| 60 | 089 | 19 | NHEIKKVLVPGSHGSEPSII | 0.2855 | D |
| 61 | 090 | 20 | GSHGSEPSIIHRGKPFQLEA | 0.8368 | A |
| 73 | 102 | 20 | GSHGSDPSIIHRGKPFTLEA | 0.7825 | A |
| 249 | 002 | 20 | SIIHRGKPFQLEA | 0.8497 | A |
| 62 | 091 | 21 | HRGKPFQLEAVFEANQNTKT | 0.9851 | A |
| 63 | 092 | 22 | VFEANQNTKTAKIEIKASID | | |
| 77 | 106 | 23 | GLEIDVPGIDTNASHFMKSP | | B |
| 67 | 096 | 24 | LVKGQQYDIKYTWNVPKIAP | 0.8233 | A |
| 271 | 131 | 24 | LVKGQQYDIKYTWNVPKIAPK | | A |
| 79 | 108 | 24 | LVKGQQYDAKYTWNVPKIAP | | B |
| 256 | 031 | 24 | QQYDIKYTWNVPKIA | 0.8233 | A |
| 270 | 126 | 24 | KGQQYDIKYTWNVPKIA | | A |
| 81 | 109 | 25 | KSENVVVTVKLVGDNGVLAS | 0.4565 | A |
| 70 | 099 | 26 | VMGDDGVLASAIATHAKIRD | 0.9688 | A |
| 269 | 125 | 26 | VMGD<u>N</u>GVLASAIATHAKIRD | | A |
| 82 | 110 | 26 | LVGDNGVLASAIATHAKIRD | 0.9864 | A |
| 253 | 012 | 26 | VLASAIATHAKIRD | 0.9154 | A |
| 257 | 117 | p4 | EIYNMVKFRMIAGQE | 0.9921 | C |

TABLE 13

List of peptides of known peptide combination

| ID No | Species | Sequence | Belong to Peptide group No: | Predicted WW HLA coverage | Rating |
|---|---|---|---|---|---|
| HDM03W | p1 | ELVDSASQHG | (8)* | 0 | |
| HDM101A | p1 | NYSQIYPPNVNKIREA | 12 | 0.1604 | |
| HDM201 | p1 | ESVKYVQSNGGAI | None | 0.3357 | |
| HDM203B | p1 | DLRQMRTVTPIRMQGGSGS | 4 | 0.8626 | A |
| HDM205 | p1 | SYYRYVAREQS | 10 | 0.3441 | |
| HDM26B | p2 | GVLASAIATHAKIR | 26 | 0.9588 | A |
| HDM35A | p7 | RGLKQMKRVGDANV | None | 0 | |

*Peptide HDM03W has less than 15 amino acid residues in overlap with a parent peptide of peptide group 8, and thus not a variant peptide of a parent peptide of peptide group 8.

Example 6

Assembling Peptide Combinations

Several peptide combinations (Table 14) with predicted high WW HLA Class II coverage were assembled from the peptides selected in Table 12. Similar peptide combinations can be assembled using another peptide (substitute peptide) from the same peptide group, i.e. another peptide from the same peptide group shown in Tables 9 and 10.

TABLE 14

Peptide Combinations

| SEQ ID NO: | Parent peptide | group Species | No: | 3 | 4 | 5 | 6 | 7 | 8 | 9 | 10 | 11 | 12 | 13 | 14 | 15 | 16 | 18 | 19 | 20 | 21 | 22 | 23 |
|---|---|---|---|---|---|---|---|---|---|---|---|---|---|---|---|---|---|---|---|---|---|---|---|
| 249 | 002 | p2 | 20 | | x | | | | | | | | | | | | | | | | x | x | |
| 250 | 009 | p1 | None | | | | | | | | | | | | | | | | | | x | | |
| 251 | 010 | p1 | 17 | | | | | | | x | | | | | x | x | x | | x | x | x | x | |
| 252 | 011 | p1 | 17 | X | | X | x | | | | | | | | | | | | | | | | |
| 253 | 012 | p2 | 26 | X | x | X | x | x | | x | | | | | | | | | | | | | |
| 254 | 022 | f1 | 7 | | x | X | x | x | | x | | | | | | | | | | | x | x | |
| 255 | 025 | p1 | 9 | | | | x | x | | | | | | | | | | | | | | | |
| 256 | 031 | p2 | 24 | X | | X | x | | | x | | | | | | | | | | | | | |
| 9 | 041 | p1 | 3 | | | | | | | | | | | | | | | x | x | | | | |
| 10 | 042 | p1 | 4 | | | | | | | | | | | | | | | | | | | | |
| 11 | 043 | pf1 | 5 | | | | | | | | | x | X | | x | x | | | | | | | |
| 12 | 044 | pf1 | 6 | | | | | | | | x | | X | x | | | x | x | | | | | x |
| 17 | 049 | p1 | 9 | | | | | | | | | | X | | | | | x | | | | | |
| 18 | 050 | p1 | 10 | | | | | | | | | | | | x | | | | x | x | | | |
| 20 | 052 | p1 | 12 | | | | | | | | | | | | | | | | | | | | |
| 22 | 054 | p1 | 14 | | | | | | | | | | | | | | | | | | | | |
| 26 | 058 | p1 | 16 | | | | | | | | x | x | | | | | | | | | | | |
| 46 | 075 | f1 | 9 | | | | | | | | x | x | | | | | | | | | | | x |
| 49 | 078 | f1 | 12 | | | | | | | | | | | | | | | | | | | | |
| 52 | 081 | f1 | 15 | | | | | | | | | | | | | | | | | | | | |
| 60 | 089 | p2 | 19 | | | | | | | | x | | | | | | | | | | | | |
| 62 | 091 | p2 | 21 | | | | | | | | | | | | | | | | | | | | |
| 70 | 099 | p2 | 26 | | | | | | | | x | | X | x | x | x | x | x | x | x | | | |
| 71 | 100 | f2 | 18 | | | | | | | | | | | | | | | | | | | | x |
| 73 | 102 | f2 | 20 | | | | | | | | | | | | | | | | | | | | x |
| 81 | 109 | f2 | 25 | | | | | | | | | x | | | | | | | | x | | | |
| 82 | 110 | f2 | 26 | | | | | | | | | x | X | x | x | x | | x | x | x | | | x |
| 257 | 117 | p4 | | X | x | | x | x | | | | | | | | | | | | | | | |
| 258 | 122 | p1 | 10 | X | x | X | x | x | | x | | | | | | | | | | | | | |
| 266 | 123 | p1 | 9 | | | | | | | | | | | | | | | | | | | | |
| 268 | 130 | p2 | 14 | | | | | | | | | | | | | | | | | | | | |
| 271 | 131 | p2 | 24 | | | | | | | | | | | | | | | | | | | | |
| | No of Peptides: | | | 5 | 5 | 5 | 7 | 5 | 7 | 5 | 5 | 5 | 5 | 3 | 5 | 4 | 3 | 5 | 5 | 4 | 5 | 5 | 5 |

| SEQ ID NO: | Parent peptide | Group Species | No: | 24 | 25 | 17 | 17a | 17b | 17c | 17d | 17f | 17p | 17l | 17q | 17s | 17t | 17u | 17v | 17x* |
|---|---|---|---|---|---|---|---|---|---|---|---|---|---|---|---|---|---|---|---|
| 249 | 002 | p2 | 20 | | | | | | | | | | | | | | | | |
| 250 | 009 | p1 | None | | | | | | | | | | | | | | | | |
| 251 | 010 | p1 | 17 | | | | | | | | | | | | | | | | |
| 252 | 011 | p1 | 17 | | | | | | | | | | | | | | | | |
| 253 | 012 | p2 | 26 | | | | | | | | | | | | | | | | |
| 254 | 022 | f1 | 7 | | | | | | | | | | | | | | | | |
| 255 | 025 | p1 | 9 | | | | | | | | | | | | | | | | |
| 256 | 031 | p2 | 24 | | | | | | | | | | | | | | | | |
| 9 | 041 | p1 | 3 | | | | X | | x | x | | | | | | | | | |
| 10 | 042 | p1 | 4 | | | | | | | | | | | | | | | | |
| 11 | 043 | pf1 | 5 | | | | | | | | | | | | | | | | |
| 12 | 044 | pf1 | 6 | X | x | | | | | | | | | | | | | | |
| 17 | 049 | p1 | 9 | | x | | | | | | | | | | | | | | |
| 18 | 050 | p1 | 10 | X | | | | | | | | | | | | | | | |
| 20 | 052 | p1 | 12 | | x | | | | | | | | | | | | | | |
| 22 | 054 | p1 | 14 | | | | | x | | | x | | | | | | | | |
| 26 | 058 | p1 | 16 | | | | X | x | x | x | x | X | | x | X | | X | X | x |
| 46 | 075 | f1 | 9 | | | | X | x | | x | | X | | x | | X | x | X | |
| 49 | 078 | f1 | 12 | X | | | | | | | | | | | | | | | |
| 52 | 081 | f1 | 15 | | | | | | x | | x | | | | | | | | |
| 60 | 089 | p2 | 19 | | | | | | | | | | | | | | | | |
| 62 | 091 | p2 | 21 | | x | | | | | x | | x | | x | X | X | | x | x |
| 70 | 099 | p2 | 26 | | | | | | | | | | | | | | | | |
| 71 | 100 | f2 | 18 | X | | | | | | | | | | | | | | | |
| 73 | 102 | f2 | 20 | X | | | | | | | | | | | | | | | |
| 81 | 109 | f2 | 25 | | | | X | x | x | | | | | | | | | | |
| 82 | 110 | f2 | 26 | | x | X | x | x | x | x | X | x | X | x | | | x | x | |
| 257 | 117 | p4 | | | | | | | | | | | | | | | | | |

TABLE 14-continued

Peptide Combinations

| 258 | 122 | p1 | 10 | | | | | | | | | | | | | | | |
|-----|-----|-----|-----|---|---|---|---|---|---|---|---|---|---|---|---|---|---|---|
| 266 | 123 | p1 | 9 | | | | | | | | x | X | X | | X | | X | | X |
| 268 | 130 | p2 | 14 | | | | | | | X | x | | X | X | x | X | x | | |
| 271 | 131 | p2 | 24 | | | | | | | X | x | X | x | X | | x | x | X | |
| | No of Peptides: | | | 5 | 5 | 5 | 5 | 5 | 5 | 5 | 5 | 5 | 5 | 5 | 5 | 5 | 5 | 5 |

*Peptide combination number 17x also contain pep-053 (shown in Table 12)

Table 14 shows examples of peptide combinations ("X" indicates that the peptide is present in the peptide combination) with predicted broad WW HLA class II coverage. Peptide combination number 8 contains the seven peptides of Table 13.

Example 7

T Cell Responses of Peptide Combinations

Peptide combinations number 3, 4, 5, 8, 9, 10, 13, 16-25 of Table 14 were initially tested for in vitro T cell responses as described above for single peptides. As shown in FIG. 9a the majority of the peptide combinations produce T cell responses in a high fraction of the donor population, such as more than about 60% to 70% of the donor population. Two peptide combinations, combination number 17 (5-peptide mix) and combination number 23 (5-peptide mix) produce T cell responses in a higher fraction of the donor population (such as above 80% of the donor population) than other peptide combinations. Also of note is that two of the peptide combinations only contain 3 peptides (peptide combination number 13 and 16), but still produce a T cell response in a high fraction of the population (more than 70% of the donor population). Such peptide combinations could be improved to produce a T cell response in an even higher fraction of the donor population, for example by adding a peptide listed in Table 12.

Additional peptide combinations were tested in T cell response assays together with peptide combination number 17 using a subset of 22 donors having about 88% worldwide HLA Class II coverage. FIG. 9b shows that peptide combination number 17f produces a T cell response in about 100% of the donor population tested in comparison to the 85% donor response to peptide combination number 17 (FIG. 9c). T cell responses for single peptides of combination 17f are also shown in FIG. 9b and indicates that peptide numbers 110 (a peptide group 26 peptide), 131 (a peptide group 24 peptide) and 054 (a peptide group 14 peptide) resulted in a higher percentage donor response than the other peptides of peptide combination 17f (FIG. 9c). The individual data of each peptide can be used to calculate the percentage of donors responding to the peptide combinations 17 and 17f in that there is a positive donor response if there is a response to at least one peptide in the combination. As shown here, the calculated fraction of donors responding to peptide combinations 17 and 17f based on individual peptide data correlates with the fraction of donors responding to the same peptide combinations tested in T cell assays. Thus, the percentage of responders recognizing a peptide combination can be calculated using information about the individual peptides that produce an in vitro T cell response in each of the donors tested.

This allows for calculating the percentage responders to other peptide combinations comprising peptides of peptide combination 17f and 17. FIG. 9d shows the percentage donor response as calculated for peptide combinations 17l, 17p, 17q, 17s, 17t, 17u and 17v (compositions shown in Table 14) and shows that these will produce a T cell response in about 80% to 90% of the donor population.

Figure 9F:
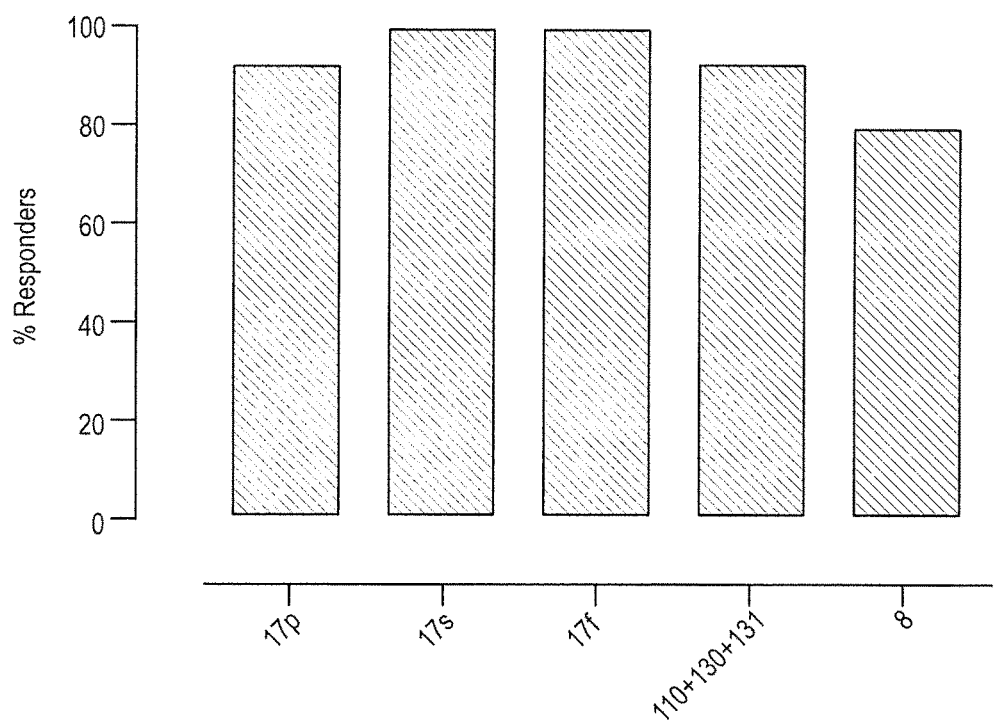
FIG. 9f: This figure shows % responders in a T cell assay to peptide combinations 17p, 17s, 17f, and 8, respectively, and a peptide combination consisting of only peptides pep-110, pep-130 and pep-131.
Figure 9G:
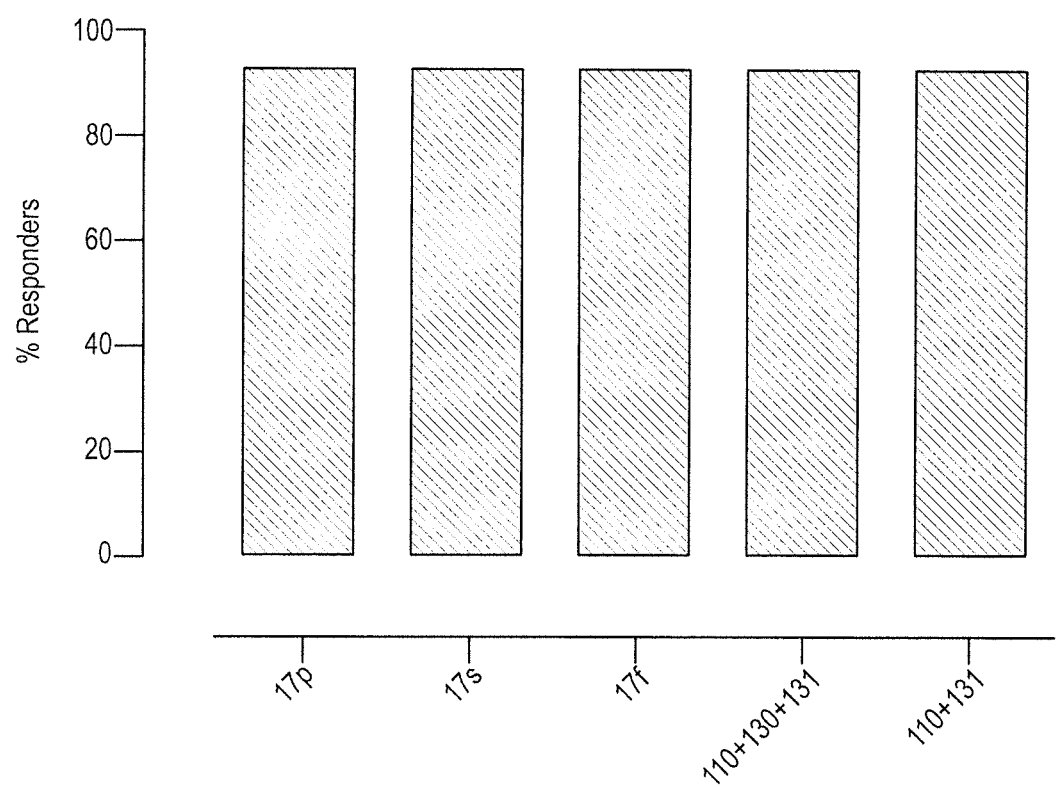
FIG. 9g: This figure shows % responders (as calculated based on individual peptides) to peptide combinations 17p, 17s, 17f, 3-pep-mix of 110+130+131 and 2-pep-mix of 110 and 131.

Further peptide combinations were evaluated using a subset of peptides (pep-058, pep-075, pep-091, pep-110, pep-123, pep-130 and pep-131) and a subset of 31 donors having a worldwide HLA Class II coverage of about 88%. FIG. 9f shows the percentage of responding donors shown to respond to peptide combinations 17p, 17s, 17f, and 8 and a peptide combination consisting of only peptides pep-110, pep-130 and pep-131, when analyzed in a T cell assay. FIG. 9g shows the calculated percentage of responders based on the individual peptide data to peptide combinations 17p, 17s, 17f, 3-pep-mix of 110+130+131 and 2-pep-mix of 110 and 131, which data indicate that all the peptide combinations suggested in FIG. 9g will produce a T cell response in about the same fraction of the donor population, such as between 80 to 90% of the donor population.

Figure 9H:
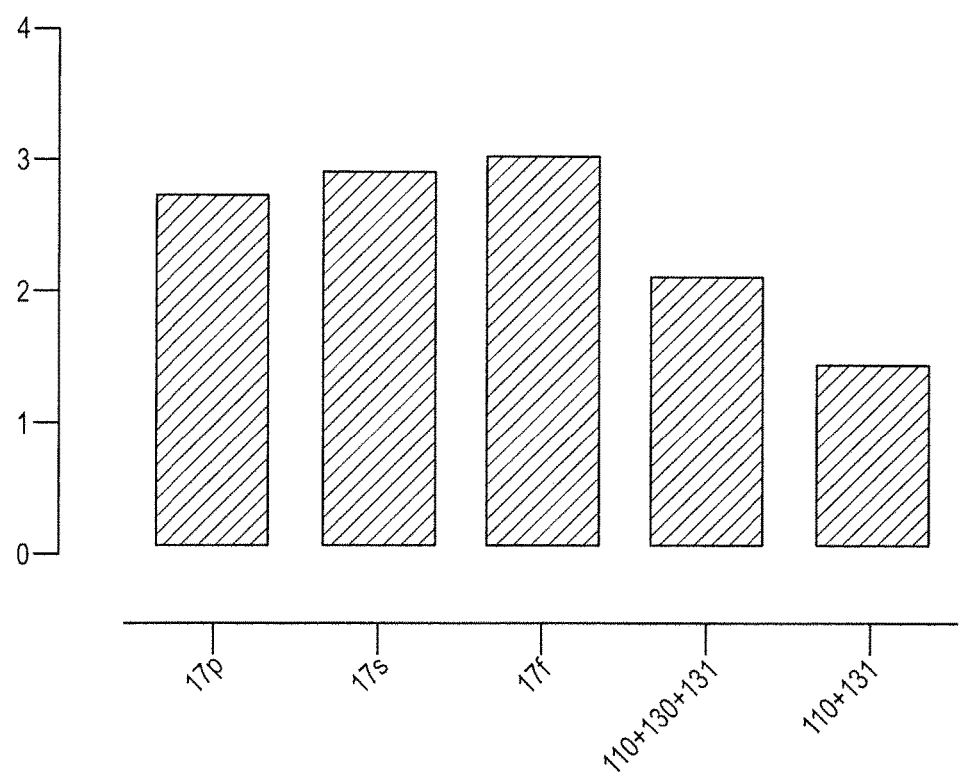

The number of peptides that a donor of the donor population in average responds to may also be calculated using the information about how many of the peptides in the peptide combination a donor is able to respond to. FIG. 9h shows the average number of peptides in peptide combinations 17p, 17s, 17f, 3-pep-mix 110+130-131 and the 2-pep-mix 110+131 that a donor of the test population is able to respond to. The data indicates that the average number of peptides in mixes 17p, 17s and 17f is between 2.5 to 3, while the average number of peptides decreases with fewer peptides in the combination.

Figure 9I:
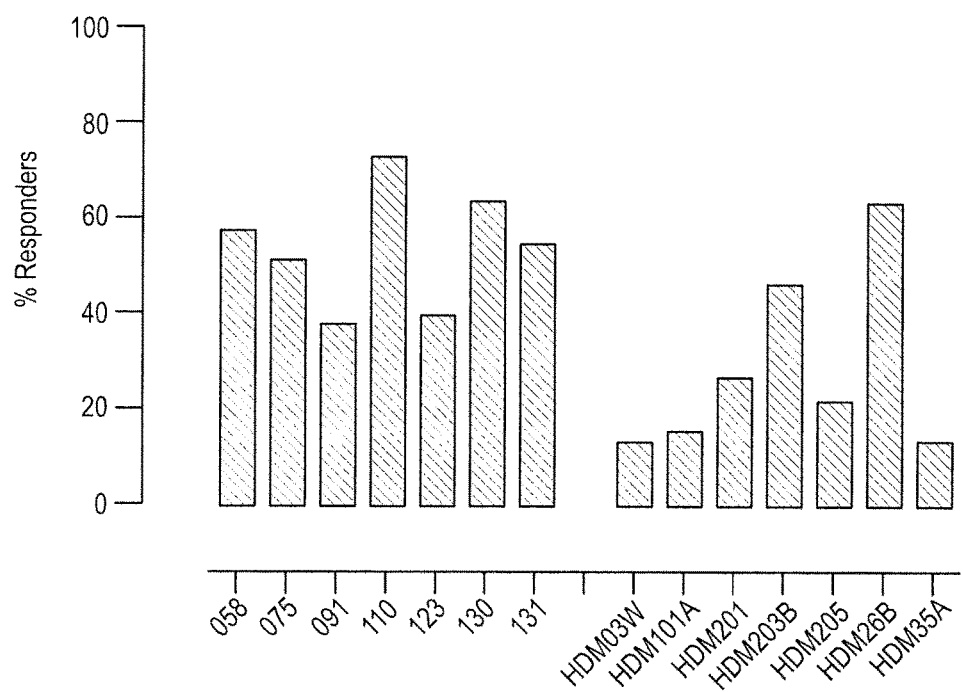
FIG. 9i: This figure shows % responders of individual peptides 058, 075, 110, 123, 130, 131 and the peptides of peptide combination 8 (HDM03W, HDM101A, HDM203B, HDM205, HDM26B and HDM35A) when tested in a T cell assay using a subset of the original donor population.
Figure 9J:
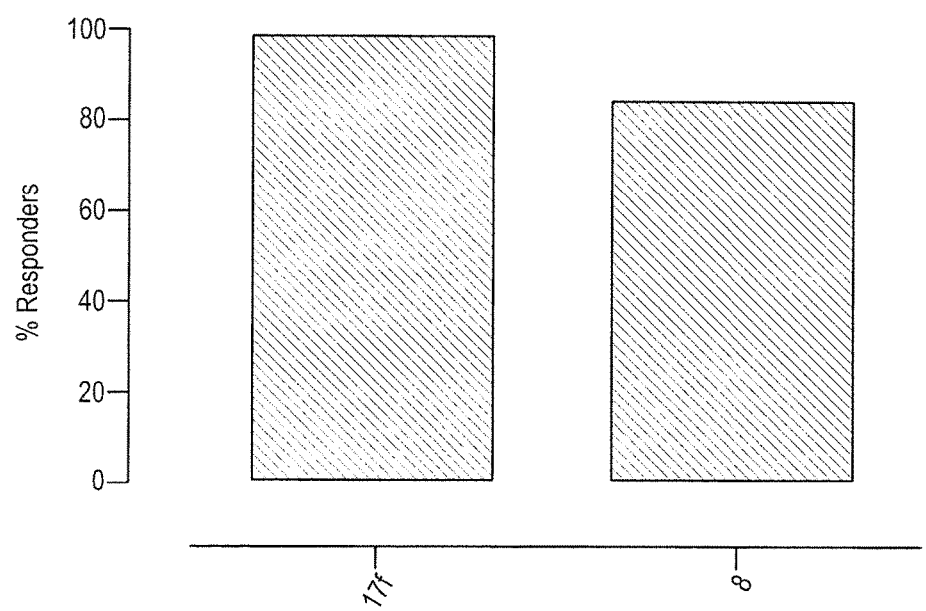
FIG. 9j: This figure shows the % responders in a T cell assay to peptide combinations 17f and 8.
Figure 9K:
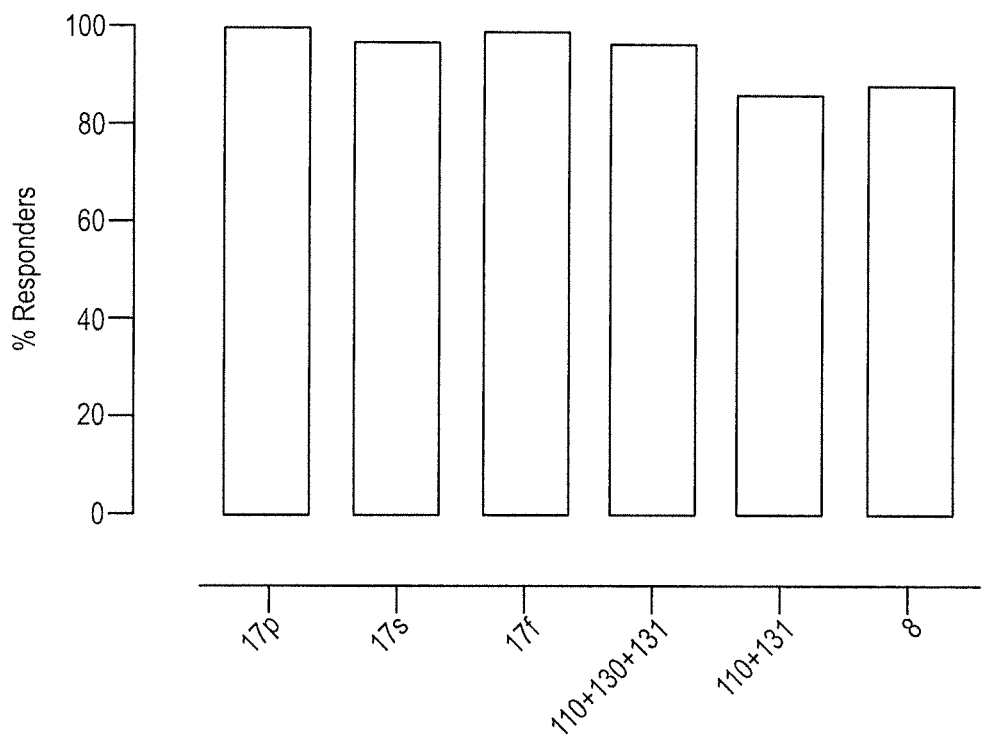
FIG. 9k: This figure shows % responders (as calculated based on % responders to individual peptides to peptide combinations 17p, 17s, 17f, 8, the three combination (110+130+131) and the two peptide combination (110+131) based on T cell assay with a subset of 22 donors having about 78% worldwide HLA Class II coverage.
Figure 9I:
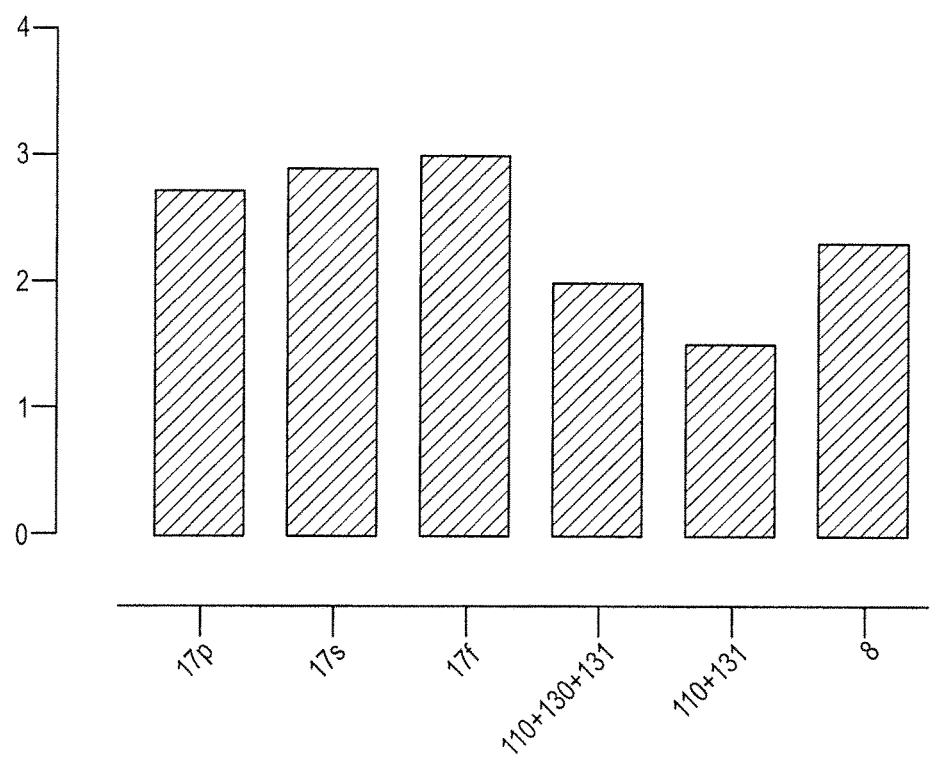

In still another experiment, the individual peptides 058, 075, 110, 123, 130, 131 and the peptides of peptide combination 8 (HDM03W, HDM101A, HDM203B, HDM205, HDM26B and HDM35A) were tested in a T cell assay using a subset of the original donor population. FIG. 9i shows the percentage of donors responding to each of the peptides tested. In the same T cell assay the peptide combination 17f and 8 were analyzed again (shown in FIG. 9j). FIG. 9k shows the calculated percentage donors responding to the further peptide combinations were evaluated using a subset of peptides (pep-058, pep-075, pep-091, pep-110, pep-123, pep-130 and pep-131) and a subset of 22 donors having about 78% worldwide HLA Class II coverage. FIG. 9l shows the percentage of responding donors shown to respond to peptide combinations 17p, 17s, 17f, and 8 and a peptide combination consisting of only peptides pep-110, pep-130 and pep-131, when analyzed in a T cell assay using a subset of 31 donors having about 88% worldwide HLA Class II coverage.

Example 8

First Choice Peptides

This example lists "first choice" peptides that may be used for assembling peptide combinations producing a T cell response in a high fraction of donors. These peptides have been shown to possess medium to high HLA Class II coverage and/or medium to high percentage responders in T cell assays, but also appear to possess suitable pharmaceutical properties, such as satisfactorily solubility in aqueous solution in the pH range of 4 to 9 and to be manufacturable.

TABLE 15

List of first choice peptides

| SEQ ID NO | Peptide No | Peptide group | pI | Sequence shown in Table(s): |
|---|---|---|---|---|
| 17 | 049 | 9 | | 9, 12 |
| 266 | 123 | 9 | 9.3 | 9, 12 |
| 46 | 075* | 9 | 4.6 | 9, 12 |
| 279 | 139 | 9 | 7.0 | 11b |
| 280 | 140 | 9 | 9.4 | 11b |
| 281 | 141 | 9 | 9.9 | 11b |
| 282 | 142 | 9 | 10.4 | 11b |
| 272 | 134 | 9 | | 11b |
| | 148 | 9 | 9.4 | 11c |
| | 152 | 9 | 9.8 | 11c |
| 18 | 050 | 10 | | 9, 12 |
| 267 | 124 | 10 | 9.9 | 11a |
| 21 | 053 | 13 | 9.7 | 9, 12 |
| 22 | 054 | 14 | | 9, 12 |
| 268 | 130* | 14 | 5.3 | 9, 12 |
| 283 | 143 | 14 | 7.8 | 11b |
| 284 | 144 | 14 | 10.1 | 11b |
| 285 | 145 | 14 | 11.2 | 11b |
| 286 | 146 | 14 | 11.8 | 11b |
| | 150 | 14 | 9.9 | 11c |
| 273 | 135 | 14 | | 11a |
| 26 | 058* | 16 | 7.7 | 9, 12 |
| 276 | 136 | 16 | 9.6 | 11b |
| 277 | 137 | 16 | 10.2 | 11b |
| 278 | 138 | 16 | 11.1 | 11b |
| 274 | 132 | 16 | | 11b |
| 275 | 133 | 16 | 11.8 | 11b |
| | 147 | 16 | 9.6 | 11a |
| 61 | 090 | 20 | 8.0 | 10, 12 |
| 73 | 102 | 20 | 8.0 | 10, 12 |
| 62 | 091 | 21 | 9.9 | 10, 12 |
| | 151 | 21 | 10.6 | 11c |
| 256 | 031 | 24 | | 10, 12 |
| 67 | 096 | 24 | | 10, 12 |
| 270 | 126 | 24 | 9.9 | 11a |
| 271 | 131 | 24 | | 10, 12, 11a |
| 81 | 109 | 25 | 7.0 | 10, 12 |
| 253 | 012 | 26 | | 10, 12 |
| 70 | 099 | 26 | | 10, 12 |
| 82 | 110 | 26 | | 10, 12 |
| 269 | 125 | 26 | 7.8 | 11a |
| | 149 | 26 | 10.1 | 11c |

*peptides marked with an asterisk may cause some solubility problems in which case a variant of the peptide may be used instead, e.g. a modification comprising one or more lysine or arginine residues at the N- and/or C-terminal end or amidation.

Example 9

In Vitro HLA Class II Binding Analysis of Peptides

This example describes how to determine the HLA class II binding of peptides of the invention. The assay employed is a competitive MHC class II binding assay, wherein each peptide is analyzed for its ability to displace a known control binder from each of the human MHC class II allotypes shown in Table 8. Due to the nature of the competitive assay, the data for each peptide is determined as a ratio of its own IC50 to that of the control peptide. Thus, a peptide that has an IC50 value that is parity to the control peptide has an identical binding affinity, while peptides with a ratio less than one have a higher affinity and those with a ratio greater than one have a lower affinity. The ratio of IC50 may be determined at different cutoff concentrations, for example at 300 or 1000 nM.

Assays to quantitatively measure peptide binding to purified class II MHC molecules are based on the inhibition of binding of a high affinity radiolabeled peptide to purified MHC molecules, and were performed essentially as detailed elsewhere (Sidney et al. 2008; Sidney et al. 2010b, a; Greenbaum et al. 2011; Sidney et al. 2001, Sidney et al 2013, McKinney et al 2013). Briefly, 0.1-1 nM of radiolabeled peptide was co-incubated at room temperature or 37° C. with purified MHC in the presence of a cocktail of protease inhibitors. Following a two- to four-day incubation, MHC bound radioactivity was determined by capturing MHC/peptide complexes on monoclonal Ab coated Lumitrac 600 plates (Greiner Bio-one, Frickenhausen, Germany), and measuring bound cpm using the TopCount (Packard Instrument Co., Meriden, Conn.) microscintillation counter. In the case of competitive assays, the concentration of peptide yielding 50% inhibition of the binding of the radiolabeled peptide was calculated. Under the conditions utilized, where [label]<[MHC] and IC50≥[MHC], the measured IC50 values are reasonable approximations of the true Kd values (Cheng and Prusoff 1973; Gulukota et al. 1997). Each peptide was tested at six different concentrations covering a 100,000-fold dose range in three or more independent experiments. As a positive control, the unlabeled version of the radiolabeled probe was also tested in each experiment.

Table 16a shows the HLA Class II alleles for which the HLA binding affinity of a selection of peptides has been measured. A positive binding is indicated in the Table with an "x", which refers to a binding affinity IC50<1000 nM.

Table 16b shows the minimal number of alleles bound by each of the peptides and the Class II HLA phenotypic coverage in a worldwide population based on the alleles found to bind each peptide. These alleles can be used to calculate the HLA phenotypic coverage of a peptide or a peptide combination.

TABLE 16a

Table 16a - In vitro HLA Class II binding analysis of some peptides

| Peptide ID | DRB1_0101 | DRB1_0301 | DRB1_0401 | DRB1_0405 | DRB1_0701 | DRB1_0802 | DRB1_0901 | DRB1_1101 |
|---|---|---|---|---|---|---|---|---|
| HDM03W | | | | | | | | |
| HDM101A | x | | | | x | | | |
| HDM201 | x | | x | x | x | x | x | |
| HDM203B | x | x | x | x | x | x | x | x |
| HDM205 | | x | | x | x | x | x | x |
| HDM26B | x | x | | | x | x | x | |
| HDM35A | x | | | | | x | | x |
| 002 | x | | | | x | | x | |
| 009 | x | | x | x | x | x | x | |
| 010 | x | | x | x | x | x | | |
| 011 | x | | x | x | x | | | |
| 012 | x | | | | x | | x | |
| 020 | x | | x | x | x | | x | |
| 022 | x | | x | x | x | x | x | |
| 025 | x | | x | x | x | x | x | |

TABLE 16a-continued

Table 16a - In vitro HLA Class II binding analysis of some peptides

| Peptide ID | | | | | | | | |
|---|---|---|---|---|---|---|---|---|
| 031 | | x | x | | x | x | x | |
| 041 | | | | | | | | |
| 044 | x | | x | x | x | | x | x |
| 049 | | x | x | x | x | | x | x |
| 050 | | x | x | | | | | x |
| 053 | x | | N | | x | | x | |
| 058 | | | x | x | x | x | x | x |
| 075 | x | x | | x | | | | |
| 089 | | | | | | x | | |
| 090 | x | | N | | x | | x | |
| 091 | x | | N | x | | x | x | |
| 099 | x | | x | | | x | x | |
| 102 | x | | N | | x | | x | |
| 109 | | x | x | | | x | | x |
| 110 | x | x | x | | | x | x | |
| 117 | x | x | x | x | x | x | x | x |
| 122 | x | | x | x | x | x | x | x |
| 123 | x | | N | x | x | x | x | x |
| 124 | | | N | | x | x | | x |
| 125 | x | | N | | | x | x | |
| 126 | x | | N | | x | x | x | |
| 130 | x | | N | x | x | x | x | |
| 131 | x | | N | | x | x | x | |

| Peptide ID | DRB1_1201 | DRB1_1302 | DRB1_1501 | DRB3_0101 | DRB3_0202 | DRB4_0101 | DRB5_0101 | HLA-DQA10501-QB10201 |
|---|---|---|---|---|---|---|---|---|
| HDM03W | | | | | | | | |
| HDM101A | | x | x | | x | | | |
| HDM201 | | x | x | x | | x | | |
| HDM203B | x | x | x | | | x | x | |
| HDM205 | | x | x | | | x | | |
| HDM26B | | x | x | | x | x | x | |
| HDM35A | | | | | | | | |
| 002 | | x | x | | | x | | |
| 009 | | x | x | | x | x | x | |
| 010 | | x | x | x | x | x | | x |
| 011 | | x | | | x | x | x | x |
| 012 | | | x | | | | x | |
| 020 | | | x | | | | | x |
| 022 | | | x | | | | | |
| 025 | x | x | x | | | x | | |
| 031 | x | x | x | | x | x | x | |
| 041 | | x | | x | x | | | x |
| 044 | | x | x | | x | | | x |
| 049 | x | x | x | x | x | | x | x |
| 050 | | | | | | | x | |
| 053 | | | | | | x | x | |
| 058 | | x | x | x | | x | | x |
| 075 | x | x | | x | x | | | x |
| 089 | | | | | | x | | |
| 090 | | x | x | | | x | | |
| 091 | | x | | | x | x | | x |
| 099 | | x | | | | | x | |
| 102 | | | x | | | x | | |
| 109 | | x | | x | | x | | |
| 110 | | x | | x | | x | x | |
| 117 | x | | x | | | x | x | |
| 122 | x | | | | x | | x | |
| 123 | x | x | x | | x | | x | x |
| 124 | | | | | | | x | |
| 125 | | | | | | | x | |
| 126 | | x | | | x | | x | |
| 130 | x | x | | | | x | x | x |
| 131 | | x | | | x | | x | |

| Peptide ID | HLA-DQA10501-DQB10301 | HLA-DQA10301-DQB10302 | HLA-DQA10401-DQB10402 | HLA-DQA10101-DQB10501 | HLA-DQA10102-DQB10602 | HLA-DPA10201-DPB10101 | HLA-DPA10103-DPB10201 | HLA-DPA10103-DPB10301 |
|---|---|---|---|---|---|---|---|---|
| HDM03W | | | | | | | | |
| HDM101A | | | | | | | | |
| HDM201 | | | | | | | | |
| HDM203B | | | | | x | | x | x |
| HDM205 | | | | | | | | |
| HDM26B | x | | | | x | | | |
| HDM35A | | | | | | | | |

TABLE 16a-continued

Table 16a - In vitro HLA Class II binding analysis of some peptides

| Peptide ID | C1 | C2 | C3 | C4 | C5 | C6 | C7 | C8 |
|---|---|---|---|---|---|---|---|---|
| 002 | x | | | | | | | |
| 009 | | | | x | | x | | |
| 010 | x | x | x | x | x | | x | |
| 011 | x | x | x | x | | | | |
| 012 | x | | | | | | | |
| 020 | x | x | x | | | N | | |
| 022 | | | | x | | | | |
| 025 | x | | | | x | | | |
| 031 | | | | x | | | x | |
| 041 | | | x | | | N | | |
| 044 | x | x | x | x | x | N | | x |
| 049 | x | | | | x | N | x | |
| 050 | | | | | | N | | x |
| 053 | x | | | | x | N | | |
| 058 | x | | | x | x | N | | x |
| 075 | | | x | | x | N | | |
| 089 | | | | | | N | | |
| 090 | x | | | | x | N | | |
| 091 | | | | x | | N | x | |
| 099 | x | | | | x | N | | |
| 102 | x | | | | x | N | | |
| 109 | | | | | | N | | |
| 110 | x | | | | x | N | | |
| 117 | | | | x | | | x | |
| 122 | | | | | | | | x |
| 123 | x | | | | x | N | x | |
| 124 | | | | | | N | x | x |
| 125 | x | x | | | | N | | |
| 126 | | | | x | | N | | x |
| 130 | x | x | | x | x | N | x | x |
| 131 | | | | x | | N | x | x |

| Peptide ID | HLA-DPA10103-DPB10401 | HLA-DPA10202-DPB10501 | HLA-DPA10201-DPB11401 | HLA-DPA10103-DPB10402 |
|---|---|---|---|---|
| HDM03W | | | | |
| HDM101A | | | | x |
| HDM201 | | | | |
| HDM203B | | | | |
| HDM205 | | | | |
| HDM26B | | x | | |
| HDM35A | | | | |
| 002 | | | | |
| 009 | x | | | |
| 010 | x | | | x |
| 011 | | | | x |
| 012 | | x | | |
| 020 | | | | |
| 022 | | | | |
| 025 | | | | |
| 031 | | x | x | |
| 041 | | | | |
| 044 | | | | x |
| 049 | x | | | |
| 050 | | | | |
| 053 | | | | |
| 058 | | | | |
| 075 | | | | |
| 089 | | | | |
| 090 | | | | |
| 091 | | | | |
| 099 | | x | | |
| 102 | | | | |
| 109 | | | | |
| 110 | | x | x | |
| 117 | x | | | |
| 122 | | | | |
| 123 | x | | | |
| 124 | | | | |
| 125 | | x | | |
| 126 | | | | |
| 130 | | | | x |
| 131 | | | | |

N: indicates that data was not available.

TABLE 16b

Table 16b - HLA Class II phenotypic coverage of some peptides

| Peptide ID | bCutoff 1000 nM | | Cutoff: 300 nM | |
|---|---|---|---|---|
| | Number of alleles | Population Coverage | Number of alleles | Population Coverage |
| 010 | 20 | 99.5% | 16 | 96.8% |
| 130 | 16 | 97.7% | 11 | 91.3% |
| 011 | 15 | 97.6% | 9 | 74.1% |
| 044 | 17 | 97.5% | 12 | 87.5% |
| 123 | 16 | 97.3% | 12 | 94.3% |
| 049 | 16 | 97.0% | 9 | 77.2% |
| 058 | 15 | 94.3% | 12 | 86.7% |
| 009 | 13 | 92.0% | 10 | 76.7% |
| 031 | 14 | 91.9% | 7 | 69.9% |
| 117 | 14 | 91.7% | 10 | 77.5% |
| HDM26B | 12 | 91.7% | 9 | 84.1% |
| 110 | 12 | 91.5% | 8 | 77.7% |
| HDM203B | 15 | 89.9% | 11 | 79.5% |
| 025 | 12 | 86.1% | 6 | 37.3% |
| 091 | 10 | 84.0% | 5 | 71.0% |
| 090 | 8 | 81.7% | 6 | 76.5% |
| 053 | 6 | 81.3% | 5 | 67.9% |
| 075 | 10 | 81.0% | 5 | 33.6% |
| 102 | 8 | 80.9% | 7 | 76.5% |
| 020 | 10 | 80.8% | 4 | 37.5% |
| 131 | 9 | 79.6% | 6 | 66.8% |
| HDM201 | 10 | 79.5% | 7 | 48.9% |
| 002 | 7 | 77.7% | 7 | 77.7% |
| HDM101A | 6 | 75.4% | 3 | 25.5% |
| HDM205 | 9 | 74.9% | 3 | 51.4% |
| 099 | 8 | 74.5% | 5 | 56.5% |
| 125 | 6 | 73.9% | 4 | 64.0% |
| 109 | 7 | 73.7% | 6 | 54.9% |
| 126 | 8 | 73.4% | 4 | 44.8% |
| 012 | 6 | 71.5% | 4 | 55.1% |
| 122 | 10 | 71.2% | 6 | 45.6% |
| 041 | 5 | 68.1% | 2 | 18.1% |
| 124 | 5 | 60.2% | 3 | 39.2% |
| 022 | 8 | 54.6% | 6 | 43.5% |
| 050 | 4 | 48.1% | 2 | 35.9% |
| 089 | 2 | 44.7% | 2 | 44.7% |
| HDM35A | 3 | 21.5% | 0 | 0.0% |
| HDM03W | 0 | 0.0% | 0 | 0.0% |

Example 10

Prediction and Calculation of HLA Class II Phenotypic Coverage of Peptide Combinations This example describes how HLA Class II allele coverage can be determined for individual peptides and peptide combination disclosed herein, In order to elicit a T-cell response a given peptide must be able to bind to at least one HLA class II molecule in a given individual. Each individual express several HLA molecules, and globally, thousands of different alleles exist. Each HLA molecule can bind a limited number of different peptides and not all HLAs bind the same peptides. In order to estimate the potential coverage of a peptide in a given population, the frequency of the different HLA class II molecules present in the population, and the binding affinity of peptide towards each of these molecules must be available. The peptide binding to a specific HLA molecule can be measured, for example as described in Example 9, or predicted using in silico algorithms as e.g. NetMHCII and NetMHCIIpan (as disclosed in Example 2 or as described in Nielsen et al 2010 or Nielsen et al 2009).

The exact affinity necessary for an immune response is not known, but is generally assumed to be in the range of 300 nM-1000 nM. The calculated phenotypic coverage of alleles determined to bind to each peptide is presented using either 300 nM or 1000 nM are presented in Table 16a. For predicted affinities is used a binding threshold of 300 nM together with a percentile rank score reported by the prediction algorithm, of at least 30.

This example also describes how peptide combinations can be compared with respect to the average fraction of donors (% of patients) having HLA Class II alleles potentially able to bind a given number of peptides (0, 1, 2, 3, 4, or 5 peptides) in a peptide combination disclosed herein (herein named valency of a peptide combination).

The HLA coverage and valency may be estimated using HLA Class II alleles represented in a worldwide population or in a subset thereof, for example the subset of alleles shown in Table 16a.

To estimate the valency, a system was created that generates virtual patients (VP). Each VP was generated using the 83 allele frequencies from Table 17 as probabilities at each locus to have this particular allele. As not all alleles in the world are considered, some of the generated VPs will lack one or more HLAs. To estimate the average fraction of patients reacting against a certain number of peptides, 1000 VPs were generated. Using the prediction method and HLA binding affinity thresholds (300 nM and 30% fractile) earlier described herein, the number of peptides that an average VP would react against was predicted. In addition, the overall fraction of how many VPs would react against 0, 1, 2, 3, 4 and 5 peptides, respectively, were calculated based on predicted HLA binding compared to the measured HLA binding affinities.

Figure 10A:
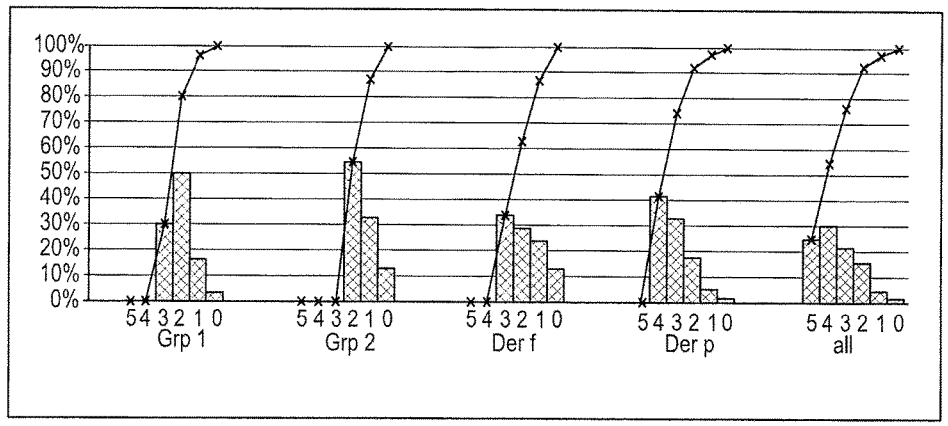
FIG. 10a shows valency for peptide combination 5, wherein the estimation is based on predicted HLA allele coverage of alleles shown in Table 8.
Figure 10B:
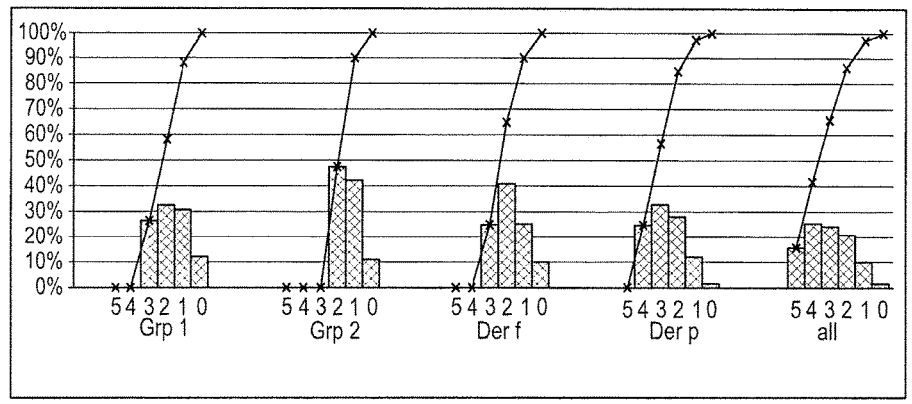
FIG. 10b shows valency for peptide combination 5, wherein the estimation is based on measured HLA allele coverage of alleles shown in Table 8.
Figure 11A:
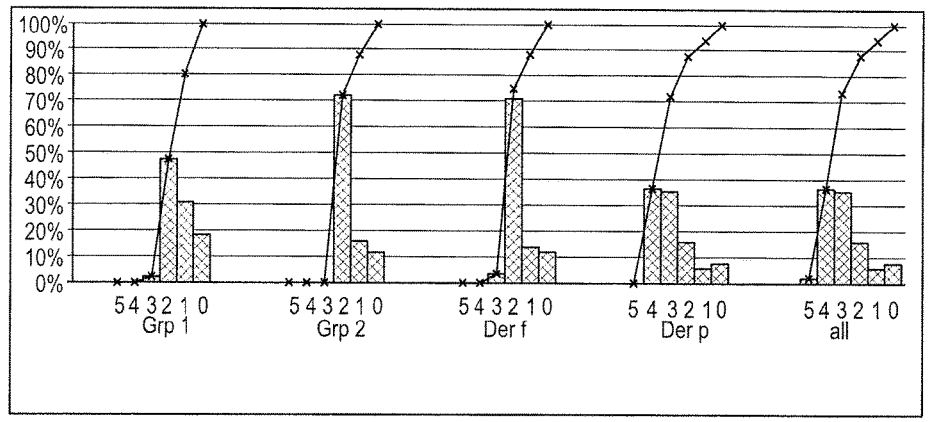
FIG. 11a shows valency for peptide combination 17f, wherein the estimation is based on predicted HLA allele coverage of alleles shown in Table 8.
Figure 11B:
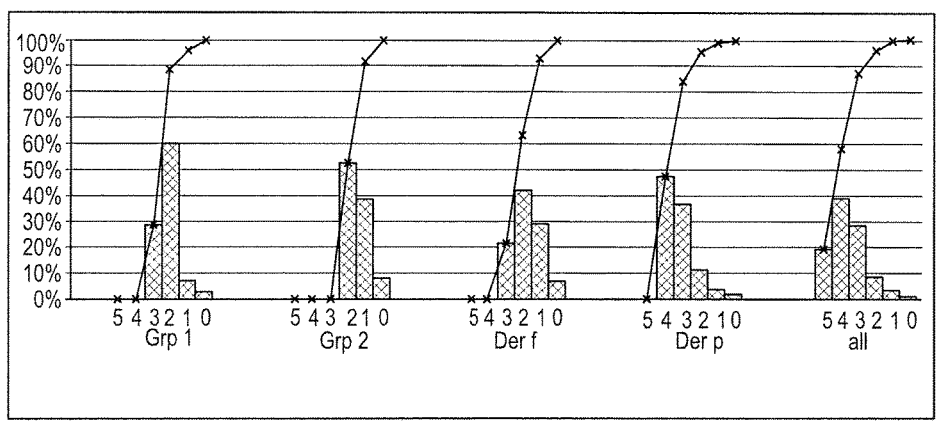
FIG. 11b shows valency for peptide combination 17f, wherein the estimation is based on measured HLA allele coverage of alleles shown in Table 8.
Figure 12A:
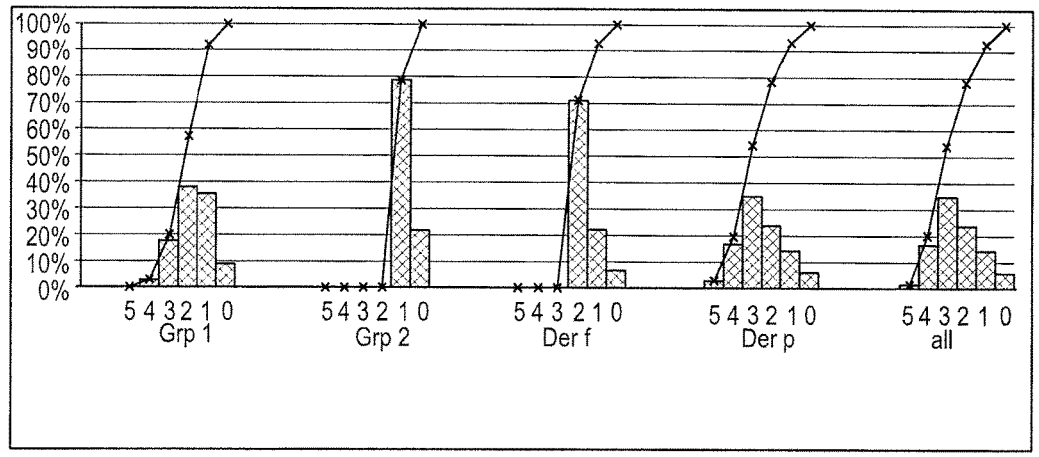
FIG. 12a shows valency for peptide combination 8, wherein the estimation is based on predicted HLA allele coverage of alleles shown in Table 8.
Figure 12B:
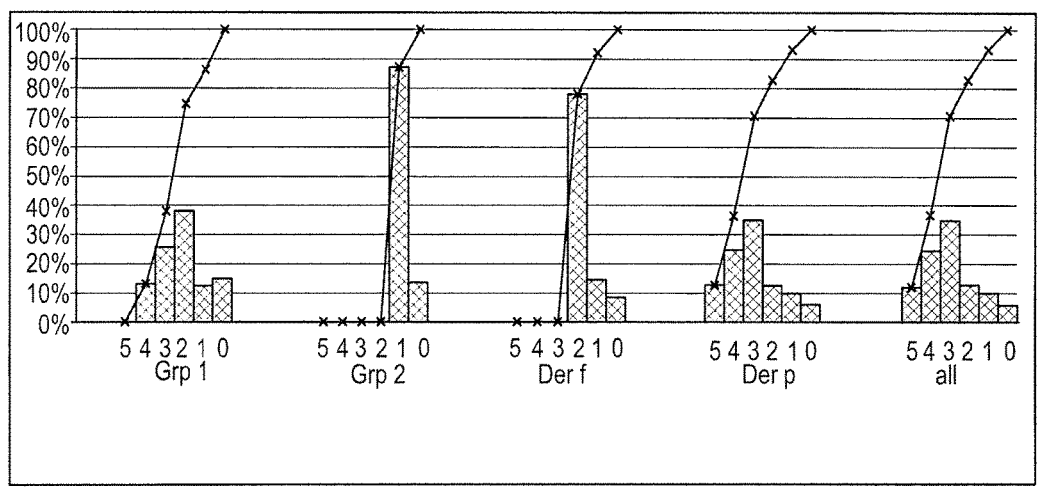
FIG. 12b shows valency for peptide combination 8, wherein the estimation is based on measured HLA allele coverage of alleles shown in Table 8.
Figure 13:
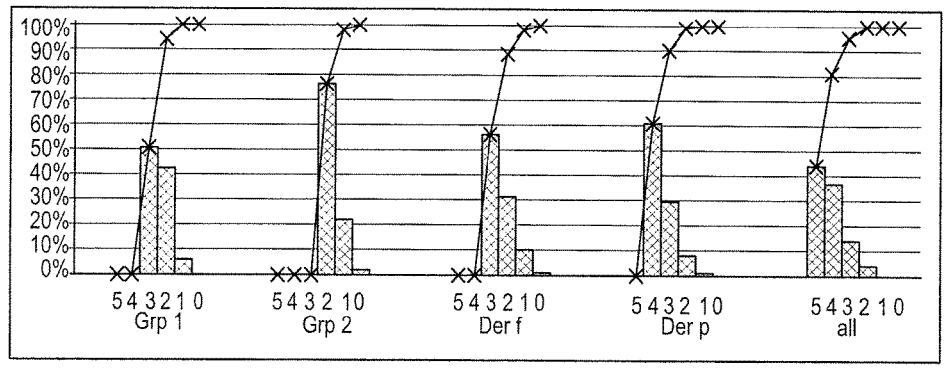
Figure 14:
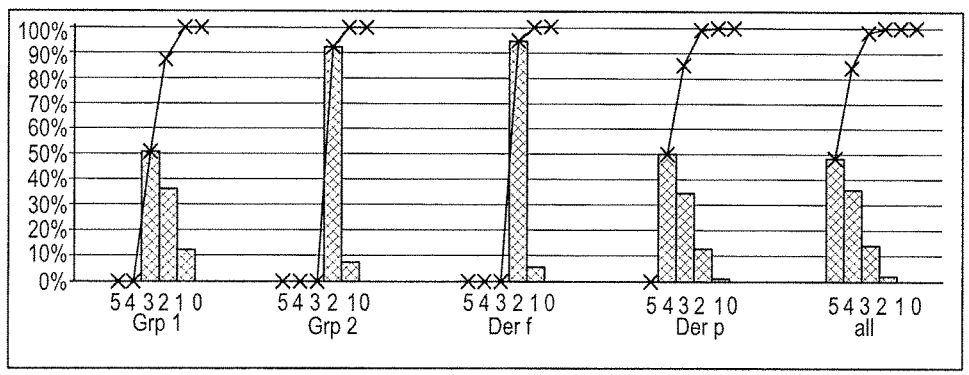
Figure 15:
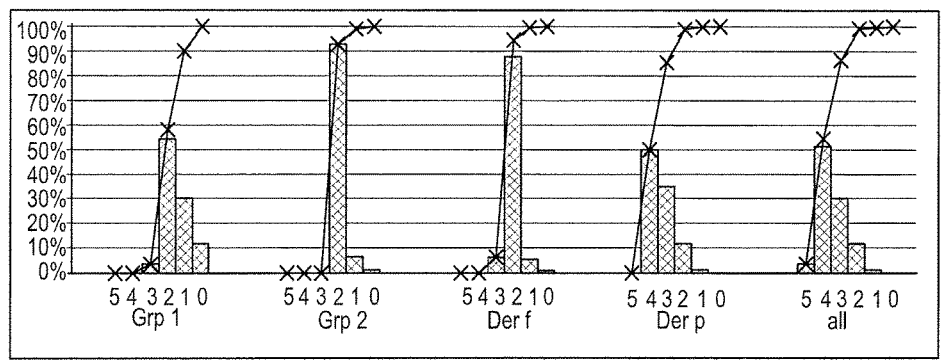
Figure 16:
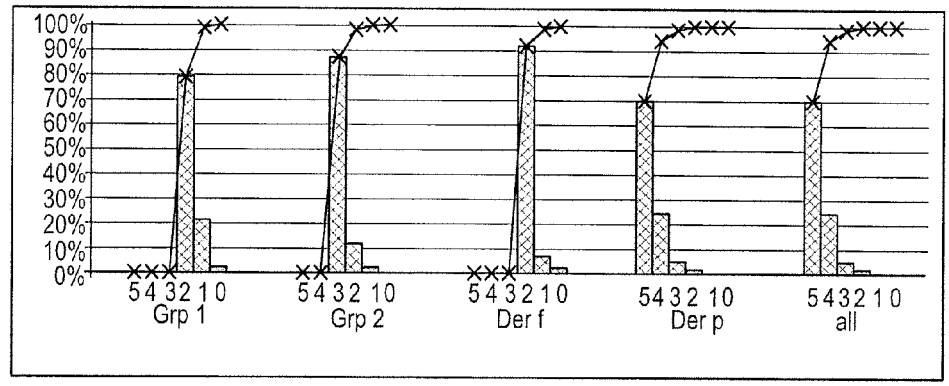
Figure 17:
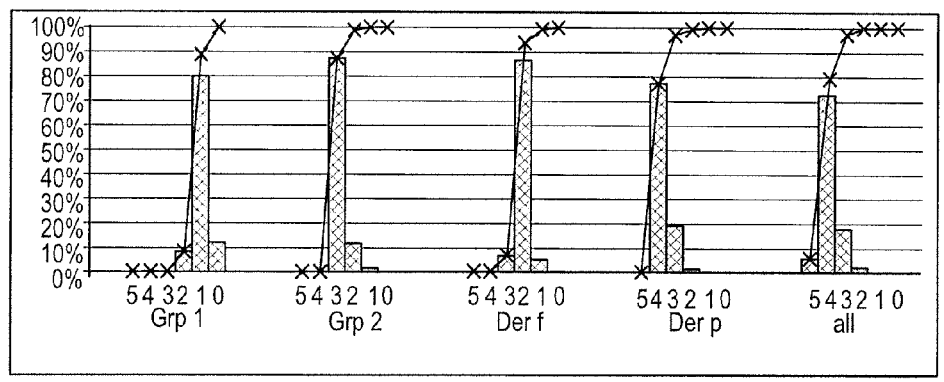

FIGS. 10a, 11a, 12a show the estimated valency of peptide combinations 5, 17f and 8 based on the peptides predicted HLA allele coverage to the HLA alleles shown in Table 16a, whereas FIGS. 10b, 11b and 12b show the estimated valency of the same peptide combinations based on the peptides measured HLA allele coverage to the same alleles. The data indicates high correlation between the valency data based on predicted HLA allele coverage and measured HLA allele coverage.

FIGS. 13 to 19 show the estimated valency of peptide combinations 9 17d, 17f, 17p, 17s, 17x and 23 that patients in a virtual patient population may respond to, wherein the estimation is based on predicted binding to the 83 HLA alleles shown in Table 17. The estimation may include the following: for each peptide or peptide combination the alleles found to be binding the given peptide, or at least one peptide in the peptide combination, is considered for the coverage calculation. Assuming that alleles at different loci are independently distributed, which is not entirely true, but is a reasonably approximation, the phenotypic coverage of the binding alleles can now be calculated using standard methods known in the art. For example, For each HLA locus (DRB1, DRB3, DRB4, DRB5) or locus combination (DQA1-DQB1, DPA1-DPB1), the HLA allele frequencies of all the alleles from the given locus found to bind the given peptide is summed ($f_{sum,locus}$). The total phenotypic coverage for each locus, n ($C_n$) is calculated as $(2 \times f_{sum,locus}) - (f_{sum,locus})^2$.

The total phenotypic coverage of all binding alleles from n loci can be calculated as $$K_n = 1 - \sum_{i=1}^{n} (1 - K_{(i-1)}) \times C_i$$

where $K_0 = 0$

The FIGS. 10a to 19 show the fraction of the virtual patients (Y-axis=% patients) that have HLA Class II alleles potentially able to bind (i.e. able to respond to) 0, 1, 2, 3, 4 and 5 peptides, respectively, in the combination (Data indicated with bars). Valency data are shown both with respect to peptides only derived from the HDM group 1 allergens Der p 1 or Der f 1 (indicated at the x-axis as Grp 1); peptides only derived from the HDM group 2 allergens Der p 2 or Der f 2 (indicated at the x-axis as Grp 2); peptides derived only from Der p (i.e. allergens Der p 1 or Der p 2 (indicated at the x-axis as Der p) and peptides derived only from Der f (i.e. allergens Der f 1 or Der f 2 (indicated at the x-axis as Der f). Finally, the valency is also shown for the all peptides in the combination (indicated at the X-axis as "all"). The Figures also show the predicted fraction of patients (% patients) that will have HLA alleles potentially able to bind a given number of peptides or more in the peptide combination (data points shown as X)

For example, the measured valency data of the 5-peptide combination 17f (FIG. 11b) shows that 20% of the patients potentially are able to respond to 5 peptides, 40% of the population potentially are able to respond to 4 peptides (data indicated with bars), that 60% of the population potentially are able to bind to at least 4 peptides (data point from curve) and that about 95% of the patients potentially are able to bind at least 2 of the 5 peptides in the combination.

The measured valency data of the 7-peptide combination 8 (FIG. 12b) shows that about 10% of the patients potentially are able to respond to 5 peptides, 25% of the population potentially are able to respond to 4 peptides (data indicated with bars), that 35% of the population potentially are able to bind to at least 4 peptides (data point from curve) and that about 82% of the patients potentially are able to bind at least 2 of the 6 peptides in the combination that derives from Der p 1, Der p1, Der f1 or Der f2. Peptide combination 8 contains a peptide derived from Der p 7 (HDM35A), which has poor HLA allele coverage (Table 16a).

TABLE 17

Table 17 - 83 HLA Class II alleles and their frequencies for use in HLA coverage predictions

| HLA Alleles | Frequency |
| --- | --- |
| DRB1_0101 | 0.0428 |
| DRB1_0102 | 0.0233 |
| DRB1_0103 | 0.0048 |
| DRB1_0301 | 0.0773 |
| DRB1_0302 | 0.0175 |
| DRB1_0307 | 0.0003 |
| DRB1_0401 | 0.0338 |
| DRB1_0402 | 0.0078 |
| DRB1_0403 | 0.0158 |
| DRB1_0404 | 0.0275 |
| DRB1_0405 | 0.0233 |
| DRB1_0406 | 0.0063 |
| DRB1_0407 | 0.0245 |
| DRB1_0408 | 0.0025 |
| DRB1_0410 | 0.0025 |
| DRB1_0411 | 0.0035 |
| DRB1_0417 | 0.0003 |
| DRB1_0701 | 0.1015 |
| DRB1_0801 | 0.0113 |
| DRB1_0802 | 0.0273 |
| DRB1_0803 | 0.0140 |
| DRB1_0804 | 0.0163 |
| DRB1_0806 | 0.0015 |
| DRB1_0809 | 0.0005 |
| DRB1_0811 | 0.0005 |
| DRB1_0901 | 0.0395 |
| DRB1_1001 | 0.0170 |
| DRB1_1101 | 0.0570 |
| DRB1_1102 | 0.0133 |
| DRB1_1103 | 0.0028 |
| DRB1_1104 | 0.0185 |
| DRB1_1106 | 0.0008 |
| DRB1_1110 | 0.0008 |
| DRB1_1111 | 0.0003 |
| DRB1_1128 | 0.0000 |
| DRB1_1201 | 0.0233 |
| DRB1_1202 | 0.0195 |
| DRB1_1301 | 0.0458 |
| DRB1_1302 | 0.0445 |
| DRB1_1303 | 0.0153 |
| DRB1_1304 | 0.0040 |
| DRB1_1305 | 0.0020 |
| DRB1_1307 | 0.0000 |
| DRB1_1311 | 0.0003 |
| DRB1_1312 | 0.0010 |
| DRB1_1323 | 0.0003 |
| DRB1_1331 | 0.0003 |
| DRB1_1401 | 0.0228 |
| DRB1_1402 | 0.0093 |
| DRB1_1403 | 0.0013 |
| DRB1_1404 | 0.0053 |
| DRB1_1405 | 0.0045 |
| DRB1_1406 | 0.0100 |
| DRB1_1407 | 0.0010 |
| DRB1_1418 | 0.0003 |
| DRB1_1419 | 0.0003 |
| DRB1_1424 | 0.0003 |
| DRB1_1501 | 0.0740 |
| DRB1_1502 | 0.0258 |
| DRB1_1503 | 0.0313 |
| DRB1_1504 | 0.0003 |
| DRB1_1506 | 0.0010 |
| DRB1_1519 | 0.0000 |
| DRB1_1601 | 0.0043 |
| DRB1_1602 | 0.0173 |
| DRB1_1607 | 0.0003 |
| DRB3_0101 | 0.1400 |
| DRB3_0202 | 0.1890 |
| DRB4_0101 | 0.2370 |
| DRB5_0101 | 0.0830 |
| DPA10103-DPB10201 | 0.0920 |
| DPA10103-DPB10301 | 0.0700 |
| DPA10103-DPB10401 | 0.2010 |
| DPA10103-DPB1040 | 0.2360 |
| DPA10201-DPB10101 | 0.0840 |
| DPA10201-DPB11401 | 0.0380 |
| DPA10202-DPB10501 | 0.1150 |
| DQA10101-DQB10501 | 0.0760 |
| DQA10102-DQB10602 | 0.0760 |
| DQA10301-DQ810302 | 0.1000 |
| DQA10401-DQB10402 | 0.0660 |
| DQA10501-DQB10201 | 0.0580 |
| DQA10501-DQB10301 | 0.1950 |

The invention claimed is:

1. A composition comprising at least three peptides, wherein at least one of the three peptides is selected from each of the following peptide groups:
   i. a parent peptide consisting of the amino acid sequence SEQ ID NO: 82 (pep-110) or a variant thereof;
   ii. a parent peptide consisting of the amino acid sequence SEQ ID NO: 271 (pep-131) or a variant thereof; and
   iii. a parent peptide consisting of the amino acid sequence SEQ ID NO: 268 (pep-130) or a variant thereof;
   wherein the variant peptides each consist of 15-25 amino acid residues and each comprise an amino acid sequence having at least 90% sequence identity over at least 15 contiguous amino acids of the corresponding parent peptide.

2. The composition according to claim 1, said composition further comprising an additional peptide selected from any one of the following groups:
   iv. a parent peptide consisting of the amino acid sequence SEQ ID NO: 266 (pep-123) or a variant thereof;
   v. a parent peptide consisting of the amino acid sequence SEQ ID NO: 26 (pep-058) or a variant thereof; and
   vi. a parent peptide consisting of the amino acid sequence SEQ ID NO: 62 (pep-091) or a variant thereof;
   and wherein the variant peptides each consist of 15-25 amino acid residues and each comprise an amino acid sequence having at least 90% sequence identity over at least 15 contiguous amino acids of the corresponding parent peptide.

3. The composition according to claim 1, said composition further comprising at least two peptides selected from the groups consisting of
   a parent peptide consisting of the amino acid sequence SEQ ID NO: 266 (pep-123) or a variant thereof,
   a parent peptide consisting of the amino acid sequence SEQ ID NO: 26 (pep-058) or a variant thereof, and
   a parent peptide consisting of the amino acid sequence SEQ ID NO: 62 (pep-091) or a variant thereof,
   wherein each peptide in said composition is selected from a different group, and wherein the variant peptides each consist of 15-25 amino acid residues and each comprise an amino acid sequence having at least 90% sequence identity over at least 15 contiguous amino acids of the corresponding parent peptide.

4. The composition according to claim 1, said composition further comprising
   a parent peptide consisting of the amino acid sequence SEQ ID NO: 266 (pep-123) or a variant thereof; and
   a parent peptide consisting of the amino acid sequence SEQ ID NO: 26 (pep-058) or a variant thereof,
   wherein the variant peptides each consists of 15-25 amino acid residues and each comprise an amino acid sequence having at least 90% sequence identity over at least 15 contiguous amino acids of the corresponding parent peptide.

5. The composition according to claim 1, said composition further comprising
   a parent peptide consisting of the amino acid sequence SEQ ID NO: 266 (pep-123) or a variant thereof; and
   a parent peptide consisting of the amino acid sequence SEQ ID NO: 62 (pep-091) or a variant thereof,
   wherein the variant peptides each consist of 15-25 amino acid residues and each comprise an amino acid sequence having at least 90% sequence identity over at least 15 contiguous amino acids of the parent peptide.

6. The composition according to claim 1, said composition further comprising
   a parent peptide consisting of the amino acid sequence SEQ ID NO: 26 (pep-058) or a variant thereof; and
   a parent peptide consisting of the amino acid sequence SEQ ID NO: 62 (pep-091) or a variant thereof, wherein the variant peptides each consist of 15-25 amino acid residues and each comprise an amino acid sequence having at least 90% sequence identity over at least 15 contiguous amino acids of the corresponding parent peptide.

7. The composition according to claim 1, wherein the parent peptide or the variant thereof is amidated at the C-terminal end, or wherein the parent peptide or the variant thereof is a salt.

8. The composition according to claim 1, wherein the parent peptide or the variant thereof is amidated at the C-terminal end.

9. The composition according to claim 1, wherein the parent peptide or the variant thereof is a salt.

10. The composition according to claim 1, wherein the composition is a pharmaceutical composition.

11. The pharmaceutical composition according to claim 10, further comprising a pharmaceutically acceptable carrier, excipient and/or adjuvant.

12. A method for relieving or reducing an immune response triggered by an allergen of a dust mite in a subject in need thereof, comprising administering to the subject a therapeutically effective amount of the composition according to claim 1.

13. A method for relieving one or more symptoms of an immune response triggered by an allergen of a dust mite in a subject in need thereof, comprising administering to the subject a therapeutically effective amount of the composition according to claim 1.

14. A composition comprising at least three peptides, wherein at least one of the peptides is selected from each of the following peptide groups i, ii, and iii:
  i.) a peptide consisting of the amino acid sequence SEQ ID NO: 82 (pep-110) or a variant thereof selected from the group consisting of: SEQ ID NO: 70 and SEQ ID NO:269;
  ii.) a parent peptide consisting of the amino acid sequence SEQ ID NO: 271 (pep-131) or a variant thereof selected from the group consisting of peptides of SEQ ID NO: 67, SEQ ID NO: 79, SEQ ID NO: 256 and SEQ ID NO: 270; and
  iii.) a parent peptide consisting of the amino acid sequence SEQ ID NO: 268 (pep-130) or a variant thereof selected from the group consisting of peptides of SEQ ID NO: 22, SEQ ID NO: 283, SEQ ID NO: 284, SEQ ID NO: 285 and SEQ ID NO: 286.

15. The composition according to claim 14, said composition further comprising:
  iv.) a parent peptide consisting of the amino acid sequence SEQ ID NO: 266 (pep-123) or a variant thereof selected from the group consisting of peptides of SEQ ID NO: 17, SEQ ID NO: 279, SEQ ID NO: 280, SEQ ID NO: 281, SEQ ID NO: 282 and SEQ ID NO: 272; and
  v.) a parent peptide consisting of the amino acid sequence SEQ ID NO: 62 (pep-091).

* * * * *

SEQUENCE LISTING

<160> NUMBER OF SEQ ID NOS: 354

<210> SEQ ID NO 1
<211> LENGTH: 20
<212> TYPE: PRT

<213> ORGANISM: Dermatophagoides pteronyssinus

<400> SEQUENCE: 1

Arg Pro Ser Ser Ile Lys Thr Phe Glu Glu Tyr Lys Lys Ala Phe Asn
1               5                   10                  15

Lys Ser Tyr Ala
            20

<210> SEQ ID NO 2
<211> LENGTH: 20
<212> TYPE: PRT
<213> ORGANISM: Dermatophagoides pteronyssinus

<400> SEQUENCE: 2

Tyr Lys Lys Ala Phe Asn Lys Ser Tyr Ala Thr Phe Glu Asp Glu Glu
1               5                   10                  15

Ala Ala Arg Lys
            20

<210> SEQ ID NO 3
<211> LENGTH: 20
<212> TYPE: PRT
<213> ORGANISM: Dermatophagoides pteronyssinus

<400> SEQUENCE: 3

Thr Phe Glu Asp Glu Glu Ala Ala Arg Lys Asn Phe Leu Glu Ser Val
1               5                   10                  15

Lys Tyr Val Gln
            20

<210> SEQ ID NO 4
<211> LENGTH: 20
<212> TYPE: PRT
<213> ORGANISM: Dermatophagoides pteronyssinus

<400> SEQUENCE: 4

Asn Phe Leu Glu Ser Val Lys Tyr Val Gln Ser Asn Gly Gly Ala Ile
1               5                   10                  15

Asn His Leu Ser
            20

<210> SEQ ID NO 5
<211> LENGTH: 20
<212> TYPE: PRT
<213> ORGANISM: Dermatophagoides pteronyssinus

<400> SEQUENCE: 5

Ser Asn Gly Gly Ala Ile Asn His Leu Ser Asp Leu Ser Leu Asp Glu
1               5                   10                  15

Phe Lys Asn Arg
            20

<210> SEQ ID NO 6
<211> LENGTH: 20
<212> TYPE: PRT
<213> ORGANISM: Dermatophagoides pteronyssinus

<400> SEQUENCE: 6

Asp Leu Ser Leu Asp Glu Phe Lys Asn Arg Phe Leu Met Ser Ala Glu
1               5                   10                  15

Ala Phe Glu His
            20

<210> SEQ ID NO 7
<211> LENGTH: 20
<212> TYPE: PRT
<213> ORGANISM: Dermatophagoides pteronyssinus

<400> SEQUENCE: 7

```
Phe Leu Met Ser Ala Glu Ala Phe Glu His Leu Lys Thr Gln Phe Asp
1               5                   10                  15

Leu Asn Ala Glu
            20
```

<210> SEQ ID NO 8
<211> LENGTH: 19
<212> TYPE: PRT
<213> ORGANISM: Dermatophagoides pteronyssinus

<400> SEQUENCE: 8

```
Leu Lys Thr Gln Phe Asp Leu Asn Ala Glu Thr Asn Ala Ser Ser Ile
1               5                   10                  15

Asn Gly Asn
```

<210> SEQ ID NO 9
<211> LENGTH: 19
<212> TYPE: PRT
<213> ORGANISM: Dermatophagoides pteronyssinus

<400> SEQUENCE: 9

```
Thr Asn Ala Ser Ser Ile Asn Gly Asn Ala Pro Ala Glu Ile Asp Leu
1               5                   10                  15

Arg Gln Met
```

<210> SEQ ID NO 10
<211> LENGTH: 20
<212> TYPE: PRT
<213> ORGANISM: Dermatophagoides pteronyssinus

<400> SEQUENCE: 10

```
Ala Pro Ala Glu Ile Asp Leu Arg Gln Met Arg Thr Val Thr Pro Ile
1               5                   10                  15

Arg Met Gln Gly
            20
```

<210> SEQ ID NO 11
<211> LENGTH: 20
<212> TYPE: PRT
<213> ORGANISM: Dermatophagoides pteronyssinus

<400> SEQUENCE: 11

```
Arg Thr Val Thr Pro Ile Arg Met Gln Gly Gly Ser Gly Ser Ser Trp
1               5                   10                  15

Ala Phe Ser Gly
            20
```

<210> SEQ ID NO 12
<211> LENGTH: 20
<212> TYPE: PRT
<213> ORGANISM: Dermatophagoides pteronyssinus

<400> SEQUENCE: 12

```
Gly Ser Gly Ser Ser Trp Ala Phe Ser Gly Val Ala Ala Thr Glu Ser
1               5                   10                  15
```

Ala Tyr Leu Ala
        20

<210> SEQ ID NO 13
<211> LENGTH: 20
<212> TYPE: PRT
<213> ORGANISM: Dermatophagoides pteronyssinus

<400> SEQUENCE: 13

Val Ala Ala Thr Glu Ser Ala Tyr Leu Ala Tyr Arg Asn Gln Ser Leu
1               5                   10                  15

Asp Leu Ala Glu
        20

<210> SEQ ID NO 14
<211> LENGTH: 20
<212> TYPE: PRT
<213> ORGANISM: Dermatophagoides pteronyssinus

<400> SEQUENCE: 14

Tyr Arg Asn Gln Ser Leu Asp Leu Ala Glu Gln Glu Leu Val Asp Ser
1               5                   10                  15

Ala Ser Gln His
        20

<210> SEQ ID NO 15
<211> LENGTH: 20
<212> TYPE: PRT
<213> ORGANISM: Dermatophagoides pteronyssinus

<400> SEQUENCE: 15

Gln Glu Leu Val Asp Ser Ala Ser Gln His Gly Ser His Gly Asp Thr
1               5                   10                  15

Ile Pro Arg Gly
        20

<210> SEQ ID NO 16
<211> LENGTH: 20
<212> TYPE: PRT
<213> ORGANISM: Dermatophagoides pteronyssinus

<400> SEQUENCE: 16

Gly Ser His Gly Asp Thr Ile Pro Arg Gly Ile Glu Tyr Ile Gln His
1               5                   10                  15

Asn Gly Val Val
        20

<210> SEQ ID NO 17
<211> LENGTH: 20
<212> TYPE: PRT
<213> ORGANISM: Dermatophagoides pteronyssinus

<400> SEQUENCE: 17

Ile Glu Tyr Ile Gln His Asn Gly Val Val Gln Glu Ser Tyr Tyr Arg
1               5                   10                  15

Tyr Val Ala Arg
        20

<210> SEQ ID NO 18
<211> LENGTH: 20
<212> TYPE: PRT
<213> ORGANISM: Dermatophagoides pteronyssinus

```
<400> SEQUENCE: 18

Gln Glu Ser Tyr Tyr Arg Tyr Val Ala Arg Glu Gln Ser Ser Arg Arg
1               5                   10                  15

Pro Asn Ala Gln
            20

<210> SEQ ID NO 19
<211> LENGTH: 20
<212> TYPE: PRT
<213> ORGANISM: Dermatophagoides pteronyssinus

<400> SEQUENCE: 19

Glu Gln Ser Ser Arg Arg Pro Asn Ala Gln Arg Phe Gly Ile Ser Asn
1               5                   10                  15

Tyr Ser Gln Ile
            20

<210> SEQ ID NO 20
<211> LENGTH: 20
<212> TYPE: PRT
<213> ORGANISM: Dermatophagoides pteronyssinus

<400> SEQUENCE: 20

Arg Phe Gly Ile Ser Asn Tyr Ser Gln Ile Tyr Pro Pro Asn Ala Asn
1               5                   10                  15

Lys Ile Arg Glu
            20

<210> SEQ ID NO 21
<211> LENGTH: 20
<212> TYPE: PRT
<213> ORGANISM: Dermatophagoides pteronyssinus

<400> SEQUENCE: 21

Tyr Pro Pro Asn Ala Asn Lys Ile Arg Glu Ala Leu Ala Gln Thr His
1               5                   10                  15

Ser Ala Ile Ala
            20

<210> SEQ ID NO 22
<211> LENGTH: 20
<212> TYPE: PRT
<213> ORGANISM: Dermatophagoides pteronyssinus

<400> SEQUENCE: 22

Ala Leu Ala Gln Thr His Ser Ala Ile Ala Val Ile Ile Gly Ile Lys
1               5                   10                  15

Asp Leu Asp Ala
            20

<210> SEQ ID NO 23
<211> LENGTH: 20
<212> TYPE: PRT
<213> ORGANISM: Dermatophagoides pteronyssinus

<400> SEQUENCE: 23

Val Ile Ile Gly Ile Lys Asp Leu Asp Ala Phe Arg His Tyr Asp Gly
1               5                   10                  15

Arg Thr Ile Ile
            20
```

```
<210> SEQ ID NO 24
<211> LENGTH: 20
<212> TYPE: PRT
<213> ORGANISM: Dermatophagoides pteronyssinus

<400> SEQUENCE: 24

Phe Arg His Tyr Asp Gly Arg Thr Ile Ile Gln Arg Asp Asn Gly Tyr
1               5                   10                  15

Gln Pro Asn Tyr
            20

<210> SEQ ID NO 25
<211> LENGTH: 20
<212> TYPE: PRT
<213> ORGANISM: Dermatophagoides pteronyssinus

<400> SEQUENCE: 25

Gln Arg Asp Asn Gly Tyr Gln Pro Asn Tyr His Ala Val Asn Ile Val
1               5                   10                  15

Gly Tyr Ser Asn
            20

<210> SEQ ID NO 26
<211> LENGTH: 20
<212> TYPE: PRT
<213> ORGANISM: Dermatophagoides pteronyssinus

<400> SEQUENCE: 26

His Ala Val Asn Ile Val Gly Tyr Ser Asn Ala Gln Gly Val Asp Tyr
1               5                   10                  15

Trp Ile Val Arg
            20

<210> SEQ ID NO 27
<211> LENGTH: 20
<212> TYPE: PRT
<213> ORGANISM: Dermatophagoides pteronyssinus

<400> SEQUENCE: 27

Ala Gln Gly Val Asp Tyr Trp Ile Val Arg Asn Ser Trp Asp Thr Asn
1               5                   10                  15

Trp Gly Asp Asn
            20

<210> SEQ ID NO 28
<211> LENGTH: 20
<212> TYPE: PRT
<213> ORGANISM: Dermatophagoides pteronyssinus

<400> SEQUENCE: 28

Asn Ser Trp Asp Thr Asn Trp Gly Asp Asn Gly Tyr Gly Tyr Phe Ala
1               5                   10                  15

Ala Asn Ile Asp
            20

<210> SEQ ID NO 29
<211> LENGTH: 23
<212> TYPE: PRT
<213> ORGANISM: Dermatophagoides pteronyssinus

<400> SEQUENCE: 29

Gly Tyr Gly Tyr Phe Ala Ala Asn Ile Asp Leu Met Met Ile Glu Glu
```

```
                   1               5                  10                 15
Tyr Pro Tyr Val Val Ile Leu
            20

<210> SEQ ID NO 30
<211> LENGTH: 20
<212> TYPE: PRT
<213> ORGANISM: Dermatophagoides farinae

<400> SEQUENCE: 30

Arg Pro Ala Ser Ile Lys Thr Phe Glu Glu Phe Lys Lys Ala Phe Asn
1               5                  10                  15

Lys Asn Tyr Ala
            20

<210> SEQ ID NO 31
<211> LENGTH: 20
<212> TYPE: PRT
<213> ORGANISM: Dermatophagoides farinae

<400> SEQUENCE: 31

Phe Lys Lys Ala Phe Asn Lys Asn Tyr Ala Thr Val Glu Glu Glu Glu
1               5                  10                  15

Val Ala Arg Lys
            20

<210> SEQ ID NO 32
<211> LENGTH: 20
<212> TYPE: PRT
<213> ORGANISM: Dermatophagoides farinae

<400> SEQUENCE: 32

Thr Val Glu Glu Glu Glu Val Ala Arg Lys Asn Phe Leu Glu Ser Leu
1               5                  10                  15

Lys Tyr Val Glu
            20

<210> SEQ ID NO 33
<211> LENGTH: 20
<212> TYPE: PRT
<213> ORGANISM: Dermatophagoides farinae

<400> SEQUENCE: 33

Asn Phe Leu Glu Ser Leu Lys Tyr Val Glu Ala Asn Lys Gly Ala Ile
1               5                  10                  15

Asn His Leu Ser
            20

<210> SEQ ID NO 34
<211> LENGTH: 20
<212> TYPE: PRT
<213> ORGANISM: Dermatophagoides farinae

<400> SEQUENCE: 34

Ala Asn Lys Gly Ala Ile Asn His Leu Ser Asp Leu Ser Leu Asp Glu
1               5                  10                  15

Phe Lys Asn Arg
            20

<210> SEQ ID NO 35
<211> LENGTH: 20
<212> TYPE: PRT
```

<213> ORGANISM: Dermatophagoides farinae

<400> SEQUENCE: 35

Asp Leu Ser Leu Asp Glu Phe Lys Asn Arg Tyr Leu Met Ser Ala Glu
1               5                   10                  15

Ala Phe Glu Gln
            20

<210> SEQ ID NO 36
<211> LENGTH: 20
<212> TYPE: PRT
<213> ORGANISM: Dermatophagoides farinae

<400> SEQUENCE: 36

Tyr Leu Met Ser Ala Glu Ala Phe Glu Gln Leu Lys Thr Gln Phe Asp
1               5                   10                  15

Leu Asn Ala Glu
            20

<210> SEQ ID NO 37
<211> LENGTH: 20
<212> TYPE: PRT
<213> ORGANISM: Dermatophagoides farinae

<400> SEQUENCE: 37

Leu Lys Thr Gln Phe Asp Leu Asn Ala Glu Thr Ser Ala Ser Arg Ile
1               5                   10                  15

Asn Ser Val Asn
            20

<210> SEQ ID NO 38
<211> LENGTH: 20
<212> TYPE: PRT
<213> ORGANISM: Dermatophagoides farinae

<400> SEQUENCE: 38

Thr Ser Ala Ser Arg Ile Asn Ser Val Asn Val Pro Ser Glu Leu Asp
1               5                   10                  15

Leu Arg Ser Leu
            20

<210> SEQ ID NO 39
<211> LENGTH: 20
<212> TYPE: PRT
<213> ORGANISM: Dermatophagoides farinae

<400> SEQUENCE: 39

Val Pro Ser Glu Leu Asp Leu Arg Ser Leu Arg Thr Val Thr Pro Ile
1               5                   10                  15

Arg Met Gln Gly
            20

<210> SEQ ID NO 40
<211> LENGTH: 20
<212> TYPE: PRT
<213> ORGANISM: Dermatophagoides farinae

<400> SEQUENCE: 40

Arg Thr Val Thr Pro Ile Arg Met Gln Gly Gly Ser Gly Ser Ser Trp
1               5                   10                  15

Ala Phe Ser Gly
            20

<210> SEQ ID NO 41
<211> LENGTH: 20
<212> TYPE: PRT
<213> ORGANISM: Dermatophagoides farinae

<400> SEQUENCE: 41

Gly Ser Gly Ser Ser Trp Ala Phe Ser Gly Val Ala Ala Thr Glu Ser
1               5                   10                  15

Ala Tyr Leu Ala
            20

<210> SEQ ID NO 42
<211> LENGTH: 20
<212> TYPE: PRT
<213> ORGANISM: Dermatophagoides farinae

<400> SEQUENCE: 42

Val Ala Ala Thr Glu Ser Ala Tyr Leu Ala Tyr Arg Asn Thr Ser Leu
1               5                   10                  15

Asp Leu Ser Glu
            20

<210> SEQ ID NO 43
<211> LENGTH: 20
<212> TYPE: PRT
<213> ORGANISM: Dermatophagoides farinae

<400> SEQUENCE: 43

Tyr Arg Asn Thr Ser Leu Asp Leu Ser Glu Gln Glu Leu Val Asp Ser
1               5                   10                  15

Ala Ser Gln His
            20

<210> SEQ ID NO 44
<211> LENGTH: 20
<212> TYPE: PRT
<213> ORGANISM: Dermatophagoides farinae

<400> SEQUENCE: 44

Gln Glu Leu Val Asp Ser Ala Ser Gln His Gly Ser His Gly Asp Thr
1               5                   10                  15

Ile Pro Arg Gly
            20

<210> SEQ ID NO 45
<211> LENGTH: 20
<212> TYPE: PRT
<213> ORGANISM: Dermatophagoides farinae

<400> SEQUENCE: 45

Gly Ser His Gly Asp Thr Ile Pro Arg Gly Ile Glu Tyr Ile Gln Gln
1               5                   10                  15

Asn Gly Val Val
            20

<210> SEQ ID NO 46
<211> LENGTH: 20
<212> TYPE: PRT
<213> ORGANISM: Dermatophagoides farinae

<400> SEQUENCE: 46

-continued

Ile Glu Tyr Ile Gln Gln Asn Gly Val Val Glu Arg Ser Tyr Pro
1               5                   10                  15

Tyr Val Ala Arg
            20

<210> SEQ ID NO 47
<211> LENGTH: 20
<212> TYPE: PRT
<213> ORGANISM: Dermatophagoides farinae

<400> SEQUENCE: 47

Glu Glu Arg Ser Tyr Pro Tyr Val Ala Arg Glu Gln Gln Ser Arg Arg
1               5                   10                  15

Pro Asn Ser Gln
            20

<210> SEQ ID NO 48
<211> LENGTH: 20
<212> TYPE: PRT
<213> ORGANISM: Dermatophagoides farinae

<400> SEQUENCE: 48

Glu Gln Gln Ser Arg Arg Pro Asn Ser Gln His Tyr Gly Ile Ser Asn
1               5                   10                  15

Tyr Ser Gln Ile
            20

<210> SEQ ID NO 49
<211> LENGTH: 20
<212> TYPE: PRT
<213> ORGANISM: Dermatophagoides farinae

<400> SEQUENCE: 49

His Tyr Gly Ile Ser Asn Tyr Ser Gln Ile Tyr Pro Pro Asp Val Lys
1               5                   10                  15

Gln Ile Arg Glu
            20

<210> SEQ ID NO 50
<211> LENGTH: 20
<212> TYPE: PRT
<213> ORGANISM: Dermatophagoides farinae

<400> SEQUENCE: 50

Tyr Pro Pro Asp Val Lys Gln Ile Arg Glu Ala Leu Thr Gln Thr His
1               5                   10                  15

Thr Ala Ile Ala
            20

<210> SEQ ID NO 51
<211> LENGTH: 20
<212> TYPE: PRT
<213> ORGANISM: Dermatophagoides farinae

<400> SEQUENCE: 51

Ala Leu Thr Gln Thr His Thr Ala Ile Ala Val Ile Ile Gly Ile Lys
1               5                   10                  15

Asp Leu Arg Ala
            20

<210> SEQ ID NO 52
<211> LENGTH: 20

```
<212> TYPE: PRT
<213> ORGANISM: Dermatophagoides farinae

<400> SEQUENCE: 52

Val Ile Ile Gly Ile Lys Asp Leu Arg Ala Phe Gln His Tyr Asp Gly
1               5                   10                  15

Arg Thr Ile Ile
            20

<210> SEQ ID NO 53
<211> LENGTH: 20
<212> TYPE: PRT
<213> ORGANISM: Dermatophagoides farinae

<400> SEQUENCE: 53

Phe Gln His Tyr Asp Gly Arg Thr Ile Ile Gln His Asp Asn Gly Tyr
1               5                   10                  15

Gln Pro Asn Tyr
            20

<210> SEQ ID NO 54
<211> LENGTH: 20
<212> TYPE: PRT
<213> ORGANISM: Dermatophagoides farinae

<400> SEQUENCE: 54

Gln His Asp Asn Gly Tyr Gln Pro Asn Tyr His Ala Val Asn Ile Val
1               5                   10                  15

Gly Tyr Gly Ser
            20

<210> SEQ ID NO 55
<211> LENGTH: 20
<212> TYPE: PRT
<213> ORGANISM: Dermatophagoides farinae

<400> SEQUENCE: 55

His Ala Val Asn Ile Val Gly Tyr Gly Ser Thr Gln Gly Val Asp Tyr
1               5                   10                  15

Trp Ile Val Arg
            20

<210> SEQ ID NO 56
<211> LENGTH: 20
<212> TYPE: PRT
<213> ORGANISM: Dermatophagoides farinae

<400> SEQUENCE: 56

Thr Gln Gly Val Asp Tyr Trp Ile Val Arg Asn Ser Trp Asp Thr Thr
1               5                   10                  15

Trp Gly Asp Ser
            20

<210> SEQ ID NO 57
<211> LENGTH: 20
<212> TYPE: PRT
<213> ORGANISM: Dermatophagoides farinae

<400> SEQUENCE: 57

Asn Ser Trp Asp Thr Thr Trp Gly Asp Ser Gly Tyr Gly Tyr Phe Gln
1               5                   10                  15

Ala Gly Asn Asn
```

<210> SEQ ID NO 58
<211> LENGTH: 23
<212> TYPE: PRT
<213> ORGANISM: Dermatophagoides farinae

<400> SEQUENCE: 58

Gly Tyr Gly Tyr Phe Gln Ala Gly Asn Asn Leu Met Met Ile Glu Gln
1               5                   10                  15

Tyr Pro Tyr Val Val Ile Met
            20

<210> SEQ ID NO 59
<211> LENGTH: 19
<212> TYPE: PRT
<213> ORGANISM: Dermatophagoides pteronyssinus

<400> SEQUENCE: 59

Asp Gln Val Asp Val Lys Asp Ser Ala Asn His Glu Ile Lys Lys Val
1               5                   10                  15

Leu Val Pro

<210> SEQ ID NO 60
<211> LENGTH: 20
<212> TYPE: PRT
<213> ORGANISM: Dermatophagoides pteronyssinus

<400> SEQUENCE: 60

Asn His Glu Ile Lys Lys Val Leu Val Pro Gly Ser His Gly Ser Glu
1               5                   10                  15

Pro Ser Ile Ile
            20

<210> SEQ ID NO 61
<211> LENGTH: 20
<212> TYPE: PRT
<213> ORGANISM: Dermatophagoides pteronyssinus

<400> SEQUENCE: 61

Gly Ser His Gly Ser Glu Pro Ser Ile Ile His Arg Gly Lys Pro Phe
1               5                   10                  15

Gln Leu Glu Ala
            20

<210> SEQ ID NO 62
<211> LENGTH: 20
<212> TYPE: PRT
<213> ORGANISM: Dermatophagoides pteronyssinus

<400> SEQUENCE: 62

His Arg Gly Lys Pro Phe Gln Leu Glu Ala Val Phe Glu Ala Asn Gln
1               5                   10                  15

Asn Thr Lys Thr
            20

<210> SEQ ID NO 63
<211> LENGTH: 20
<212> TYPE: PRT
<213> ORGANISM: Dermatophagoides pteronyssinus

<400> SEQUENCE: 63

```
Val Phe Glu Ala Asn Gln Asn Thr Lys Thr Ala Lys Ile Glu Ile Lys
1               5                   10                  15

Ala Ser Ile Asp
            20
```

<210> SEQ ID NO 64
<211> LENGTH: 20
<212> TYPE: PRT
<213> ORGANISM: Dermatophagoides pteronyssinus

<400> SEQUENCE: 64

```
Ala Lys Ile Glu Ile Lys Ala Ser Ile Asp Gly Leu Glu Val Asp Val
1               5                   10                  15

Pro Gly Ile Asp
            20
```

<210> SEQ ID NO 65
<211> LENGTH: 20
<212> TYPE: PRT
<213> ORGANISM: Dermatophagoides pteronyssinus

<400> SEQUENCE: 65

```
Gly Leu Glu Val Asp Val Pro Gly Ile Asp Pro Asn Ala Ser His Tyr
1               5                   10                  15

Met Lys Ser Pro
            20
```

<210> SEQ ID NO 66
<211> LENGTH: 20
<212> TYPE: PRT
<213> ORGANISM: Dermatophagoides pteronyssinus

<400> SEQUENCE: 66

```
Pro Asn Ala Ser His Tyr Met Lys Ser Pro Leu Val Lys Gly Gln Gln
1               5                   10                  15

Tyr Asp Ile Lys
            20
```

<210> SEQ ID NO 67
<211> LENGTH: 20
<212> TYPE: PRT
<213> ORGANISM: Dermatophagoides pteronyssinus

<400> SEQUENCE: 67

```
Leu Val Lys Gly Gln Gln Tyr Asp Ile Lys Tyr Thr Trp Asn Val Pro
1               5                   10                  15

Lys Ile Ala Pro
            20
```

<210> SEQ ID NO 68
<211> LENGTH: 20
<212> TYPE: PRT
<213> ORGANISM: Dermatophagoides pteronyssinus

<400> SEQUENCE: 68

```
Tyr Thr Trp Asn Val Pro Lys Ile Ala Pro Lys Ser Glu Asn Val Val
1               5                   10                  15

Val Thr Val Lys
            20
```

<210> SEQ ID NO 69
<211> LENGTH: 20

-continued

```
<212> TYPE: PRT
<213> ORGANISM: Dermatophagoides pteronyssinus

<400> SEQUENCE: 69

Lys Ser Glu Asn Val Val Thr Val Lys Val Met Gly Asp Asp Gly
1               5                   10                  15

Val Leu Ala Ser
            20

<210> SEQ ID NO 70
<211> LENGTH: 20
<212> TYPE: PRT
<213> ORGANISM: Dermatophagoides pteronyssinus

<400> SEQUENCE: 70

Val Met Gly Asp Asp Gly Val Leu Ala Ser Ala Ile Ala Thr His Ala
1               5                   10                  15

Lys Ile Arg Asp
            20

<210> SEQ ID NO 71
<211> LENGTH: 19
<212> TYPE: PRT
<213> ORGANISM: Dermatophagoides farinae

<400> SEQUENCE: 71

Asp Gln Val Asp Val Lys Asp Ser Ala Asn Asn Glu Ile Lys Lys Val
1               5                   10                  15

Met Val Asp

<210> SEQ ID NO 72
<211> LENGTH: 20
<212> TYPE: PRT
<213> ORGANISM: Dermatophagoides farinae

<400> SEQUENCE: 72

Asn Asn Glu Ile Lys Lys Val Met Val Asp Gly Ser His Gly Ser Asp
1               5                   10                  15

Pro Ser Ile Ile
            20

<210> SEQ ID NO 73
<211> LENGTH: 20
<212> TYPE: PRT
<213> ORGANISM: Dermatophagoides farinae

<400> SEQUENCE: 73

Gly Ser His Gly Ser Asp Pro Ser Ile Ile His Arg Gly Lys Pro Phe
1               5                   10                  15

Thr Leu Glu Ala
            20

<210> SEQ ID NO 74
<211> LENGTH: 19
<212> TYPE: PRT
<213> ORGANISM: Dermatophagoides farinae

<400> SEQUENCE: 74

His Arg Gly Lys Pro Phe Thr Leu Glu Ala Leu Phe Asp Ala Asn Gln
1               5                   10                  15

Asn Thr Lys
```

<210> SEQ ID NO 75
<211> LENGTH: 20
<212> TYPE: PRT
<213> ORGANISM: Dermatophagoides farinae

<400> SEQUENCE: 75

Leu Phe Asp Ala Asn Gln Asn Thr Lys Thr Ala Lys Ile Glu Ile Lys
1               5                   10                  15

Ala Ser Leu Asp
            20

<210> SEQ ID NO 76
<211> LENGTH: 20
<212> TYPE: PRT
<213> ORGANISM: Dermatophagoides farinae

<400> SEQUENCE: 76

Ala Lys Ile Glu Ile Lys Ala Ser Leu Asp Gly Leu Glu Ile Asp Val
1               5                   10                  15

Pro Gly Ile Asp
            20

<210> SEQ ID NO 77
<211> LENGTH: 20
<212> TYPE: PRT
<213> ORGANISM: Dermatophagoides farinae

<400> SEQUENCE: 77

Gly Leu Glu Ile Asp Val Pro Gly Ile Asp Thr Asn Ala Ser His Phe
1               5                   10                  15

Met Lys Ser Pro
            20

<210> SEQ ID NO 78
<211> LENGTH: 20
<212> TYPE: PRT
<213> ORGANISM: Dermatophagoides farinae

<400> SEQUENCE: 78

Thr Asn Ala Ser His Phe Met Lys Ser Pro Leu Val Lys Gly Gln Gln
1               5                   10                  15

Tyr Asp Ala Lys
            20

<210> SEQ ID NO 79
<211> LENGTH: 20
<212> TYPE: PRT
<213> ORGANISM: Dermatophagoides farinae

<400> SEQUENCE: 79

Leu Val Lys Gly Gln Gln Tyr Asp Ala Lys Tyr Thr Trp Asn Val Pro
1               5                   10                  15

Lys Ile Ala Pro
            20

<210> SEQ ID NO 80
<211> LENGTH: 20
<212> TYPE: PRT
<213> ORGANISM: Dermatophagoides farinae

<400> SEQUENCE: 80

Tyr Thr Trp Asn Val Pro Lys Ile Ala Pro Lys Ser Glu Asn Val Val

Val Thr Val Lys
        20

<210> SEQ ID NO 81
<211> LENGTH: 20
<212> TYPE: PRT
<213> ORGANISM: Dermatophagoides farinae

<400> SEQUENCE: 81

Lys Ser Glu Asn Val Val Thr Val Lys Leu Val Gly Asp Asn Gly
1               5                   10                  15

Val Leu Ala Ser
        20

<210> SEQ ID NO 82
<211> LENGTH: 20
<212> TYPE: PRT
<213> ORGANISM: Dermatophagoides farinae

<400> SEQUENCE: 82

Leu Val Gly Asp Asn Gly Val Leu Ala Ser Ala Ile Ala Thr His Ala
1               5                   10                  15

Lys Ile Arg Asp
        20

<210> SEQ ID NO 83
<211> LENGTH: 15
<212> TYPE: PRT
<213> ORGANISM: Dermatophagoides pteronyssinus

<400> SEQUENCE: 83

Arg Pro Ser Ser Ile Lys Thr Phe Glu Glu Tyr Lys Lys Ala Phe
1               5                   10                  15

<210> SEQ ID NO 84
<211> LENGTH: 15
<212> TYPE: PRT
<213> ORGANISM: Dermatophagoides pteronyssinus

<400> SEQUENCE: 84

Lys Thr Phe Glu Glu Tyr Lys Lys Ala Phe Asn Lys Ser Tyr Ala
1               5                   10                  15

<210> SEQ ID NO 85
<211> LENGTH: 15
<212> TYPE: PRT
<213> ORGANISM: Dermatophagoides pteronyssinus

<400> SEQUENCE: 85

Tyr Lys Lys Ala Phe Asn Lys Ser Tyr Ala Thr Phe Glu Asp Glu
1               5                   10                  15

<210> SEQ ID NO 86
<211> LENGTH: 15
<212> TYPE: PRT
<213> ORGANISM: Dermatophagoides pteronyssinus

<400> SEQUENCE: 86

Asn Lys Ser Tyr Ala Thr Phe Glu Asp Glu Glu Ala Ala Arg Lys
1               5                   10                  15

<210> SEQ ID NO 87

-continued

```
<211> LENGTH: 15
<212> TYPE: PRT
<213> ORGANISM: Dermatophagoides pteronyssinus

<400> SEQUENCE: 87

Thr Phe Glu Asp Glu Glu Ala Ala Arg Lys Asn Phe Leu Glu Ser
1               5                   10                  15

<210> SEQ ID NO 88
<211> LENGTH: 15
<212> TYPE: PRT
<213> ORGANISM: Dermatophagoides pteronyssinus

<400> SEQUENCE: 88

Glu Ala Ala Arg Lys Asn Phe Leu Glu Ser Val Lys Tyr Val Gln
1               5                   10                  15

<210> SEQ ID NO 89
<211> LENGTH: 15
<212> TYPE: PRT
<213> ORGANISM: Dermatophagoides pteronyssinus

<400> SEQUENCE: 89

Asn Phe Leu Glu Ser Val Lys Tyr Val Gln Ser Asn Gly Gly Ala
1               5                   10                  15

<210> SEQ ID NO 90
<211> LENGTH: 15
<212> TYPE: PRT
<213> ORGANISM: Dermatophagoides pteronyssinus

<400> SEQUENCE: 90

Val Lys Tyr Val Gln Ser Asn Gly Gly Ala Ile Asn His Leu Ser
1               5                   10                  15

<210> SEQ ID NO 91
<211> LENGTH: 15
<212> TYPE: PRT
<213> ORGANISM: Dermatophagoides pteronyssinus

<400> SEQUENCE: 91

Ser Asn Gly Gly Ala Ile Asn His Leu Ser Asp Leu Ser Leu Asp
1               5                   10                  15

<210> SEQ ID NO 92
<211> LENGTH: 15
<212> TYPE: PRT
<213> ORGANISM: Dermatophagoides pteronyssinus

<400> SEQUENCE: 92

Ile Asn His Leu Ser Asp Leu Ser Leu Asp Glu Phe Lys Asn Arg
1               5                   10                  15

<210> SEQ ID NO 93
<211> LENGTH: 15
<212> TYPE: PRT
<213> ORGANISM: Dermatophagoides pteronyssinus

<400> SEQUENCE: 93

Asp Leu Ser Leu Asp Glu Phe Lys Asn Arg Phe Leu Met Ser Ala
1               5                   10                  15

<210> SEQ ID NO 94
<211> LENGTH: 15
<212> TYPE: PRT
```

<213> ORGANISM: Dermatophagoides pteronyssinus

<400> SEQUENCE: 94

Glu Phe Lys Asn Arg Phe Leu Met Ser Ala Glu Ala Phe Glu His
1               5                   10                  15

<210> SEQ ID NO 95
<211> LENGTH: 15
<212> TYPE: PRT
<213> ORGANISM: Dermatophagoides pteronyssinus

<400> SEQUENCE: 95

Phe Leu Met Ser Ala Glu Ala Phe Glu His Leu Lys Thr Gln Phe
1               5                   10                  15

<210> SEQ ID NO 96
<211> LENGTH: 15
<212> TYPE: PRT
<213> ORGANISM: Dermatophagoides pteronyssinus

<400> SEQUENCE: 96

Glu Ala Phe Glu His Leu Lys Thr Gln Phe Asp Leu Asn Ala Glu
1               5                   10                  15

<210> SEQ ID NO 97
<211> LENGTH: 15
<212> TYPE: PRT
<213> ORGANISM: Dermatophagoides pteronyssinus

<400> SEQUENCE: 97

Leu Lys Thr Gln Phe Asp Leu Asn Ala Glu Thr Asn Ala Cys Ser
1               5                   10                  15

<210> SEQ ID NO 98
<211> LENGTH: 15
<212> TYPE: PRT
<213> ORGANISM: Dermatophagoides pteronyssinus

<400> SEQUENCE: 98

Asp Leu Asn Ala Glu Thr Asn Ala Cys Ser Ile Asn Gly Asn Ala
1               5                   10                  15

<210> SEQ ID NO 99
<211> LENGTH: 14
<212> TYPE: PRT
<213> ORGANISM: Dermatophagoides pteronyssinus

<400> SEQUENCE: 99

Thr Asn Ala Cys Ser Ile Asn Gly Asn Ala Pro Ala Glu Ile
1               5                   10

<210> SEQ ID NO 100
<211> LENGTH: 14
<212> TYPE: PRT
<213> ORGANISM: Dermatophagoides pteronyssinus

<400> SEQUENCE: 100

Ile Asn Gly Asn Ala Pro Ala Glu Ile Asp Leu Arg Gln Met
1               5                   10

<210> SEQ ID NO 101
<211> LENGTH: 14
<212> TYPE: PRT
<213> ORGANISM: Dermatophagoides pteronyssinus

<400> SEQUENCE: 101

Pro Ala Glu Ile Asp Leu Arg Gln Met Arg Thr Val Thr Pro
1               5                   10

<210> SEQ ID NO 102
<211> LENGTH: 15
<212> TYPE: PRT
<213> ORGANISM: Dermatophagoides pteronyssinus

<400> SEQUENCE: 102

Asp Leu Arg Gln Met Arg Thr Val Thr Pro Ile Arg Met Gln Gly
1               5                   10                  15

<210> SEQ ID NO 103
<211> LENGTH: 15
<212> TYPE: PRT
<213> ORGANISM: Dermatophagoides pteronyssinus

<400> SEQUENCE: 103

Arg Thr Val Thr Pro Ile Arg Met Gln Gly Gly Cys Gly Ser Cys
1               5                   10                  15

<210> SEQ ID NO 104
<211> LENGTH: 15
<212> TYPE: PRT
<213> ORGANISM: Dermatophagoides pteronyssinus

<400> SEQUENCE: 104

Ile Arg Met Gln Gly Gly Cys Gly Ser Cys Trp Ala Phe Ser Gly
1               5                   10                  15

<210> SEQ ID NO 105
<211> LENGTH: 15
<212> TYPE: PRT
<213> ORGANISM: Dermatophagoides pteronyssinus

<400> SEQUENCE: 105

Gly Cys Gly Ser Cys Trp Ala Phe Ser Gly Val Ala Ala Thr Glu
1               5                   10                  15

<210> SEQ ID NO 106
<211> LENGTH: 15
<212> TYPE: PRT
<213> ORGANISM: Dermatophagoides pteronyssinus

<400> SEQUENCE: 106

Trp Ala Phe Ser Gly Val Ala Ala Thr Glu Ser Ala Tyr Leu Ala
1               5                   10                  15

<210> SEQ ID NO 107
<211> LENGTH: 15
<212> TYPE: PRT
<213> ORGANISM: Dermatophagoides pteronyssinus

<400> SEQUENCE: 107

Val Ala Ala Thr Glu Ser Ala Tyr Leu Ala Tyr Arg Asn Gln Ser
1               5                   10                  15

<210> SEQ ID NO 108
<211> LENGTH: 15
<212> TYPE: PRT
<213> ORGANISM: Dermatophagoides pteronyssinus

<400> SEQUENCE: 108

```
Ser Ala Tyr Leu Ala Tyr Arg Asn Gln Ser Leu Asp Leu Ala Glu
1               5                   10                  15

<210> SEQ ID NO 109
<211> LENGTH: 15
<212> TYPE: PRT
<213> ORGANISM: Dermatophagoides pteronyssinus

<400> SEQUENCE: 109

Tyr Arg Asn Gln Ser Leu Asp Leu Ala Glu Gln Glu Leu Val Asp
1               5                   10                  15

<210> SEQ ID NO 110
<211> LENGTH: 15
<212> TYPE: PRT
<213> ORGANISM: Dermatophagoides pteronyssinus

<400> SEQUENCE: 110

Leu Asp Leu Ala Glu Gln Glu Leu Val Asp Cys Ala Ser Gln His
1               5                   10                  15

<210> SEQ ID NO 111
<211> LENGTH: 15
<212> TYPE: PRT
<213> ORGANISM: Dermatophagoides pteronyssinus

<400> SEQUENCE: 111

Gln Glu Leu Val Asp Cys Ala Ser Gln His Gly Cys His Gly Asp
1               5                   10                  15

<210> SEQ ID NO 112
<211> LENGTH: 15
<212> TYPE: PRT
<213> ORGANISM: Dermatophagoides pteronyssinus

<400> SEQUENCE: 112

Cys Ala Ser Gln His Gly Cys His Gly Asp Thr Ile Pro Arg Gly
1               5                   10                  15

<210> SEQ ID NO 113
<211> LENGTH: 15
<212> TYPE: PRT
<213> ORGANISM: Dermatophagoides pteronyssinus

<400> SEQUENCE: 113

Gly Cys His Gly Asp Thr Ile Pro Arg Gly Ile Glu Tyr Ile Gln
1               5                   10                  15

<210> SEQ ID NO 114
<211> LENGTH: 15
<212> TYPE: PRT
<213> ORGANISM: Dermatophagoides pteronyssinus

<400> SEQUENCE: 114

Thr Ile Pro Arg Gly Ile Glu Tyr Ile Gln His Asn Gly Val Val
1               5                   10                  15

<210> SEQ ID NO 115
<211> LENGTH: 15
<212> TYPE: PRT
<213> ORGANISM: Dermatophagoides pteronyssinus

<400> SEQUENCE: 115

Ile Glu Tyr Ile Gln His Asn Gly Val Val Gln Glu Ser Tyr Tyr
1               5                   10                  15
```

<210> SEQ ID NO 116
<211> LENGTH: 15
<212> TYPE: PRT
<213> ORGANISM: Dermatophagoides pteronyssinus

<400> SEQUENCE: 116

His Asn Gly Val Val Gln Glu Ser Tyr Tyr Arg Tyr Val Ala Arg
1               5                   10                  15

<210> SEQ ID NO 117
<211> LENGTH: 15
<212> TYPE: PRT
<213> ORGANISM: Dermatophagoides pteronyssinus

<400> SEQUENCE: 117

Gln Glu Ser Tyr Tyr Arg Tyr Val Ala Arg Glu Gln Ser Cys Arg
1               5                   10                  15

<210> SEQ ID NO 118
<211> LENGTH: 15
<212> TYPE: PRT
<213> ORGANISM: Dermatophagoides pteronyssinus

<400> SEQUENCE: 118

Arg Tyr Val Ala Arg Glu Gln Ser Cys Arg Arg Pro Asn Ala Gln
1               5                   10                  15

<210> SEQ ID NO 119
<211> LENGTH: 15
<212> TYPE: PRT
<213> ORGANISM: Dermatophagoides pteronyssinus

<400> SEQUENCE: 119

Glu Gln Ser Cys Arg Arg Pro Asn Ala Gln Arg Phe Gly Ile Ser
1               5                   10                  15

<210> SEQ ID NO 120
<211> LENGTH: 15
<212> TYPE: PRT
<213> ORGANISM: Dermatophagoides pteronyssinus

<400> SEQUENCE: 120

Arg Pro Asn Ala Gln Arg Phe Gly Ile Ser Asn Tyr Cys Gln Ile
1               5                   10                  15

<210> SEQ ID NO 121
<211> LENGTH: 15
<212> TYPE: PRT
<213> ORGANISM: Dermatophagoides pteronyssinus

<400> SEQUENCE: 121

Arg Phe Gly Ile Ser Asn Tyr Cys Gln Ile Tyr Pro Pro Asn Ala
1               5                   10                  15

<210> SEQ ID NO 122
<211> LENGTH: 15
<212> TYPE: PRT
<213> ORGANISM: Dermatophagoides pteronyssinus

<400> SEQUENCE: 122

Asn Tyr Cys Gln Ile Tyr Pro Pro Asn Ala Asn Lys Ile Arg Glu
1               5                   10                  15

```
<210> SEQ ID NO 123
<211> LENGTH: 15
<212> TYPE: PRT
<213> ORGANISM: Dermatophagoides pteronyssinus

<400> SEQUENCE: 123

Tyr Pro Pro Asn Ala Asn Lys Ile Arg Glu Ala Leu Ala Gln Thr
1               5                   10                  15

<210> SEQ ID NO 124
<211> LENGTH: 15
<212> TYPE: PRT
<213> ORGANISM: Dermatophagoides pteronyssinus

<400> SEQUENCE: 124

Asn Lys Ile Arg Glu Ala Leu Ala Gln Thr His Ser Ala Ile Ala
1               5                   10                  15

<210> SEQ ID NO 125
<211> LENGTH: 15
<212> TYPE: PRT
<213> ORGANISM: Dermatophagoides pteronyssinus

<400> SEQUENCE: 125

Ala Leu Ala Gln Thr His Ser Ala Ile Ala Val Ile Ile Gly Ile
1               5                   10                  15

<210> SEQ ID NO 126
<211> LENGTH: 15
<212> TYPE: PRT
<213> ORGANISM: Dermatophagoides pteronyssinus

<400> SEQUENCE: 126

His Ser Ala Ile Ala Val Ile Ile Gly Ile Lys Asp Leu Asp Ala
1               5                   10                  15

<210> SEQ ID NO 127
<211> LENGTH: 15
<212> TYPE: PRT
<213> ORGANISM: Dermatophagoides pteronyssinus

<400> SEQUENCE: 127

Val Ile Ile Gly Ile Lys Asp Leu Asp Ala Phe Arg His Tyr Asp
1               5                   10                  15

<210> SEQ ID NO 128
<211> LENGTH: 15
<212> TYPE: PRT
<213> ORGANISM: Dermatophagoides pteronyssinus

<400> SEQUENCE: 128

Lys Asp Leu Asp Ala Phe Arg His Tyr Asp Gly Arg Thr Ile Ile
1               5                   10                  15

<210> SEQ ID NO 129
<211> LENGTH: 15
<212> TYPE: PRT
<213> ORGANISM: Dermatophagoides pteronyssinus

<400> SEQUENCE: 129

Phe Arg His Tyr Asp Gly Arg Thr Ile Ile Gln Arg Asp Asn Gly
1               5                   10                  15

<210> SEQ ID NO 130
<211> LENGTH: 15
```

<212> TYPE: PRT
<213> ORGANISM: Dermatophagoides pteronyssinus

<400> SEQUENCE: 130

Gly Arg Thr Ile Ile Gln Arg Asp Asn Gly Tyr Gln Pro Asn Tyr
1               5                   10                  15

<210> SEQ ID NO 131
<211> LENGTH: 15
<212> TYPE: PRT
<213> ORGANISM: Dermatophagoides pteronyssinus

<400> SEQUENCE: 131

Gln Arg Asp Asn Gly Tyr Gln Pro Asn Tyr His Ala Val Asn Ile
1               5                   10                  15

<210> SEQ ID NO 132
<211> LENGTH: 15
<212> TYPE: PRT
<213> ORGANISM: Dermatophagoides pteronyssinus

<400> SEQUENCE: 132

Tyr Gln Pro Asn Tyr His Ala Val Asn Ile Val Gly Tyr Ser Asn
1               5                   10                  15

<210> SEQ ID NO 133
<211> LENGTH: 15
<212> TYPE: PRT
<213> ORGANISM: Dermatophagoides pteronyssinus

<400> SEQUENCE: 133

His Ala Val Asn Ile Val Gly Tyr Ser Asn Ala Gln Gly Val Asp
1               5                   10                  15

<210> SEQ ID NO 134
<211> LENGTH: 15
<212> TYPE: PRT
<213> ORGANISM: Dermatophagoides pteronyssinus

<400> SEQUENCE: 134

Val Gly Tyr Ser Asn Ala Gln Gly Val Asp Tyr Trp Ile Val Arg
1               5                   10                  15

<210> SEQ ID NO 135
<211> LENGTH: 15
<212> TYPE: PRT
<213> ORGANISM: Dermatophagoides pteronyssinus

<400> SEQUENCE: 135

Ala Gln Gly Val Asp Tyr Trp Ile Val Arg Asn Ser Trp Asp Thr
1               5                   10                  15

<210> SEQ ID NO 136
<211> LENGTH: 15
<212> TYPE: PRT
<213> ORGANISM: Dermatophagoides pteronyssinus

<400> SEQUENCE: 136

Tyr Trp Ile Val Arg Asn Ser Trp Asp Thr Asn Trp Gly Asp Asn
1               5                   10                  15

<210> SEQ ID NO 137
<211> LENGTH: 15
<212> TYPE: PRT
<213> ORGANISM: Dermatophagoides pteronyssinus

<400> SEQUENCE: 137

Asn Ser Trp Asp Thr Asn Trp Gly Asp Asn Gly Tyr Gly Tyr Phe
1               5                   10                  15

<210> SEQ ID NO 138
<211> LENGTH: 15
<212> TYPE: PRT
<213> ORGANISM: Dermatophagoides pteronyssinus

<400> SEQUENCE: 138

Asn Trp Gly Asp Asn Gly Tyr Gly Tyr Phe Ala Ala Asn Ile Asp
1               5                   10                  15

<210> SEQ ID NO 139
<211> LENGTH: 15
<212> TYPE: PRT
<213> ORGANISM: Dermatophagoides pteronyssinus

<400> SEQUENCE: 139

Gly Tyr Gly Tyr Phe Ala Ala Asn Ile Asp Leu Met Met Ile Glu
1               5                   10                  15

<210> SEQ ID NO 140
<211> LENGTH: 15
<212> TYPE: PRT
<213> ORGANISM: Dermatophagoides pteronyssinus

<400> SEQUENCE: 140

Ala Ala Asn Ile Asp Leu Met Met Ile Glu Glu Tyr Pro Tyr Val
1               5                   10                  15

<210> SEQ ID NO 141
<211> LENGTH: 15
<212> TYPE: PRT
<213> ORGANISM: Dermatophagoides pteronyssinus

<400> SEQUENCE: 141

Ile Asp Leu Met Met Ile Glu Glu Tyr Pro Tyr Val Val Ile Leu
1               5                   10                  15

<210> SEQ ID NO 142
<211> LENGTH: 15
<212> TYPE: PRT
<213> ORGANISM: Dermatophagoides farinae

<400> SEQUENCE: 142

Arg Pro Ala Ser Ile Lys Thr Phe Glu Glu Phe Lys Lys Ala Phe
1               5                   10                  15

<210> SEQ ID NO 143
<211> LENGTH: 15
<212> TYPE: PRT
<213> ORGANISM: Dermatophagoides farinae

<400> SEQUENCE: 143

Lys Thr Phe Glu Glu Phe Lys Lys Ala Phe Asn Lys Asn Tyr Ala
1               5                   10                  15

<210> SEQ ID NO 144
<211> LENGTH: 15
<212> TYPE: PRT
<213> ORGANISM: Dermatophagoides farinae

<400> SEQUENCE: 144

```
Phe Lys Lys Ala Phe Asn Lys Asn Tyr Ala Thr Val Glu Glu Glu
1               5                   10                  15
```

<210> SEQ ID NO 145
<211> LENGTH: 15
<212> TYPE: PRT
<213> ORGANISM: Dermatophagoides farinae

<400> SEQUENCE: 145

```
Asn Lys Asn Tyr Ala Thr Val Glu Glu Glu Val Ala Arg Lys
1               5                   10                  15
```

<210> SEQ ID NO 146
<211> LENGTH: 15
<212> TYPE: PRT
<213> ORGANISM: Dermatophagoides farinae

<400> SEQUENCE: 146

```
Thr Val Glu Glu Glu Val Ala Arg Lys Asn Phe Leu Glu Ser
1               5                   10                  15
```

<210> SEQ ID NO 147
<211> LENGTH: 15
<212> TYPE: PRT
<213> ORGANISM: Dermatophagoides farinae

<400> SEQUENCE: 147

```
Glu Val Ala Arg Lys Asn Phe Leu Glu Ser Leu Lys Tyr Val Glu
1               5                   10                  15
```

<210> SEQ ID NO 148
<211> LENGTH: 15
<212> TYPE: PRT
<213> ORGANISM: Dermatophagoides farinae

<400> SEQUENCE: 148

```
Asn Phe Leu Glu Ser Leu Lys Tyr Val Glu Ala Asn Lys Gly Ala
1               5                   10                  15
```

<210> SEQ ID NO 149
<211> LENGTH: 15
<212> TYPE: PRT
<213> ORGANISM: Dermatophagoides farinae

<400> SEQUENCE: 149

```
Leu Lys Tyr Val Glu Ala Asn Lys Gly Ala Ile Asn His Leu Ser
1               5                   10                  15
```

<210> SEQ ID NO 150
<211> LENGTH: 15
<212> TYPE: PRT
<213> ORGANISM: Dermatophagoides farinae

<400> SEQUENCE: 150

```
Ala Asn Lys Gly Ala Ile Asn His Leu Ser Asp Leu Ser Leu Asp
1               5                   10                  15
```

<210> SEQ ID NO 151
<211> LENGTH: 15
<212> TYPE: PRT
<213> ORGANISM: Dermatophagoides farinae

<400> SEQUENCE: 151

```
Ile Asn His Leu Ser Asp Leu Ser Leu Asp Glu Phe Lys Asn Arg
```

```
1               5                   10                  15
```

<210> SEQ ID NO 152
<211> LENGTH: 15
<212> TYPE: PRT
<213> ORGANISM: Dermatophagoides farinae

<400> SEQUENCE: 152

```
Asp Leu Ser Leu Asp Glu Phe Lys Asn Arg Tyr Leu Met Ser Ala
1               5                   10                  15
```

<210> SEQ ID NO 153
<211> LENGTH: 15
<212> TYPE: PRT
<213> ORGANISM: Dermatophagoides farinae

<400> SEQUENCE: 153

```
Glu Phe Lys Asn Arg Tyr Leu Met Ser Ala Glu Ala Phe Glu Gln
1               5                   10                  15
```

<210> SEQ ID NO 154
<211> LENGTH: 15
<212> TYPE: PRT
<213> ORGANISM: Dermatophagoides farinae

<400> SEQUENCE: 154

```
Tyr Leu Met Ser Ala Glu Ala Phe Glu Gln Leu Lys Thr Gln Phe
1               5                   10                  15
```

<210> SEQ ID NO 155
<211> LENGTH: 15
<212> TYPE: PRT
<213> ORGANISM: Dermatophagoides farinae

<400> SEQUENCE: 155

```
Glu Ala Phe Glu Gln Leu Lys Thr Gln Phe Asp Leu Asn Ala Glu
1               5                   10                  15
```

<210> SEQ ID NO 156
<211> LENGTH: 15
<212> TYPE: PRT
<213> ORGANISM: Dermatophagoides farinae

<400> SEQUENCE: 156

```
Leu Lys Thr Gln Phe Asp Leu Asn Ala Glu Thr Ser Ala Cys Arg
1               5                   10                  15
```

<210> SEQ ID NO 157
<211> LENGTH: 15
<212> TYPE: PRT
<213> ORGANISM: Dermatophagoides farinae

<400> SEQUENCE: 157

```
Asp Leu Asn Ala Glu Thr Ser Ala Cys Arg Ile Asn Ser Val Asn
1               5                   10                  15
```

<210> SEQ ID NO 158
<211> LENGTH: 15
<212> TYPE: PRT
<213> ORGANISM: Dermatophagoides farinae

<400> SEQUENCE: 158

```
Thr Ser Ala Cys Arg Ile Asn Ser Val Asn Val Pro Ser Glu Leu
1               5                   10                  15
```

<210> SEQ ID NO 159
<211> LENGTH: 15
<212> TYPE: PRT
<213> ORGANISM: Dermatophagoides farinae

<400> SEQUENCE: 159

Ile Asn Ser Val Asn Val Pro Ser Glu Leu Asp Leu Arg Ser Leu
1               5                   10                  15

<210> SEQ ID NO 160
<211> LENGTH: 15
<212> TYPE: PRT
<213> ORGANISM: Dermatophagoides farinae

<400> SEQUENCE: 160

Val Pro Ser Glu Leu Asp Leu Arg Ser Leu Arg Thr Val Thr Pro
1               5                   10                  15

<210> SEQ ID NO 161
<211> LENGTH: 15
<212> TYPE: PRT
<213> ORGANISM: Dermatophagoides farinae

<400> SEQUENCE: 161

Asp Leu Arg Ser Leu Arg Thr Val Thr Pro Ile Arg Met Gln Gly
1               5                   10                  15

<210> SEQ ID NO 162
<211> LENGTH: 15
<212> TYPE: PRT
<213> ORGANISM: Dermatophagoides farinae

<400> SEQUENCE: 162

Arg Thr Val Thr Pro Ile Arg Met Gln Gly Gly Cys Gly Ser Cys
1               5                   10                  15

<210> SEQ ID NO 163
<211> LENGTH: 15
<212> TYPE: PRT
<213> ORGANISM: Dermatophagoides farinae

<400> SEQUENCE: 163

Ile Arg Met Gln Gly Gly Cys Gly Ser Cys Trp Ala Phe Ser Gly
1               5                   10                  15

<210> SEQ ID NO 164
<211> LENGTH: 15
<212> TYPE: PRT
<213> ORGANISM: Dermatophagoides farinae

<400> SEQUENCE: 164

Gly Cys Gly Ser Cys Trp Ala Phe Ser Gly Val Ala Ala Thr Glu
1               5                   10                  15

<210> SEQ ID NO 165
<211> LENGTH: 15
<212> TYPE: PRT
<213> ORGANISM: Dermatophagoides farinae

<400> SEQUENCE: 165

Trp Ala Phe Ser Gly Val Ala Ala Thr Glu Ser Ala Tyr Leu Ala
1               5                   10                  15

<210> SEQ ID NO 166

```
<211> LENGTH: 15
<212> TYPE: PRT
<213> ORGANISM: Dermatophagoides farinae

<400> SEQUENCE: 166

Val Ala Ala Thr Glu Ser Ala Tyr Leu Ala Tyr Arg Asn Thr Ser
1               5                   10                  15

<210> SEQ ID NO 167
<211> LENGTH: 15
<212> TYPE: PRT
<213> ORGANISM: Dermatophagoides farinae

<400> SEQUENCE: 167

Ser Ala Tyr Leu Ala Tyr Arg Asn Thr Ser Leu Asp Leu Ser Glu
1               5                   10                  15

<210> SEQ ID NO 168
<211> LENGTH: 15
<212> TYPE: PRT
<213> ORGANISM: Dermatophagoides farinae

<400> SEQUENCE: 168

Tyr Arg Asn Thr Ser Leu Asp Leu Ser Glu Gln Glu Leu Val Asp
1               5                   10                  15

<210> SEQ ID NO 169
<211> LENGTH: 15
<212> TYPE: PRT
<213> ORGANISM: Dermatophagoides farinae

<400> SEQUENCE: 169

Leu Asp Leu Ser Glu Gln Glu Leu Val Asp Cys Ala Ser Gln His
1               5                   10                  15

<210> SEQ ID NO 170
<211> LENGTH: 15
<212> TYPE: PRT
<213> ORGANISM: Dermatophagoides farinae

<400> SEQUENCE: 170

Gln Glu Leu Val Asp Cys Ala Ser Gln His Gly Cys His Gly Asp
1               5                   10                  15

<210> SEQ ID NO 171
<211> LENGTH: 15
<212> TYPE: PRT
<213> ORGANISM: Dermatophagoides farinae

<400> SEQUENCE: 171

Cys Ala Ser Gln His Gly Cys His Gly Asp Thr Ile Pro Arg Gly
1               5                   10                  15

<210> SEQ ID NO 172
<211> LENGTH: 15
<212> TYPE: PRT
<213> ORGANISM: Dermatophagoides farinae

<400> SEQUENCE: 172

Gly Cys His Gly Asp Thr Ile Pro Arg Gly Ile Glu Tyr Ile Gln
1               5                   10                  15

<210> SEQ ID NO 173
<211> LENGTH: 15
<212> TYPE: PRT
```

<213> ORGANISM: Dermatophagoides farinae

<400> SEQUENCE: 173

Thr Ile Pro Arg Gly Ile Glu Tyr Ile Gln Gln Asn Gly Val Val
1               5                   10                  15

<210> SEQ ID NO 174
<211> LENGTH: 15
<212> TYPE: PRT
<213> ORGANISM: Dermatophagoides farinae

<400> SEQUENCE: 174

Ile Glu Tyr Ile Gln Gln Asn Gly Val Val Glu Glu Arg Ser Tyr
1               5                   10                  15

<210> SEQ ID NO 175
<211> LENGTH: 15
<212> TYPE: PRT
<213> ORGANISM: Dermatophagoides farinae

<400> SEQUENCE: 175

Gln Asn Gly Val Val Glu Glu Arg Ser Tyr Pro Tyr Val Ala Arg
1               5                   10                  15

<210> SEQ ID NO 176
<211> LENGTH: 15
<212> TYPE: PRT
<213> ORGANISM: Dermatophagoides farinae

<400> SEQUENCE: 176

Glu Glu Arg Ser Tyr Pro Tyr Val Ala Arg Glu Gln Gln Cys Arg
1               5                   10                  15

<210> SEQ ID NO 177
<211> LENGTH: 15
<212> TYPE: PRT
<213> ORGANISM: Dermatophagoides farinae

<400> SEQUENCE: 177

Pro Tyr Val Ala Arg Glu Gln Gln Cys Arg Arg Pro Asn Ser Gln
1               5                   10                  15

<210> SEQ ID NO 178
<211> LENGTH: 15
<212> TYPE: PRT
<213> ORGANISM: Dermatophagoides farinae

<400> SEQUENCE: 178

Glu Gln Gln Cys Arg Arg Pro Asn Ser Gln His Tyr Gly Ile Ser
1               5                   10                  15

<210> SEQ ID NO 179
<211> LENGTH: 15
<212> TYPE: PRT
<213> ORGANISM: Dermatophagoides farinae

<400> SEQUENCE: 179

Arg Pro Asn Ser Gln His Tyr Gly Ile Ser Asn Tyr Cys Gln Ile
1               5                   10                  15

<210> SEQ ID NO 180
<211> LENGTH: 15
<212> TYPE: PRT
<213> ORGANISM: Dermatophagoides farinae

<400> SEQUENCE: 180

His Tyr Gly Ile Ser Asn Tyr Cys Gln Ile Tyr Pro Pro Asp Val
1               5                   10                  15

<210> SEQ ID NO 181
<211> LENGTH: 15
<212> TYPE: PRT
<213> ORGANISM: Dermatophagoides farinae

<400> SEQUENCE: 181

Asn Tyr Cys Gln Ile Tyr Pro Pro Asp Val Lys Gln Ile Arg Glu
1               5                   10                  15

<210> SEQ ID NO 182
<211> LENGTH: 15
<212> TYPE: PRT
<213> ORGANISM: Dermatophagoides farinae

<400> SEQUENCE: 182

Tyr Pro Pro Asp Val Lys Gln Ile Arg Glu Ala Leu Thr Gln Thr
1               5                   10                  15

<210> SEQ ID NO 183
<211> LENGTH: 15
<212> TYPE: PRT
<213> ORGANISM: Dermatophagoides farinae

<400> SEQUENCE: 183

Lys Gln Ile Arg Glu Ala Leu Thr Gln Thr His Thr Ala Ile Ala
1               5                   10                  15

<210> SEQ ID NO 184
<211> LENGTH: 15
<212> TYPE: PRT
<213> ORGANISM: Dermatophagoides farinae

<400> SEQUENCE: 184

Ala Leu Thr Gln Thr His Thr Ala Ile Ala Val Ile Ile Gly Ile
1               5                   10                  15

<210> SEQ ID NO 185
<211> LENGTH: 15
<212> TYPE: PRT
<213> ORGANISM: Dermatophagoides farinae

<400> SEQUENCE: 185

His Thr Ala Ile Ala Val Ile Ile Gly Ile Lys Asp Leu Arg Ala
1               5                   10                  15

<210> SEQ ID NO 186
<211> LENGTH: 15
<212> TYPE: PRT
<213> ORGANISM: Dermatophagoides farinae

<400> SEQUENCE: 186

Val Ile Ile Gly Ile Lys Asp Leu Arg Ala Phe Gln His Tyr Asp
1               5                   10                  15

<210> SEQ ID NO 187
<211> LENGTH: 15
<212> TYPE: PRT
<213> ORGANISM: Dermatophagoides farinae

<400> SEQUENCE: 187

```
Lys Asp Leu Arg Ala Phe Gln His Tyr Asp Gly Arg Thr Ile Ile
1               5                   10                  15

<210> SEQ ID NO 188
<211> LENGTH: 15
<212> TYPE: PRT
<213> ORGANISM: Dermatophagoides farinae

<400> SEQUENCE: 188

Phe Gln His Tyr Asp Gly Arg Thr Ile Ile Gln His Asp Asn Gly
1               5                   10                  15

<210> SEQ ID NO 189
<211> LENGTH: 15
<212> TYPE: PRT
<213> ORGANISM: Dermatophagoides farinae

<400> SEQUENCE: 189

Gly Arg Thr Ile Ile Gln His Asp Asn Gly Tyr Gln Pro Asn Tyr
1               5                   10                  15

<210> SEQ ID NO 190
<211> LENGTH: 15
<212> TYPE: PRT
<213> ORGANISM: Dermatophagoides farinae

<400> SEQUENCE: 190

Gln His Asp Asn Gly Tyr Gln Pro Asn Tyr His Ala Val Asn Ile
1               5                   10                  15

<210> SEQ ID NO 191
<211> LENGTH: 15
<212> TYPE: PRT
<213> ORGANISM: Dermatophagoides farinae

<400> SEQUENCE: 191

Tyr Gln Pro Asn Tyr His Ala Val Asn Ile Val Gly Tyr Gly Ser
1               5                   10                  15

<210> SEQ ID NO 192
<211> LENGTH: 15
<212> TYPE: PRT
<213> ORGANISM: Dermatophagoides farinae

<400> SEQUENCE: 192

His Ala Val Asn Ile Val Gly Tyr Gly Ser Thr Gln Gly Val Asp
1               5                   10                  15

<210> SEQ ID NO 193
<211> LENGTH: 15
<212> TYPE: PRT
<213> ORGANISM: Dermatophagoides farinae

<400> SEQUENCE: 193

Val Gly Tyr Gly Ser Thr Gln Gly Val Asp Tyr Trp Ile Val Arg
1               5                   10                  15

<210> SEQ ID NO 194
<211> LENGTH: 15
<212> TYPE: PRT
<213> ORGANISM: Dermatophagoides farinae

<400> SEQUENCE: 194

Thr Gln Gly Val Asp Tyr Trp Ile Val Arg Asn Ser Trp Asp Thr
1               5                   10                  15
```

<210> SEQ ID NO 195
<211> LENGTH: 15
<212> TYPE: PRT
<213> ORGANISM: Dermatophagoides farinae

<400> SEQUENCE: 195

Tyr Trp Ile Val Arg Asn Ser Trp Asp Thr Thr Trp Gly Asp Ser
1               5                   10                  15

<210> SEQ ID NO 196
<211> LENGTH: 15
<212> TYPE: PRT
<213> ORGANISM: Dermatophagoides farinae

<400> SEQUENCE: 196

Asn Ser Trp Asp Thr Thr Trp Gly Asp Ser Gly Tyr Gly Tyr Phe
1               5                   10                  15

<210> SEQ ID NO 197
<211> LENGTH: 15
<212> TYPE: PRT
<213> ORGANISM: Dermatophagoides farinae

<400> SEQUENCE: 197

Thr Trp Gly Asp Ser Gly Tyr Gly Tyr Phe Gln Ala Gly Asn Asn
1               5                   10                  15

<210> SEQ ID NO 198
<211> LENGTH: 15
<212> TYPE: PRT
<213> ORGANISM: Dermatophagoides farinae

<400> SEQUENCE: 198

Gly Tyr Gly Tyr Phe Gln Ala Gly Asn Asn Leu Met Met Ile Glu
1               5                   10                  15

<210> SEQ ID NO 199
<211> LENGTH: 15
<212> TYPE: PRT
<213> ORGANISM: Dermatophagoides farinae

<400> SEQUENCE: 199

Gln Ala Gly Asn Asn Leu Met Met Ile Glu Gln Tyr Pro Tyr Val
1               5                   10                  15

<210> SEQ ID NO 200
<211> LENGTH: 15
<212> TYPE: PRT
<213> ORGANISM: Dermatophagoides farinae

<400> SEQUENCE: 200

Asn Asn Leu Met Met Ile Glu Gln Tyr Pro Tyr Val Val Ile Met
1               5                   10                  15

<210> SEQ ID NO 201
<211> LENGTH: 15
<212> TYPE: PRT
<213> ORGANISM: Dermatophagoides pteronyssinus

<400> SEQUENCE: 201

Asp Gln Val Asp Val Lys Asp Cys Ala Asn His Glu Ile Lys Lys
1               5                   10                  15

```
<210> SEQ ID NO 202
<211> LENGTH: 15
<212> TYPE: PRT
<213> ORGANISM: Dermatophagoides pteronyssinus

<400> SEQUENCE: 202

Lys Asp Cys Ala Asn His Glu Ile Lys Lys Val Leu Val Pro Gly
1               5                   10                  15

<210> SEQ ID NO 203
<211> LENGTH: 15
<212> TYPE: PRT
<213> ORGANISM: Dermatophagoides pteronyssinus

<400> SEQUENCE: 203

His Glu Ile Lys Lys Val Leu Val Pro Gly Cys His Gly Ser Glu
1               5                   10                  15

<210> SEQ ID NO 204
<211> LENGTH: 15
<212> TYPE: PRT
<213> ORGANISM: Dermatophagoides pteronyssinus

<400> SEQUENCE: 204

Val Leu Val Pro Gly Cys His Gly Ser Glu Pro Cys Ile Ile His
1               5                   10                  15

<210> SEQ ID NO 205
<211> LENGTH: 15
<212> TYPE: PRT
<213> ORGANISM: Dermatophagoides pteronyssinus

<400> SEQUENCE: 205

Cys His Gly Ser Glu Pro Cys Ile Ile His Arg Gly Lys Pro Phe
1               5                   10                  15

<210> SEQ ID NO 206
<211> LENGTH: 15
<212> TYPE: PRT
<213> ORGANISM: Dermatophagoides pteronyssinus

<400> SEQUENCE: 206

Pro Cys Ile Ile His Arg Gly Lys Pro Phe Gln Leu Glu Ala Val
1               5                   10                  15

<210> SEQ ID NO 207
<211> LENGTH: 15
<212> TYPE: PRT
<213> ORGANISM: Dermatophagoides pteronyssinus

<400> SEQUENCE: 207

Arg Gly Lys Pro Phe Gln Leu Glu Ala Val Phe Glu Ala Asn Gln
1               5                   10                  15

<210> SEQ ID NO 208
<211> LENGTH: 15
<212> TYPE: PRT
<213> ORGANISM: Dermatophagoides pteronyssinus

<400> SEQUENCE: 208

Gln Leu Glu Ala Val Phe Glu Ala Asn Gln Asn Thr Lys Thr Ala
1               5                   10                  15

<210> SEQ ID NO 209
<211> LENGTH: 15
```

<212> TYPE: PRT
<213> ORGANISM: Dermatophagoides pteronyssinus

<400> SEQUENCE: 209

Phe Glu Ala Asn Gln Asn Thr Lys Thr Ala Lys Ile Glu Ile Lys
1               5                   10                  15

<210> SEQ ID NO 210
<211> LENGTH: 15
<212> TYPE: PRT
<213> ORGANISM: Dermatophagoides pteronyssinus

<400> SEQUENCE: 210

Asn Thr Lys Thr Ala Lys Ile Glu Ile Lys Ala Ser Ile Asp Gly
1               5                   10                  15

<210> SEQ ID NO 211
<211> LENGTH: 15
<212> TYPE: PRT
<213> ORGANISM: Dermatophagoides pteronyssinus

<400> SEQUENCE: 211

Lys Ile Glu Ile Lys Ala Ser Ile Asp Gly Leu Glu Val Asp Val
1               5                   10                  15

<210> SEQ ID NO 212
<211> LENGTH: 15
<212> TYPE: PRT
<213> ORGANISM: Dermatophagoides pteronyssinus

<400> SEQUENCE: 212

Ala Ser Ile Asp Gly Leu Glu Val Asp Val Pro Gly Ile Asp Pro
1               5                   10                  15

<210> SEQ ID NO 213
<211> LENGTH: 15
<212> TYPE: PRT
<213> ORGANISM: Dermatophagoides pteronyssinus

<400> SEQUENCE: 213

Leu Glu Val Asp Val Pro Gly Ile Asp Pro Asn Ala Cys His Tyr
1               5                   10                  15

<210> SEQ ID NO 214
<211> LENGTH: 15
<212> TYPE: PRT
<213> ORGANISM: Dermatophagoides pteronyssinus

<400> SEQUENCE: 214

Pro Gly Ile Asp Pro Asn Ala Cys His Tyr Met Lys Cys Pro Leu
1               5                   10                  15

<210> SEQ ID NO 215
<211> LENGTH: 15
<212> TYPE: PRT
<213> ORGANISM: Dermatophagoides pteronyssinus

<400> SEQUENCE: 215

Asn Ala Cys His Tyr Met Lys Cys Pro Leu Val Lys Gly Gln Gln
1               5                   10                  15

<210> SEQ ID NO 216
<211> LENGTH: 15
<212> TYPE: PRT
<213> ORGANISM: Dermatophagoides pteronyssinus

<400> SEQUENCE: 216

Met Lys Cys Pro Leu Val Lys Gly Gln Gln Tyr Asp Ile Lys Tyr
1               5                   10                  15

<210> SEQ ID NO 217
<211> LENGTH: 15
<212> TYPE: PRT
<213> ORGANISM: Dermatophagoides pteronyssinus

<400> SEQUENCE: 217

Val Lys Gly Gln Gln Tyr Asp Ile Lys Tyr Thr Trp Asn Val Pro
1               5                   10                  15

<210> SEQ ID NO 218
<211> LENGTH: 15
<212> TYPE: PRT
<213> ORGANISM: Dermatophagoides pteronyssinus

<400> SEQUENCE: 218

Tyr Asp Ile Lys Tyr Thr Trp Asn Val Pro Lys Ile Ala Pro Lys
1               5                   10                  15

<210> SEQ ID NO 219
<211> LENGTH: 15
<212> TYPE: PRT
<213> ORGANISM: Dermatophagoides pteronyssinus

<400> SEQUENCE: 219

Thr Trp Asn Val Pro Lys Ile Ala Pro Lys Ser Glu Asn Val Val
1               5                   10                  15

<210> SEQ ID NO 220
<211> LENGTH: 15
<212> TYPE: PRT
<213> ORGANISM: Dermatophagoides pteronyssinus

<400> SEQUENCE: 220

Lys Ile Ala Pro Lys Ser Glu Asn Val Val Thr Val Lys Val
1               5                   10                  15

<210> SEQ ID NO 221
<211> LENGTH: 15
<212> TYPE: PRT
<213> ORGANISM: Dermatophagoides pteronyssinus

<400> SEQUENCE: 221

Ser Glu Asn Val Val Val Thr Val Lys Val Met Gly Asp Asp Gly
1               5                   10                  15

<210> SEQ ID NO 222
<211> LENGTH: 15
<212> TYPE: PRT
<213> ORGANISM: Dermatophagoides pteronyssinus

<400> SEQUENCE: 222

Val Thr Val Lys Val Met Gly Asp Asp Gly Val Leu Ala Cys Ala
1               5                   10                  15

<210> SEQ ID NO 223
<211> LENGTH: 15
<212> TYPE: PRT
<213> ORGANISM: Dermatophagoides pteronyssinus

<400> SEQUENCE: 223

Met Gly Asp Asp Gly Val Leu Ala Cys Ala Ile Ala Thr His Ala
1               5                   10                  15

<210> SEQ ID NO 224
<211> LENGTH: 15
<212> TYPE: PRT
<213> ORGANISM: Dermatophagoides pteronyssinus

<400> SEQUENCE: 224

Gly Val Leu Ala Cys Ala Ile Ala Thr His Ala Lys Ile Arg Asp
1               5                   10                  15

<210> SEQ ID NO 225
<211> LENGTH: 15
<212> TYPE: PRT
<213> ORGANISM: Dermatophagoides farinae

<400> SEQUENCE: 225

Asp Gln Val Asp Val Lys Asp Cys Ala Asn Asn Glu Ile Lys Lys
1               5                   10                  15

<210> SEQ ID NO 226
<211> LENGTH: 15
<212> TYPE: PRT
<213> ORGANISM: Dermatophagoides farinae

<400> SEQUENCE: 226

Lys Asp Cys Ala Asn Asn Glu Ile Lys Lys Val Met Val Asp Gly
1               5                   10                  15

<210> SEQ ID NO 227
<211> LENGTH: 15
<212> TYPE: PRT
<213> ORGANISM: Dermatophagoides farinae

<400> SEQUENCE: 227

Asn Glu Ile Lys Lys Val Met Val Asp Gly Cys His Gly Ser Asp
1               5                   10                  15

<210> SEQ ID NO 228
<211> LENGTH: 15
<212> TYPE: PRT
<213> ORGANISM: Dermatophagoides farinae

<400> SEQUENCE: 228

Val Met Val Asp Gly Cys His Gly Ser Asp Pro Cys Ile Ile His
1               5                   10                  15

<210> SEQ ID NO 229
<211> LENGTH: 15
<212> TYPE: PRT
<213> ORGANISM: Dermatophagoides farinae

<400> SEQUENCE: 229

Cys His Gly Ser Asp Pro Cys Ile Ile His Arg Gly Lys Pro Phe
1               5                   10                  15

<210> SEQ ID NO 230
<211> LENGTH: 15
<212> TYPE: PRT
<213> ORGANISM: Dermatophagoides farinae

<400> SEQUENCE: 230

Pro Cys Ile Ile His Arg Gly Lys Pro Phe Thr Leu Glu Ala Leu

<210> SEQ ID NO 231
<211> LENGTH: 15
<212> TYPE: PRT
<213> ORGANISM: Dermatophagoides farinae

<400> SEQUENCE: 231

Arg Gly Lys Pro Phe Thr Leu Glu Ala Leu Phe Asp Ala Asn Gln
1               5                   10                  15

<210> SEQ ID NO 232
<211> LENGTH: 15
<212> TYPE: PRT
<213> ORGANISM: Dermatophagoides farinae

<400> SEQUENCE: 232

Thr Leu Glu Ala Leu Phe Asp Ala Asn Gln Asn Thr Lys Thr Ala
1               5                   10                  15

<210> SEQ ID NO 233
<211> LENGTH: 15
<212> TYPE: PRT
<213> ORGANISM: Dermatophagoides farinae

<400> SEQUENCE: 233

Phe Asp Ala Asn Gln Asn Thr Lys Thr Ala Lys Ile Glu Ile Lys
1               5                   10                  15

<210> SEQ ID NO 234
<211> LENGTH: 15
<212> TYPE: PRT
<213> ORGANISM: Dermatophagoides farinae

<400> SEQUENCE: 234

Asn Thr Lys Thr Ala Lys Ile Glu Ile Lys Ala Ser Leu Asp Gly
1               5                   10                  15

<210> SEQ ID NO 235
<211> LENGTH: 15
<212> TYPE: PRT
<213> ORGANISM: Dermatophagoides farinae

<400> SEQUENCE: 235

Lys Ile Glu Ile Lys Ala Ser Leu Asp Gly Leu Glu Ile Asp Val
1               5                   10                  15

<210> SEQ ID NO 236
<211> LENGTH: 15
<212> TYPE: PRT
<213> ORGANISM: Dermatophagoides farinae

<400> SEQUENCE: 236

Ala Ser Leu Asp Gly Leu Glu Ile Asp Val Pro Gly Ile Asp Thr
1               5                   10                  15

<210> SEQ ID NO 237
<211> LENGTH: 15
<212> TYPE: PRT
<213> ORGANISM: Dermatophagoides farinae

<400> SEQUENCE: 237

Leu Glu Ile Asp Val Pro Gly Ile Asp Thr Asn Ala Cys His Phe
1               5                   10                  15

<210> SEQ ID NO 238
<211> LENGTH: 15
<212> TYPE: PRT
<213> ORGANISM: Dermatophagoides farinae

<400> SEQUENCE: 238

Pro Gly Ile Asp Thr Asn Ala Cys His Phe Met Lys Cys Pro Leu
1               5                   10                  15

<210> SEQ ID NO 239
<211> LENGTH: 15
<212> TYPE: PRT
<213> ORGANISM: Dermatophagoides farinae

<400> SEQUENCE: 239

Asn Ala Cys His Phe Met Lys Cys Pro Leu Val Lys Gly Gln Gln
1               5                   10                  15

<210> SEQ ID NO 240
<211> LENGTH: 15
<212> TYPE: PRT
<213> ORGANISM: Dermatophagoides farinae

<400> SEQUENCE: 240

Met Lys Cys Pro Leu Val Lys Gly Gln Gln Tyr Asp Ala Lys Tyr
1               5                   10                  15

<210> SEQ ID NO 241
<211> LENGTH: 15
<212> TYPE: PRT
<213> ORGANISM: Dermatophagoides farinae

<400> SEQUENCE: 241

Val Lys Gly Gln Gln Tyr Asp Ala Lys Tyr Thr Trp Asn Val Pro
1               5                   10                  15

<210> SEQ ID NO 242
<211> LENGTH: 15
<212> TYPE: PRT
<213> ORGANISM: Dermatophagoides farinae

<400> SEQUENCE: 242

Tyr Asp Ala Lys Tyr Thr Trp Asn Val Pro Lys Ile Ala Pro Lys
1               5                   10                  15

<210> SEQ ID NO 243
<211> LENGTH: 15
<212> TYPE: PRT
<213> ORGANISM: Dermatophagoides farinae

<400> SEQUENCE: 243

Thr Trp Asn Val Pro Lys Ile Ala Pro Lys Ser Glu Asn Val Val
1               5                   10                  15

<210> SEQ ID NO 244
<211> LENGTH: 15
<212> TYPE: PRT
<213> ORGANISM: Dermatophagoides farinae

<400> SEQUENCE: 244

Lys Ile Ala Pro Lys Ser Glu Asn Val Val Thr Val Lys Leu
1               5                   10                  15

<210> SEQ ID NO 245

```
<211> LENGTH: 15
<212> TYPE: PRT
<213> ORGANISM: Dermatophagoides farinae

<400> SEQUENCE: 245

Ser Glu Asn Val Val Thr Val Lys Leu Val Gly Asp Asn Gly
1               5                   10                  15

<210> SEQ ID NO 246
<211> LENGTH: 15
<212> TYPE: PRT
<213> ORGANISM: Dermatophagoides farinae

<400> SEQUENCE: 246

Val Thr Val Lys Leu Val Gly Asp Asn Gly Val Leu Ala Cys Ala
1               5                   10                  15

<210> SEQ ID NO 247
<211> LENGTH: 15
<212> TYPE: PRT
<213> ORGANISM: Dermatophagoides farinae

<400> SEQUENCE: 247

Val Gly Asp Asn Gly Val Leu Ala Cys Ala Ile Ala Thr His Ala
1               5                   10                  15

<210> SEQ ID NO 248
<211> LENGTH: 15
<212> TYPE: PRT
<213> ORGANISM: Dermatophagoides farinae

<400> SEQUENCE: 248

Gly Val Leu Ala Cys Ala Ile Ala Thr His Ala Lys Ile Arg Asp
1               5                   10                  15

<210> SEQ ID NO 249
<211> LENGTH: 13
<212> TYPE: PRT
<213> ORGANISM: Dermatophagoides pteronyssinus

<400> SEQUENCE: 249

Ser Ile Ile His Arg Gly Lys Pro Phe Gln Leu Glu Ala
1               5                   10

<210> SEQ ID NO 250
<211> LENGTH: 16
<212> TYPE: PRT
<213> ORGANISM: Dermatophagoides pteronyssinus

<400> SEQUENCE: 250

Glu Ser Ala Tyr Leu Ala Tyr Arg Asn Gln Ser Leu Asp Leu Ala Glu
1               5                   10                  15

<210> SEQ ID NO 251
<211> LENGTH: 18
<212> TYPE: PRT
<213> ORGANISM: Dermatophagoides pteronyssinus

<400> SEQUENCE: 251

Asp Asn Gly Tyr Gly Tyr Phe Ala Ala Asn Ile Asp Leu Met Met Ile
1               5                   10                  15

Glu Glu

<210> SEQ ID NO 252
```

```
<211> LENGTH: 14
<212> TYPE: PRT
<213> ORGANISM: Dermatophagoides pteronyssinus

<400> SEQUENCE: 252

Asn Gly Tyr Gly Tyr Phe Ala Ala Asn Ile Asp Leu Met Met
1               5                   10

<210> SEQ ID NO 253
<211> LENGTH: 14
<212> TYPE: PRT
<213> ORGANISM: Dermatophagoides pteronyssinus

<400> SEQUENCE: 253

Val Leu Ala Ser Ala Ile Ala Thr His Ala Lys Ile Arg Asp
1               5                   10

<210> SEQ ID NO 254
<211> LENGTH: 15
<212> TYPE: PRT
<213> ORGANISM: Dermatophagoides farinae

<400> SEQUENCE: 254

Ala Thr Glu Ser Ala Tyr Leu Ala Tyr Arg Asn Thr Ser Leu Asp
1               5                   10                  15

<210> SEQ ID NO 255
<211> LENGTH: 15
<212> TYPE: PRT
<213> ORGANISM: Dermatophagoides pteronyssinus

<400> SEQUENCE: 255

Arg Gly Ile Glu Tyr Ile Gln His Asn Gly Val Val Gln Glu Ser
1               5                   10                  15

<210> SEQ ID NO 256
<211> LENGTH: 15
<212> TYPE: PRT
<213> ORGANISM: Dermatophagoides pteronyssinus

<400> SEQUENCE: 256

Gln Gln Tyr Asp Ile Lys Tyr Thr Trp Asn Val Pro Lys Ile Ala
1               5                   10                  15

<210> SEQ ID NO 257
<211> LENGTH: 15
<212> TYPE: PRT
<213> ORGANISM: Dermatophagoides pteronyssinus

<400> SEQUENCE: 257

Glu Ile Tyr Asn Met Val Lys Phe Arg Met Ile Ala Gly Gln Glu
1               5                   10                  15

<210> SEQ ID NO 258
<211> LENGTH: 16
<212> TYPE: PRT
<213> ORGANISM: Dermatophagoides pteronyssinus

<400> SEQUENCE: 258

Gln Glu Ser Tyr Tyr Arg Tyr Val Ala Arg Glu Gln Ser Ser Arg Arg
1               5                   10                  15

<210> SEQ ID NO 259
<211> LENGTH: 19
<212> TYPE: PRT
```

<213> ORGANISM: Dermatophagoides pteronyssinus

<400> SEQUENCE: 259

Asp Leu Arg Gln Met Arg Thr Val Thr Pro Ile Arg Met Gln Gly Gly
1               5                   10                  15

Ser Gly Ser

<210> SEQ ID NO 260
<211> LENGTH: 10
<212> TYPE: PRT
<213> ORGANISM: Dermatophagoides pteronyssinus

<400> SEQUENCE: 260

Glu Leu Val Asp Ser Ala Ser Gln His Gly
1               5                   10

<210> SEQ ID NO 261
<211> LENGTH: 16
<212> TYPE: PRT
<213> ORGANISM: Dermatophagoides pteronyssinus

<400> SEQUENCE: 261

Asn Tyr Ser Gln Ile Tyr Pro Pro Asn Val Asn Lys Ile Arg Glu Ala
1               5                   10                  15

<210> SEQ ID NO 262
<211> LENGTH: 13
<212> TYPE: PRT
<213> ORGANISM: Dermatophagoides pteronyssinus

<400> SEQUENCE: 262

Glu Ser Val Lys Tyr Val Gln Ser Asn Gly Gly Ala Ile
1               5                   10

<210> SEQ ID NO 263
<211> LENGTH: 11
<212> TYPE: PRT
<213> ORGANISM: Dermatophagoides pteronyssinus

<400> SEQUENCE: 263

Ser Tyr Tyr Arg Tyr Val Ala Arg Glu Gln Ser
1               5                   10

<210> SEQ ID NO 264
<211> LENGTH: 14
<212> TYPE: PRT
<213> ORGANISM: Dermatophagoides pteronyssinus

<400> SEQUENCE: 264

Gly Val Leu Ala Ser Ala Ile Ala Thr His Ala Lys Ile Arg
1               5                   10

<210> SEQ ID NO 265
<211> LENGTH: 14
<212> TYPE: PRT
<213> ORGANISM: Dermatophagoides pteronyssinus

<400> SEQUENCE: 265

Arg Gly Leu Lys Gln Met Lys Arg Val Gly Asp Ala Asn Val
1               5                   10

<210> SEQ ID NO 266
<211> LENGTH: 22
<212> TYPE: PRT

```
<213> ORGANISM: Dermatophagoides pteronyssinus

<400> SEQUENCE: 266

Arg Gly Ile Glu Tyr Ile Gln His Asn Gly Val Val Gln Glu Ser Tyr
1               5                   10                  15

Tyr Arg Tyr Val Ala Arg
            20

<210> SEQ ID NO 267
<211> LENGTH: 21
<212> TYPE: PRT
<213> ORGANISM: Dermatophagoides pteronyssinus

<400> SEQUENCE: 267

Val Gln Glu Ser Tyr Tyr Arg Tyr Val Ala Arg Glu Gln Ser Ser Arg
1               5                   10                  15

Arg Pro Asn Ala Gln
            20

<210> SEQ ID NO 268
<211> LENGTH: 22
<212> TYPE: PRT
<213> ORGANISM: Dermatophagoides pteronyssinus

<400> SEQUENCE: 268

Arg Glu Ala Leu Ala Gln Thr His Ser Ala Ile Ala Val Ile Ile Gly
1               5                   10                  15

Ile Lys Asp Leu Asp Ala
            20

<210> SEQ ID NO 269
<211> LENGTH: 20
<212> TYPE: PRT
<213> ORGANISM: Dermatophagoides pteronyssinus

<400> SEQUENCE: 269

Val Met Gly Asp Asn Gly Val Leu Ala Ser Ala Ile Ala Thr His Ala
1               5                   10                  15

Lys Ile Arg Asp
        20

<210> SEQ ID NO 270
<211> LENGTH: 17
<212> TYPE: PRT
<213> ORGANISM: Dermatophagoides pteronyssinus

<400> SEQUENCE: 270

Lys Gly Gln Gln Tyr Asp Ile Lys Tyr Thr Trp Asn Val Pro Lys Ile
1               5                   10                  15

Ala

<210> SEQ ID NO 271
<211> LENGTH: 21
<212> TYPE: PRT
<213> ORGANISM: Dermatophagoides pteronyssinus

<400> SEQUENCE: 271

Leu Val Lys Gly Gln Gln Tyr Asp Ile Lys Tyr Thr Trp Asn Val Pro
1               5                   10                  15

Lys Ile Ala Pro Lys
            20
```

<210> SEQ ID NO 272
<211> LENGTH: 22
<212> TYPE: PRT
<213> ORGANISM: Artificial Sequence
<220> FEATURE:
<223> OTHER INFORMATION: Synthetic peptide

<400> SEQUENCE: 272

Arg Gly Ile Glu Tyr Ile Gln Gln Asn Gly Val Val Glu Glu Arg Ser
1               5                   10                  15

Tyr Pro Tyr Val Ala Arg
            20

<210> SEQ ID NO 273
<211> LENGTH: 24
<212> TYPE: PRT
<213> ORGANISM: Artificial Sequence
<220> FEATURE:
<223> OTHER INFORMATION: Synthetic peptide

<400> SEQUENCE: 273

Lys Ile Arg Glu Ala Leu Ala Gln Thr His Ser Ala Ile Ala Val Ile
1               5                   10                  15

Ile Gly Ile Lys Asp Leu Asp Ala
            20

<210> SEQ ID NO 274
<211> LENGTH: 24
<212> TYPE: PRT
<213> ORGANISM: Artificial Sequence
<220> FEATURE:
<223> OTHER INFORMATION: Synthetic peptide

<400> SEQUENCE: 274

Arg Arg Arg Arg His Ala Val Asn Ile Val Gly Tyr Ser Asn Ala Gln
1               5                   10                  15

Gly Val Asp Tyr Trp Ile Val Arg
            20

<210> SEQ ID NO 275
<211> LENGTH: 24
<212> TYPE: PRT
<213> ORGANISM: Artificial Sequence
<220> FEATURE:
<223> OTHER INFORMATION: Synthetic peptide

<400> SEQUENCE: 275

Arg Arg His Ala Val Asn Ile Val Gly Tyr Ser Asn Ala Gln Gly Val
1               5                   10                  15

Asp Tyr Trp Ile Val Arg Arg Arg
            20

<210> SEQ ID NO 276
<211> LENGTH: 21
<212> TYPE: PRT
<213> ORGANISM: Artificial Sequence
<220> FEATURE:
<223> OTHER INFORMATION: Synthetic peptide

<400> SEQUENCE: 276

Arg His Ala Val Asn Ile Val Gly Tyr Ser Asn Ala Gln Gly Val Asp
1               5                   10                  15

Tyr Trp Ile Val Arg
            20

<210> SEQ ID NO 277
<211> LENGTH: 22
<212> TYPE: PRT
<213> ORGANISM: Artificial Sequence
<220> FEATURE:
<223> OTHER INFORMATION: Synthetic peptide

<400> SEQUENCE: 277

Arg His Ala Val Asn Ile Val Gly Tyr Ser Asn Ala Gln Gly Val Asp
1               5                   10                  15

Tyr Trp Ile Val Arg Arg
            20

<210> SEQ ID NO 278
<211> LENGTH: 23
<212> TYPE: PRT
<213> ORGANISM: Artificial Sequence
<220> FEATURE:
<223> OTHER INFORMATION: Synthetic peptide

<400> SEQUENCE: 278

Arg Arg His Ala Val Asn Ile Val Gly Tyr Ser Asn Ala Gln Gly Val
1               5                   10                  15

Asp Tyr Trp Ile Val Arg Arg
            20

<210> SEQ ID NO 279
<211> LENGTH: 21
<212> TYPE: PRT
<213> ORGANISM: Artificial Sequence
<220> FEATURE:
<223> OTHER INFORMATION: Synthetic peptide

<400> SEQUENCE: 279

Arg Ile Glu Tyr Ile Gln Gln Asn Gly Val Val Glu Glu Arg Ser Tyr
1               5                   10                  15

Pro Tyr Val Ala Arg
            20

<210> SEQ ID NO 280
<211> LENGTH: 22
<212> TYPE: PRT
<213> ORGANISM: Artificial Sequence
<220> FEATURE:
<223> OTHER INFORMATION: Synthetic peptide

<400> SEQUENCE: 280

Arg Ile Glu Tyr Ile Gln Gln Asn Gly Val Val Glu Glu Arg Ser Tyr
1               5                   10                  15

Pro Tyr Val Ala Arg Arg
            20

<210> SEQ ID NO 281
<211> LENGTH: 23
<212> TYPE: PRT
<213> ORGANISM: Artificial Sequence
<220> FEATURE:
<223> OTHER INFORMATION: Synthetic peptide

<400> SEQUENCE: 281

Arg Arg Ile Glu Tyr Ile Gln Gln Asn Gly Val Val Glu Glu Arg Ser
1               5                   10                  15

Tyr Pro Tyr Val Ala Arg Arg

20

<210> SEQ ID NO 282
<211> LENGTH: 24
<212> TYPE: PRT
<213> ORGANISM: Artificial Sequence
<220> FEATURE:
<223> OTHER INFORMATION: Synthetic peptide

<400> SEQUENCE: 282

Arg Arg Ile Glu Tyr Ile Gln Gln Asn Gly Val Val Glu Glu Arg Ser
1               5                   10                  15

Tyr Pro Tyr Val Ala Arg Arg Arg
            20

<210> SEQ ID NO 283
<211> LENGTH: 23
<212> TYPE: PRT
<213> ORGANISM: Artificial Sequence
<220> FEATURE:
<223> OTHER INFORMATION: Synthetic peptide

<400> SEQUENCE: 283

Arg Arg Glu Ala Leu Ala Gln Thr His Ser Ala Ile Ala Val Ile Ile
1               5                   10                  15

Gly Ile Lys Asp Leu Asp Ala
            20

<210> SEQ ID NO 284
<211> LENGTH: 24
<212> TYPE: PRT
<213> ORGANISM: Artificial Sequence
<220> FEATURE:
<223> OTHER INFORMATION: Synthetic peptide

<400> SEQUENCE: 284

Arg Arg Glu Ala Leu Ala Gln Thr His Ser Ala Ile Ala Val Ile Ile
1               5                   10                  15

Gly Ile Lys Asp Leu Asp Ala Arg
            20

<210> SEQ ID NO 285
<211> LENGTH: 25
<212> TYPE: PRT
<213> ORGANISM: Artificial Sequence
<220> FEATURE:
<223> OTHER INFORMATION: Synthetic peptide

<400> SEQUENCE: 285

Arg Arg Arg Glu Ala Leu Ala Gln Thr His Ser Ala Ile Ala Val Ile
1               5                   10                  15

Ile Gly Ile Lys Asp Leu Asp Ala Arg
            20                  25

<210> SEQ ID NO 286
<211> LENGTH: 26
<212> TYPE: PRT
<213> ORGANISM: Artificial Sequence
<220> FEATURE:
<223> OTHER INFORMATION: Synthetic peptide

<400> SEQUENCE: 286

Arg Arg Arg Glu Ala Leu Ala Gln Thr His Ser Ala Ile Ala Val Ile
1               5                   10                  15

Ile Gly Ile Lys Asp Leu Asp Ala Arg Arg
         20                  25

<210> SEQ ID NO 287
<211> LENGTH: 302
<212> TYPE: PRT
<213> ORGANISM: Dermatophagoides pteronyssinus

<400> SEQUENCE: 287

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
                35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala His Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 288
<211> LENGTH: 302
<212> TYPE: PRT
<213> ORGANISM: Dermatophagoides pteronyssinus

<400> SEQUENCE: 288

Arg Pro Ser Ser Ile Lys Thr Phe Glu Glu Tyr Lys Lys Ala Phe Gln
1               5                   10                  15

-continued

```
Lys Ser Tyr Ala Thr Phe Glu Asp Glu Ala Ala Arg Lys Asn Phe
                20                  25                  30
Leu Glu Ser Val Lys Tyr Val Gln Ser Asn Gly Gly Ala Ile Asn His
        35                  40                  45
Leu Ser Asp Leu Ser Leu Asp Glu Phe Lys Asn Arg Phe Leu Met Ser
    50                  55                  60
Ala Glu Ala Phe Glu His Leu Lys Thr Gln Phe Asp Leu Asn Ala Glu
65                  70                  75                  80
Thr Asn Ala Ser Ser Ile Asn Gly Asn Ala Pro Ala Glu Ile Asp Leu
                85                  90                  95
Arg Gln Met Arg Thr Val Thr Pro Ile Arg Met Gln Gly Gly Ser Gly
            100                 105                 110
Ser Ser Trp Ala Phe Ser Gly Val Ala Ala Thr Glu Ser Ala Tyr Leu
        115                 120                 125
Ala Tyr Arg Asn Gln Ser Leu Asp Leu Ala Glu Gln Glu Leu Val Asp
    130                 135                 140
Ser Ala Ser Gln His Gly Ser His Gly Asp Thr Ile Pro Arg Gly Ile
145                 150                 155                 160
Glu Tyr Ile Gln His Asn Gly Val Val Gln Glu Ser Tyr Tyr Arg Tyr
                165                 170                 175
Val Ala Arg Glu Gln Ser Ser Arg Arg Pro Asn Ala Gln Arg Phe Gly
            180                 185                 190
Ile Ser Asn Tyr Ser Gln Ile Tyr Pro Pro Asn Val Asn Lys Ile Arg
        195                 200                 205
Glu Ala Leu Ala Gln Thr His Ser Ala Ile Ala Val Ile Ile Gly Ile
    210                 215                 220
Lys Asp Leu Asp Ala Phe Arg His Tyr Asp Gly Arg Thr Ile Ile Gln
225                 230                 235                 240
Arg Asp Asn Gly Tyr Gln Pro Asn Tyr His Ala Val Asn Ile Val Gly
                245                 250                 255
Tyr Ser Asn Ala Gln Gly Val Asp Tyr Trp Ile Val Arg Asn Ser Trp
            260                 265                 270
Asp Thr Asn Trp Gly Asp Asn Gly Tyr Gly Tyr Phe Ala Ala Asn Ile
        275                 280                 285
Asp Leu Met Met Ile Glu Glu Tyr Pro Tyr Val Val Ile Leu
    290                 295                 300

<210> SEQ ID NO 289
<211> LENGTH: 302
<212> TYPE: PRT
<213> ORGANISM: Dermatophagoides pteronyssinus

<400> SEQUENCE: 289

Arg Pro Ser Ser Ile Lys Thr Phe Glu Glu Tyr Lys Lys Ala Phe Gln
1               5                   10                  15
Lys Ser Tyr Ala Thr Phe Glu Asp Glu Ala Ala Arg Lys Asn Phe
                20                  25                  30
Leu Glu Ser Val Lys Tyr Val Gln Ser Asn Gly Gly Ala Ile Asn His
        35                  40                  45
Leu Ser Asp Leu Ser Leu Asp Glu Phe Lys Asn Arg Phe Leu Met Ser
    50                  55                  60
Ala Glu Ala Phe Glu His Leu Lys Thr Gln Phe Asp Leu Asn Ala Glu
65                  70                  75                  80
Thr Asn Ala Ser Ser Ile Asn Gly Asn Ala Pro Ala Glu Ile Asp Leu
                85                  90                  95
```

```
Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Lys Tyr Ile Gln His Asn Gly Val Val Gln Glu Ser Tyr Tyr Arg Tyr
                    165                 170                 175

Val Ala Arg Glu Gln Ser Ser Arg Pro Asn Ala Gln Arg Phe Gly
            180                 185                 190

Ile Ser Asn Tyr Ser Gln Ile Tyr Pro Pro Asn Val Asn Lys Ile Arg
                    195                 200                 205

Glu Ala Leu Ala Gln Thr His Ser Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                    245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
                    275                 280                 285

Asp Leu Met Met Ile Glu Glu Tyr Pro Tyr Val Val Ile Leu
            290                 295                 300

<210> SEQ ID NO 290
<211> LENGTH: 302
<212> TYPE: PRT
<213> ORGANISM: Dermatophagoides pteronyssinus

<400> SEQUENCE: 290

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
            115                 120                 125

Ala His Arg Asn Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
```

```
            165                 170                 175
Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
            195                 200                 205

Glu Ala Leu Ala Gln Thr His Thr Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
            245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Gln Tyr Pro Tyr Val Val Ile Leu
            290                 295                 300
```

<210> SEQ ID NO 291
<211> LENGTH: 302
<212> TYPE: PRT
<213> ORGANISM: Dermatophagoides pteronyssinus

<400> SEQUENCE: 291

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
        50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
            85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
            165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
            195                 200                 205

Glu Ala Leu Ala Gln Thr His Ser Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240
```

```
Arg Asp Asn Gly Tyr Gln Pro Asn Tyr His Ala Val Asn Ile Val Gly
            245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu
            290                 295                 300
```

<210> SEQ ID NO 292
<211> LENGTH: 302
<212> TYPE: PRT
<213> ORGANISM: Dermatophagoides pteronyssinus

<400> SEQUENCE: 292

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
        130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Val Asn Lys Ile Arg
            195                 200                 205

Glu Ala Leu Ala Gln Thr His Ser Ala Ile Ala Val Ile Ile Gly Ile
        210                 215                 220

Lys Asp Leu Asp Ala Phe Arg His Tyr Asp Gly Arg Thr Ile Ile Gln
225                 230                 235                 240

His Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu
            290                 295                 300
```

<210> SEQ ID NO 293

<211> LENGTH: 302
<212> TYPE: PRT
<213> ORGANISM: Dermatophagoides pteronyssinus

<400> SEQUENCE: 293

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Thr Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300
```

<210> SEQ ID NO 294
<211> LENGTH: 302
<212> TYPE: PRT
<213> ORGANISM: Dermatophagoides pteronyssinus

<400> SEQUENCE: 294

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45
```

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Leu Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Val Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 295
<211> LENGTH: 302
<212> TYPE: PRT
<213> ORGANISM: Dermatophagoides pteronyssinus

<400> SEQUENCE: 295

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Pro Val Thr Pro Ile Arg Met Gln Gly Gly Ser Gly
            100                 105                 110

Ser Ser Trp Ala Phe Ser Gly Val Ala Ala Thr Glu Ser Ala Tyr Leu

```
            115                 120                 125
Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 296
<211> LENGTH: 302
<212> TYPE: PRT
<213> ORGANISM: Dermatophagoides pteronyssinus

<400> SEQUENCE: 296

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Asp Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190
```

```
Ile Ser Asn Tyr Ser Gln Ile Tyr Pro Pro Asn Ala Asn Lys Ile Arg
            195                 200                 205

Glu Ala Leu Ala Gln Thr His Ser Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
            245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu
            290                 295                 300

<210> SEQ ID NO 297
<211> LENGTH: 302
<212> TYPE: PRT
<213> ORGANISM: Dermatophagoides pteronyssinus

<400> SEQUENCE: 297

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
            85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
            165                 170                 175

Val Ala Arg Glu Gln Ser Ser Arg Pro Asn Ala Gln Arg Phe Gly
            180                 185                 190

Ile Ser Asn Tyr Ser Gln Ile Tyr Pro Pro Asn Ala Ser Lys Ile Arg
            195                 200                 205

Glu Ala Leu Ala Gln Thr His Ser Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
            245                 250                 255

Tyr Ser Asn Ala Gln Gly Val Asp Tyr Trp Ile Val Arg Asn Ser Trp
            260                 265                 270
```

```
Asp Thr Asn Trp Gly Asp Asn Gly Tyr Gly Tyr Phe Ala Ala Asn Ile
    275                 280                 285

Asp Leu Met Met Ile Glu Lys Tyr Pro Tyr Val Val Ile Leu
    290                 295                 300
```

<210> SEQ ID NO 298
<211> LENGTH: 302
<212> TYPE: PRT
<213> ORGANISM: Dermatophagoides pteronyssinus

<400> SEQUENCE: 298

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
                20                  25                  30

Leu Glu Ser Val Lys Tyr Val Gln Ser Asn Gly Gly Ala Ile Asn His
                35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
                100                 105                 110

Ser Ser Trp Ala Phe Ser Gly Val Ala Ala Thr Glu Ser Ala Tyr Leu
                115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
                180                 185                 190

Ile Ser Asn Tyr Ser Gln Ile Tyr Pro Pro Asn Val Asn Lys Ile Arg
                195                 200                 205

Lys Ala Leu Ala Gln Thr His Ser Ala Met Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
                260                 265                 270

Asp Thr Asn Trp Gly Asp Asn Gly Tyr Gly Tyr Phe Ala Ala Asn Ile
    275                 280                 285

Asp Leu Met Met Ile Glu Lys Tyr Pro Tyr Val Val Ile Leu
    290                 295                 300
```

<210> SEQ ID NO 299
<211> LENGTH: 302
<212> TYPE: PRT
<213> ORGANISM: Dermatophagoides pteronyssinus

<400> SEQUENCE: 299

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Ile Arg Thr Val Thr Pro Ile Arg Met Gln Gly Gly Ser Gly
                100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Ser Lys Ile Arg
            195                 200                 205

Glu Ala Leu Ala Gln Thr His Ser Ala Ile Ala Val Ile Ile Gly Ile
210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Gly Tyr Pro Tyr Val Val Ile Leu
            290                 295                 300
```

<210> SEQ ID NO 300
<211> LENGTH: 302
<212> TYPE: PRT
<213> ORGANISM: Dermatophagoides pteronyssinus

<400> SEQUENCE: 300

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
```

| | | | | 65 | | | | 70 | | | | 75 | | | | 80 |

Thr Asn Ala Ser Ser Ile Asn Gly Asn Ala Pro Ala Glu Ile Asp Leu
                        85                      90                  95

Arg Gln Met Arg Thr Val Thr Pro Ile Arg Met Gln Gly Gly Ser Gly
              100                    105                  110

Ser Ser Trp Ala Phe Ser Gly Val Ala Ala Thr Glu Ser Ala Tyr Leu
        115                      120                  125

Ala Tyr Arg Asn Gln Ser Leu Asp Leu Ala Glu Gln Glu Leu Val Asp
130                        135                      140

Ser Ala Ser Gln His Gly Ser His Gly Asp Thr Ile Pro Arg Gly Ile
145                      150                      155                  160

Ala Tyr Ile Gln His Asn Gly Val Val Gln Glu Ser Tyr Tyr Arg Tyr
              165                    170                  175

Val Ala Arg Glu Gln Ser Ser Arg Arg Pro Asn Ala Gln Arg Phe Gly
        180                      185                  190

Ile Ser Asn Tyr Ser Gln Ile Tyr Pro Pro Asn Ala Asn Lys Ile Arg
            195                    200                  205

Glu Ala Leu Ala Gln Thr His Ser Ala Ile Ala Val Ile Ile Gly Ile
210                        215                      220

Lys Asp Leu Asp Ala Phe Arg His Tyr Asp Gly Arg Thr Ile Ile Gln
225                      230                      235                  240

Arg Asp Asn Gly Tyr Gln Pro Asn Tyr His Ala Val Asn Ile Val Gly
              245                    250                  255

Tyr Ser Asn Ala Gln Gly Val Asp Tyr Trp Ile Val Arg Asn Ser Trp
        260                      265                  270

Asp Thr Asn Trp Gly Asp Asn Gly Tyr Gly Tyr Phe Ala Ala Asn Ile
            275                    280                  285

Asp Leu Met Met Ile Glu Glu Tyr Pro Tyr Val Val Ile Leu
290                        295                      300

<210> SEQ ID NO 301
<211> LENGTH: 302
<212> TYPE: PRT
<213> ORGANISM: Dermatophagoides pteronyssinus

<400> SEQUENCE: 301

Arg Pro Ser Ser Ile Lys Thr Phe Glu Glu Tyr Lys Lys Ala Phe Gln
1                      5                      10                  15

Lys Ser Tyr Ala Thr Phe Glu Asp Glu Glu Ala Ala Arg Lys Asn Phe
              20                    25                  30

Leu Glu Ser Val Lys Tyr Val Gln Ser Asn Gly Gly Ala Ile Asn His
        35                      40                  45

Leu Ser Asp Leu Ser Leu Asp Glu Phe Lys Asn Arg Phe Leu Met Ser
    50                      55                    60

Ala Glu Ala Phe Glu His Leu Lys Thr Gln Phe Asp Leu Asn Ala Glu
65                        70                      75                  80

Thr Asn Ala Ser Ser Ile Asn Gly Asn Ala Pro Ala Glu Ile Asp Leu
                      85                      90                  95

Arg Gln Met Arg Thr Val Thr Pro Ile Arg Met Gln Gly Gly Ser Gly
              100                    105                  110

Ser Ser Trp Ala Phe Ser Gly Val Ala Ala Thr Glu Ser Ala Tyr Leu
        115                      120                  125

Ala Tyr Arg Asn Gln Ser Leu Asp Leu Ala Glu Gln Glu Leu Val Asp
130                        135                      140

```
Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Thr Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 302
<211> LENGTH: 302
<212> TYPE: PRT
<213> ORGANISM: Dermatophagoides pteronyssinus

<400> SEQUENCE: 302

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Leu Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220
```

Lys Asp Leu Asp Ala Phe Arg His Tyr Asp Gly Arg Thr Ile Ile Gln
225                 230                 235                 240

Arg Asp Asn Gly Tyr Gln Pro Asn Tyr Tyr Ala Val Asn Ile Val Gly
            245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu
290                 295                 300

<210> SEQ ID NO 303
<211> LENGTH: 302
<212> TYPE: PRT
<213> ORGANISM: Dermatophagoides pteronyssinus

<400> SEQUENCE: 303

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
            85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
            165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
            195                 200                 205

Glu Ala Leu Thr Gln Thr His Ser Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
            245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu

<210> SEQ ID NO 304
<211> LENGTH: 302
<212> TYPE: PRT
<213> ORGANISM: Dermatophagoides pteronyssinus

<400> SEQUENCE: 304

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Ile Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 305
<211> LENGTH: 302
<212> TYPE: PRT
<213> ORGANISM: Dermatophagoides pteronyssinus

<400> SEQUENCE: 305

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe

```
                20                  25                  30
Leu Glu Ser Val Lys Tyr Val Gln Ser Asn Gly Gly Ala Ile Asn His
         35                  40                  45

Leu Ser Asp Leu Ser Leu Asp Glu Phe Lys Asn Arg Phe Leu Met Ser
 50                  55                  60

Ala Glu Ala Phe Glu His Leu Lys Thr Gln Phe Asp Leu Asn Ala Glu
 65                  70                  75                  80

Thr Asn Ala Ser Ser Ile Asn Gly Asn Ala Pro Ala Glu Ile Asp Leu
             85                  90                  95

Arg Gln Met Arg Thr Val Thr Pro Ile Arg Met Gln Gly Ser Gly
             100                 105                 110

Ser Ser Trp Ala Phe Ser Gly Val Ala Ala Thr Glu Ser Ala Tyr Leu
         115                 120                 125

Ala Tyr Arg Asn Gln Ser Leu Asp Leu Ala Glu Gln Glu Leu Val Asp
         130                 135                 140

Ser Ala Ser Gln His Gly Ser His Gly Asp Thr Ile Pro Arg Gly Ile
145                 150                 155                 160

Gly Tyr Ile Gln His Asn Gly Val Val Gln Glu Ser Tyr Tyr Arg Tyr
                 165                 170                 175

Val Ala Arg Glu Gln Ser Ser Arg Arg Pro Asn Ala Gln Arg Phe Gly
             180                 185                 190

Ile Ser Asn Tyr Ser Gln Ile Tyr Pro Pro Asn Val Asn Lys Ile Arg
         195                 200                 205

Glu Ala Leu Ala Gln Thr His Ser Ala Ile Ala Val Ile Ile Gly Ile
         210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
             245                 250                 255

Tyr Ser Asn Ala Gln Gly Val Asp Tyr Trp Ile Val Arg Asn Ser Trp
         260                 265                 270

Asp Thr Asn Trp Gly Asp Asn Gly Tyr Gly Tyr Phe Ala Ala Asn Ile
         275                 280                 285

Asp Leu Met Met Ile Glu Glu Tyr Pro Tyr Val Val Ile Leu
         290                 295                 300

<210> SEQ ID NO 306
<211> LENGTH: 302
<212> TYPE: PRT
<213> ORGANISM: Dermatophagoides pteronyssinus

<400> SEQUENCE: 306

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
             20                  25                  30

Leu Glu Ser Val Lys Tyr Val Gln Ser Asn Gly Gly Ala Ile Asn His
         35                  40                  45

Leu Ser Asp Leu Ser Leu Asp Glu Phe Lys Asn Arg Phe Leu Met Ser
 50                  55                  60

Ala Glu Ala Phe Glu His Leu Lys Thr Gln Phe Asp Leu Asn Ala Glu
 65                  70                  75                  80

Thr Asn Ala Ser Ser Ile Asn Gly Asn Ala Pro Ala Glu Ile Asp Leu
             85                  90                  95
```

```
Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Arg
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300

<210> SEQ ID NO 307
<211> LENGTH: 302
<212> TYPE: PRT
<213> ORGANISM: Dermatophagoides pteronyssinus

<400> SEQUENCE: 307

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Ser Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175
```

```
Val Ala Arg Glu Gln Ser Ser Arg Pro Asn Ala Gln Arg Phe Gly
            180                 185                 190

Ile Ser Asn Tyr Ser Gln Ile Tyr Pro Pro Asn Val Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Gly Tyr Pro Tyr Val Val Ile Leu
    290                 295                 300
```

<210> SEQ ID NO 308
<211> LENGTH: 302
<212> TYPE: PRT
<213> ORGANISM: Dermatophagoides pteronyssinus

<400> SEQUENCE: 308

```
Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
            85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
        115                 120                 125

Ala Tyr Arg Asn Gln Ser Leu Asp Leu Ala Glu Gln Glu Leu Val Asp
    130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Pro Asn Ala Gln Arg Phe Gly
            180                 185                 190

Thr Ser Asn Tyr Ser Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
```

```
                        245                 250                 255
Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Glu Tyr Pro Tyr Val Val Ile Leu
            290                 295                 300

<210> SEQ ID NO 309
<211> LENGTH: 302
<212> TYPE: PRT
<213> ORGANISM: Dermatophagoides pteronyssinus

<400> SEQUENCE: 309

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
            85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
            165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
            195                 200                 205

Glu Ala Leu Ala Gln Thr His Ser Ala Ile Ala Val Ile Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
            245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
            275                 280                 285

Asp Leu Met Met Ile Glu Gly Tyr Pro Tyr Val Val Ile Leu
            290                 295                 300

<210> SEQ ID NO 310
<211> LENGTH: 302
```

```
<212> TYPE: PRT
<213> ORGANISM: Dermatophagoides pteronyssinus

<400> SEQUENCE: 310

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
                20                  25                  30

Leu Glu Ser Val Lys Tyr Val Gln Ser Asn Gly Gly Ala Ile Asn His
            35                  40                  45

Leu Ser Asp Leu Ser Leu Asp Glu Phe Lys Asn Arg Phe Leu Met Ser
50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
                100                 105                 110

Ser Ser Trp Ala Phe Ser Gly Val Ala Ala Thr Glu Ser Ala Tyr Leu
            115                 120                 125

Ala Tyr Arg Asn Gln Ser Leu Asp Leu Ala Glu Gln Glu Leu Val Asp
130                 135                 140

Ser Ala Ser Gln His Gly Ser Asn Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Arg Pro Asn Ala Gln Arg Phe Gly
            180                 185                 190

Ile Ser Asn Tyr Ser Gln Ile Tyr Pro Pro Asn Ala Asn Lys Ile Arg
                195                 200                 205

Glu Ala Leu Ala Gln Thr His Ser Ala Ile Ala Val Ile Ile Gly Ile
210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
                275                 280                 285

Asp Leu Met Met Ile Glu Glu Tyr Pro Tyr Val Val Ile Leu
290                 295                 300

<210> SEQ ID NO 311
<211> LENGTH: 302
<212> TYPE: PRT
<213> ORGANISM: Dermatophagoides pteronyssinus

<400> SEQUENCE: 311

Arg Pro Ser Ser Ile Lys Thr Phe Glu Glu Tyr Lys Lys Ala Phe Gln
1               5                   10                  15

Lys Ser Tyr Ala Thr Phe Glu Asp Glu Glu Ala Ala Arg Lys Asn Phe
                20                  25                  30

Leu Glu Ser Val Lys Tyr Val Gln Ser Asn Gly Gly Ala Ile Asn His
            35                  40                  45
```

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Ser Ser Ile Asn Gly Asn Ala Pro Ala Glu Ile Asp Leu
                85                  90                  95

Arg Gln Met Arg Thr Val Thr Pro Ile Arg Met Gln Gly Gly Ser Gly
            100                 105                 110

Ser Ser Trp Ala Phe Ser Gly Val Ala Ala Thr Glu Ser Ala Tyr Leu
                115                 120                 125

Ala Tyr Arg Glu Gln Ser Leu Asp Leu Ala Glu Gln Glu Leu Val Asp
            130                 135                 140

Ser Ala Ser Gln His Gly Ser His Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Ser Arg Pro Asn Ala Gln Arg Phe Gly
            180                 185                 190

Ile Ser Asn Tyr Ser Gln Ile Tyr Pro Pro Asn Ala Asn Lys Ile Arg
                195                 200                 205

Glu Ala Leu Ala Gln Thr His Ser Ala Ile Ala Val Ile Gly Ile
            210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
                275                 280                 285

Asp Leu Met Met Ile Glu Glu Tyr Pro Tyr Val Val Ile Leu
            290                 295                 300

<210> SEQ ID NO 312
<211> LENGTH: 303
<212> TYPE: PRT
<213> ORGANISM: Dermatophagoides farinae

<400> SEQUENCE: 312

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
                35                  40                  45

Leu Ser Asp Leu Ser Leu Asp Glu Phe Lys Asn Arg Tyr Leu Met Ser
            50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
                115                 120                 125

Leu Ala Tyr Arg Asn Thr Ser Leu Asp Leu Ser Glu Gln Glu Leu Val
            130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Ser Arg Arg Pro Asn Ser Gln His Tyr
            180                 185                 190

Gly Ile Ser Asn Tyr Ser Gln Ile Tyr Pro Pro Asp Val Lys Gln Ile
        195                 200                 205

Arg Glu Ala Leu Thr Gln Thr His Thr Ala Ile Ala Val Ile Ile Gly
210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
290                 295                 300

<210> SEQ ID NO 313
<211> LENGTH: 303
<212> TYPE: PRT
<213> ORGANISM: Dermatophagoides farinae

<400> SEQUENCE: 313

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
            130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Ser Arg Arg Pro Asn Ser Gln His Tyr
            180                 185                 190

Gly Ile Ser Asn Tyr Ser Gln Ile Tyr Pro Pro Asp Val Lys Gln Ile

```
            195                 200                 205
Arg Glu Ala Leu Thr Gln Thr His Thr Ala Ile Ala Val Ile Ile Gly
    210                 215                 220

Ile Lys Asp Leu Arg Ala Phe Gln His Tyr Asp Gly Arg Thr Ile Ile
225                 230                 235                 240

Gln Arg Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
                260                 265                 270

Trp Asp Thr Thr Trp Gly Asp Ser Gly Tyr Gly Tyr Phe Gln Ala Gly
                275                 280                 285

Asn Asn Leu Met Met Ile Glu Gln Tyr Pro Tyr Val Val Ile Met
                290                 295                 300

<210> SEQ ID NO 314
<211> LENGTH: 303
<212> TYPE: PRT
<213> ORGANISM: Dermatophagoides farinae

<400> SEQUENCE: 314

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Ser Arg Arg Pro Asn Ser Gln His Tyr
            180                 185                 190

Gly Ile Ser Asn Tyr Ser Gln Ile Tyr Pro Pro Asp Val Lys Gln Ile
        195                 200                 205

Arg Glu Ala Leu Thr Gln Thr His Thr Ala Ile Ala Val Ile Ile Gly
    210                 215                 220

Ile Lys Asp Leu Arg Ala Phe Gln His Tyr Gly Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
                260                 265                 270
```

```
Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
    290                 295                 300
```

<210> SEQ ID NO 315
<211> LENGTH: 303
<212> TYPE: PRT
<213> ORGANISM: Dermatophagoides farinae

<400> SEQUENCE: 315

```
Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
    50                  55                  60

Ala Glu Ala Phe Glu Gln Leu Lys Thr Gln Phe Asp Leu Asn Ala Glu
65                  70                  75                  80

Ile Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
    130                 135                 140

Asp Ser Ala Ser Gln His Gly Arg His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Ser Arg Arg Pro Asn Ser Gln His Tyr
            180                 185                 190

Gly Ile Ser Asn Tyr Ser Gln Ile Tyr Pro Pro Asp Val Lys Gln Ile
        195                 200                 205

Arg Glu Ala Leu Thr Gln Thr His Thr Ala Ile Ala Val Ile Ile Gly
    210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
    290                 295                 300
```

<210> SEQ ID NO 316
<211> LENGTH: 303
<212> TYPE: PRT
<213> ORGANISM: Dermatophagoides farinae

<400> SEQUENCE: 316

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
            35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
            85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
            115                 120                 125

Leu Ala Tyr Arg Asn Thr Ser Leu Asp Leu Ser Glu Gln Glu Leu Val
            130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
            165                 170                 175

Tyr Val Ala Arg Glu Gln Ser Arg Arg Pro Asn Ser Gln His Tyr
            180                 185                 190

Asp Ile Ser Asn Tyr Ser Gln Ile Tyr Pro Pro Asp Val Lys Gln Ile
            195                 200                 205

Arg Glu Ala Leu Thr Gln Thr His Thr Ala Ile Ala Val Ile Ile Gly
210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
            245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
            275                 280                 285

Asn Asn Leu Met Met Ile Glu Gln Tyr Pro Tyr Val Val Ile Met
            290                 295                 300

<210> SEQ ID NO 317
<211> LENGTH: 303
<212> TYPE: PRT
<213> ORGANISM: Dermatophagoides farinae

<400> SEQUENCE: 317

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
            35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
            115                 120                 125

Leu Ala Tyr Arg Asn Thr Ser Leu Asp Leu Ser Glu Gln Glu Leu Val
130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Arg Ser Arg Arg Pro Asn Ser Gln His Tyr
            180                 185                 190

Gly Ile Ser Asn Tyr Ser Gln Ile Tyr Pro Pro Asp Val Lys Gln Ile
            195                 200                 205

Arg Glu Ala Leu Thr Gln Thr His Thr Ala Ile Ala Val Ile Ile Gly
210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Asp Asp Tyr Trp Ile Val Arg Asn Ser
            260                 265                 270

Trp Asp Thr Thr Trp Gly Asp Ser Gly Tyr Gly Tyr Phe Gln Ala Gly
            275                 280                 285

Asn Asn Leu Met Met Ile Glu Gln Tyr Pro Tyr Val Val Ile Met
290                 295                 300

<210> SEQ ID NO 318
<211> LENGTH: 303
<212> TYPE: PRT
<213> ORGANISM: Dermatophagoides farinae

<400> SEQUENCE: 318

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
            35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
            115                 120                 125

Leu Ala Tyr Arg Asn Thr Ser Leu Asp Leu Ser Glu Gln Glu Leu Val
130                 135                 140

Asp Ser Ala Ser Gln His Gly Ser His Gly Asp Thr Ile Pro Arg Gly

```
145                 150                 155                 160
Ile Glu Tyr Ile Gln Gln Asn Gly Val Glu Glu Arg Ser Tyr Pro
                165                 170                 175

Tyr Val Ala Arg Glu Gln Arg Ser Arg Arg Pro Asn Ser Gln His Tyr
                180                 185                 190

Gly Ile Ser Asn Tyr Ser Gln Ile Tyr Pro Pro Asp Val Lys Gln Ile
                195                 200                 205

Arg Glu Ala Leu Thr Gln Thr His Thr Ala Ile Ala Val Ile Ile Gly
210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
                260                 265                 270

Trp Asp Thr Thr Trp Gly Asp Ser Gly Tyr Gly Tyr Phe Gln Ala Gly
                275                 280                 285

Asn Asn Leu Met Met Ile Glu Gln Tyr Pro Tyr Val Val Ile Met
                290                 295                 300

<210> SEQ ID NO 319
<211> LENGTH: 303
<212> TYPE: PRT
<213> ORGANISM: Dermatophagoides farinae

<400> SEQUENCE: 319

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
                20                  25                  30

Leu Glu Ser Leu Lys Tyr Val Glu Ala Asn Lys Gly Ala Ile Asn His
                35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Ala Thr Pro Ile Arg Met Gln Gly Gly Ser
                100                 105                 110

Gly Ser Ser Trp Ala Phe Ser Gly Val Ala Ala Thr Glu Ser Ala Tyr
                115                 120                 125

Leu Ala Tyr Arg Asn Thr Ser Leu Asp Leu Ser Glu Gln Glu Leu Val
                130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Glu Glu Arg Ser Tyr Pro
                165                 170                 175

Tyr Val Ala Arg Glu Gln Gln Ser Arg Arg Pro Asn Ser Gln His Tyr
                180                 185                 190

Gly Ile Ser Asn Tyr Ser Gln Ile Tyr Pro Pro Asp Val Lys Gln Ile
                195                 200                 205

Arg Glu Ala Leu Thr Gln Thr His Thr Ala Ile Ala Val Ile Ile Gly
210                 215                 220
```

```
Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
            245                 250                 255

Gly Tyr Gly Ser Thr Gln Gly Val Asp Tyr Trp Ile Val Arg Asn Ser
        260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
290                 295                 300
```

<210> SEQ ID NO 320
<211> LENGTH: 303
<212> TYPE: PRT
<213> ORGANISM: Dermatophagoides farinae

<400> SEQUENCE: 320

```
Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Lys Leu Val
130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Ser Arg Arg Pro Asn Ser Gln His Tyr
            180                 185                 190

Gly Ile Ser Asn Tyr Ser Gln Ile Tyr Pro Pro Asp Val Lys Gln Ile
        195                 200                 205

Arg Glu Ala Leu Thr Gln Thr His Thr Ala Ile Ala Val Ile Ile Gly
210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
290                 295                 300
```

<210> SEQ ID NO 321
<211> LENGTH: 303
<212> TYPE: PRT
<213> ORGANISM: Dermatophagoides farinae

<400> SEQUENCE: 321

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
50                  55                  60

Ala Glu Ala Phe Glu Gln Leu Lys Thr Gln Phe Asp Leu Asn Ala Glu
65                  70                  75                  80

Thr Ser Ala Ser Arg Ile Asn Ser Val Asn Val Pro Ser Glu Leu Asp
                85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
    130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175

Tyr Val Ala Arg Glu Gln Gln Ser Arg Arg Pro Asn Ser Gln His Tyr
            180                 185                 190

Gly Ile Ser Asn Tyr Ser Gln Ile Tyr Pro Pro Asp Val Lys Gln Ile
        195                 200                 205

Arg Glu Ala Leu Thr Gln Thr His Thr Ala Ile Ala Val Ile Ile Gly
    210                 215                 220

Ile Lys Asp Leu Arg Ala Phe Gln His Tyr Asp Gly Arg Thr Ile Ile
225                 230                 235                 240

Arg His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
    290                 295                 300

<210> SEQ ID NO 322
<211> LENGTH: 303
<212> TYPE: PRT
<213> ORGANISM: Dermatophagoides farinae

<400> SEQUENCE: 322

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

-continued

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
 50                  55                  60

Ala Glu Ala Phe Glu Gln Leu Lys Thr Gln Phe Asp Leu Asn Ala Glu
 65                  70                  75                  80

Thr Ser Ala Ser Arg Ile Asn Ser Val Asn Val Pro Ser Glu Leu Asp
             85                  90                  95

Leu Arg Ser Leu Arg Thr Val Thr Pro Ile Arg Met Gln Gly Gly Ser
            100                 105                 110

Gly Ser Ser Trp Ala Phe Ser Gly Val Ala Ala Thr Glu Ser Ala Tyr
            115                 120                 125

Leu Ala Tyr Arg Gln Thr Ser Leu Asp Leu Ser Glu Gln Glu Leu Val
        130                 135                 140

Asp Ser Ala Ser Gln His Gly Ser His Gly Asp Thr Ile Pro Arg Gly
145                 150                 155                 160

Ile Glu Tyr Ile Gln Gln Asn Gly Val Val Glu Arg Ser Tyr Pro
                165                 170                 175

Tyr Val Ala Arg Glu Gln Arg Ser Arg Arg Pro Asn Ser Gln His Tyr
            180                 185                 190

Gly Ile Ser Asn Tyr Ser Gln Ile Tyr Pro Pro Asp Val Lys Gln Ile
        195                 200                 205

Arg Glu Ala Leu Thr Gln Thr His Thr Ala Ile Ala Val Ile Ile Gly
210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Val Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
    290                 295                 300

<210> SEQ ID NO 323
<211> LENGTH: 129
<212> TYPE: PRT
<213> ORGANISM: Dermatophagoides pteronyssinus

<400> SEQUENCE: 323

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
 50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
            85                  90                  95

Ile Ala Pro Lys Ser Glu Asn Val Val Val Thr Val Lys Val Met Gly

```
            100                 105                 110

Asp Asp Gly Val Leu Ala Ser Ala Ile Ala Thr His Ala Lys Ile Arg
        115                 120                 125

Asp

<210> SEQ ID NO 324
<211> LENGTH: 129
<212> TYPE: PRT
<213> ORGANISM: Dermatophagoides pteronyssinus

<400> SEQUENCE: 324

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asn Gly Val Leu Ala Ser Ala Ile Ala Thr His Ala Lys Leu Arg
        115                 120                 125

Asp

<210> SEQ ID NO 325
<211> LENGTH: 129
<212> TYPE: PRT
<213> ORGANISM: Dermatophagoides pteronyssinus

<400> SEQUENCE: 325

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Leu Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asn Gly Val Leu Ala Ser Ala Ile Ala Thr His Ala Lys Ile Arg
        115                 120                 125

Asp

<210> SEQ ID NO 326
<211> LENGTH: 129
<212> TYPE: PRT
```

<213> ORGANISM: Dermatophagoides pteronyssinus

<400> SEQUENCE: 326

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Leu Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Leu Gly
            100                 105                 110

Asp Asn Gly Val Leu Ala Ser Ala Ile Ala Thr His Ala Lys Ile Arg
        115                 120                 125

Asp

<210> SEQ ID NO 327
<211> LENGTH: 129
<212> TYPE: PRT
<213> ORGANISM: Dermatophagoides pteronyssinus

<400> SEQUENCE: 327

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Leu Phe Glu Ala Asn Gln Asn Ser Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asp Gly Val Leu Ala Ser Ala Ile Ala Thr His Ala Lys Ile Arg
        115                 120                 125

Asp

<210> SEQ ID NO 328
<211> LENGTH: 129
<212> TYPE: PRT
<213> ORGANISM: Dermatophagoides pteronyssinus

<400> SEQUENCE: 328

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Thr Lys

```
                35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Met Lys Ser Pro Leu
 65                  70                  75                  80

Val Lys Gly Gln Gln Tyr Asp Ile Lys Tyr Thr Trp Asn Val Pro Lys
                85                  90                  95

Ile Thr Pro Lys Ser Glu Asn Val Val Thr Val Lys Val Met Gly
            100                 105                 110

Asp Asp Gly Val Leu Ala Ser Ala Ile Ala Thr His Ala Lys Ile Arg
        115                 120                 125

Asp

<210> SEQ ID NO 329
<211> LENGTH: 129
<212> TYPE: PRT
<213> ORGANISM: Dermatophagoides pteronyssinus

<400> SEQUENCE: 329

Asp Gln Val Asp Val Lys Asp Ser Ala Asn His Glu Ile Lys Lys Val
 1               5                  10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Ser Lys
                35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Met Lys Ser Pro Leu
 65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Val Met Gly
            100                 105                 110

Asp Asp Gly Val Leu Ala Ser Ala Ile Ala Thr His Ala Lys Ile Arg
        115                 120                 125

Asp

<210> SEQ ID NO 330
<211> LENGTH: 129
<212> TYPE: PRT
<213> ORGANISM: Dermatophagoides pteronyssinus

<400> SEQUENCE: 330

Asp Gln Val Asp Val Lys Asp Ser Ala Asn His Glu Ile Lys Lys Val
 1               5                  10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Ser Lys
                35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Met Lys Ser Pro Leu
 65                  70                  75                  80

Val Lys Gly Gln Gln Tyr Asp Ile Lys Tyr Thr Trp Asn Val Pro Lys
                85                  90                  95
```

```
Ile Ala Pro Lys Ser Glu Asn Val Val Val Thr Val Lys Val Met Gly
            100                 105                 110

Asp Asp Gly Ala Leu Ala Ser Ala Ile Ala Thr His Ala Lys Ile Arg
            115                 120                 125

Asp

<210> SEQ ID NO 331
<211> LENGTH: 129
<212> TYPE: PRT
<213> ORGANISM: Dermatophagoides pteronyssinus

<400> SEQUENCE: 331

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Ser Lys
            35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Leu Gly
            100                 105                 110

Asp Asn Gly Val Leu Ala Ser Ala Ile Ala Thr His Ala Lys Ile Arg
            115                 120                 125

Asp

<210> SEQ ID NO 332
<211> LENGTH: 129
<212> TYPE: PRT
<213> ORGANISM: Dermatophagoides pteronyssinus

<400> SEQUENCE: 332

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Ser Lys
            35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Leu Gly
            100                 105                 110

Asp Asn Gly Val Leu Ala Ser Ala Ile Ala Thr His Ala Lys Ile Arg
            115                 120                 125

Asp

<210> SEQ ID NO 333
<211> LENGTH: 129
```

```
<212> TYPE: PRT
<213> ORGANISM: Dermatophagoides pteronyssinus

<400> SEQUENCE: 333

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
                20                  25                  30

Lys Pro Phe Gln Leu Glu Ala Leu Phe Glu Ala Asn Gln Asn Ser Lys
            35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110

Asp Asn Gly Val Leu Ala Ser Ala Ile Ala Thr His Ala Lys Ile Arg
        115                 120                 125

Asp

<210> SEQ ID NO 334
<211> LENGTH: 129
<212> TYPE: PRT
<213> ORGANISM: Dermatophagoides pteronyssinus

<400> SEQUENCE: 334

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
                20                  25                  30

Lys Pro Phe Gln Leu Glu Ala Val Phe Glu Ala Asn Gln Asn Thr Lys
            35                  40                  45

Thr Ala Lys Ile Glu Ile Lys Ala Ser Ile Asp Gly Leu Glu Val Asp
        50                  55                  60

Val Pro Gly Ile Asp Pro Asn Ala Ser His Tyr Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Ile Gly
            100                 105                 110

Asp Asn Gly Val Leu Ala Ser Ala Ile Ala Thr His Ala Lys Ile Arg
        115                 120                 125

Asp

<210> SEQ ID NO 335
<211> LENGTH: 129
<212> TYPE: PRT
<213> ORGANISM: Dermatophagoides pteronyssinus

<400> SEQUENCE: 335

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
                20                  25                  30
```

Lys Pro Phe Gln Leu Glu Ala Val Phe Glu Ala Asn Gln Asn Thr Lys
            35                  40                  45

Asn Ala Lys Ile Glu Ile Lys Ala Ser Ile Asp Gly Leu Glu Val Asp
    50                  55                  60

Val Pro Gly Ile Asp Pro Asn Ala Ser His Tyr Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Val Met Gly
            100                 105                 110

Asp Asn Gly Val Leu Ala Ser Ala Ile Ala Thr His Ala Lys Ile Arg
            115                 120                 125

Asp

<210> SEQ ID NO 336
<211> LENGTH: 129
<212> TYPE: PRT
<213> ORGANISM: Dermatophagoides pteronyssinus

<400> SEQUENCE: 336

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Leu Phe Glu Ala Asn Gln Asn Thr Lys
            35                  40                  45

Asn Ala Lys Ile Glu Ile Lys Ala Ser Ile Asp Gly Leu Glu Val Asp
    50                  55                  60

Val Pro Gly Ile Asp Pro Asn Ala Ser His Tyr Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Val Leu Gly
            100                 105                 110

Asp Asn Gly Val Leu Ala Ser Ala Ile Ala Thr His Ala Lys Ile Arg
            115                 120                 125

Asp

<210> SEQ ID NO 337
<211> LENGTH: 129
<212> TYPE: PRT
<213> ORGANISM: Dermatophagoides pteronyssinus

<400> SEQUENCE: 337

Asp Gln Val Asp Val Lys Asp Ser Ala Asn His Glu Ile Lys Lys Val
1               5                   10                  15

Leu Val Pro Gly Ser His Gly Ser Glu Pro Ser Ile Ile His Arg Gly
            20                  25                  30

Lys Pro Phe Gln Leu Glu Ala Val Phe Glu Ala Asn Gln Asn Ser Lys
            35                  40                  45

Thr Ala Lys Ile Glu Ile Lys Ala Ser Ile Asp Gly Leu Glu Val Asp
    50                  55                  60

Val Pro Gly Ile Asp Pro Asn Ala Ser His Tyr Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Val Met Gly
            100                 105                 110

Asp Asn Gly Val Leu Ala Ser Ala Ile Ala Thr His Ala Lys Ile Arg
            115                 120                 125

Asp

<210> SEQ ID NO 338
<211> LENGTH: 129
<212> TYPE: PRT
<213> ORGANISM: Dermatophagoides farinae

<400> SEQUENCE: 338

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Ser His Phe Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Ser Ala Ile Ala Thr His Gly Lys Ile Arg
            115                 120                 125

Asp

<210> SEQ ID NO 339
<211> LENGTH: 129
<212> TYPE: PRT
<213> ORGANISM: Dermatophagoides farinae

<400> SEQUENCE: 339

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Ser His Phe Met Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Ser Ala Ile Ala Thr His Gly Lys Ile Arg
            115                 120                 125

Asp

<210> SEQ ID NO 340

```
<211> LENGTH: 129
<212> TYPE: PRT
<213> ORGANISM: Dermatophagoides farinae

<400> SEQUENCE: 340

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Ser Leu Asp Gly Leu Glu Ile Asp
    50                  55                  60

Val Pro Gly Ile Asp Thr Asn Ala Ser His Phe Met Lys Ser Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Thr Val Lys Leu Val Gly
            100                 105                 110

Asp Asn Gly Val Leu Ala Ser Ala Ile Ala Thr His Ala Lys Ile Arg
        115                 120                 125

Asp

<210> SEQ ID NO 341
<211> LENGTH: 129
<212> TYPE: PRT
<213> ORGANISM: Dermatophagoides farinae

<400> SEQUENCE: 341

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Thr Glu Ile Lys Ala Ser Leu Asp Gly Leu Glu Ile Asp
    50                  55                  60

Val Pro Gly Ile Asp Thr Asn Ala Ser His Phe Met Lys Ser Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Ser Ala Ile Ala Thr His Ala Lys Ile Arg
        115                 120                 125

Asp

<210> SEQ ID NO 342
<211> LENGTH: 129
<212> TYPE: PRT
<213> ORGANISM: Dermatophagoides farinae

<400> SEQUENCE: 342

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30
```

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
 50                  55                  60

Val Pro Gly Ile Asp Thr Asn Ala Ser His Phe Met Lys Ser Pro Leu
 65                  70                  75                  80

Val Lys Gly Gln Gln Tyr Asp Ala Lys Tyr Thr Trp Asn Val Pro Lys
                85                  90                  95

Ile Ala Pro Glu Ser Glu Asn Val Val Thr Val Lys Leu Val Gly
            100                 105                 110

Asp Asn Gly Val Leu Ala Ser Ala Ile Ala Thr His Ala Lys Ile Arg
            115                 120                 125

Asp

<210> SEQ ID NO 343
<211> LENGTH: 129
<212> TYPE: PRT
<213> ORGANISM: Dermatophagoides farinae

<400> SEQUENCE: 343

Asp Gln Val Asp Val Lys Asp Ser Ala Asn His Glu Ile Lys Lys Val
 1               5                  10                  15

Met Val Asp Gly Ser His Gly Ser Asp Pro Ser Ile Ile His Arg Gly
            20                  25                  30

Lys Pro Phe Asn Leu Glu Ala Ile Phe Asp Ala Asn Gln Asn Thr Lys
            35                  40                  45

Thr Ala Lys Ile Glu Ile Lys Ala Asn Ile Asp Gly Leu Glu Val Asp
 50                  55                  60

Val Pro Gly Ile Asp Thr Asn Ala Ser His Tyr Ile Lys Ser Pro Leu
 65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Ser Ala Ile Ala Thr His Ala Lys Ile Arg
            115                 120                 125

Asp

<210> SEQ ID NO 344
<211> LENGTH: 129
<212> TYPE: PRT
<213> ORGANISM: Dermatophagoides farinae

<400> SEQUENCE: 344

Asp Gln Val Asp Val Lys Asp Ser Ala Asn Asn Glu Ile Lys Lys Val
 1               5                  10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asn Gly Leu Glu Val Asp
 50                  55                  60

Val Pro Gly Ile Asp Thr Asn Ala Ser His Tyr Ile Lys Ser Pro Leu
 65                  70                  75                  80

Val Lys Gly Gln Gln Tyr Asp Ala Lys Tyr Thr Trp Asn Val Pro Lys

```
                85                  90                  95
Ile Ala Pro Lys Ser Glu Asn Val Val Thr Val Lys Leu Ile Gly
            100                 105                 110

Asp Asn Gly Val Leu Ala Ser Ala Ile Ala Thr His Ala Lys Ile Arg
            115                 120                 125

Asp

<210> SEQ ID NO 345
<211> LENGTH: 129
<212> TYPE: PRT
<213> ORGANISM: Dermatophagoides farinae

<400> SEQUENCE: 345

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asp Gly Leu Glu Val Asp
        50                  55                  60

Val Pro Gly Ile Asp Thr Asn Ala Ser His Tyr Ile Lys Ser Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Thr Val Lys Leu Val Gly
            100                 105                 110

Asp Asn Gly Val Leu Ala Ser Ala Ile Ala Thr His Ala Lys Ile Arg
            115                 120                 125

Asp

<210> SEQ ID NO 346
<211> LENGTH: 129
<212> TYPE: PRT
<213> ORGANISM: Dermatophagoides farinae

<400> SEQUENCE: 346

Asp Gln Val Asp Val Lys Asp Ser Ala Asn Asn Glu Ile Lys Lys Val
1               5                   10                  15

Met Val Asp Gly Arg His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asn Gly Leu Glu Val Asp
        50                  55                  60

Val Pro Gly Ile Asp Thr Asn Ala Ser His Phe Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Thr Val Lys Leu Ile Gly
            100                 105                 110

Asp Asn Gly Val Leu Ala Ser Ala Ile Ala Thr His Ala Lys Ile Arg
            115                 120                 125

Asp
```

```
<210> SEQ ID NO 347
<211> LENGTH: 129
<212> TYPE: PRT
<213> ORGANISM: Dermatophagoides farinae

<400> SEQUENCE: 347

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Asn Ile Asn Gly Leu Glu Ala Asp
    50                  55                  60

Val Pro Gly Ile Asp Thr Asn Ala Ser His Tyr Ile Lys Ser Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Ser Ala Ile Ala Thr His Ala Lys Ile Arg
        115                 120                 125

Asp

<210> SEQ ID NO 348
<211> LENGTH: 129
<212> TYPE: PRT
<213> ORGANISM: Dermatophagoides farinae

<400> SEQUENCE: 348

Asp Gln Val Asp Val Lys Asp Ser Ala Asn Asn Glu Ile Lys Lys Val
1               5                   10                  15

Met Val Asp Gly Arg His Gly Ser Asp Pro Ser Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Ile Lys Ala Asn Ile Asn Gly Leu Glu Val Asp
    50                  55                  60

Val Pro Gly Ile Asp Thr Asn Ala Ser His Phe Val Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Ser Ala Ile Ala Thr His Ala Lys Ile Arg
        115                 120                 125

Asp

<210> SEQ ID NO 349
<211> LENGTH: 129
<212> TYPE: PRT
<213> ORGANISM: Dermatophagoides farinae

<400> SEQUENCE: 349

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
```

```
                    20                  25                  30
Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Ile Asp
        50                  55                  60

Val Pro Gly Ile Asp Thr Asn Ala Ser His Phe Met Lys Ser Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Thr Val Lys Leu Val Gly
            100                 105                 110

Asp Asn Gly Val Leu Ala Ser Ala Ile Ala Thr His Gly Lys Ile Arg
        115                 120                 125

Asp

<210> SEQ ID NO 350
<211> LENGTH: 129
<212> TYPE: PRT
<213> ORGANISM: Dermatophagoides farinae

<400> SEQUENCE: 350

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
                20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Ser Leu Asp Gly Leu Glu Thr Asp
        50                  55                  60

Val Pro Gly Ile Asp Thr Asn Ala Ser His Phe Met Lys Ser Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Thr Val Lys Leu Ile Gly
            100                 105                 110

Asp Asn Gly Val Leu Ala Ser Ala Ile Ala Thr His Gly Lys Ile Arg
        115                 120                 125

Asp

<210> SEQ ID NO 351
<211> LENGTH: 129
<212> TYPE: PRT
<213> ORGANISM: Dermatophagoides farinae

<400> SEQUENCE: 351

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
                20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asn Gly Leu Glu Val Asp
        50                  55                  60

Val Pro Gly Ile Asp Thr Asn Ala Ser His Phe Val Lys Ser Pro Leu
65                  70                  75                  80
```

Val Lys Gly Gln Gln Tyr Asp Ile Lys Tyr Thr Trp Asn Val Pro Lys
            85                  90                  95

Ile Ala Pro Lys Ser Glu Asn Val Val Thr Val Lys Leu Ile Gly
            100                 105                 110

Asp Asn Gly Val Leu Ala Ser Ala Ile Ala Thr His Gly Lys Ile Arg
            115                 120                 125

Asp

<210> SEQ ID NO 352
<211> LENGTH: 129
<212> TYPE: PRT
<213> ORGANISM: Dermatophagoides farinae

<400> SEQUENCE: 352

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asn Gly Leu Glu Val Asp
        50                  55                  60

Val Pro Gly Ile Asp Thr Asn Ala Ser His Phe Val Lys Ser Pro Leu
65                  70                  75                  80

Val Lys Gly Gln Gln Tyr Asp Ile Lys Tyr Thr Trp Asn Val Pro Lys
            85                  90                  95

Ile Ala Pro Lys Ser Glu Asn Val Val Thr Val Lys Leu Ile Gly
            100                 105                 110

Asp Asn Gly Val Leu Ala Ser Ala Ile Ala Thr His Gly Lys Ile Ser
            115                 120                 125

Asp

<210> SEQ ID NO 353
<211> LENGTH: 129
<212> TYPE: PRT
<213> ORGANISM: Dermatophagoides farinae

<400> SEQUENCE: 353

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asn Gly Leu Glu Val Asp
        50                  55                  60

Val Pro Gly Ile Asp Thr Asn Ala Ser His Tyr Ile Lys Ser Pro Leu
65                  70                  75                  80

Val Lys Gly Gln Gln Tyr Asp Ala Lys Tyr Thr Trp Asn Val Pro Lys
            85                  90                  95

Ile Ala Pro Lys Ser Glu Asn Val Val Thr Val Lys Leu Ile Gly
            100                 105                 110

Asp Asn Gly Val Leu Ala Ser Ala Ile Ala Thr His Gly Lys Ile Arg
            115                 120                 125

Asp

```
<210> SEQ ID NO 354
<211> LENGTH: 129
<212> TYPE: PRT
<213> ORGANISM: Dermatophagoides farinae

<400> SEQUENCE: 354

Asp Gln Val Asp Val Lys Asp Ser Ala Asn Asn Glu Ile Lys Lys Val
1               5                   10                  15

Met Val Asp Gly Ser His Gly Ser Asp Pro Ser Ile Ile His Arg Gly
            20                  25                  30

Lys Pro Phe Thr Leu Glu Ala Leu Phe Asp Ala Asn Gln Asn Thr Lys
            35                  40                  45

Thr Ala Lys Ile Glu Ile Lys Ala Asn Ile Asn Gly Leu Glu Val Asp
        50                  55                  60

Val Pro Gly Ile Asp Thr Asn Ala Ser His Tyr Ile Lys Ser Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Ser Ala Ile Ala Thr His Gly Lys Ile Arg
            115                 120                 125

Asp
```